US012766107B2

(12) United States Patent
Yue et al.

(10) Patent No.: US 12,766,107 B2
(45) Date of Patent: Oct. 20, 2026

(54) PHARMACEUTICAL COMPOSITION COMPRISING ANTIBODY DRUG CONJUGATE AND USE THEREOF

(71) Applicants: JIANGSU HENGRUI PHARMACEUTICALS CO., LTD., Lianyungan (CN); SHANGHAI HENGRUI PHARMACEUTICAL CO., LTD., Shanghai (CN)

(72) Inventors: Zhanlong Yue, Shanghai (CN); Zhen Yan, Shanghai (CN); Xun Liu, Shanghai (CN)

(73) Assignees: JIANGSU HENGRUI PHARMACEUTICALS CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 1016 days.

(21) Appl. No.: 17/914,087

(22) PCT Filed: Mar. 25, 2021

(86) PCT No.: PCT/CN2021/082854
§ 371 (c)(1),
(2) Date: Sep. 23, 2022

(87) PCT Pub. No.: WO2021/190581
PCT Pub. Date: Sep. 30, 2021

(65) Prior Publication Data

US 2023/0165969 A1 Jun. 1, 2023

(30) Foreign Application Priority Data

Mar. 25, 2020 (CN) ......................... 202010219601.7
Mar. 17, 2021 (CN) ......................... 202110287012.7

(51) Int. Cl.

| | |
|---|---|
| ***A61K 39/395*** | (2006.01) |
| ***A61K 9/19*** | (2006.01) |
| ***A61K 47/26*** | (2006.01) |
| ***A61K 47/68*** | (2017.01) |
| ***A61P 35/04*** | (2006.01) |
| ***C07K 16/32*** | (2006.01) |

(52) U.S. Cl.
CPC ................ *A61K 9/19* (2013.01); *A61K 47/26* (2013.01); *A61K 47/68037* (2023.08); *A61K 47/6855* (2017.08); *A61K 47/6865* (2017.08); *A61K 47/6889* (2017.08); *A61P 35/04* (2018.01); *C07K 16/32* (2013.01)

(58) Field of Classification Search
None
See application file for complete search history.

(56) References Cited

U.S. PATENT DOCUMENTS

| | | | | |
|---|---|---|---|---|
| 4,970,198 | A | 11/1990 | Lee et al. | |
| 5,079,233 | A | 1/1992 | Lee | |
| 5,585,089 | A | 12/1996 | Queen et al. | |
| 5,606,040 | A | 2/1997 | McGahren et al. | |
| 5,693,762 | A | 12/1997 | Queen et al. | |
| 5,739,116 | A | 4/1998 | Hamann et al. | |
| 5,767,285 | A | 6/1998 | Hamann et al. | |
| 5,773,001 | A | 6/1998 | Hamann et al. | |
| 7,090,843 | B1 | 8/2006 | Francisco et al. | |
| 7,659,241 | B2 | 2/2010 | Senter et al. | |
| 8,088,387 | B2 | 1/2012 | Steeves et al. | |
| 2005/0020645 | A1 | 1/2005 | Ohta et al. | |
| 2007/0031402 | A1 * | 2/2007 | Zhang .............. | A61K 47/68033 424/178.1 |

(Continued)

FOREIGN PATENT DOCUMENTS

| | | | |
|---|---|---|---|
| CN | 104755494 | A | 7/2015 |
| CN | 105829346 | A | 8/2016 |
| CN | 108853514 | A | 11/2018 |

(Continued)

OTHER PUBLICATIONS

Mullard A, (2013) Nature Reviews Drug Discovery, 12:329-332.

(Continued)

*Primary Examiner* — Yunsoo Kim
(74) *Attorney, Agent, or Firm* — Morgan, Lewis & Bockius LLP

(57) ABSTRACT

A pharmaceutical composition, comprising an antibody drug conjugate in a buffer solution. The antibody drug conjugate has a structure represented by the general formula (Pc-L-Y-D). The pharmaceutical composition further comprises sugar and a surfactant.

(Pc-L-Y-D)

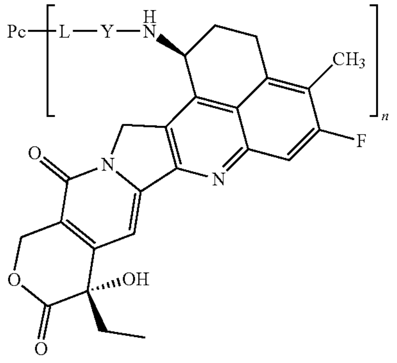

24 Claims, 5 Drawing Sheets

Specification includes a Sequence Listing.

(56) References Cited

U.S. PATENT DOCUMENTS

2018/0147292 A1 * 5/2018 Noguchi ................ A61K 31/40

FOREIGN PATENT DOCUMENTS

| | | | |
|---|---|---|---|
| EP | 0737686 | A1 | 10/1996 |
| EP | 2907824 | A1 | 8/2015 |
| WO | 2005001038 | A2 | 1/2005 |
| WO | 2004010957 | A2 | 2/2005 |
| WO | 2005037992 | A2 | 4/2005 |
| WO | 2008025020 | A2 | 2/2008 |
| WO | 201396771 | A1 | 6/2013 |
| WO | 2013106717 | A1 | 7/2013 |
| WO | 2014057687 | A1 | 4/2014 |

OTHER PUBLICATIONS

DiJoseph JF, Armellino DC, (2004) Blood, 103:1807-1814).
Nat. Biotechnol (2003) 21(7):778-784.
Clinical Cancer Research (2016)22 (20):5097-5108.
Cancer Sci (2016) 107: 1039-1046.
Tetrahedron Letters, 25(12), 1269-72; 1984.
Journal of the American Chemical Society, 2014, vol. 136, #22, p. 8138-8142.
Journal of Medicinal Chemistry, 2013, vol. 56, # 13, p. 5541-5552.

* cited by examiner

SEQUENCE LISTING

```
<160> NUMBER OF SEQ ID NOS: 6

<210> SEQ ID NO 1
<211> LENGTH: 214
<212> TYPE: PRT
<213> ORGANISM: Artificial Sequence
<220> FEATURE:
<223> OTHER INFORMATION: Light chain of trastuzumab

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

-continued

210

<210> SEQ ID NO 2
<211> LENGTH: 450
<212> TYPE: PRT
<213> ORGANISM: Artificial Sequence
<220> FEATURE:
<223> OTHER INFORMATION: Heavy chain of trastuzumab

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 3
<211> LENGTH: 214
<212> TYPE: PRT
<213> ORGANISM: Artificial Sequence
<220> FEATURE:
<223> OTHER INFORMATION: Light chain of pertuzumab

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 4
<211> LENGTH: 449
<212> TYPE: PRT
<213> ORGANISM: Artificial Sequence
<220> FEATURE:
<223> OTHER INFORMATION: Heavy chain of pertuzumab
```

<400> SEQUENCE: 4

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Thr Met Asp Trp Val Arg Gln Ala Pro Gly Lys Gly Leu Glu Trp Val
35 40 45

Ala Asp Val Asn Pro Asn Ser Gly Gly Ser Ile Tyr Asn Gln Arg Phe
50 55 60

Lys Gly Arg Phe Thr Leu Ser Val Asp Arg Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asn Leu Gly Pro Ser Phe Tyr Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys

```
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 5
<211> LENGTH: 215
<212> TYPE: PRT
<213> ORGANISM: Artificial Sequence
<220> FEATURE:
<223> OTHER INFORMATION: Light chain of B7H3 antibody 1F9DS

<400> SEQUENCE: 5

Asp Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215


<210> SEQ ID NO 6
<211> LENGTH: 449
<212> TYPE: PRT
<213> ORGANISM: Artificial Sequence
<220> FEATURE:
<223> OTHER INFORMATION: Heavy chain of B7H3 antibody 1F9DS

<400> SEQUENCE: 6

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
```

-continued

```
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
            100                 105                 110

Ala Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

PHARMACEUTICAL COMPOSITION COMPRISING ANTIBODY DRUG CONJUGATE AND USE THEREOF

CROSS-REFERENCE TO RELATED APPLICATIONS

The present application is a national stage application of International Patent Application No. PCT/CN2021/082854, filed on Mar. 25, 2021, which claims the benefit of and priority to Chinese Patent Application No. (CN202010219601.7 filed on Mar. 25, 2020, and Chinese Patent Application No. (CN202110287012.7) filed on Mar. 17, 2021.

SEQUENCE LISTING

The instant application contains a Sequence Listing which has been submitted electronically in ASCII format and is hereby incorporated by reference in its entirety. Said ASCII copy, created on Sep. 2, 2022, is named "721021CPUS_126268-5042-US_ST25_Sequence_Listing.TXT" and is approximately 18 kilobytes in size.

TECHNICAL FIELD

The present disclosure belongs to the field of pharmaceutical formulations, and in particular relates to a pharmaceutical composition comprising an antibody drug conjugate and use thereof as an anti-cancer medicament.

BACKGROUND

The statements herein merely provide background information related to the present disclosure and may not necessarily constitute the prior art.

Antibody drug conjugate (ADC) links a monoclonal antibody or an antibody fragment to a biologically active cytotoxin via a stable chemical linker compound, fully exploiting the binding specificity of the antibody to surface antigens of normal cells and tumor cells and the high-efficiency of the cytotoxin, and also avoiding the former's disadvantage of having a poor therapeutic effect, the latter's disadvantage of having serious toxic side effects, and the like. This means that the antibody drug conjugate can bind to tumor cells more precisely and has a reduced effect on normal cells compared to conventional chemotherapeutic drugs in the past (Mullard A, (2013) *Nature Reviews Drug Discovery,* 12:329-332; DiJoseph J F, Armellino D C, (2004) *Blood,* 103:1807-1814).

Mylotarg® (gemtuzumab ozogamicin, Wyeth Pharmaceutical Co., Ltd.), the first antibody drug conjugate, was approved by U.S. FDA in 2000 for the treatment of acute myelocytic leukemia (*Drugs of the Future* (2000) 25(7):686; U.S. Pat. Nos. 4,970,198; 5,079,233; 5,585,089; 5,606,040; 5,693,762; 5,739,116; 5,767,285; 5,773,001).

Adcetris® (brentuximab vedotin, Seattle Genetics) was approved by fast track review designed by U.S. FDA in August 2011 for the treatment of Hodgkin lymphoma and recurrent anaplastic large cell lymphoma (*Nat. Biotechnol* (2003) 21(7):778-784; WO2004010957; WO2005001038; U.S. Pat. Nos. 7,090,843A; 7,659,241; WO2008025020). Adcetris® is a novel ADC-targeted drug that can enable the drug to directly act on target CD30 on lymphoma cells and then carry out endocytosis so as to induce apoptosis of the tumor cells.

Both Mylotarg® and Adcetris® are targeted therapies against hematological tumors which are relatively simple in tissue structure compared to solid tumors. Kadcyla® (ado-trastuzumab emtansine, T-DM1) was approved by U.S. FDA in February 2013 for the treatment of HER2-positive patients with advanced or metastatic breast cancer and having drug resistance to tratuzumab (trade name: Herceptin) and paclitaxel (WO2005037992; U.S. Pat. No. 8,088,387). Kadcyla® is the first ADC drug approved by U.S. FDA for the treatment of solid tumors.

There are several classes of small molecules with cytotoxicity for antibody drug conjugates, one of which is camptothecin derivatives having an antitumor effect by inhibiting topoisomerase I. In WO2014057687; *Clinical Cancer Research* (2016) 22(20):5097-5108; and *Cancer Sci* (2016) 107:1039-1046, it was reported that camptothecin derivative exatecan (chemical name (1S,9S)-1-amino-9-ethyl-5-fluoro-2,3-dihydro-9-hydroxy-4-methyl-1H,12H-benzo[de]pyrano[3',4': 6,7]imidazo[1,2-b]quinoline-10,13 (9H,15H)-dione) was applied to antibody drug conjugates (ADCs). There is still a need to further develop ADC drugs with better therapeutic effects. However, ADCs are of more complicated heterostructures than antibodies, and therefore, a greater challenge has been posed to ADC formulations for therapeutic purposes.

SUMMARY

The present disclosure provides a pharmaceutical composition comprising an antibody drug conjugate and a buffer, wherein the antibody drug conjugate has a structure of general formula (Pc-L-Y-D):

(Pc-L-Y-D)

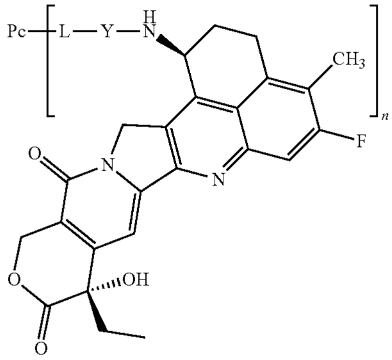

;

wherein:

Y is selected from the group consisting of —O—$(CR^aR^b)_m$—$CR^1R^2$—C(O)—, —O—$CR^1R^2$—$(CR^aR^b)_m$—, —O—$CR^1R^2$—, —NH—$(CR^aR^b)_m$—$CR^1R^2$—C(O)— and —S—$(CR^aR^b)_m$—$CR^1R^2$—C(O)—;

$R^a$ and $R^b$ are identical or different and are each independently selected from the group consisting of hydrogen, deuterium, halogen, alkyl, haloalkyl, deuterated alkyl, alkoxy, hydroxy, amino, cyano, nitro, hydroxyalkyl, cycloalkyl and heterocyclyl;

or, $R^a$ and $R^b$, together with carbon atoms linked thereto, form cycloalkyl or heterocyclyl;

$R^1$ is selected from the group consisting of halogen, haloalkyl, deuterated alkyl, cycloalkyl, cycloalkylalkyl, alkoxyalkyl, heterocyclyl, aryl and heteroaryl;

$R^2$ is selected from the group consisting of hydrogen, halogen, haloalkyl, deuterated alkyl, cycloalkyl, cycloalkylalkyl, alkoxyalkyl, heterocyclyl, aryl and heteroaryl;

or, $R^1$ and $R^2$, together with carbon atoms linked thereto, form cycloalkyl or heterocyclyl;

or, $R^a$ and $R^2$, together with carbon atoms connected thereto, form cycloalkyl or heterocyclyl;

m is an integer from 0 to 4;

n is a decimal or an integer from 1 to 10;

L is a linker unit;

Pc is an antibody or an antigen-binding fragment thereof;

the composition is at a pH of about 4.5 to about 6.0, preferably a pH of about 4.8 to about 5.3, and more preferably a pH of about 5.0 to about 5.1.

In an alternative embodiment, the buffer in the pharmaceutical composition is at a pH of about 4.5 to about 6.0; non-limiting examples include about 4.5, about 4.6, about 4.7, about 4.8, about 4.9, about 5.0, about 5.1, about 5.2, about 5.3, about 5.4, about 5.5, about 5.6, about 5.7, about 5.8, about 5.9 and about 6.0; about 4.8 to about 5.3 is preferred, and about 5.0 to about 5.1 is more preferred. In some embodiments, the pharmaceutical composition is at a pH of 4.5 to 5.2, preferably a pH of 4.8 to 5.2, and more preferably a pH of 5.0 to 5.1. In some embodiments, the pharmaceutical composition is at a pH of 5.0. In an alternative embodiment, the pharmaceutical composition further comprises a surfactant, which may be selected from the group consisting of polysorbate, polysorbate 20, polysorbate 80, poloxamer, Triton, sodium dodecyl sulfonate, sodium lauryl sulfonate, sodium octyl glycoside, lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauramido propyl-betaine, cocaramide propyl-betaine, linoleinamide propyl-betaine, myristylamide propyl-betaine, palmitamide propyl-betaine, isostearamide propyl-betaine, myristylamide propyl-dimethylamine, palmitamide propyl-dimethylamine, isostearamide propyl-dimethylamine, sodium methyl cocoyl, sodium methyl oleyl taurate, polyethylene glycol, polypropylene glycol, copolymer of ethylene and propylene glycol, and the like. The surfactant is preferably polysorbate 80 or polysorbate 20, more preferably polysorbate 80.

In an alternative embodiment, the surfactant in the pharmaceutical composition is at a concentration of about 0.01 mg/mL to about 1.0 mg/mL. In an alternative embodiment, the surfactant in the pharmaceutical composition is at a concentration of about 0.05 mg/mL to about 0.5 mg/mL, preferably about 0.1 mg/mL to about 0.3 mg/mL, about 0.2 mg/mL to about 0.6 mg/mL, about 0.2 mg/mL to about 0.5 mg/mL, or about 0.2 mg/mL to about 0.3 mg/mL, and more preferably about 0.2 mg/mL; non-limiting examples include 0.1 mg/mL, 0.15 mg/mL, 0.2 mg/mL, 0.25 mg/mL, 0.3 mg/mL, 0.35 mg/mL, 0.4 mg/mL, 0.45 mg/mL, 0.5 mg/mL and 0.6 mg/mL.

In an alternative embodiment, the aforementioned pharmaceutical composition further comprises a saccharide. "Saccharide" of the present disclosure includes the general composition ($CH_2O$) and derivatives thereof, including monosaccharides, disaccharides, trisaccharides, polysaccharides, sugar alcohols, reducing sugars, non-reducing sugars, etc. The saccharide may be selected from the group consisting of glucose, sucrose, trehalose, lactose, fructose, maltose, dextran, glycerin, erythritol, glycerol, arabitol, sylitol, sorbitol, mannitol, mellibiose, melezitose, raffinose, mannotriose, stachyose, maltose, lactulose, maltulose, glucitol, maltitol, lactitol, iso-maltulose, etc. The saccharide is preferably non-reducing disaccharide, more preferably trehalose or sucrose, and most preferably sucrose.

In an alternative embodiment, the saccharide in the aforementioned pharmaceutical compositions is at a concentration of about 60 mg/mL to about 90 mg/mL; non-limiting examples include 60 mg/mL, 65 mg/mL, 70 mg/mL, 75 mg/mL, 80 mg/mL, 85 mg/mL and 90 mg/mL; 80 mg/mL is preferred. In some embodiments, the saccharide is at a concentration of 70 mg/mL to 90 mg/mL.

In an alternative embodiment, the antibody drug conjugate in the pharmaceutical composition is at a concentration of about 1 mg/mL to about 100 mg/mL; non-limiting examples include 1 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 40 mg/mL, 50 mg/mL, 60 mg/mL, 70 mg/mL, 80 mg/mL, 90 mg/mL and 100 mg/mL; about 10 mg/mL to about 30 mg/mL is preferred, and about 20 mg/mL to about 22 mg/mL is more preferred. Specifically, non-limiting examples include 20.1 mg/mL, 20.2 mg/mL, 20.3 mg/mL, 20.4 mg/mL, 20.5 mg/mL, 20.6 mg/mL, 20.7 mg/mL, 20.8 mg/mL, 20.81 mg/mL, 20.82 mg/mL, 20.83 mg/mL, 20.84 mg/mL, 20.85 mg/mL, 20.86 mg/mL, 20.87 mg/mL, 20.88 mg/mL, 20.89 mg/mL, 20.9 mg/mL, 20.9 mg/mL, 20.91 mg/mL, 20.92 mg/mL, 20.93 mg/mL, 20.94 mg/mL, 20.95 mg/mL, 20.96 mg/mL, 20.97 mg/mL, 20.98 mg/mL, 20.99 mg/mL and 21 mg/mL. In an alternative embodiment, the antibody drug conjugate in the pharmaceutical composition is at a concentration of about 10 mg/mL to about 30 mg/mL, preferably about 20 mg/mL, based on the naked antibody (i.e., the antibody portion of the ADC).

In an alternative embodiment, the buffer in the aforementioned pharmaceutical composition is selected from the group consisting of a histidine salt buffer, a succinate buffer and a citrate buffer, preferably a succinate buffer, and more preferably succinic acid-sodium succinate buffer.

In an alternative embodiment, the buffer in the pharmaceutical composition is at a concentration of about 5 mM to about 50 mM; non-limiting examples include 1 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 30 mM, 40 mM and 50 mM; about 5 mM to about 20 mM is preferred, and about 10 mM is most preferred.

In an alternative embodiment, the drug loading (n) may range from 3 to 8, 4 to 8, 5 to 7, more preferably 5.3 to 6.1, 5.7 cytotoxic drugs binding to each antibody or an antigen-binding fragment (Pc) thereof. n is a decimal or an integer.

In an alternative embodiment, the pharmaceutical composition comprises:

(a) the antibody drug conjugate at about 10 mg/mL to about 30 mg/mL, (b) a polysorbate at about 0.05 mg/mL to about 0.5 mg/mL, (c) a saccharide at about 60 mg/mL to about 90 mg/mL, and (d) a buffer at about 5 mM to about 20 mM; the pharmaceutical composition being at a pH of about 4.8 to about 5.3.

In an alternative embodiment, the pharmaceutical composition comprises:

(a) the antibody drug conjugate at about 10 mg/mL to about 30 mg/mL, (b) a polysorbate at about 0.05 mg/mL to about 0.5 mg/mL, (c) a saccharide at about 60 mg/mL to about 90 mg/mL, and (d) a buffer at about 5 mM to about 20 mM; the pharmaceutical composition being at a pH of 4.8 to 5.2.

In an alternative embodiment, the pharmaceutical composition comprises:

(a) the antibody drug conjugate at about 20 mg/mL to about 22 mg/mL, (b) polysorbate 80 at about 0.2 mg/mL, (c) sucrose at 80 mg/mL, and (d) a succinate buffer at 10 mM; the pharmaceutical composition being at a pH of about 5.0 to about 5.1. In some embodiments, the pharmaceutical composition is at a pH of 5.0 to 5.1.

In an alternative embodiment, in the aforementioned antibody drug conjugate,

—Y— is —O—$(CR^aR^b)$m-$CR^1R^2$—C(O)—;

$R^a$ and $R^b$ are identical or different and are each independently selected from the group consisting of hydrogen, deuterium, halogen and alkyl;

$R^1$ is $C_{3-7}$ cycloalkylalkyl or $C_{3-7}$ cycloalkyl;

$R^2$ is selected from the group consisting of hydrogen, haloalkyl and $C_{3-7}$ cycloalkyl, preferably hydrogen;

or, $R^1$ and $R^2$, together with carbon atoms linked thereto, form $C_{3-7}$ cycloalkyl;

m is 0 or 1.

In an alternative embodiment, in the aforementioned antibody drug conjugate,

—Y— is —O—$(CH_2)$m-$CR^1R^2$—C(O)—;

$R^1$ is $C_{3-7}$ cycloalkylalkyl or $C_{3-7}$ cycloalkyl;

$R^2$ is selected from the group consisting of hydrogen, haloalkyl and $C_{3-7}$ cycloalkyl;

or, $R^1$ and $R^2$, together with carbon atoms linked thereto, form $C_{3-7}$ cycloalkyl;

m is 0 or 1.

In an alternative embodiment, in the aforementioned antibody drug conjugate,

—Y— is —O—$(CH_2)$m-$CR^1R^2$—C(O)—;

$R^1$ is $C_{3-7}$ cycloalkylalkyl or $C_{3-7}$ cycloalkyl;

$R^2$ is hydrogen;

or, $R^1$ and $R^2$, together with carbon atoms linked thereto, form $C_{3-7}$ cycloalkyl;

m is 0 or 1.

In an alternative embodiment, in the aforementioned antibody drug conjugate,

—Y— is —O—$(CH_2)$m-$CR^1R^2$—C(O)—;

$R^1$ is $C_{3-7}$ cycloalkylalkyl or $C_{3-7}$ cycloalkyl;

$R^2$ is hydrogen;

or, $R^1$ and $R^2$, together with carbon atoms linked thereto, form $C_{3-7}$ cycloalkyl;

m is 0.

In an alternative embodiment, in the aforementioned antibody drug conjugate,

—Y— is selected from the group consisting of:

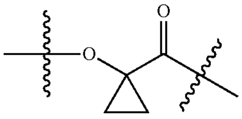
,
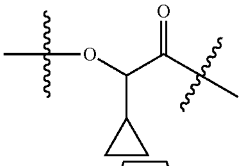
,
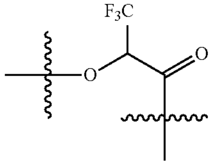
,
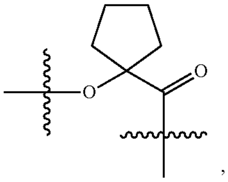
,
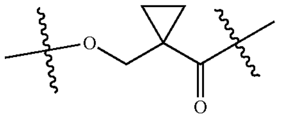
,

-continued

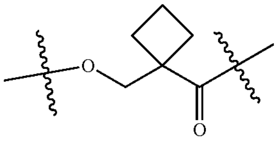
, and
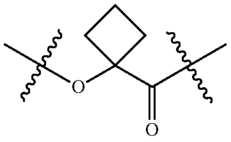
,

In an alternative embodiment, in the aforementioned antibody drug conjugate, a O end of Y is linked to the linker unit L.

In an alternative embodiment, in the aforementioned antibody drug conjugate,

—Y— is selected from the group consisting of:

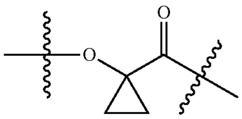
,
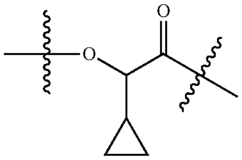
,
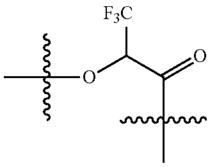
,
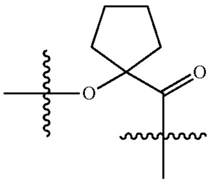
,
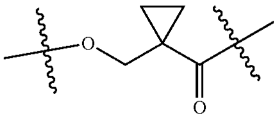
,
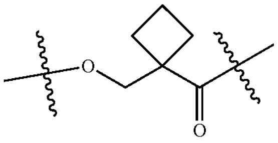
, and
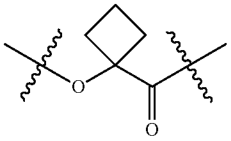
, In an alternative embodiment, the aforementioned antibody drug conjugate has a structure of general formula (Pc-L-$D_1$):

(Pc-L-D1)

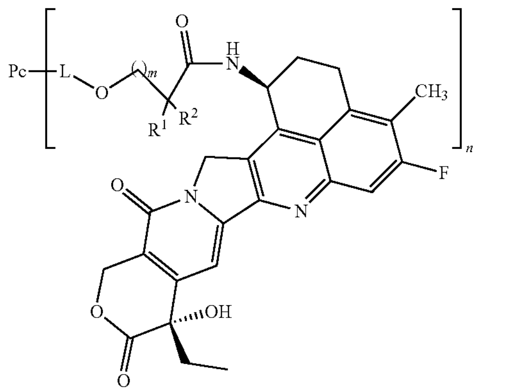

wherein:

$R^1$ is cycloalkylalkyl or cycloalkyl, preferably $C_{3-7}$ cycloalkylalkyl or $C_{3-7}$ cycloalkyl;

$R^2$ is selected from the group consisting of hydrogen, haloalkyl and $C_{3-7}$ cycloalkyl, preferably hydrogen;

or, $R^1$ and $R^2$, together with carbon atoms linked thereto, form $C_{3-7}$ cycloalkyl;

m is 0 or 1;

n may be an integer or a decimal from 1 to 10;

Pc is an antibody or an antigen-binding fragment thereof; and L is a linker unit.

In an alternative embodiment, in the aforementioned antibody drug conjugate, n may be an integer or a decimal from 2 to 8, preferably an integer or a decimal from 3 to 8.

In an alternative embodiment, in the aforementioned antibody drug conjugate, the linker unit -L- is $-L^1-L^2-L^3-L^4-$, wherein:

$L^1$ is selected from the group consisting of -(succinimidyl-3-yl-N)—W—C(O)—, —$CH_2$—C(O)—$NR^3$—W—C(O)— and —C(O)—W—C(O)—, wherein W is selected from the group consisting of $C_{1-8}$ alkyl, $C_{1-8}$ alkyl-cycloalkyl and linear heteroalkyl of 1 to 8 atoms, and the heteroalkyl comprises 1 to 3 heteroatoms selected from the group consisting of N, O and S, wherein the $C_{1-8}$ alkyl, cycloalkyl and linear heteroalkyl are each independently optionally further substituted with one or more substituents selected from the group consisting of halogen, hydroxy, cyano, amino, alkyl, chloroalkyl, deuterated alkyl, alkoxy and cycloalkyl;

$L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20; $L^2$ is preferably a chemical bond;

$L^3$ is a peptide residue consisting of 2 to 7 amino acids, wherein the amino acids are optionally further substituted with one or more substituents selected from the group consisting of halogen, hydroxy, cyano, amino, alkyl, chloroalkyl, deuterated alkyl, alkoxy and cycloalkyl;

$L^4$ is selected from the group consisting of —$NR^5(CR^6R^7)_t$—, —$C(O)NR^5$, —$C(O)NR^5(CH_2)_t$— and a chemical bond, wherein t is an integer from 1 to 6; $L^4$ is preferably —$NR^5(CR^6R^7)_t$—;

$R^3$, $R^4$ and $R^5$ are identical or different and are each independently selected from the group consisting of hydrogen, alkyl, haloalkyl, deuterated alkyl and hydroxyalkyl;

$R^6$ and $R^7$ are identical or different and are each independently selected from the group consisting of hydrogen, halogen, alkyl, haloalkyl, deuterated alkyl and hydroxyalkyl.

In an alternative embodiment, in the aforementioned antibody drug conjugate, the linker unit $L^1$ is selected from the group consisting of -(succinimidin-3-yl-N)—$(CH_2)s^1$-C(O)—, -(succinimidin-3-yl-N)—$CH_2$-cyclohexyl-C(O)—, -(succinimidin-3-yl-N)—$(CH_2CH_2O)s^2$-$CH_2CH_2$—C(O)—, —$CH_2$—C(O)—$NR^3$—$(CH_2)s^3$-C(O)— and —C(O)—$(CH_2)s^4$C(O)—, wherein $s^1$ is an integer from 2 to 8, $s^2$ is an integer from 1 to 3, $s^3$ is an integer from 1 to 8, and $s^4$ is an integer from 1 to 8; $s^1$ is preferably 5.

In an alternative embodiment, in the aforementioned antibody drug conjugate, the linker unit $L^2$ is —$NR^4(CH_2CH_2O)p^1CH_2C(O)$— or a chemical bond, and $p^1$ is an integer from 6 to 12.

In an alternative embodiment, in the aforementioned antibody drug conjugate, $L^4$ is —$NR^5(CR^6R^7)t$-, $R^5$ is hydrogen or alkyl, $R^6$ and $R^7$ are identical or different and are each independently hydrogen or alkyl, and t is 1 or 2, preferably 2; $L^4$ is preferably —$NR^5CR^6R^7$—, more preferably —$NHCH_2$—.

In an alternative embodiment, in the aforementioned antibody drug conjugate, the linker unit -L- is $-L^1-L^2-L^3-L^4-$, wherein:

$L^1$ is

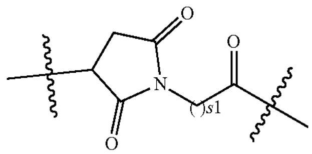

, and $s^1$ is an integer from 2 to 8;

$L^2$ is a chemical bond;

$L^3$ is a tetrapeptide residue;

$L^4$ is —$NR^5(CR^6R^7)t$-, $R^5$ is hydrogen or alkyl, $R^6$ and $R^7$ are identical or different and are each independently hydrogen or alkyl, and t is 1 or 2.

In an alternative embodiment, in the aforementioned antibody drug conjugate, the linker unit -L- is $-L^1-L^2-L^3-L^4-$, wherein:

$L^1$ is -(succinimidin-3-yl-N)—$CH_2$-cyclohexyl-C(O)—;

$L^2$ is —$NR^4(CH_2CH_2O)_9CH_2C(O)$—;

$L^3$ is a tetrapeptide residue;

$L^4$ is —$NR^5(CR^6R^7)t$-, $R^5$ is hydrogen or alkyl, $R^6$ and $R^7$ are identical or different and are each independently hydrogen or alkyl, and t is 1 or 2.

In an alternative embodiment, in the aforementioned antibody drug conjugate, the peptide residue of $L^3$ is an amino acid residue formed from one, two or more amino acids selected from the group consisting of phenylalanine (E), glycine (G), valine (V), lysine (K), citrulline, serine (S), glutamic acid (E) and aspartic acid (N), preferably an amino acid residue formed from one, two or more amino acids selected from the group consisting of phenylalanine and glycine, more preferably a tetrapeptide residue, and most preferably a tetrapeptide residue of GGFG (glycine-glycine-phenylalanine-glycine).

In an alternative embodiment, in the aforementioned antibody drug conjugate, the linker unit -L- is $-L^1-L^2-L^3-L^4-$, wherein the $L^1$ end is linked to the antibody or the antigen-binding fragment thereof, and the $L^4$ end is linked to Y.

In an alternative embodiment, in the aforementioned antibody drug conjugate, the -L-Y— is:

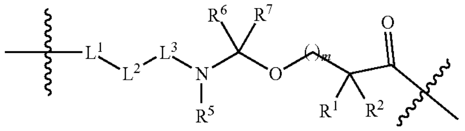

$L^1$ is -(succinimidin-3-yl-N)—$(CH_2)s^1$-C(O)— or -(succinimidin-3-yl-N)—$CH_2$-cyclohexyl-C(O)—;

$L^2$ is —$NR^4(CH_2CH_2O)p^1CH_2C(O)$— or a chemical bond, and $p^1$ is an integer from 6 to 12;

$R^4$ is selected from the group consisting of hydrogen, alkyl, haloalkyl, deuterated alkyl and hydroxyalkyl;

$L^3$ is a tetrapeptide residue of GGFG;

$R^1$ is cycloalkylalkyl or cycloalkyl, preferably $C_{3-7}$ cycloalkylalkyl or $C_{3-7}$ cycloalkyl;

$R^2$ is selected from the group consisting of hydrogen, haloalkyl and $C_{3-7}$ cycloalkyl, preferably hydrogen;

or, $R^1$ and $R^2$, together with carbon atoms linked thereto, form $C_{3-7}$ cycloalkyl;

$R^5$ is selected from the group consisting of hydrogen and alkyl, and $R^6$ and $R^7$ are identical or different and are each independently hydrogen or alkyl;

$s^1$ is an integer from 2 to 8, preferably 5;

m is an integer from 0 to 4.

In an alternative embodiment, in the aforementioned antibody drug conjugate, the -L-Y— is:

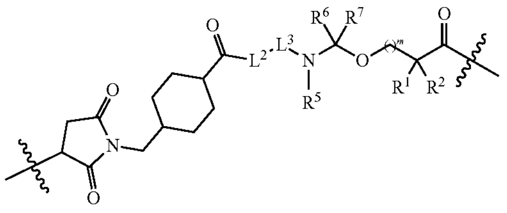

preferably:

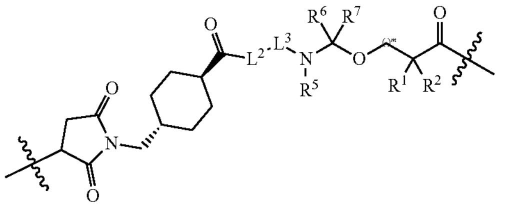

$L^2$ is —$NR^4(CH_2CH_2O)_9CH_2C(O)$—; $R^4$ is selected from the group consisting of hydrogen, alkyl, haloalkyl, deuterated alkyl and hydroxyalkyl;

$L^3$ is a tetrapeptide residue of GGFG;

$R^1$ is cycloalkylalkyl or cycloalkyl, preferably $C_{3-7}$ cycloalkylalkyl or $C_{3-7}$ cycloalkyl;

$R^2$ is selected from the group consisting of hydrogen, haloalkyl and $C_{3-7}$ cycloalkyl, preferably hydrogen;

or, $R^1$ and $R^2$, together with carbon atoms linked thereto, form $C_{3-7}$ cycloalkyl;

$R^5$ is selected from the group consisting of hydrogen and alkyl, and $R^6$ and $R^7$ are identical or different and are each independently hydrogen or alkyl;

m is an integer from 0 to 4.

In an alternative embodiment, in the aforementioned antibody drug conjugate, the -L-Y— is:

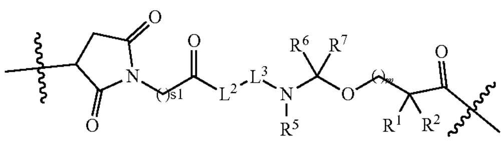

$L^2$ is a chemical bond;

$L^3$ is a tetrapeptide residue of GGFG;

$R^1$ is cycloalkylalkyl or cycloalkyl, preferably $C_{3-7}$ cycloalkylalkyl or $C_{3-7}$ cycloalkyl;

$R^2$ is selected from the group consisting of hydrogen, haloalkyl and $C_{3-7}$ cycloalkyl, preferably hydrogen;

or, $R^1$ and $R^2$, together with carbon atoms linked thereto, form $C_{3-7}$ cycloalkyl;

$R^5$ is selected from the group consisting of hydrogen and alkyl, and $R^6$ and $R^7$ are identical or different and are each independently hydrogen or alkyl;

$s^1$ is an integer from 2 to 8, preferably 5;

m is an integer from 0 to 4.

In an alternative embodiment, in the aforementioned antibody drug conjugate, the -L-Y— is:

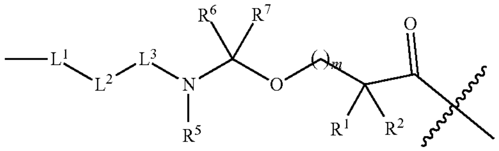

wherein:

$L^1$ is -(succinimidin-3-yl-N)—$(CH_2)s^1$-C(O)— or -(succinimidin-3-yl-N)—$CH_2$-cyclohexyl-C(O)—;

$L^2$ is —$NR^4(CH_2CH_2O)p^1CH_2C(O)$— or a chemical bond, and $p^1$ is an integer from 1 to 20;

$R^4$ is selected from the group consisting of hydrogen, alkyl, haloalkyl, deuterated alkyl and hydroxyalkyl;

$L^3$ is a tetrapeptide residue of GGFG;

$R^1$ is cycloalkylalkyl or cycloalkyl, preferably $C_{3-7}$ cycloalkylalkyl or $C_{3-7}$ cycloalkyl;

$R^2$ is selected from the group consisting of hydrogen, haloalkyl and $C_{3-7}$ cycloalkyl, preferably hydrogen;

or, $R^1$ and $R^2$, together with carbon atoms linked thereto, form $C_{3-7}$ cycloalkyl;

$R^5$, $R^6$ and $R^7$ are identical or different and are each independently hydrogen or alkyl;

$s^1$ is an integer from 2 to 8;

m is an integer from 0 to 4.

In an alternative embodiment, in the aforementioned antibody drug conjugate, the -L-Y— is:

(-L-Y-)

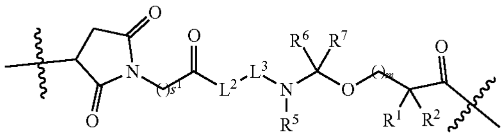

wherein:

$L^2$ is a chemical bond;

$L^3$ is a tetrapeptide residue of GGFG;

$R^1$ is cycloalkylalkyl or cycloalkyl, preferably $C_{3-7}$ cycloalkylalkyl or $C_{3-7}$ cycloalkyl;

$R^2$ is selected from the group consisting of hydrogen, haloalkyl and $C_{3-7}$ cycloalkyl, preferably hydrogen;

or, $R^1$ and $R^2$, together with carbon atoms linked thereto, form $C_{3-7}$ cycloalkyl;

$R^5$ is selected from the group consisting of hydrogen and alkyl, and $R^6$ and $R^7$ are identical or different and are each independently hydrogen or alkyl;

$s^1$ is an integer from 2 to 8;

m is an integer from 0 to 4.

In an alternative embodiment, the antibody drug conjugate has a structure of general formula (Pc-$L_a$-Y-D):

(Pc-$L_a$-Y-D)

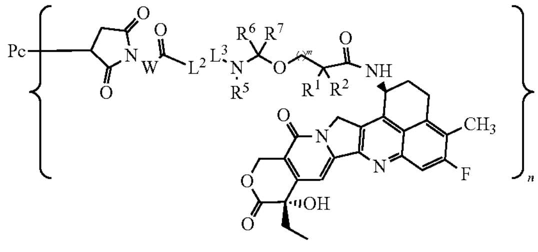

;

wherein,

W is selected from the group consisting of $C_{1-8}$ alkyl, $C_{1-8}$ alkyl-$C_{3-7}$ cycloalkyl, and a linear heteroalkyl of 1 to 8 atoms, and the heteroalkyl comprises 1 to 3 heteroatoms selected from the group consisting of N, O and S, wherein the $C_{1-8}$ alkyl, $C_{3-7}$ cycloalkyl and linear heteroalkyl are each independently optionally further substituted with one or more substituents selected from the group consisting of halogen, hydroxy, cyano, amino, $C_{1-6}$ alkyl, Cis chloroalkyl, deuterated $C_{1-6}$ alkyl, $C_{1-6}$ alkoxy, and $C_{3-7}$ cycloalkyl;

$L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20; $R^4$ is selected from the group consisting of hydrogen, alkyl, haloalkyl, deuterated alkyl, and hydroxyalkyl;

$L^3$ is a peptide residue consisting of 2 to 7 amino acid residues, wherein the amino acid residues are selected from the group consisting of amino acid residues formed from amino acids of phenylalanine (F), glycine (G), valine (V), lysine (K), citrulline, serine (S), glutamic acid (Q) and aspartic acid (D), and are optionally further substituted with one or more substituents selected from the group consisting of halogen, hydroxy, cyano, amino, $C_{1-6}$ alkyl, Cis chloroalkyl, deuterated $C_{1-6}$ alkyl, $C_{1-6}$ alkoxy and $C_{3-7}$ cycloalkyl;

$R^1$ is $C_{1-6}$ haloalkyl or $C_{3-7}$ cycloalkyl;

$R^2$ is selected from the group consisting of hydrogen, $C_{1-6}$ haloalkyl and $C_{3-7}$ cycloalkyl;

or, $R^1$ and $R^2$, together with carbon atoms linked thereto, form $C_{3-7}$ cycloalkyl;

$R^5$ is selected from the group consisting of hydrogen, $C_{1-6}$ alkyl, $C_{1-6}$ haloalkyl, deuterated $C_{1-6}$ alkyl and hydroxy $C_{1-6}$ alkyl;

$R^6$ and $R^7$ are identical or different and are each independently selected from the group consisting of hydrogen, halogen, $C_{1-6}$ alkyl, $C_{1-6}$ haloalkyl, deuterated $C_{1-6}$ alkyl and hydroxy $C_{1-6}$ alkyl;

m is 0 or 1;

n is a decimal or an integer from 3 to 8;

Pc is an antibody or an antigen-binding fragment thereof.

In an alternative embodiment, the antibody drug conjugate has a structure of general formula (Pc-Lb-Y-D):

(Pc-Lb-Y-D)

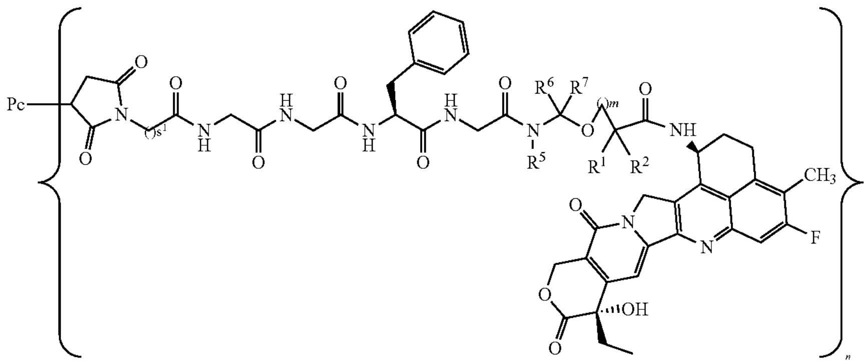

;

wherein:

$s^1$ is an integer from 2 to 8;

Pc, $R^1$, $R^2$, $R^5$, $R^6$, $R^7$, m and n are as defined in general formula (Pc-$L_a$-Y-D).

In an alternative embodiment, in the aforementioned antibody drug conjugate, the -L-Y— includes, but is not limited to:

| No. | Structure |
| --- | --- |
| -L-$Y^2$- | 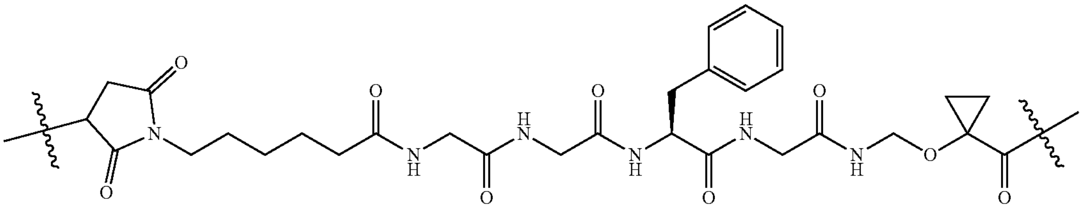 [SMILES: *C(=O)C1(OCNC(=O)CNC(=O)[C@H](Cc2ccccc2)NC(=O)CNC(=O)CNC(=O)CCCCCN2C(=O)CC(*)C2=O)CC1] |
| -L-$Y^3$- | 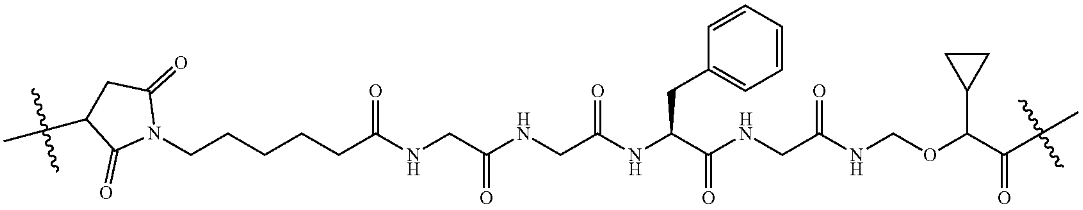 [SMILES: *C(=O)C(OCNC(=O)CNC(=O)[C@H](Cc1ccccc1)NC(=O)CNC(=O)CNC(=O)CCCCCN1C(=O)CC(*)C1=O)C1CC1] |
| -L-$Y^{3-A}$- | 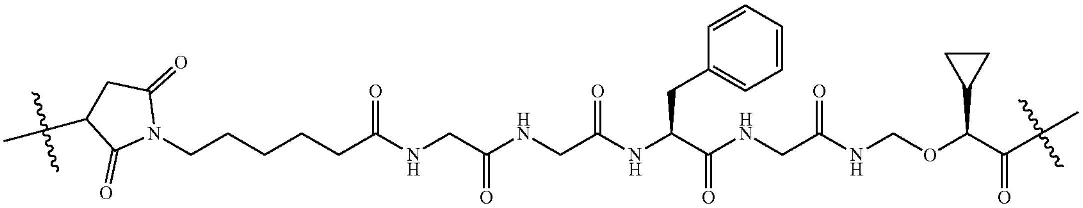 [SMILES: *C(=O)[C@@H](OCNC(=O)CNC(=O)[C@H](Cc1ccccc1)NC(=O)CNC(=O)CNC(=O)CCCCCN1C(=O)CC(*)C1=O)C1CC1] |
| -L-$Y^{3-B}$- | 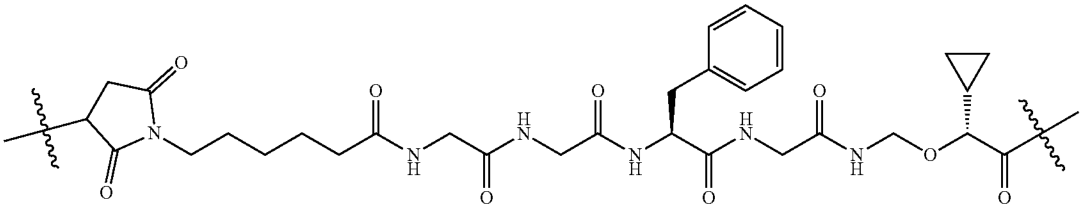 |
| -L-$Y^6$- | 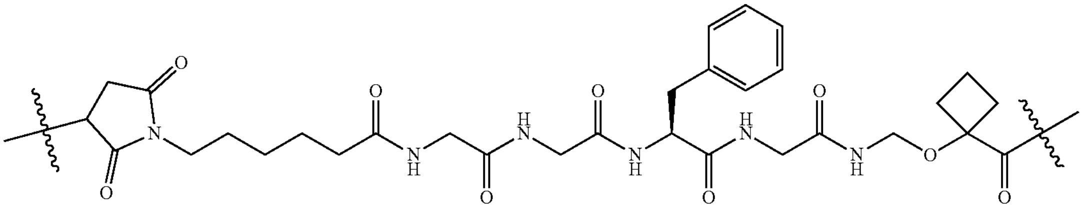 [SMILES: *C(=O)C1(OCNC(=O)CNC(=O)[C@H](Cc2ccccc2)NC(=O)CNC(=O)CNC(=O)CCCCCN2C(=O)CC(*)C2=O)CCC1] |
| -L-$Y^7$- | 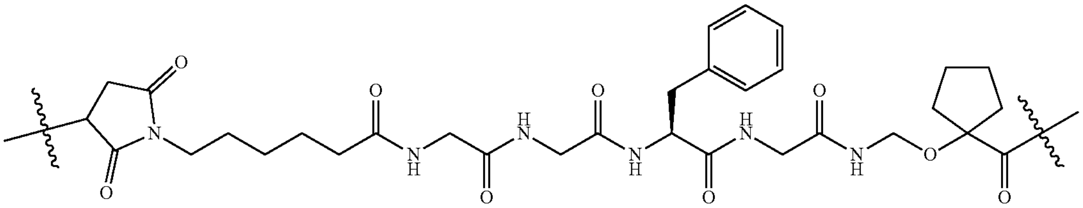 [SMILES: *C(=O)C1(OCNC(=O)CNC(=O)[C@H](Cc2ccccc2)NC(=O)CNC(=O)CNC(=O)CCCCCN2C(=O)CC(*)C2=O)CCCC1] |
| -L-$Y^8$- | 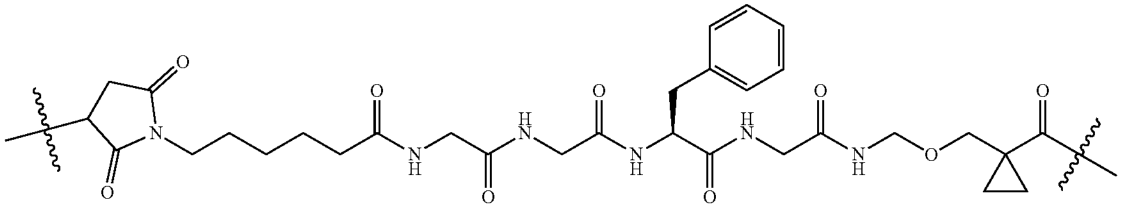 [SMILES: *C(=O)C1(COCNC(=O)CNC(=O)[C@H](Cc2ccccc2)NC(=O)CNC(=O)CNC(=O)CCCCCN2C(=O)CC(*)C2=O)CC1] |

-continued
| No. | Structure |
|---|---|
| -L-Y$^9$- | 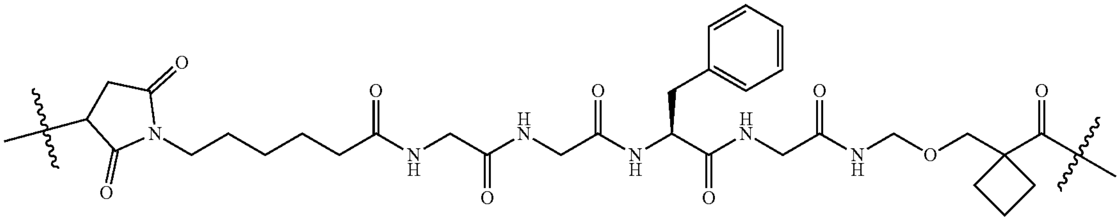 [SMILES: *C(=O)C1(COCNC(=O)CNC(=O)[C@H](Cc2ccccc2)NC(=O)CNC(=O)CNC(=O)CCCCCN2C(=O)CC(*)C2=O)CCC1] |
| -L-Y$^{10}$- | 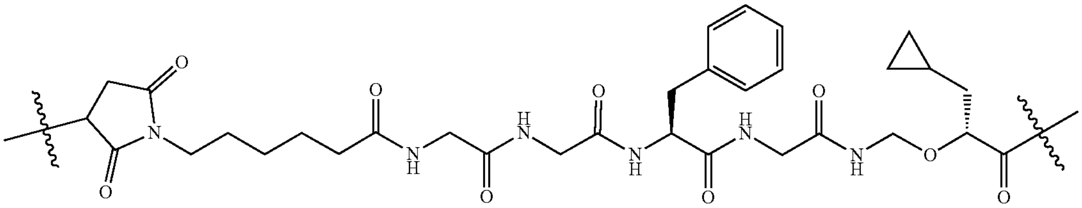 [SMILES: *C(=O)[C@@H](CC1CC1)OCNC(=O)CNC(=O)[C@H](Cc1ccccc1)NC(=O)CNC(=O)CNC(=O)CCCCCN1C(=O)CC(*)C1=O] |
| -L-Y$^{11}$- | 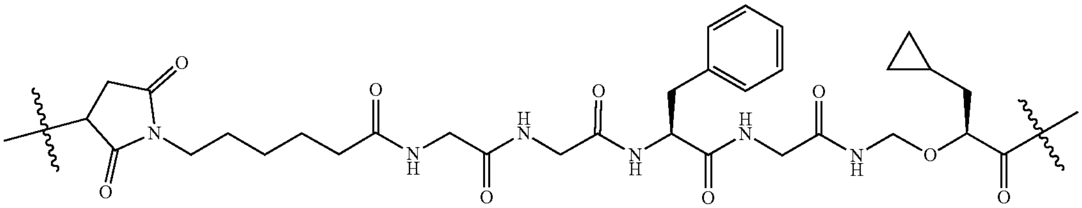 [SMILES: *C(=O)[C@H](CC1CC1)OCNC(=O)CNC(=O)[C@H](Cc1ccccc1)NC(=O)CNC(=O)CNC(=O)CCCCCN1C(=O)CC(*)C1=O] |
| -L-Y$^{12}$- | 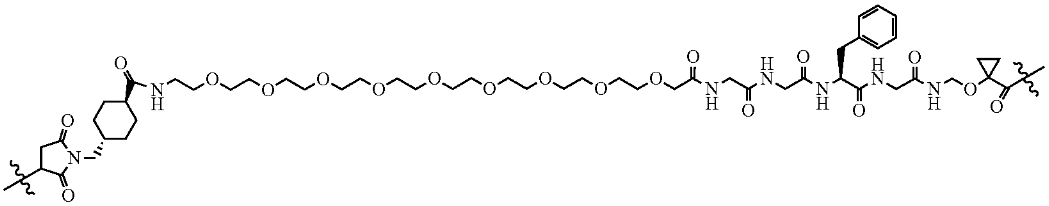 [SMILES: *C(=O)C1(OCNC(=O)CNC(=O)[C@H](Cc2ccccc2)NC(=O)CNC(=O)CNC(=O)COCCOCCOCCOCCOCCOCCOCCOCCOCCNC(=O)[C@H]2CC[C@H](CN3C(=O)CC(*)C3=O)CC2)CC1] |
| -L-Y$^{13}$- | 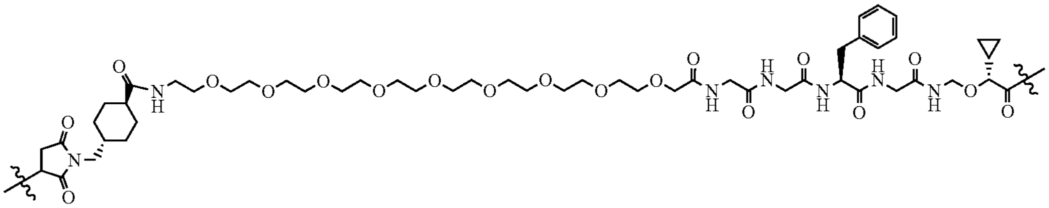 [SMILES: *C(=O)[C@H](OCNC(=O)CNC(=O)[C@H](Cc1ccccc1)NC(=O)CNC(=O)CNC(=O)COCCOCCOCCOCCOCCOCCOCCOCCOCCNC(=O)[C@H]1CC[C@H](CN2C(=O)CC(*)C2=O)CC1)C1CC1] |
| -L-Y$^{14}$- | 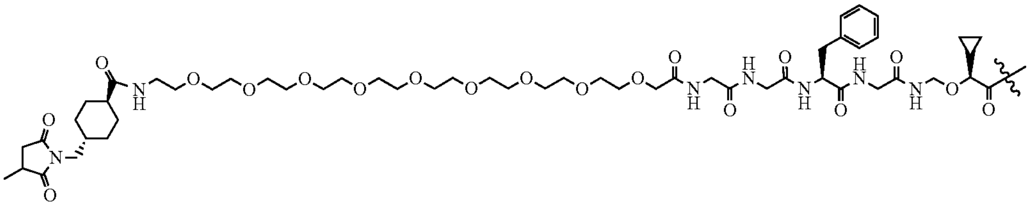 [SMILES: *C(=O)[C@@H](OCNC(=O)CNC(=O)[C@H](Cc1ccccc1)NC(=O)CNC(=O)CNC(=O)COCCOCCOCCOCCOCCOCCOCCOCCOCCNC(=O)[C@H]1CC[C@H](CN2C(=O)CC(C)C2=O)CC1)C1CC1] |

In an alternative embodiment, the aforementioned antibody drug conjugate has the following structure:
| Structure |
| --- |
| 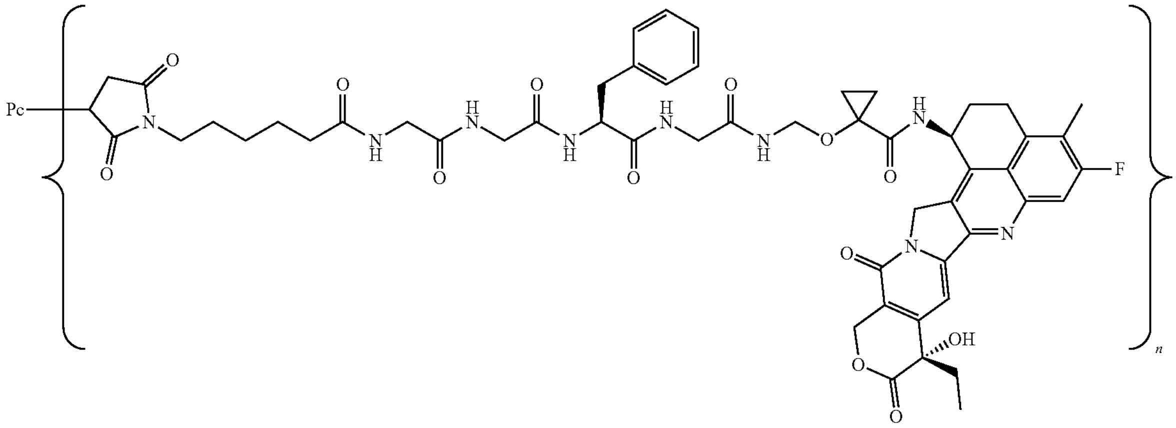 |
| 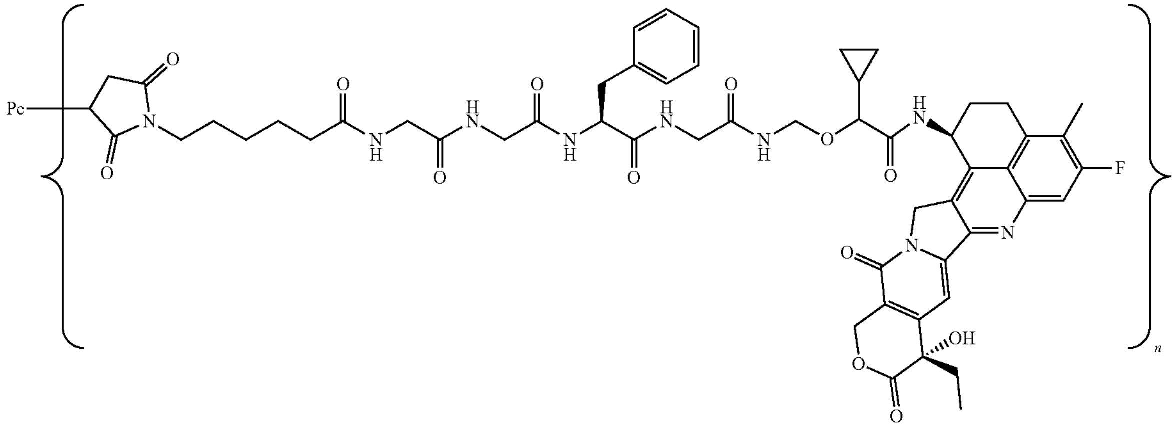 |
| 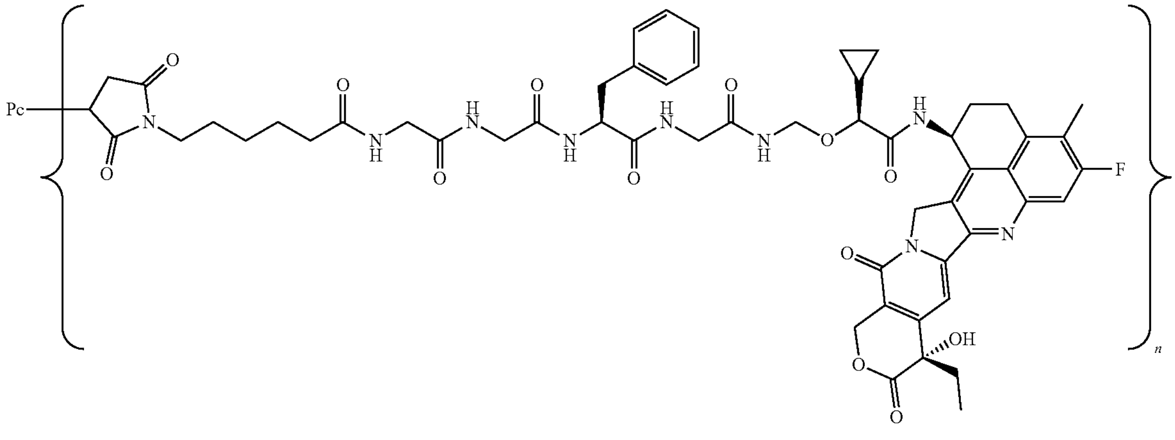 |

-continued
| Structure |
| --- |
| 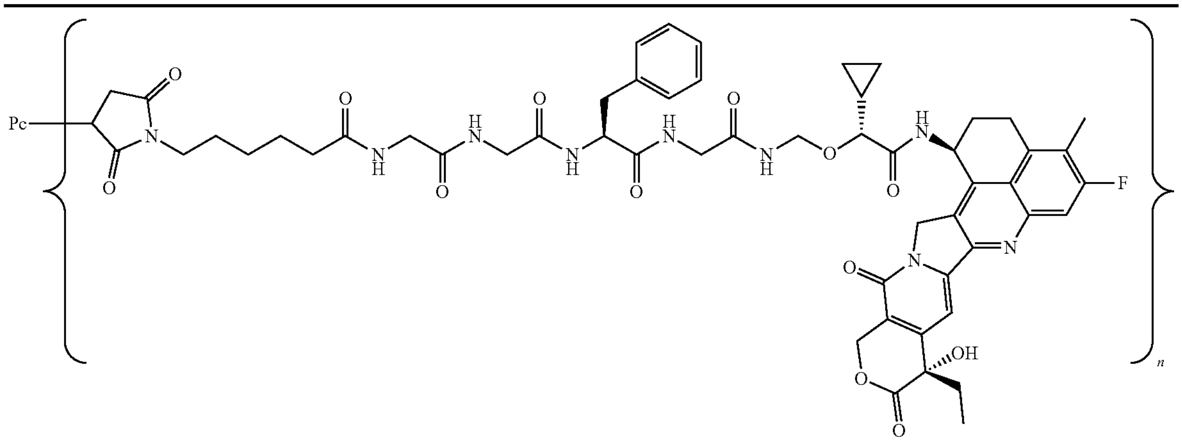 |
| 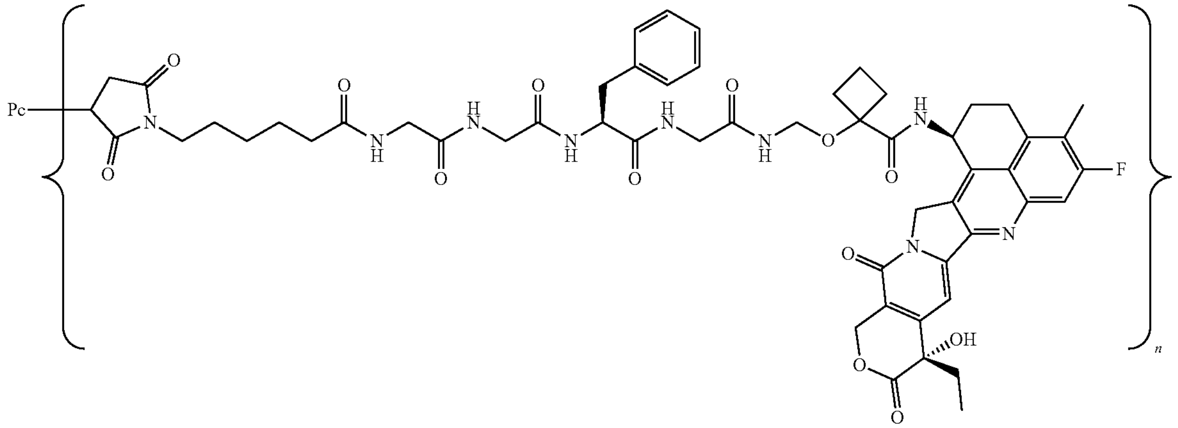 |
| 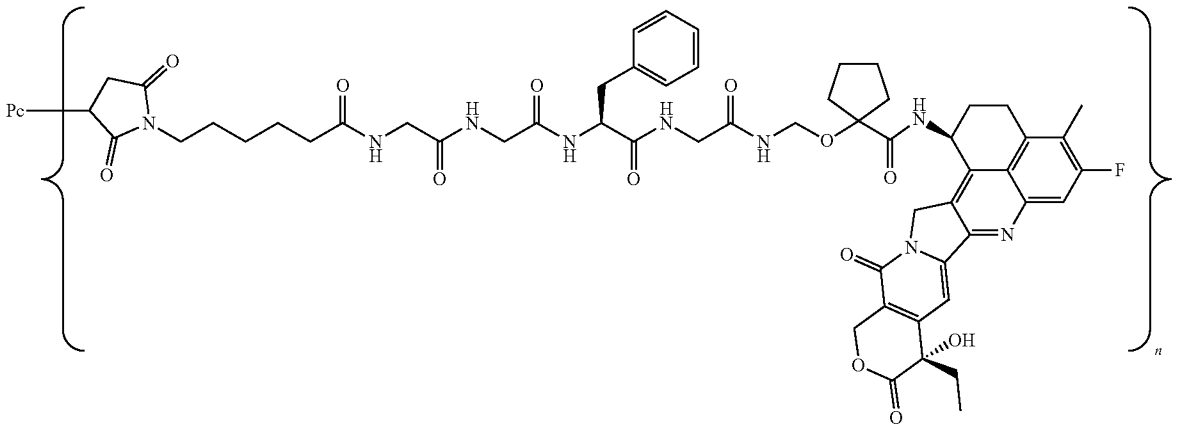 |

-continued
| Structure |
| --- |
| 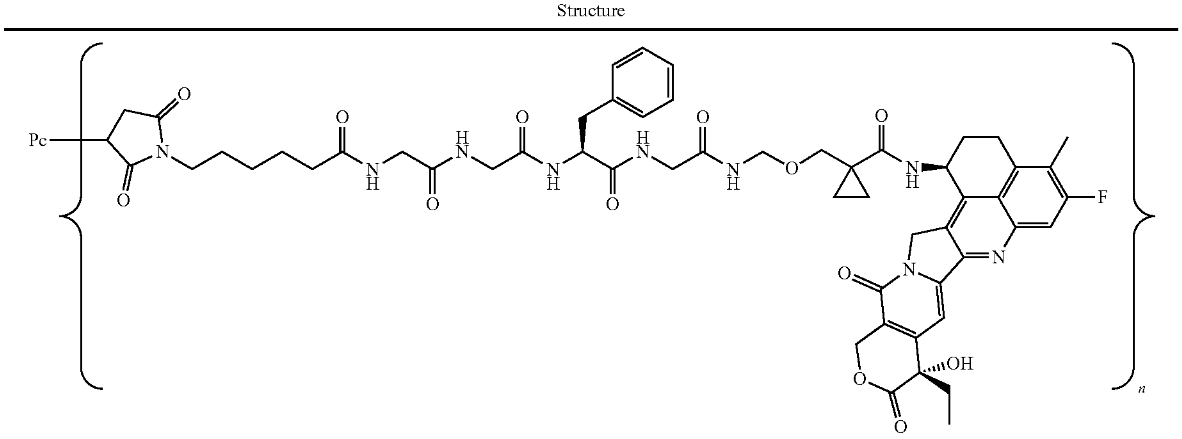 |
| 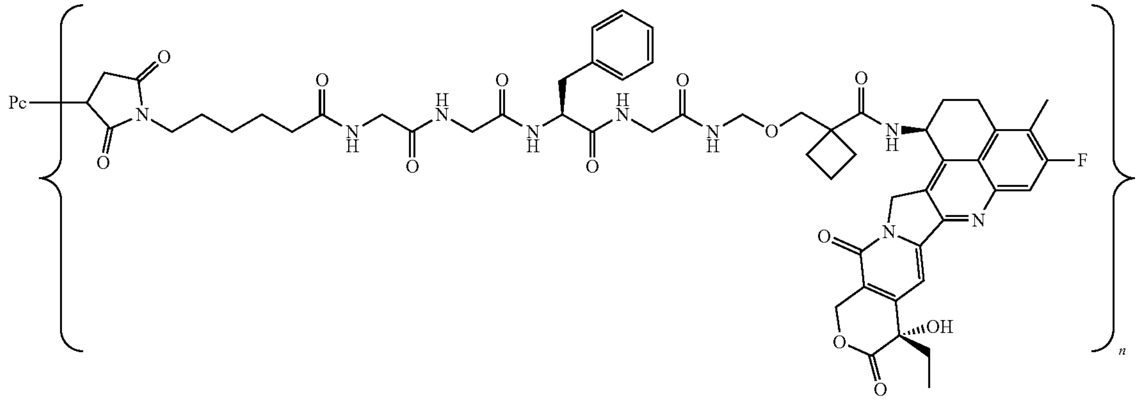 |
| 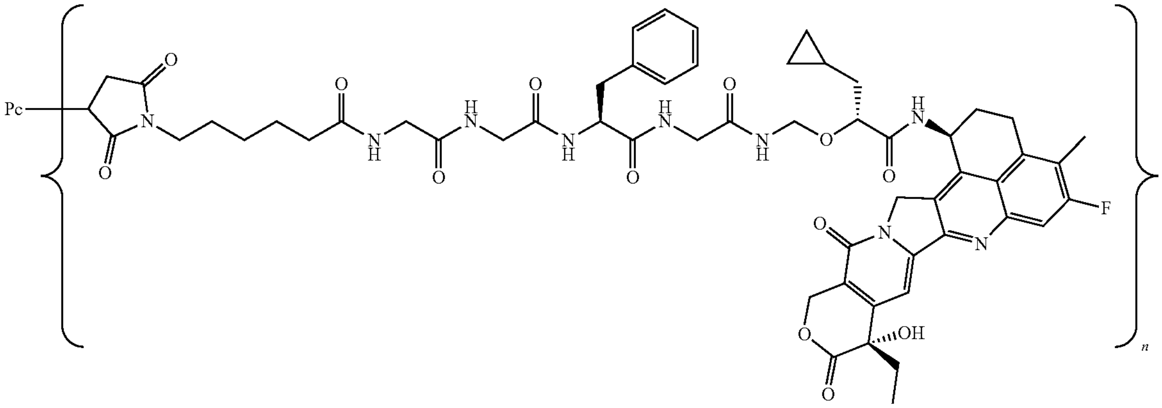 |

-continued
| Structure |
| --- |
| 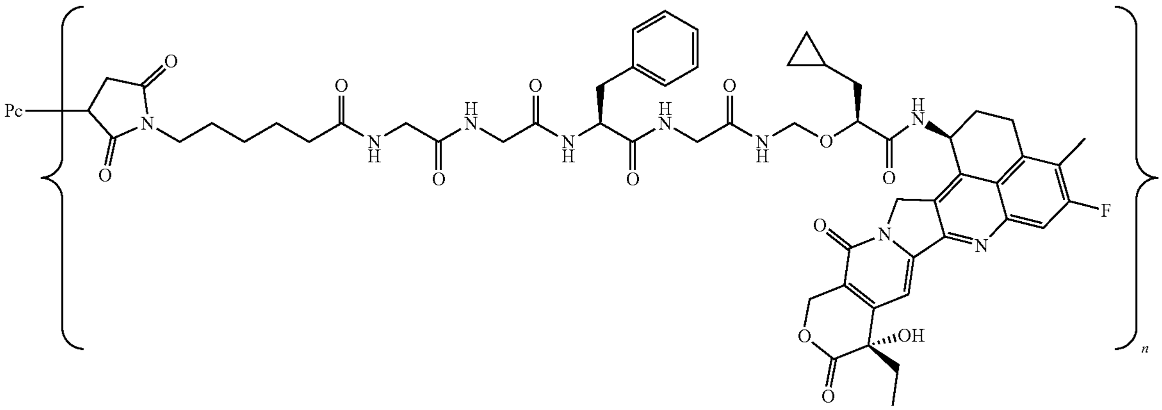 |
| 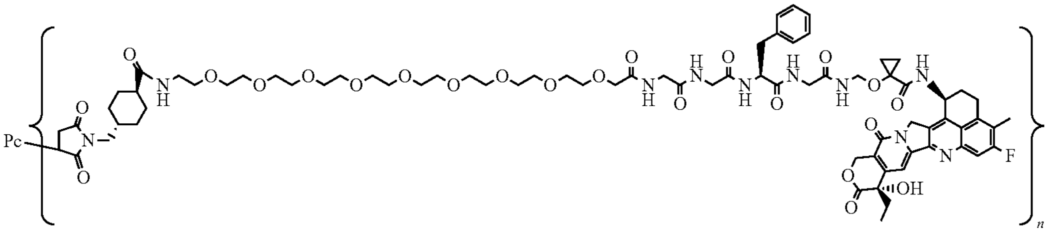 |
| 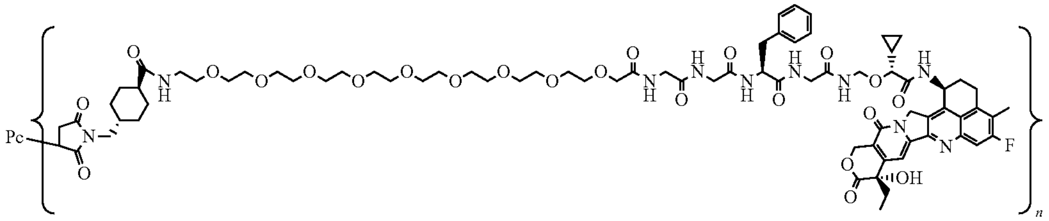 |
| 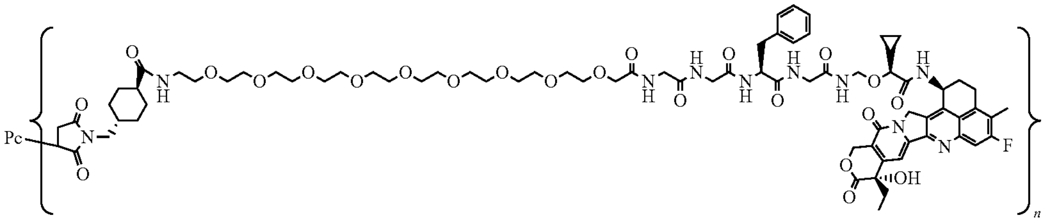 |

wherein Pc and n are as defined in general formula (Pc-$L_a$-Y-D).

In an alternative embodiment, the antibody drug conjugate has the following structure:

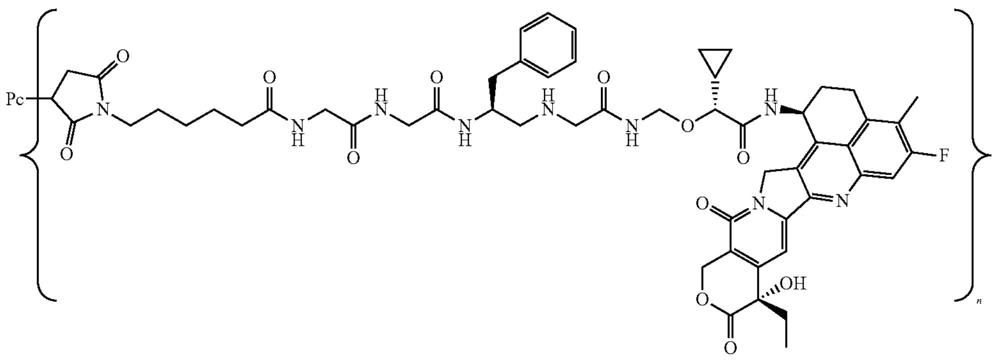

;

wherein:

n is a decimal or an integer from 3 to 8;

Pc is an antibody or an antigen-binding fragment thereof.

In an alternative embodiment, the Pc is an antibody or an antigen-binding fragment thereof, wherein the antibody is selected from the group consisting of a chimeric antibody, a humanized antibody or a fully human-derived antibody, preferably a monoclonal antibody.

In an alternative embodiment, the Pc is selected from the group consisting of an anti-HER2 (ErbB2) antibody, an anti-EGFR antibody, an anti-B7-H3 antibody, an anti-c-Met antibody, an anti-$HER_3$ (ErbB3) antibody, an anti-HER4 (ErbB4) antibody, an anti-CD20 antibody, an anti-CD22 antibody, an anti-CD30 antibody, an anti-CD33 antibody, an anti-CD44 antibody, an anti-CD56 antibody, an anti-CD70 antibody, an anti-CD73 antibody, an anti-CD105 antibody, an anti-CEA antibody, an anti-A33 antibody, an anti-Cripto antibody, an anti-EphA2 antibody, an anti-G250 antibody, an anti-MUC1 antibody, an anti-Lewis Y antibody, an anti-VEGFR antibody, an anti-GPNMB antibody, an anti-integrin antibody, an anti-PSMA antibody, an anti-tenascin-C antibody, an anti-SLC44A4 antibody and an anti-mesothelin antibody, or antigen-binding fragments thereof.

In an alternative embodiment, the antibody or the antigen-binding fragment thereof in the antibody drug conjugate is selected from the group consisting of trastuzumab, pertuzumab, nimotuzumab, enoblituzumab, emibetuzumab, inotuzumab, pinatuzumab, brentuximab, gemtuzumab, bivatuzumab, lorvotuzumab, cBR96 and glematumamab, or antigen-binding fragments thereof.

In an alternative embodiment, the antibody drug conjugate has the following structure:

| Exemplary ADC | Structural formula |
|---|---|
| ADC-3 | 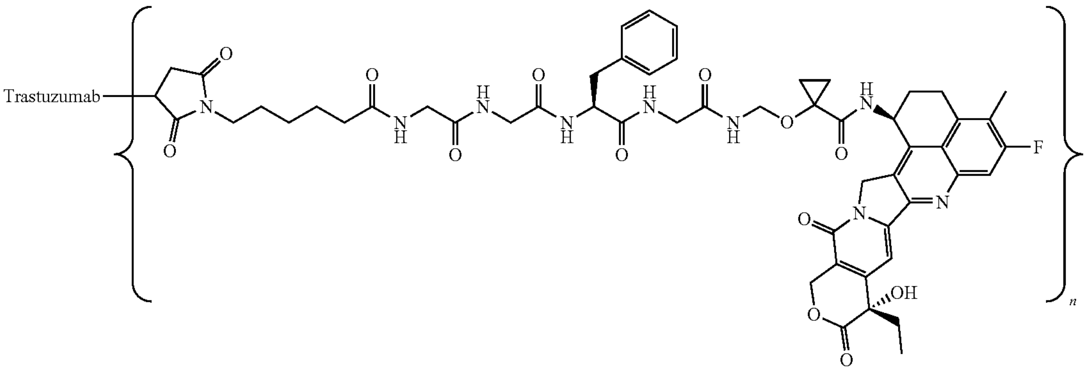 |

-continued
| Exemplary ADC | Structural formula |
|---|---|
| | 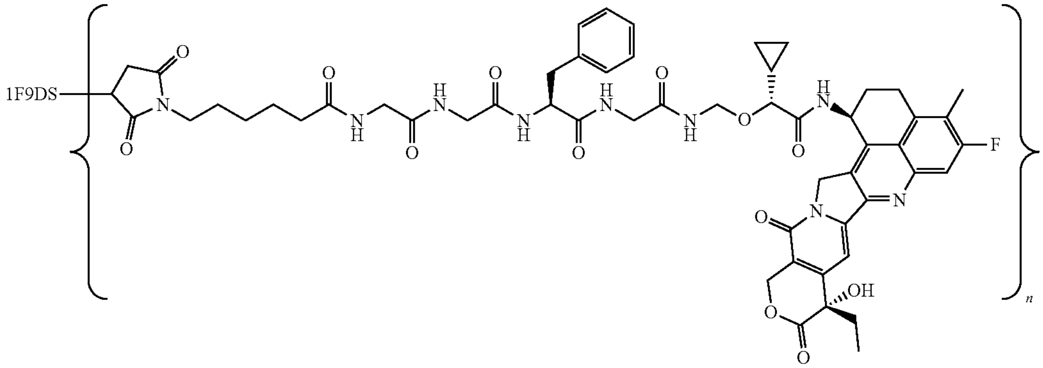 |
| ADC-6 | 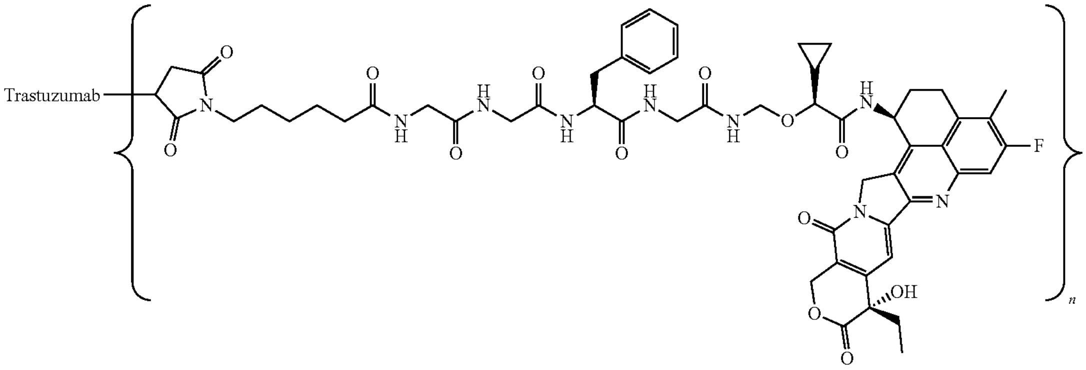 |
| ADC-4/ ADC-5/ ADC-17/ ADC-19/ ADC-22/ ADC-24/ ADC-32/ ADC-33 | 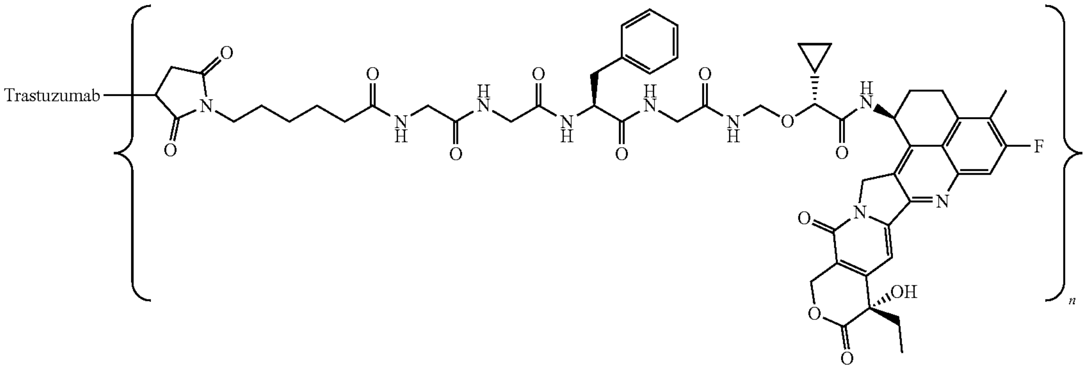 |
| ADC-7 | 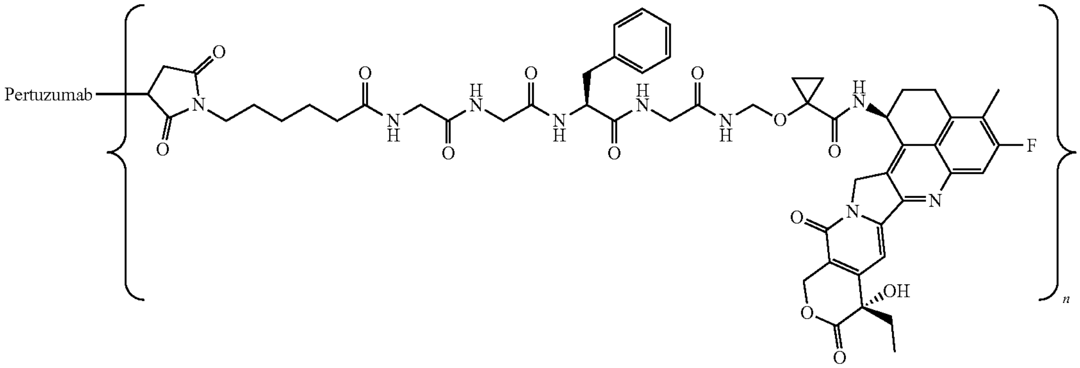 |

-continued
| Exemplary ADC | Structural formula |
| --- | --- |
| | 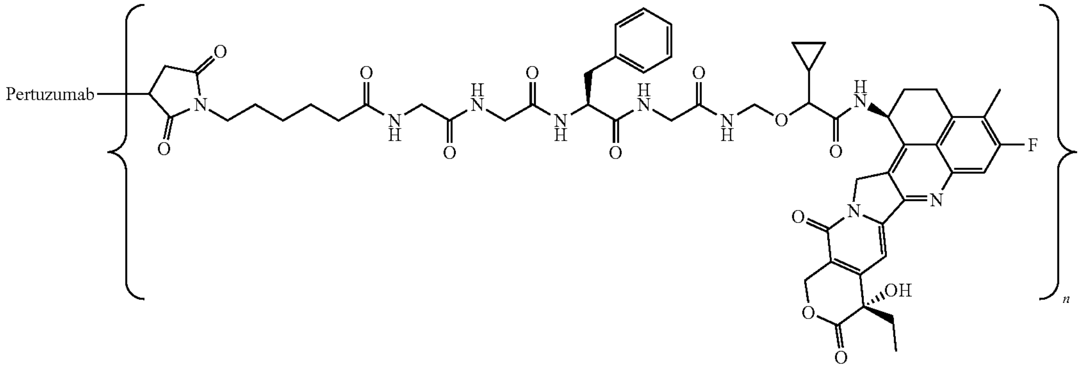 |
| | 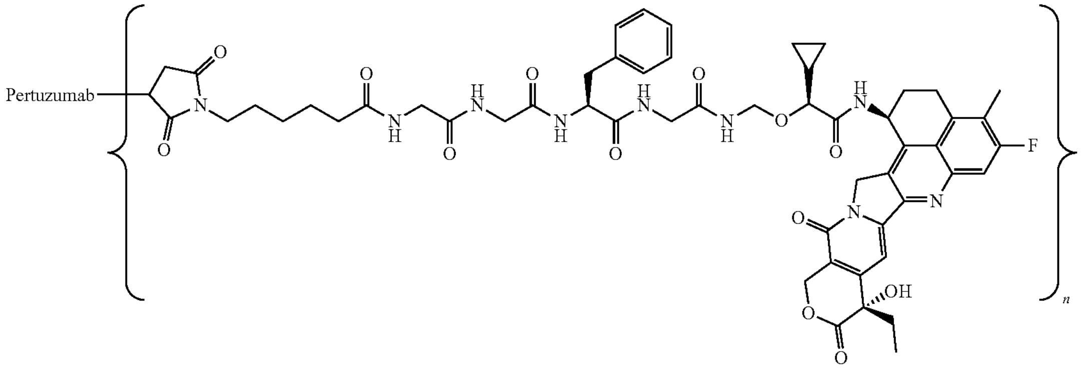 |
| | 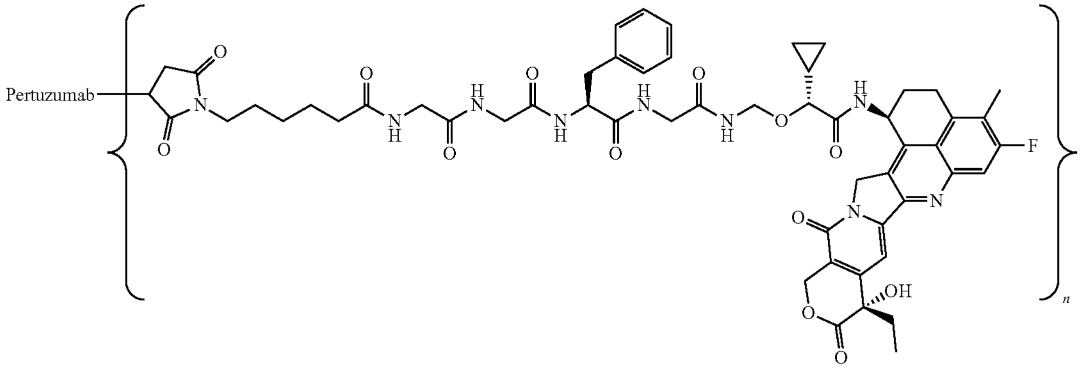 |
| ADC-10/ ADC-11 | 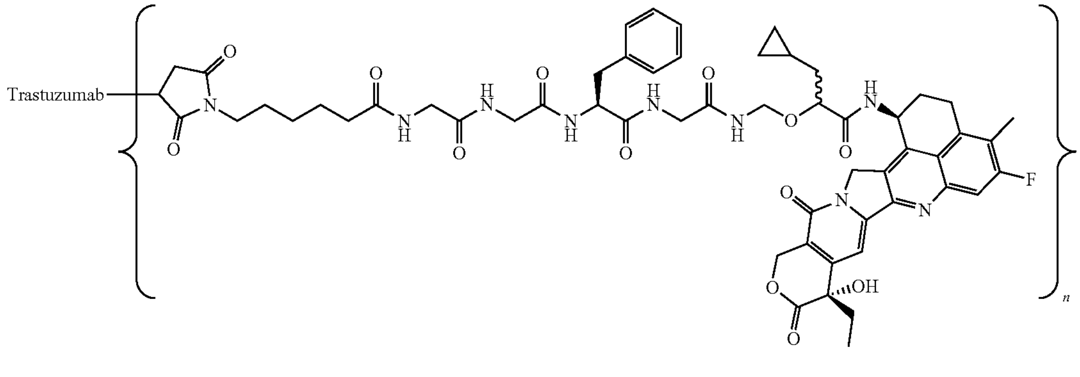 |

-continued
| Exemplary ADC | Structural formula |
| --- | --- |
| | 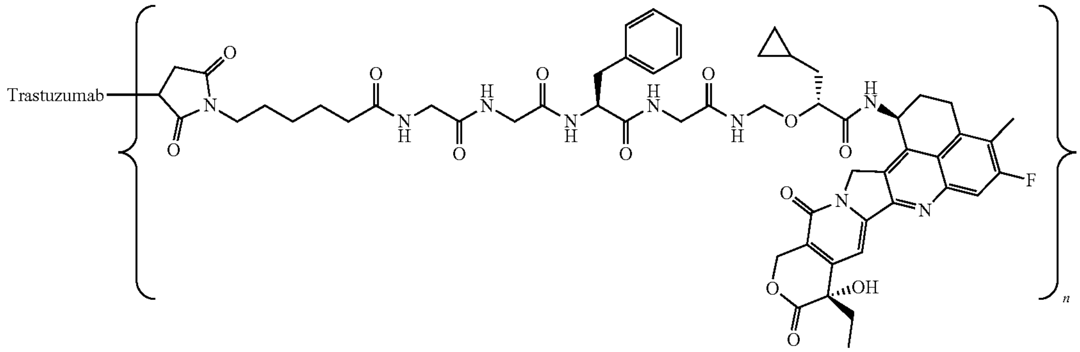 |
| | 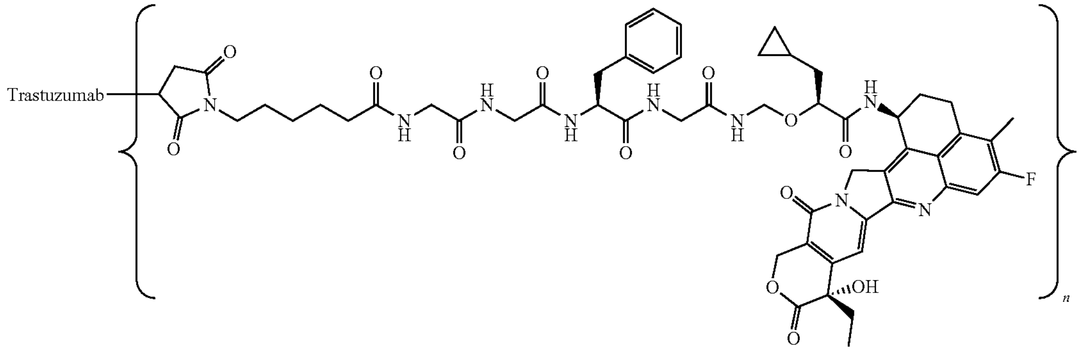 |
| ADC-12 | 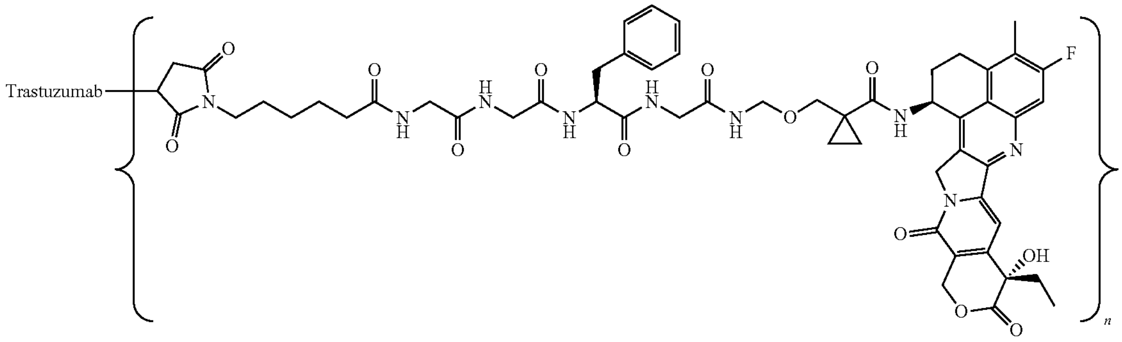 |
| ADC-13 | 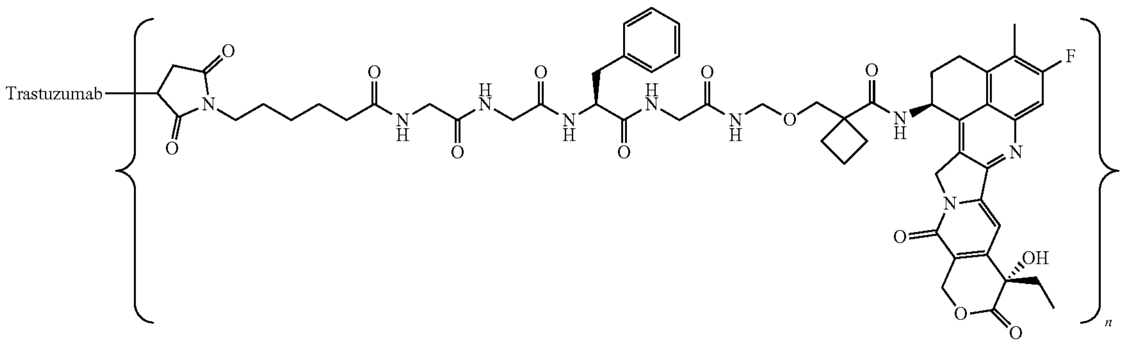 |

-continued
| Exemplary ADC | Structural formula |
| --- | --- |
| ADC-14 | 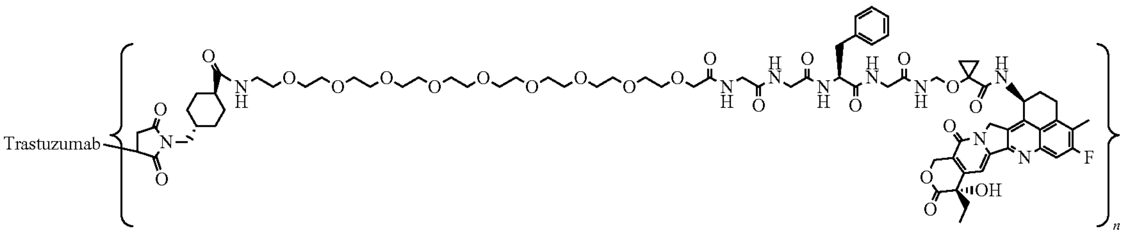 |
| ADC-15 | 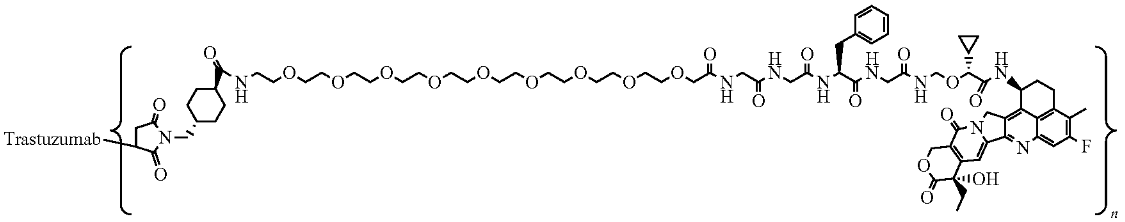 |
| ADC-16 | 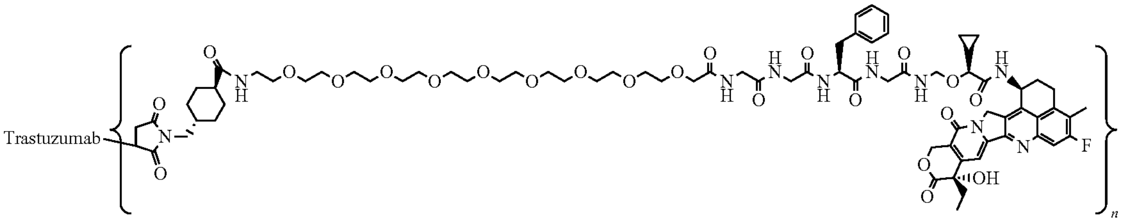 |
| ADC-25/ADC-27/ADC-29 | 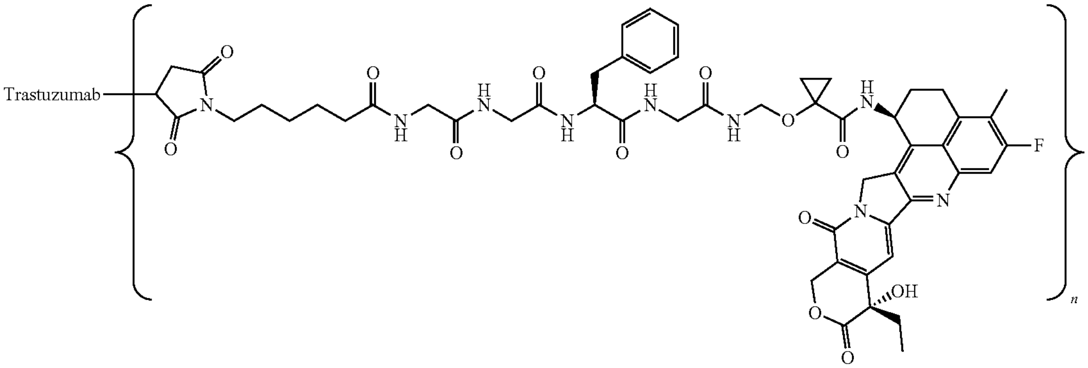 |
| ADC-31 | 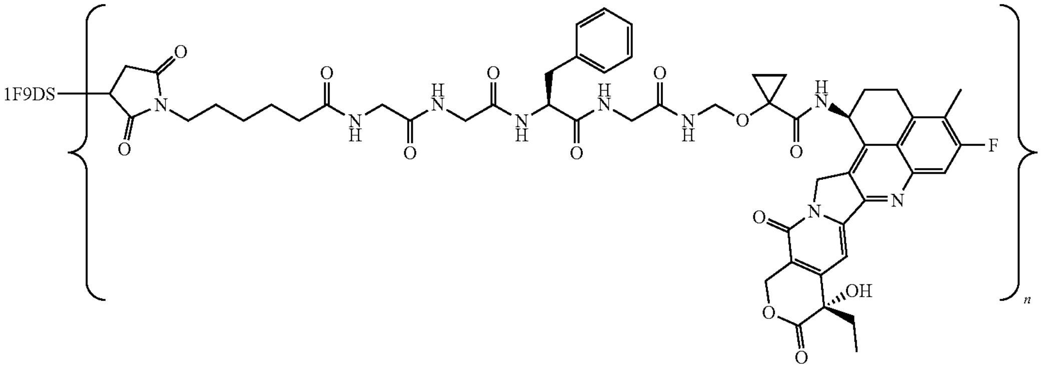 |

wherein n is a non-zero integer or a decimal from 0 to 10, preferably an integer or a decimal between 1 and 10, more preferably an integer or a decimal from 2 to 8, and most preferably an integer or a decimal from 3 to 8.

In an alternative embodiment, the antibody drug conjugate in the pharmaceutical composition has the following structure:

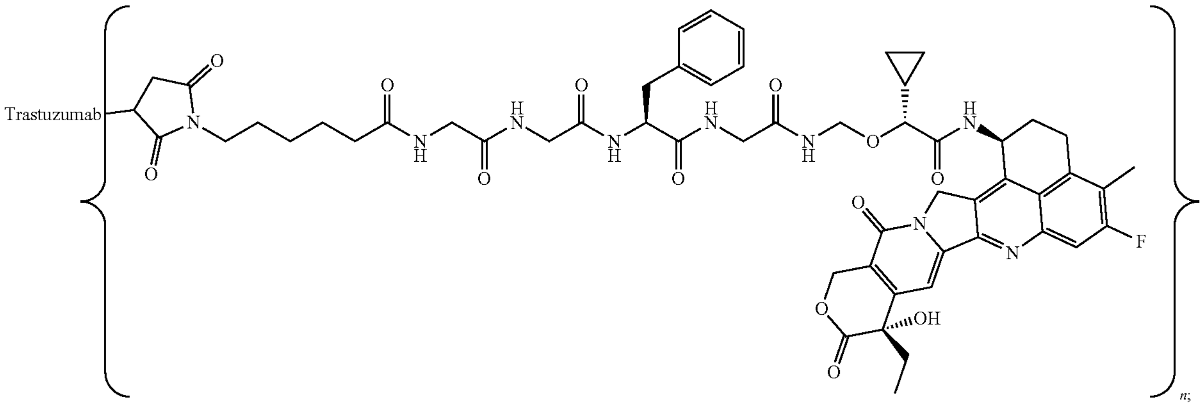

wherein n is a decimal or an integer from 3 to 8.

The present disclosure provides a pharmaceutical composition comprising: (a) the antibody drug conjugate at about 10 mg/mL to about 30 mg/mL, (b) a polysorbate at about 0.05 mg/mL to about 0.5 mg/mL, (c) a saccharide at about 60 mg/mL to about 90 mg/mL, and (d) a buffer at about 5 mM to about 20 mM; the composition being at a pH of 4.8 to 5.2;

wherein the antibody drug conjugate has the following structure:

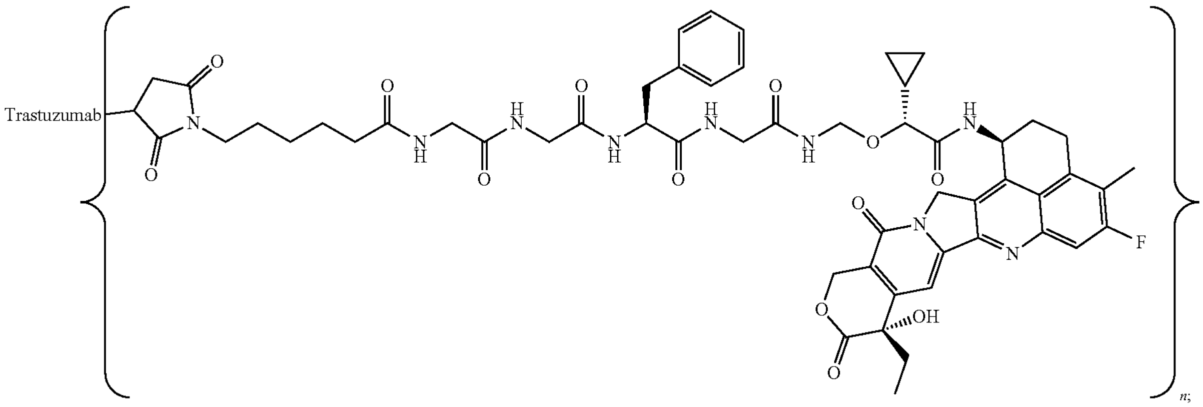

wherein n is a decimal or an integer from 3 to 8.

The present disclosure provides a pharmaceutical composition comprising: (a) an antibody drug conjugate at about 20 mg/mL to about 22 mg/mL, (b) polysorbate 80 at about 0.2 mg/mL, (c) sucrose at about 80 mg/mL, and (d) a succinate buffer at about 10 mM; the pharmaceutical composition being at a pH of 5.0 to 5.1;

wherein the antibody drug conjugate has the following structure:

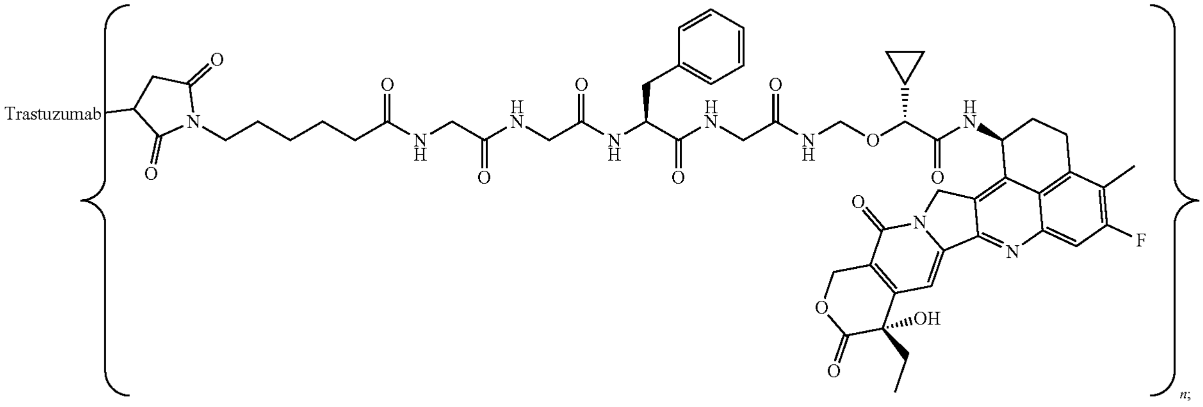

wherein n is a decimal or an integer from 3 to 8.

The present disclosure also provides a lyophilized formulation comprising an antibody drug conjugate, wherein the formulation can be reconstituted to form the pharmaceutical composition described above.

The present disclosure also provides a method for preparing a lyophilized formulation comprising an antibody drug conjugate, which comprises a step of lyophilizing the pharmaceutical composition described above.

In an alternative embodiment, the lyophilizing in the method for preparing a lyophilized formulation comprising an antibody drug conjugate comprises steps of pre-freezing, primary drying and secondary drying. Lyophilization is carried out by freezing the formulation and then subliming water at a temperature suitable for the primary drying. Under these conditions, the product is at a temperature lower than the eutectic point or the collapse temperature of the formulation. Typically, the temperature for the primary drying ranges from about −30° C. to 25° C. (assuming the product remains frozen during the primary drying). The formulation, the size and type of the container (e.g., glass vial) containing the sample, and the liquid volume determine the time required for drying, which may range from a few hours to several days (e.g., 40-60 hours). The secondary drying may be carried out at about 0-40° C., depending primarily on the type and size of the container and the type of the protein used. The time needed for the secondary drying is determined by the desired residual water content in the product, and it typically takes at least about 5 hours. Typically, the water content of the formulation lyophilized at low pressure is less than about 5%, preferably less than about 3%. The pressure may be the same as that applied to the step of primary drying; preferably, the pressure of the secondary drying is lower than that of the primary drying. The lyophilization conditions may vary with the formulation and vial size.

In an alternative embodiment of the present disclosure, 5 mL of a stock solution of the pharmaceutical composition is lyophilized, the lyophilization program being as follows: for the pre-freezing, the temperature is −5° C. or −45° C.; for the primary drying, the temperature is −20° C., and the degree of vacuum is 10 Pa; for the secondary drying, the temperature is 25° C., and the degree of vacuum is 1 Pa.

In some embodiments, the lyophilized formulation is stable at 2-8° C. for at least 3 months, at least 6 months, at least 12 months, at least 18 months, or at least 24 months. In some embodiments, the lyophilized formulation is stable at 40° C. for at least 7 days, at least 14 days, or at least 28 days.

The present disclosure also provides a lyophilized formulation comprising an antibody drug conjugate obtained by lyophilizing the pharmaceutical composition comprising an anti-HER2 antibody drug conjugate described above.

The present disclosure also provides a reconstituted solution comprising an antibody drug conjugate obtained by reconstituting the lyophilized formulation described above.

The present disclosure also provides a method for preparing the reconstituted solution described above comprising a step of reconstituting the aforementioned lyophilized formulation with a solution selected from the group consisting of, but not limited to, water for injection, normal saline or glucose solution.

In an alternative embodiment, the reconstituted solution comprises the following components:

(a) the antibody drug conjugate at about 10 mg/mL to about 30 mg/mL, (b) a polysorbate at about 0.05 mg/mL to about 0.5 mg/mL, (c) a saccharide at about 60 mg/mL to about 90 mg/mL, and (d) a buffer at about 5 mM to about 20 mM; the reconstituted solution being at a pH of 4.8 to 5.2.

In an alternative embodiment, the reconstituted solution comprises the following components:

(a) an antibody drug conjugate at about 20 mg/mL to 22 mg/mL, (b) polysorbate 80 at about 0.2 mg/mL, (c) sucrose at about 80 mg/mL, and (d) a succinate buffer at about 10 mM; the reconstituted solution being at a pH of 5.0 to 5.1.

The present disclosure also provides an article of manufacture comprising a container containing the pharmaceutical composition, the lyophilized formulation or the reconstituted solution described above. In some embodiments, the container is a tubular injection vial made of neutral borosilicate glass.

The disclosure also provides use of the aforementioned pharmaceutical composition or the lyophilized formulation or the reconstituted solution or the article of manufacture in preparing a medicament for treating or preventing tumors.

The present disclosure also provides a method for treating a disease comprising providing the aforementioned pharmaceutical composition or lyophilized formulation or reconstituted solution or article of manufacture.

The present disclosure also provides the aforementioned pharmaceutical composition, or lyophilized formulation, or reconstituted solution, or article of manufacture, as a medicament, preferably for treating or preventing a tumor disease.

In an alternative embodiment, the disease or tumor is cancer associated with HER2, HER3, B7H3 or EGFR expression.

In an alternative embodiment, the cancer is selected from the group consisting of breast cancer, ovarian cancer, cervical cancer, uterine cancer, prostate cancer, kidney cancer, urinary tract cancer, bladder cancer, liver cancer, stomach cancer, endometrial cancer, salivary gland carcinoma, esophageal cancer, melanoma, neuroglioma, neuroblastoma, sarcoma, lung cancer, colon cancer, rectal cancer, colorectal cancer, leukemia, bone cancer, skin cancer, thyroid cancer, pancreatic cancer and lymphoma.

As is well known to those skilled in the art, one, some or all of the features of the various embodiments described in the present disclosure may be further combined to form other embodiments of the present disclosure. The above embodiments of the present disclosure and other embodiments obtained by combination are further illustrated through the following detailed description.

The present disclosure provides a pharmaceutical composition that favors production and administration and is stable in properties. In particular, the pharmaceutical composition described in the present disclosure comprise an antibody drug conjugate and a buffer.

Terms

In order to facilitate the understanding of the present disclosure, some technical and scientific terms are specifically defined below. Unless otherwise specifically defined herein, all other technical and scientific terms used herein have the meanings generally understood by those of ordinary skill in the art to which the present disclosure belongs. The application PCT/CN2019/107873 (WO2020/063676) is incorporated herein by reference in its entirety.

"Antibody drug conjugate (ADC)" is formed by connecting an antibody or an antibody fragment with cytotoxin with biological activity or a small-molecule drug with cell killing activity by a stable chemical linker compound, in which case the binding specificity of the antibody to tumor cell-specific or highly expressed antigens and the high-efficiency of the cytotoxin are fully exploited, and toxic side effects on normal cells are avoided. The antibody drug conjugate can bind to tumor cells precisely and has a reduced effect on normal cells compared to conventional chemotherapeutic drugs in the past.

"Buffer" refers to a buffer that resists changes in pH by the action of its acid-base conjugate components. Examples of buffers that control the pH in an appropriate range include acetate, succinate, gluconate, histidine salt, oxalate, lactate, phosphate, citrate, tartrate, fumarate, glycylglycine and other organic acid buffers.

"Histidine salt buffer" is a buffer comprising histidine ions. Examples of histidine salt buffers include histidine-hydrochloride buffer, histidine-acetate buffer, histidine-phosphate buffer, histidine-sulfate buffer, and the like, and the histidine-acetate buffer is preferred. The histidine-acetate buffer is prepared from histidine and acetic acid, and the histidine hydrochloride buffer is prepared from histidine and hydrochloric acid.

"Citrate buffer" is a buffer comprising citrate ions. Examples of citrate buffers include citric acid-sodium citrate, citric acid-potassium citrate, citric acid-calcium citrate, citric acid-magnesium citrate, and the like. The preferred citrate buffer is citric acid-sodium citrate.

"Succinate buffer" is a buffer comprising succinate ions. Examples of succinate buffers include succinic acid-sodium succinate, succinic acid-potassium succinate, succinic acid-calcium succinate, and the like. The preferred succinate buffer is succinic acid-sodium succinate. Illustratively, the succinic acid-sodium succinate may be prepared from succinic acid and sodium hydroxide, or from succinic acid and sodium succinate.

"Phosphate buffer" is a buffer comprising phosphate ions. Examples of phosphate buffers include disodium hydrogen phosphate-sodium dihydrogen phosphate, disodium hydrogen phosphate-potassium dihydrogen phosphate, disodium hydrogen phosphate-citric acid, and the like. The preferred phosphate buffer is disodium hydrogen phosphate-sodium dihydrogen phosphate.

"Acetate buffer" is a buffer comprising acetate ions. Examples of acetate buffers include acetic acid-sodium acetate, acetic acid histidine salt, acetic acid-potassium acetate, acetic acid-calcium acetate, acetic acid-magnesium acetate, and the like. The preferred acetate buffer is acetic acid-sodium acetate.

"Pharmaceutical composition" refers to a mixture containing one or more of the antibody drug conjugates described herein or physiologically/pharmaceutically acceptable salts or prodrugs thereof, and other chemical components, and the other components are, for example, physiologically/pharmaceutically acceptable carriers and excipients. The purpose of the pharmaceutical composition is to maintain the stability of the active ingredient of the antibody and promote the administration to an organism, which facilitates the absorption of the active ingredient, thereby exerting biological activity.

As used herein, "pharmaceutical composition" and "formulation" are not mutually exclusive.

The pharmaceutical composition described in the present disclosure is in solution form, and unless otherwise specified, the solvent is water.

"Lyophilized formulation" refers to a formulation or a pharmaceutical composition obtained by vacuum lyophilization of a pharmaceutical composition or a formulation in liquid or solution form.

The terms "about" and "approximately" as used herein mean that a numerical value is within an acceptable error range for the particular value determined by one of ordinary skill in the art, and the numerical value depends in part on how the value is measured or determined (i.e., the limits of the measurement system). For example, "about" can mean within 1 or more than 1 standard deviation per the practice in the art. Or, "about" or "substantially comprising" may mean a range of up to 20%. Furthermore, particularly for biological systems or processes, the term can mean up to an order of magnitude or up to 5-fold of a numerical value. When a particular value is provided in the present application and claims, unless otherwise stated, the meaning of "about" or "substantially comprising" should be assumed to be within an acceptable error range for that particular value.

The pharmaceutical composition of the present disclosure can achieve a stable effect: a pharmaceutical composition in which the antibody drug conjugate substantially retains its physical and/or chemical stability and/or biological activity after storage; preferably, the pharmaceutical composition substantially retains its physical and chemical stability as well as its biological activity after storage. The storage period is generally selected based on a predetermined shelf life of the pharmaceutical composition. There are a variety of analytical techniques currently available for measuring protein stability, and the stability after storage for a selected period of time at a selected temperature can be measured.

A stable formulation is one in which no significant change is observed under the following conditions: stored at refrigeration temperature (2-8° C.) for at least 3 months, preferably 6 months, more preferably 1 year, and even more preferably up to 2 years. In addition, stable liquid formulations include liquid formulations that exhibit desirable features after storage at temperatures including 25° C. for periods including 1 month, 3 months and 6 months. Typical examples for stability are as follows: typically, no more than about 10%, preferably no more than about 5%, of antibody monomers aggregate or are degraded as measured by SEC-HPLC. The formulation is a pale yellow, nearly colorless and transparent liquid, or colorless, or transparent to slightly opalescent, by visual analysis. The concentration, pH and osmotic pressure of the formulation have no more than ±10% change. Typically, no more than about 10%, preferably no more than about 5%, of decrease is observed. Typically, no more than about 10%, preferably no more than about 5%, of aggregation is formed.

An antibody drug conjugate "retains its physical stability" in a pharmaceutical formulation if it shows no significant increase in aggregation, precipitation and/or denaturation upon visual examination of color and/or clarity, or as measured by UV light scattering, size exclusion chromatography (SEC) and dynamic light scattering (DLS). Changes of protein conformation can be evaluated by fluorescence spectroscopy (which determines the protein tertiary structure) and by FTIR spectroscopy (which determines the protein secondary structure).

An antibody drug conjugate "retains its chemical stability" in a pharmaceutical formulation if it shows no significant chemical change. Chemical stability can be assessed by detecting and quantifying chemically changed forms of the protein. Degradation processes that often change the chemical structure of proteins include hydrolysis or clipping (evaluated by methods such as size exclusion chromatography and CE-SDS), oxidation (evaluated by methods such as peptide mapping in conjunction with mass spectroscopy or MALDI/TOF/MS), deamidation (evaluated by methods such as ion-exchange chromatography, capillary isoelectric focusing, peptide mapping, and isoaspartic acid measurement), and isomerization (evaluated by measuring the isoaspartic acid content, peptide mapping, etc.).

An antibody drug conjugate "retains its biological activity" in a pharmaceutical formulation if the biological activity of the antibody drug conjugate at a given time is within a predetermined range of the biological activity exhibited at the time the pharmaceutical formulation was prepared.

The three-letter and single-letter codes for amino acids used in the present disclosure are described as in *J. Biol. Chem.,* 243, p 3558 (1968).

"Antibody" described herein refers to an immunoglobulin, and an intact antibody is of a tetrapeptide chain structure formed by connection between two identical heavy chains and two identical light chains by interchain disulfide bonds. The heavy chain constant regions of an immunoglobulin differ in their amino acid composition and arrangement, and thus in their antigenicity. Accordingly, immunoglobulins can be divided into five classes, otherwise called isotypes of immunoglobulins, namely IgM, IgD, IgG, IgA and IgE, with their corresponding heavy chains being μ chain, δ chain, γ chain, α chain and ε chain, respectively. Ig of the same class can be divided into different subclasses according to differences in the amino acid composition of the hinge regions and the number and positions of disulfide bonds of the heavy chains; for example, IgG may be divided into IgG1, IgG2, IgG3 and IgG4. Light chains are classified into κ or λ chains by the differences in the constant regions. Each of the five classes of Ig may have a κ chain or λ chain. The antibody described in the present disclosure is preferably specific antibodies against cell surface antigens on target cells, non-limiting examples of the antibodies being one or more of an anti-HER2 (ErbB2) antibody, an anti-EGFR antibody, an anti-B7-H3 antibody, an anti-c-Met antibody, an anti-$HER_3$ (ErbB3) antibody, an anti-HER4 (ErbB4) antibody, an anti-CD20 antibody, an anti-CD22 antibody, an anti-CD30 antibody, an anti-CD33 antibody, an anti-CD44 antibody, an anti-CD56 antibody, an anti-CD70 antibody, an anti-CD73 antibody, an anti-CD105 antibody, an anti-CEA antibody, an anti-A33 antibody, an anti-Cripto antibody, an anti-EphA2 antibody, an anti-G250 antibody, an anti-MUC1 antibody, an anti-Lewis Y antibody, an anti-VEGFR antibody, an anti-GPNMB antibody, an anti-integrin antibody, an anti-PSMA antibody, an anti-tenascin-C antibody, an anti-SLC44A4 antibody and an anti-mesothelin antibody, preferably trastuzumab (under trade name Herceptin), pertuzumab (also known as 2C4, under trade name Perjeta), nimotuzumab (under trade name Taixinsheng), enoblituzumab, emibetuzumab, inotuzumab, pinatuzumab, brentuximab, gemtuzumab, bivatuzumab, lorvotuzumab, cBR96 and glematumamab.

In the heavy and light chains of the antibody, the sequences of about 110 amino acids near the N-terminus vary considerably and thus are referred to as variable regions (Fv regions); the remaining amino acid sequences near the C-terminus are relatively stable and thus are referred to as constant regions. The variable regions comprise 3 hypervariable regions (HVRs) and 4 framework regions (FRs) with relatively conservative sequences. The 3 hypervariable regions determine the specificity of the antibody and thus are also known as complementarity determining regions (CDRs). Each light chain variable region (LCVR) or heavy chain variable region (HCVR) consists of 3 CDRs and 4 FRs arranged from the amino-terminus to the carboxy-terminus in the following order: FR1, CDR1, FR2, CDR2, FR3, CDR3 and FR4. The 3 CDRs of the light chain refer to LCDR1, LCDR2 and LCDR3, and the 3 CDRs of the heavy chain refer to HCDR1, HCDR2 and HCDR3. CDR amino acid residues of the LCVR and HCVR regions of the antibodies or antigen-binding fragments described in the present disclosure correspond with known Kabat numbering scheme (LCDRs 1-3, HCDRs 1-3) in terms of number and positions. In the present disclosure, the antibody light chain of the present disclosure may further comprise a light chain constant region comprising a human or murine κ and λ chains or variants thereof.

In the present disclosure, the antibody heavy chain of the present disclosure may further comprise a heavy chain constant region comprising human or murine IgG1, IgG2, IgG3 and IgG4 or variants thereof.

The antibody of the present disclosure includes a murine antibody, a chimeric antibody and a humanized antibody, and preferably a humanized antibody.

The term "murine antibody" used herein refers to an antibody prepared from mice according to the knowledge and skill in the art. During the preparation, a test subject is injected with a specific antigen, and then hybridomas expressing antibodies with desired sequence or functional properties are isolated.

The term "chimeric antibody" refers to an antibody obtained by fusing a variable region of a murine antibody and a constant region of a human antibody, which can reduce an immune response induced by the murine antibody. The chimeric antibody is established by firstly establishing hybridoma secreting murine specific monoclonal antibody, then cloning a variable region gene from the mouse hybridoma cells, cloning a constant region gene of human antibody as required, linking the mouse variable region gene and the human constant region gene into a chimeric gene, inserting the chimeric gene into a human vector, and finally expressing chimeric antibody molecules in a eukaryotic industrial system or prokaryotic industrial system.

The term "humanized antibody", also known as a CDR-grafted antibody, refers to an antibody produced by grafting murine CDR sequences into a human antibody variable region framework, i.e., a different type of human species antibody framework sequence.

Such antibody can overcome the strong heterogeneous reaction induced by the chimeric antibody because of carrying a large amount of mouse protein components. Such framework sequences can be obtained from public DNA databases or published references that include germline antibody gene sequences. For example, germline DNA sequences of genes of the human heavy and light chain variable regions can be found in the "VB ase" human species sequence database, as well as in Kabat, E. A. et al., 1991 *Sequences of Proteins of Immunological Interest,* 5th edition. To avoid the decrease in activity caused by the decrease in immunogenicity, the FR sequence in human antibody variable region can be subjected to minimum reverse mutation or back mutation to maintain activity. The humanized antibody of the present disclosure also include humanized antibodies which were further subjected to CDR affinity maturation by phage display.

The term "naked antibody" refers to an antibody that is not conjugated to a heterologous module (e.g., a cytotoxic module) or a radioactive label.

"Antigen-binding fragment of an antibody" described herein may refer to an Fab fragment, an Fab' fragment, an $F(ab')_2$ fragment, or an scFv fragment, an Fv fragment that binds to an antigen, which has antigen-binding activity. The Fv fragment comprises the heavy chain variable region and the light chain variable region of the antibody, but no the constant region, and has the smallest antibody fragment of the entire antigen-binding sites. Generally, the Fv antibody also comprises a polypeptide linker between the VH and VL domains, and is capable of forming the structure required for antigen binding. Two antibody variable regions can also be linked into a single polypeptide chain using different linkers, known as single chain antibody or single chain fv (sFv).

The term "antigen-binding site" disclosed herein refers to a continuous or discontinuous three-dimensional spatial site on an antigen that is recognized by an antibody or an antigen-binding fragment of the present disclosure.

"ADCC", i.e., antibody-dependent cell-mediated cytotoxicity, described herein means that the Fc receptor-expressing cells directly kill antibody-coated target cells by recognition of the Fc segment of the antibody. The ADCC effector function of the antibody may be reduced or eliminated by modification of the Fc segment of the IgG. The modification refers to a mutation in the heavy chain constant region of the antibody, such as a mutation selected from the group consisting of N297A, L234A and L235A of IgG1; IgG2/4 chimera, and F234A/L235A of IgG4.

The "mutations" in the mutant sequences described herein include, but are not limited to, "back mutation", "conservative modification" or "conservative replacement or substitution". The "conservative modification" or "conservative replacement or substitution" described herein refers to replacement of amino acids in a protein with other amino acids having similar characteristics (e.g., charge, side-chain size, hydrophobicity/hydrophilicity, or backbone conformation and rigidity), so that changes can be frequently made without changing the biological activity of the protein. Those skilled in the art know that, generally speaking, a single amino acid replacement in a non-essential region of a polypeptide does not substantially change the biological activity (see, e.g., Watson et al. (1987) *Molecular Biology of the Gene*, The Benjamin/Cummings Pub. Co., p 224, (4th edition)). In addition, the replacement of amino acids with similar structure or function is unlikely to disrupt the biological activity.

"Mutant sequence" described herein refers to a nucleotide sequence and/or amino acid sequence having a different degree of percent sequence identity to the nucleotide sequence and/or amino acid sequence of the present disclosure, when mutational modifications such as replacements, insertions or deletions are appropriately made to the nucleotide sequence and/or amino acid sequence of the present disclosure. The sequence identity described herein may be at least 85%, 90% or 95%, and preferably at least 95%. Non-limiting examples include 85%, 86%, 87%, 88%, 89%, 90%, 91%, 92%, 93%, 94%, 95%, 96%, 97%, 98%, 99% and 100%. Sequence comparison and percent identity determination between two sequences can be performed by the default settings for the BLASTN/BLASTP algorithm available on the website National Center For Biotechnology Institute.

The term "linker unit" or "linker fragment" refers to a chemical structure fragment or bond, which is linked to an antibody or antigen-binding fragment thereof at one end and to a drug at the other end, and also may be linked to an antibody or drug after being linked to another linker. In preferred embodiments of the present disclosure, they are indicated as L and $L^1$ through $L^4$, wherein the $L^1$ end is linked to an antibody, and the $L^4$ end is linked to a structure unit Y and then to a compound or toxin.

The linker includes stretcher units, spacer units and amino acid units, and may be synthesized using methods known in the art, such as those described in US2005-0238649A1. The linker may be a "cleavable linker" favoring the release of drugs in cells. For example, acid-labile linkers (e.g., hydrazones), protease-sensitive (e.g., peptidase-sensitive) linkers, photolabile linkers, dimethyl linkers or disulfide-containing linkers can be used (Chari et al., *Cancer Research* 52: 127-131(1992); U.S. Pat. No. 5,208,020). The engineered antibody or antigen-binding fragment of the present disclosure can be prepared and purified using conventional methods. For example, cDNA sequences encoding the heavy and light chains can be cloned and recombined into a GS expression vector. Recombinant immunoglobulin expression vectors can be stably transfected into CHO cells. As a more recommended prior art, mammalian expression systems may result in glycosylation of antibodies, particularly at the highly conserved N-terminal site of the Fc region. Positive clones are expanded in a serum-free medium of a bioreactor to produce antibodies. The culture with the secreted antibody can be purified using conventional techniques. For example, purification is carried out on an A or G Sepharose FF column containing an adjusted buffer. Non-specifically bound fractions are washed away. The bound antibody is eluted using pH gradient method, and the antibody fragments are detected by SDS -PAGE and collected. The antibody can be filtered and concentrated using conventional methods. Soluble mixtures and polymers can also be removed using conventional methods, such as molecular sieves and ion exchange. The resulting product needs to be immediately frozen, e.g., at −70° C., or lyophilized.

The term "alkyl" refers to a saturated aliphatic hydrocarbon group that is a linear or branched group containing 1 to 20 carbon atoms, preferably alkyl containing 1 to 12 carbon atoms, more preferably alkyl containing 1 to 10 carbon atoms, and most preferably alkyl containing 1 to 6 carbon atoms. Non-limiting examples of alkyl include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, various branched isomers thereof, etc. More preferred is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl may be substituted or unsubstituted. When substituted, the substituent may be substituted at any available connection site, wherein the substituent is preferably one or more of the following groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio and oxo.

The term "heteroalkyl" refers to alkyl containing one or more heteroatoms selected from the group consisting of N, O and S, wherein the alkyl is as defined above.

The term "alkylene" refers to a saturated linear or branched aliphatic hydrocarbon group having residues derived from the parent alkane by removal of two hydrogen atoms from the same carbon atom or two different carbon atoms. It is a linear or branched group containing 1 to 20 carbon atoms, preferably alkylene containing 1 to 12 carbon atoms, more preferably alkylene containing 1 to 6 carbon atoms. Non-limiting examples of alkylene include, but are not limited to, methylene($-CH_2-$), 1,1-ethylidene($-CH(CH_3)-$), 1,2-ethylidene($-CH_2CH_2-$), 1,1-propylidene($-CH(CH_2CH_3)-$), 1,2-propylidene($-CH_2CH(CH_3)-$), 1,3-propylidene($-CH_2CH_2CH_2-$), 1,4-butylidene($-CH_2CH_2CH_2CH_2-$), 1,5-butylidene($-CH_2CH_2CH_2CH_2CH_2-$), etc. The alkylene may be substituted or unsubstituted. When substituted, the substituent may be substituted at any available connection site with one or more substituents preferably independently optionally selected from the group consisting of alkyl, alkenyl, alkynyl, alkoxy, alkylthio, alkylamino, halogen, mercapto, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkoxy" refers to —O-(alkyl) and —O-(unsubstituted cycloalkyl), wherein the alkyl or cycloalkyl is as defined above. Non-limiting examples of alkoxy include: methoxy, ethoxy, propoxy, butoxy, cyclopropyloxy, cyclobutoxy, cyclopentyloxy and cyclohexyloxy. The alkoxy may be optionally substituted or unsubstituted, and when it is substituted, the substituent is preferably one or more of the following groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The term "cycloalkyl" refers to a saturated or partially unsaturated monocyclic or polycyclic hydrocarbon substituent. The cycloalkyl ring contains 3 to 20 carbon atoms, preferably 3 to 12 carbon atoms, more preferably 3 to 10 carbon atoms, and most preferably 3 to 7 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, and bridged cycloalkyl.

The term "heterocyclyl" refers to a saturated or partially unsaturated monocyclic or polycyclic hydrocarbon substituent containing 3 to 20 ring atoms, wherein one or more of the ring atoms are heteroatoms selected from the group consisting of nitrogen, oxygen and $S(O)_m$ (where m is an integer from 0 to 2), excluding a cyclic portion of —O—O—, —O—S— or —S—S—, and the remaining ring atoms are carbon atoms. Heterocycloalkyl preferably contains 3 to 12 ring atoms, of which 1 to 4 are heteroatoms; more preferably, a cycloalkyl ring contains 3 to 10 ring atoms. Non-limiting examples of monocyclic heterocyclyl include pyrrolidinyl, piperidinyl, piperazinyl, morpholinyl, thiomorpholinyl, homopiperazinyl, etc. Non-limiting examples of polycyclic heterocyclyl include spiro heterocyclyl, fused heterocyclyl, and bridged heterocyclyl.

The term "spiro heterocyclyl" refers to a 5- to 20-membered polycyclic heterocyclyl group in which monocyclic rings share one atom (referred to as the spiro atom), wherein one or more ring atoms are heteroatoms selected from the group consisting of nitrogen, oxygen and $S(O)_m$ (where m is an integer from 0 to 2), and the remaining ring atoms are carbon atoms. These rings may contain one or more double bonds, but none of them has a fully conjugated π-electron system. Preferably, the spiro heterocyclyl is 6- to 14-membered, and more preferably 7- to 10-membered. According to the number of Spiro atoms shared among the rings, the spiro heterocyclyl may be monospiro heterocyclyl, bispiro heterocyclyl or polyspiro heterocyclyl, preferably monospiro heterocyclyl and bispiro heterocyclyl, and more preferably 4-membered/4-membered, 4-membered/5-membered, 4-membered/6-membered, 5-membered/5-membered or 5-membered/6-membered monospiro heterocyclyl. Non-limiting examples of spiro heterocyclyl include:

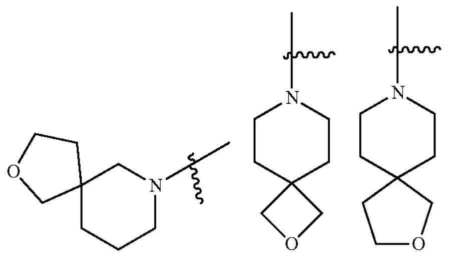

-continued

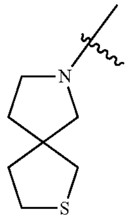

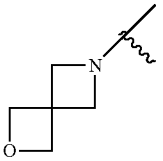

and

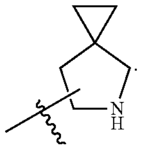

-continued

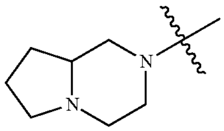

and

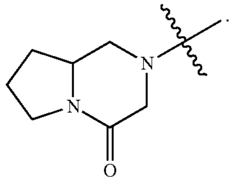

The term "fused heterocyclyl" refers to a 5- to 20-membered polycyclic heterocyclyl group in which each ring shares a pair of adjacent atoms with the other rings in the system, wherein one or more of the rings may contain one or more double bonds, but none of them has a fully conjugated π-electron system, wherein one or more of the ring atoms are heteroatoms selected from the group consisting of nitrogen, oxygen and $S(O)_m$ (where m is an integer from 0 to 2), and the remaining ring atoms are carbon atoms. Preferably, the fused heterocyclyl is 6- to 14-membered, and more preferably 7- to 10-membered. According to the number of the formed rings, the fused heterocyclyl may be bicyclic, tricyclic, tetracyclic or polycyclic fused heterocyclyl, preferably bicyclic or tricyclic fused heterocyclyl, and more preferably 5-membered/5-membered or 5-membered/6-membered bicyclic fused heterocyclyl. Non-limiting examples of fused heterocyclyl include:

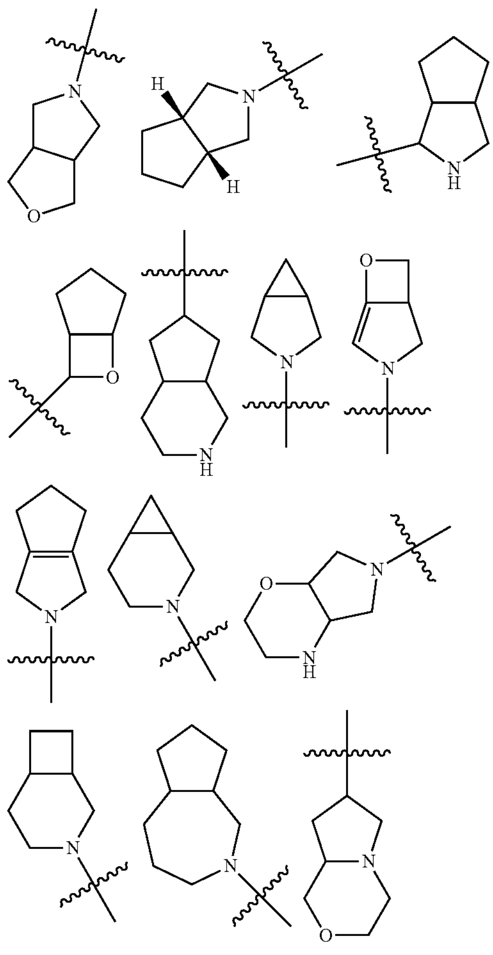

The term "bridged heterocyclyl" refers to a 5- to 14-membered polycyclic heterocyclyl group in which any two rings share two atoms that are not directly linked to each other, wherein these rings may contain one or more double bonds, but none of them has a fully conjugated π-electron system, wherein one or more of the ring atoms are heteroatoms selected from the group consisting of nitrogen, oxygen and $S(O)_m$ (where m is an integer from 0 to 2), and the remaining ring atoms are carbon atoms. Preferably, the bridged heterocyclyl is 6- to 14-membered, and more preferably 7- to 10-membered. According to the number of the formed rings, the bridged heterocyclyl may be bicyclic, tricyclic, tetracyclic or polycyclic bridged heterocyclyl, preferably bicyclic, tricyclic or tetracyclic bridged heterocyclyl, and more preferably bicyclic or tricyclic bridged heterocyclyl. Non-limiting examples of bridged heterocyclyl include:

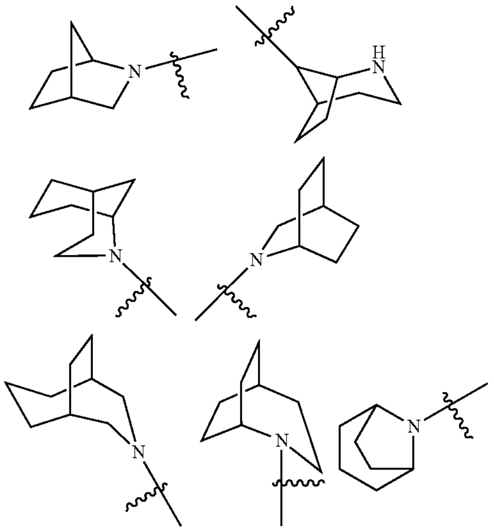

and

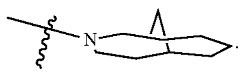

The heterocyclyl ring may be fused to an aryl, heteroaryl or cycloalkyl ring, wherein the ring linked to the parent structure is heterocyclyl. Non-limiting examples of the heterocyclyl ring include:

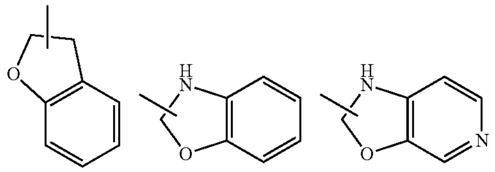

-continued

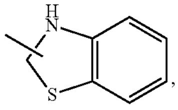, etc.

The heterocyclyl may be optionally substituted or unsubstituted, and when it is substituted, the substituent is preferably one or more of the following groups independently selected from the group consisting of: alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio and oxo.

The term "aryl" refers to a 6- to 14-membered, preferably 6- to 10-membered, carbon monocyclic or fused polycyclic (i.e., rings sharing a pair of adjacent carbon atoms) group having a conjugated π-electron system, such as phenyl and naphthyl, preferably phenyl. The aryl ring may be fused to a heteroaryl, heterocyclyl or cycloalkyl ring, wherein the ring linked to the parent structure is an aryl ring. Non-limiting examples of the aryl ring include:

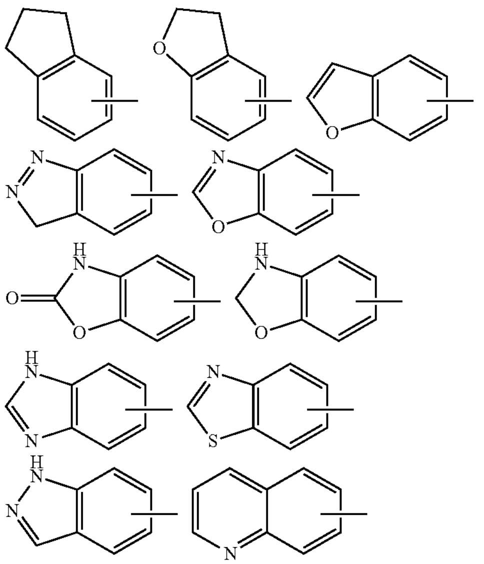

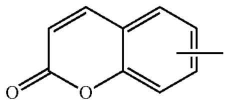 and 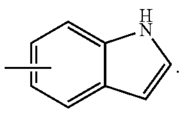.

The aryl may be substituted or unsubstituted, and when it is substituted, the substituent is preferably one or more of the following groups independently selected from the group consisting of: alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The term "heteroaryl" refers to a heteroaromatic system containing 1 to 4 heteroatoms and 5 to 14 ring atoms, wherein the heteroatoms are selected from the group consisting of oxygen, sulfur and nitrogen. The heteroaryl is preferably 5- to 10-membered, more preferably 5- or 6-membered, such as furanyl, thienyl, pyridinyl, pyrrolyl, N-alkylpyrrolyl, pyrimidinyl, pyrazinyl, imidazolyl and tetrazolyl. The heteroaryl ring may be fused to an aryl, heterocyclyl or cycloalkyl ring, wherein the ring linked to the parent structure is a heteroaryl ring. Non-limiting examples of the heteroaryl ring include:

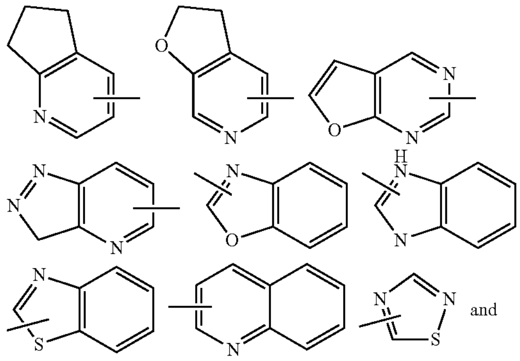 and

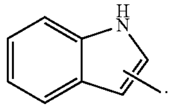.

The heteroaryl may be optionally substituted or unsubstituted, and when it is substituted, the substituent is preferably one or more of the following groups independently selected from the group consisting of: alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The term "amino protecting group" refers to a group that can be easily removed and is intended to protect an amino group from being changed when a reaction is conducted elsewhere in the molecule. Non-limiting examples of the amino protecting group include 9-fluorenylmethoxycarbonyl, tert-butoxycarbonyl, acetyl, benzyl, allyl, p-methoxybenzyl, etc. These groups may be optionally substituted with 1 to 3 substituents selected from the group consisting of halogen, alkoxy and nitro. The amino protecting group is preferably 9-fluorenylmethoxycarbonyl.

The term "cycloalkylalkyl" refers to alkyl substituted with one or more cycloalkyl groups, preferably one cycloalkyl group, wherein the alkyl is as defined above, and the cycloalkyl is as defined above.

The term "haloalkyl" refers to alkyl substituted with one or more halogens, wherein the alkyl is as defined above.

The term "deuterated alkyl" refers to alkyl substituted with one or more deuterium atoms, wherein the alkyl is as defined above.

The term "hydroxy" refers to —OH group.

The term "halogen" refers to fluorine, chlorine, bromine or iodine.

The term "amino" refers to $—NH_2$.

The term "nitro" refers to $—NO_2$.

The term "optional" or "optionally" means that the event or circumstance subsequently described may, but not necessarily, occur, and that the description includes instances where the event or circumstance occurs or does not occur. For example, "optionally comprising 1-3 antibody heavy chain variable regions" means that the antibody heavy chain variable region of a particular sequence may, but not necessarily, be present.

The term "substituted" means that one or more, preferably up to 5, more preferably 1 to 3 hydrogen atoms in the group are independently substituted with a corresponding number of substituents. It goes without saying that a substituent is only in its possible chemical position, and those skilled in the art will be able to determine (experimentally or theoretically) possible or impossible substitution without undue efforts. For example, it may be unstable when amino or hydroxy having a free hydrogen is bound to a carbon atom having an unsaturated (e.g., olefinic) bond.

The term "drug loading" refers to the mean number of cytotoxic drugs loaded on each antibody or an antigen-binding fragment thereof in antibody drug conjugate molecules, and it may also be expressed in terms of a ratio of the number of drugs to the number of antibodies. The drug loading may range from 0-12, preferably 1-10, more preferably 3-8, and most preferably 5.3-6.1 cytotoxic drugs linked to each antibody or an antigen-binding fragment (Pc) thereof. In embodiments of the present disclosure, the drug loading is represented by n, which may also be referred to as a DAR (drug-antibody ratio) value, and, illustratively, may be a mean of 1, 2, 3, 4, 5, 6, 7, 8, 9 and 10. The mean number of drugs per ADC molecule upon coupling reactions can be characterized by conventional methods such as ultraviolet-visible spectroscopy (UV-Vis), hydrophobic interaction chromatography (HIC) mass spectrometry, ELISA assays and HPLC.

The loading of the cytotoxic drug can be controlled using the following non-limiting methods, including:

(1) controlling a molar ratio of a linking reagent to a monoclonal antibody, (2) controlling reaction time and temperature, and (3) selecting different reagents.

For preparation of conventional pharmaceutical compositions, reference is made to Chinese Pharmacopoeia.

The term "carrier" for the drug of the present disclosure refers to a system that can alter the manner in which the drug gets into a human body and the distribution of the drug in the human body, control the release rate of the drug, and deliver the drug to a targeted organ. The drug carrier release and targeted system can reduce drug degradation and loss, reduce side effects and improve bioavailability. For example, polymeric surfactants that can be used as carriers can self-assemble due to their unique amphiphilic structures to form various forms of aggregates, such as micelles, microemulsions, gels, liquid crystals and vesicles, as preferred examples. The aggregates have the capability of encapsulating drug molecules and have good permeability for membranes, and therefore can be used as excellent drug carriers.

"Giving" and "treating", when applied to animals, humans, experimental subjects, cells, tissues, organs or biological fluids, refer to contact of an exogenous drug, a therapeutic agent, a diagnostic agent or a composition with the animals, humans, subjects, cells, tissues, organs or biological fluids. "Giving" and "treating" can refer to, for example, therapeutic, pharmacokinetic, diagnostic, research and experimental methods. The treatment of cells comprises contacting a reagent with the cells and contacting the reagent with a fluid. "Giving" and "treating" also refer to treating, e.g., cells by reagents, diagnosis, binding compositions or by another cell in vitro and ex vivo. "Treating", when applied to human, veterinary or research subjects, refers to therapeutic treatment, preventive or prophylactic measures, and research and diagnostic applications.

"Treating" or "treatment" refers to administering a therapeutic agent, such as a composition comprising any one of the conjugation compounds of the present disclosure, either internally or externally to a patient with one or more symptoms of a disease on which the therapeutic agent is known to have a therapeutic effect. Typically, the therapeutic agent is administered in an amount effective to alleviate one or more symptoms of the disease in the patient or population being treated to induce regression of such symptoms or to inhibit the development of such symptoms to any clinically measurable degree. The amount of therapeutic agent effective to alleviate the symptoms of any particular disease (also referred to as a "therapeutically effective amount") may vary depending on a variety of factors, such as the disease state, age, and weight of the patient, and the ability of the drug to produce a desired therapeutic effect in the patient. Whether a symptom of a disease has been alleviated can be evaluated by any clinical testing methods commonly used by doctors or other health care professionals to evaluate the severity or progression of the symptom. Although the embodiments of the present disclosure (for example, treatment methods or products) may not be effective in alleviating the symptoms of each disease of interest, they shall reduce the symptoms of a disease of interest in a statistically significant number of patients, as determined according to any statistical testing methods known in the art, such as Student t-test, chi-square test, Mann and Whitney's U test, Kruskal-Wallis test (H test), Jonckheere-Terpstra test and Wilcoxon test.

"Effective amount" comprises an amount sufficient to ameliorate or prevent a symptom or condition of a medical disease. An effective amount also refers to an amount sufficient to allow or facilitate diagnosis. The effective amount for a particular patient or veterinary subject may vary depending on the factors such as the condition to be treated, the general health of the patient, the method and route and dosage of administration, and the severity of side effects. An effective amount can be the maximum dose or administration regimen to avoid significant side effects or toxic effects.

"Exchange" refers to the exchange of a solvent system that solubilizes an antibody protein. For example, a high-salt or hypertonic solvent system comprising the antibody protein is exchanged, by physical operations, with a buffer system of a stable formulation, such that the antibody protein is present in the stable formulation. The physical operations include, but are not limited to, ultrafiltration, dialysis or reconstitution following centrifugation.

DETAILED DESCRIPTION

Figure 1A:
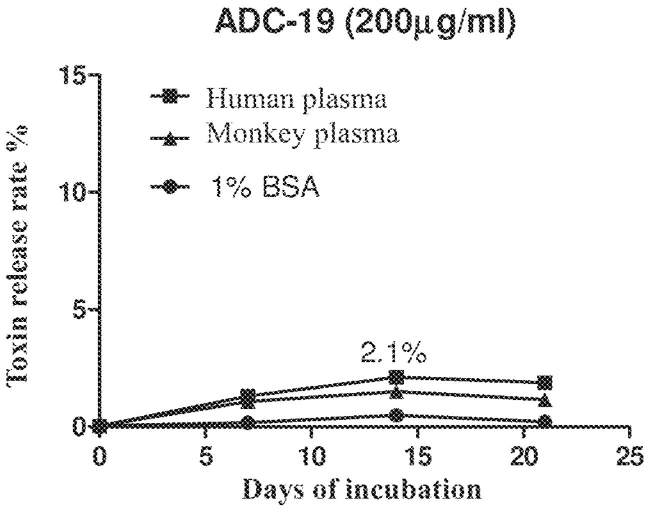
FIG. 1A shows the results of plasma stability test for ADC-19 of the present disclosure.

The present disclosure is further described below with reference to examples, which, however, are not intended to limit the scope of the present disclosure. The experimental methods in the examples of the present disclosure in which specific conditions are not specified are generally performed under conventional conditions, for example, by referring to *Antibodies: A Laboratory Manual and Molecular Cloning: A Laboratory Manual* by Cold Spring Harbor Laboratory, or under conditions recommended by the manufacturer of the raw material or the goods. Reagents without specific origins indicated are commercially available conventional reagents.

I. Antibody Drug Conjugates

The structures of the compounds were determined by nuclear magnetic resonance (NMR) or mass spectrometry (MS). NMR spectra were measured using a Bruker AVANCE-400 nuclear magnetic resonance instrument, with deuterated dimethyl sulfoxide (DMSO-d6), deuterated chloroform ($CDCl_3$) and deuterated methanol ($CD_3OD$) as determination solvents and tetramethylsilane (TMS) as internal standard. Chemical shifts were given in unit of $10^{-6}$ (ppm).

MS analysis was performed using a FINNIGAN LCQAd (ESI) mass spectrometer (manufacturer: Thermo, model: Finnigan LCQ advantage MAX).

UPLC analysis was performed using a Waters Acquity UPLC SQD liquid chromatography-mass spectrometry system.

HPLC analysis was performed using an Agilent 1200DAD high pressure liquid chromatograph (Sunfire C18 150×4.6 mm chromatography column) and a Waters 2695-2996 high pressure liquid chromatograph (Gimini C18 150×4.6 mm chromatography column).

UV-HPLC analysis was performed using a Thermo nanodrop2000 ultraviolet spectrophotometer.

Proliferation inhibition rates and $IC_{50}$ values were determined using a PHERA starFS microplate reader (BMG, Germany).

Yantai Huanghai HSGF254 or Qingdao GF254 silica gel plates of specifications 0.15 mm to 0.2 mm were adopted for thin layer chromatography (TLC) analysis and 0.4 mm to 0.5 mm for TLC separation and purification.

Yantai Huanghai silica gel of 200-300 mesh is generally used as a carrier in column chromatography.

Known starting materials of the present disclosure may be synthesized using or according to methods known in the art, or may be purchased from ABCR GmbH & Co.KG, Acros Organnics, Aldrich Chemical Company, Accela ChemBio Inc, Chembee Chemicals, etc. In the Examples, the reactions were performed in an argon atmosphere or a nitrogen atmosphere unless otherwise stated.

The argon atmosphere or nitrogen atmosphere means that the reaction flask is linked to a balloon containing about 1 L of argon or nitrogen.

The hydrogen atmosphere means that the reaction flask is linked to a balloon containing about 1 L of hydrogen.

Parr 3916EKX hydrogenator, Qinglan QL-500 hydrogenator or HC2-SS hydrogenator was used in the pressurized hydrogenation reactions.

The hydrogenation reactions usually involve 3 cycles of vacuumization and hydrogen purge.

A CEM Discover-S 908860 microwave reactor was used in the microwave reactions. In the Examples, the solution in the reaction refers to an aqueous solution unless otherwise stated.

In the Examples, the reaction temperature is room temperature unless otherwise stated. The room temperature is the optimum reaction temperature, ranging from 20° C. to 30° C. Preparation of PBS buffer at pH 6.5 in Examples: 8.5 g of $KH_2PO_4$, 8.56 g of $K_2HPO_4.3H_2O$, 5.85 g of NaCl and 1.5 g of EDTA were added to a flask, and the volume was brought to 2 L. The additions were all ultrasonically dissolved, and the solution was well mixed by shaking to give the desired buffer.

The eluent system for column chromatography and the developing solvent system for thin layer chromatography used for compound purification include: A: dichloromethane and isopropanol system, B: dichloromethane and methanol system, and C: petroleum ether and ethyl acetate system. The volume ratio of solvents was adjusted according to the polarity of the compound, or by adding a small amount of triethylamine and acidic or basic reagent.

Some of the compounds of the present disclosure are characterized by Q-TOF LC/MS. Q-TOF LC/MS analysis was performed using an Agilent 6530 accurate-mass quadrupole time-of-flight mass spectrometer and an Agilent 1290-Infinity ultra-high performance liquid chromatograph (Agilent Poroshell 300SB-C8 5 μm, 2.1×75 mm chromatography column).

Example 1-1

N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizinol[1,2-b]quinolin-1-yl)-1-hydroxycyclopropane-1-carboxamide 1

1

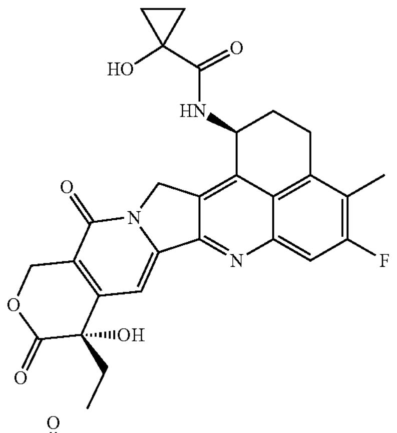

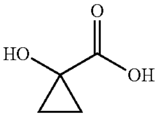

+

1a

-continued

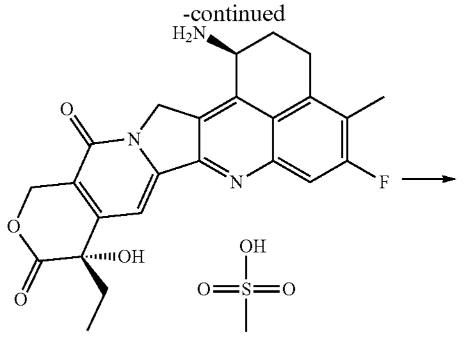

1b

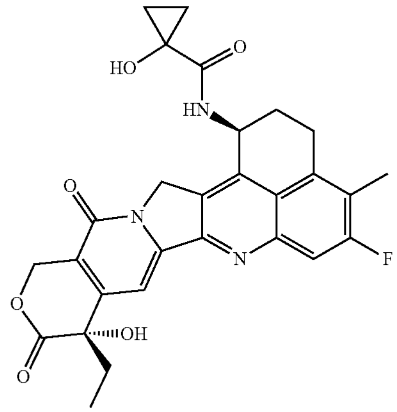

1

To exatecan mesylate 1b (2.0 mg, 3.76 μmol, prepared as disclosed in Patent Application "EP0737686A1") was added 1 mL of N,N-dimethylformamide. The mixture was cooled to 0-5° C. in an ice-water bath, and a drop of triethylamine was added. The reaction mixture was stirred until it became clear. To the reaction mixture were successively added 1-hydroxycyclopropylcarboxylic acid 1a (1.4 mg, 3.7 μmol, prepared using known method "Tetrahedron Letters, 25(12), 1269-72; 1984") and 4-(4,6-dimethoxy-1,3,5-triazin-2-yl)-4-methylmorpholinium chloride (3.8 mg, 13.7 μmol). After addition, the reaction mixture was stirred at 0-5° C. for 2 h, quenched with 5 mL of water, and extracted with ethyl acetate (8 mL×3). The organic phases were combined, washed with saturated sodium chloride solution (5 mL×2), dried over anhydrous sodium sulfate, and filtered.

The filtrate was concentrated under reduced pressure, and the resulting residue was purified by thin layer chromatography with developing solvent system B to give the title product 1 (1.6 mg, 82.1% yield).

MS m/z (ESI): 520.2 [M+1].

$^1$H NMR (400 MHz, $CDCl_3$): δ 7.90-7.84 (m, 1H), 7.80-7.68 (m, 1H), 5.80-5.70 (m, 1H), 5.62-5.54 (m, 2H), 5.44-5.32 (m, 2H), 5.28-5.10 (m, 2H), 3.40-3.15 (m, 3H), 2.44 (s, 3H), 2.23 (t, 1H), 2.06-1.75 (m, 2H), 1.68-1.56 (m, 1H), 1.22-1.18 (m, 2H), 1.04-0.98 (m, 2H), 0.89 (t, 3H).

Example 1-2

(S)-2-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxyacetamide 2-A (R)-2-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxyacetamide 2-B

2-A

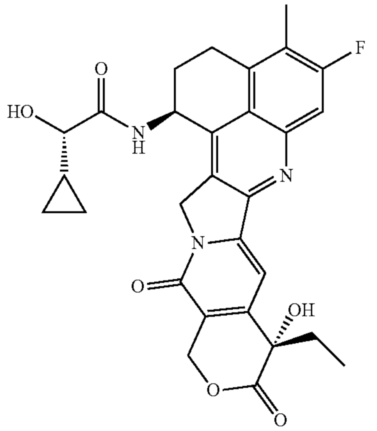

2-B

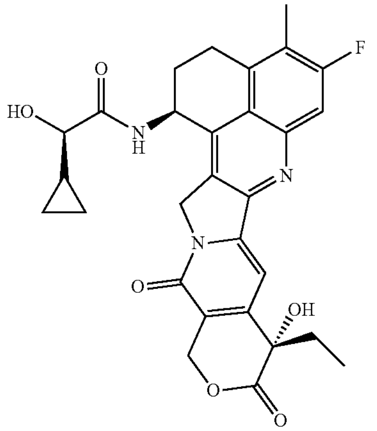

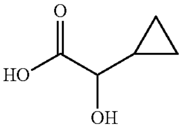

+

2a

-continued

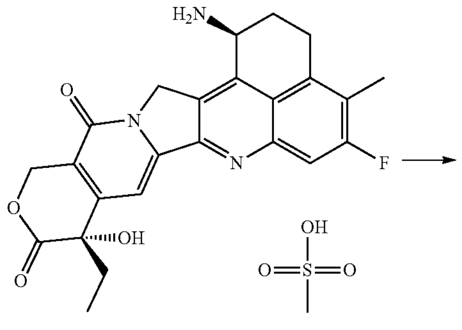

1b

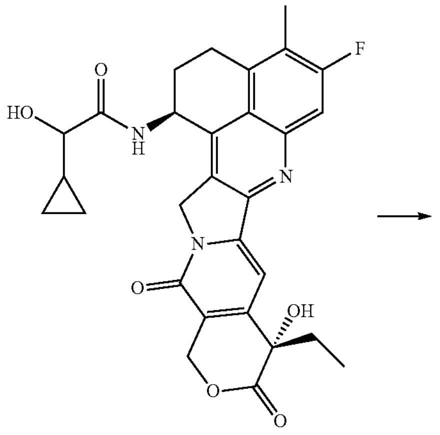

2

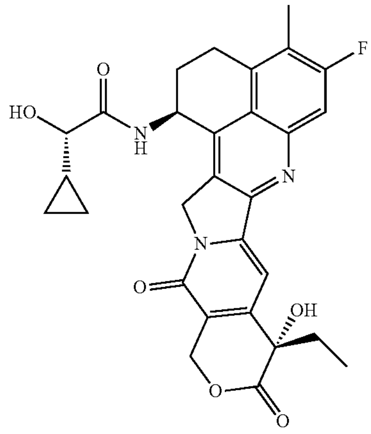

2-A

+

-continued

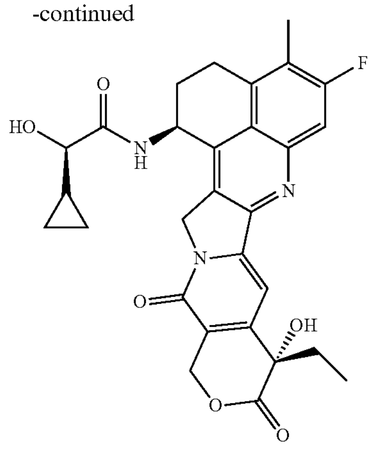

2-B

To compound 1b (4 mg, 7.53 μmol) were added 2 mL of ethanol and 0.4 mL of N,N-dimethylformamide The system was purged with argon three times, and the mixture was cooled to 0-5° C. in an ice-water bath, followed by dropwise addition of 0.3 mL of N-methylmorpholine. The reaction mixture was stirred until it became clear. To the reaction mixture were successively added 2-cyclopropyl-2-hydroxy-acetic acid 2a (2.3 mg, 19.8 μmol, prepared as disclosed in Patent Application "WO2013106717"), 1-hydroxybenzotriazole (3 mg, 22.4 μmol) and 1-(3-dimethylaminopropyl)-3-ethylcarbodiimide hydrochloride (4.3 mg, 22.4 μmol). After addition, the reaction mixture was stirred at 0-5° C. for 1 h. The ice-water bath was removed, and the reaction mixture was heated to 30° C., stirred for 2 h, and concentrated under reduced pressure. The resulting crude compound 2 was purified by high performance liquid chromatography (separation conditions: chromatography column: XBridge Prep C18 OBD 5 μm 19×250 mm; mobile phase: A-water (10 mmol of $NH_4OAc$), B-acetonitrile, gradient elution, flow rate: 18 mL/min), and the corresponding fractions were collected and concentrated under reduced pressure to give the title products (2-A: 1.5 mg, 2-B: 1.5 mg).

MS m/z (ESI): 534.0 [M+1].

Single-configuration compound 2-B (shorter retention time):

UPLC analysis: retention time: 1.06 min; purity: 88% (chromatography column: ACQUITY UPLC BEHC18 1.7 μm 2.1×50 mm; mobile phase: A-water (5 mmol of $NH_4OAc$), B-acetonitrile).

$^1H$ NMR (400 MHz, DMSO-$d_6$): δ 8.37 (d, 1H), 7.76 (d, 1H), 7.30 (s, 1H), 6.51 (s, 1H), 5.58-5.56 (m, 1H), 5.48 (d, 1H), 5.41 (s, 2H), 5.32-5.29 (m, 2H), 3.60 (t, 1H), 3.19-3.13 (m, 1H), 2.38 (s, 3H), 2.20-2.14 (m, 1H), 1.98 (q, 2H), 1.87-1.83 (m, 1H), 1.50-1.40 (m, 1H), 1.34-1.28 (m, 1H), 0.86 (t, 3H), 0.50-0.39 (m, 4H).

Single-configuration compound 2-A (longer retention time):

UPLC analysis: retention time: 1.10 min; purity: 86% (chromatography column: ACQUITY UPLC BEHC18 1.7 μm 2.1×50 mm; mobile phase: A-water (5 mmol of $NH_4OAc$), B-acetonitrile).

$^1H$ NMR (400 MHz, DMSO-$d_6$): δ 8.35 (d, 1H), 7.78 (d, 1H), 7.31 (s, 1H), 6.52 (s, 1H), 5.58-5.53 (m, 1H), 5.42 (s, 2H), 5.37 (d, 1H), 5.32 (t, 1H), 3.62 (t, 1H), 3.20-3.15 (m, 2H), 2.40 (s, 3H), 2.25-2.16 (m, 1H), 1.98 (q, 2H), 1.87-1.82 (m, 1H), 1.50-1.40 (m, 1H), 1.21-1.14 (m, 1H), 0.87 (t, 3H), 0.47-0.35 (m, 4H).

Example 1-3

(S)—N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizinol[1,2-b]quinolin-1-yl)-3,3,3-trifluoro-2-hydroxypropionamide 3-A (R)—N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizinol[1,2-b]quinolin-1-yl)-3,3,3-trifluoro-2-hydroxypropionamide 3-B

3-A

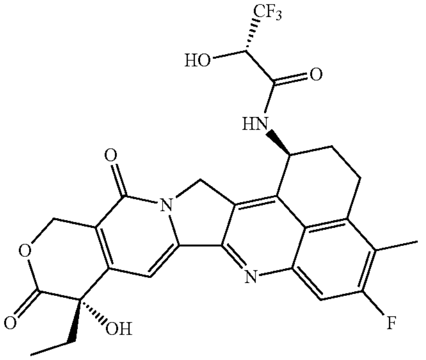

3-B

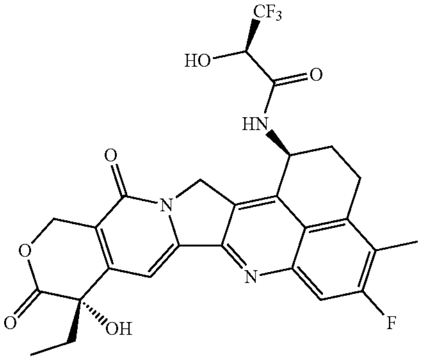

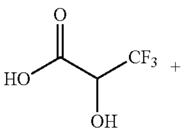

3a

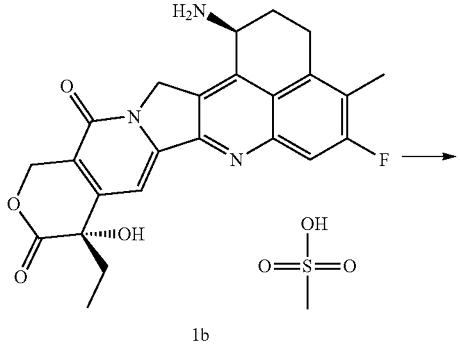

1b

-continued

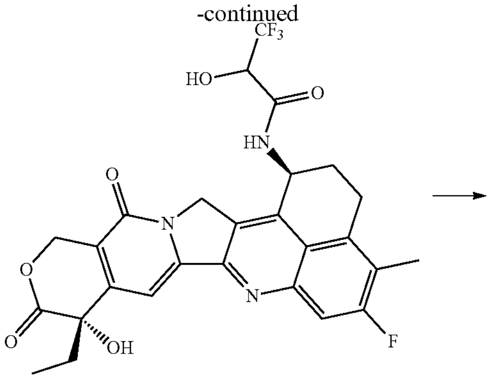

3

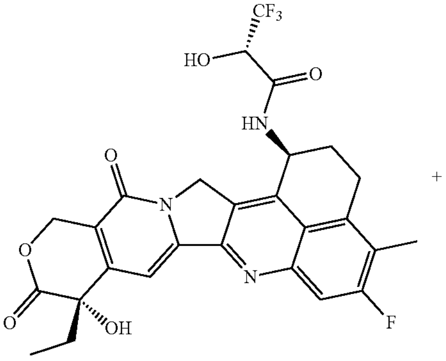

3-A

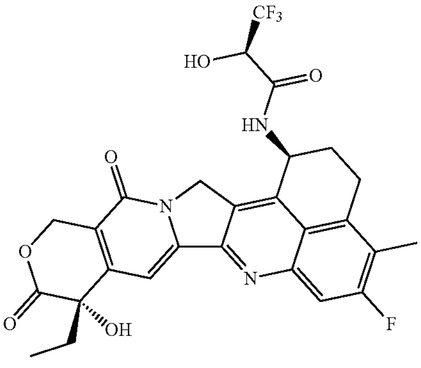

3-B

To compound 1b (5.0 mg, 9.41 μmol) were added 2 mL of ethanol and 0.4 mL of N,N-dimethylformamide, and the mixture was cooled to 0-5° C. in an ice-water bath, followed by dropwise addition of 0.3 mL of N-methylmorpholine. The reaction mixture was stirred until it became clear. To the reaction mixture were successively added 3,3,3-trifluoro-2-hydroxypropionic acid 3a (4.1 mg, 28.4 μmol, supplied by Alfa), 1-hydroxybenzotriazole (3.8 mg, 28.1 μmol) and 1-(3-dimethylaminopropyl)-3-ethylcarbodiimide hydrochloride (5.4 mg, 28.2 μmol). After addition, the reaction mixture was stirred at 0-5° C. for 10 min. The ice-water bath was removed, and the reaction mixture was heated to 30° C., stirred for 8 h, and concentrated under reduced pressure. The resulting crude compound 3 was purified by high performance liquid chromatography (separation conditions: chromatography column: XBridge Prep C18 OBD 5 μm 19×250 mm; mobile phase: A-water (10 mmol of $NH_4OAc$), B-acetonitrile, gradient elution, flow rate: 18 mL/min), and the corresponding fractions were collected and concentrated under reduced pressure to give the title products (1.5 mg, 1.5 mg).

MS m/z (ESI): 561.9 [M+1].

Single-configuration compound (shorter retention time):

UPLC analysis: retention time: 1.11 min; purity: 88% (chromatography column: ACQUITY UPLC BEHC18 1.7 μm 2.1×50 mm; mobile phase: A-water (5 mmol of $NH_4OAc$), B-acetonitrile).

$^1H$ NMR (400 MHz, DMSO-$d_6$): δ 8.94 (d, 1H), 7.80 (d, 1H), 7.32 (s, 1H), 7.20 (d, 1H), 6.53 (s, 1H), 5.61-5.55 (m, 1H), 5.45-5.23 (m, 3H), 5.15-5.06 (m, 1H), 4.66-4.57 (m, 1H), 3.18-3.12 (m, 1H), 2.40 (s, 3H), 2.26-2.20 (m, 1H), 2.16-2.08 (m, 1H), 2.02-1.94 (m, 1H), 1.89-1.82 (m, 1H), 1.50-1.40 (m, 1H), 0.87 (t, 3H).

Single-configuration compound (longer retention time):

UPLC analysis: retention time: 1.19 min; purity: 90% (chromatography column: ACQUITY UPLC BEHC18 1.7 pin 2.1×50 mm; mobile phase: A-water (5 mmol of $NH_4OAc$), B-acetonitrile).

$^1H$ NMR (400 MHz, DMSO-$d_6$): δ 8.97 (d, 1H), 7.80 (d, 1H), 7.31 (s, 1H), 7.16 (d, 1H), 6.53 (s, 1H), 5.63-5.55 (m, 1H), 5.45-5.20 (m, 3H), 5.16-5.07 (m, 1H), 4.66-4.57 (m, 1H), 3.18-3.12 (m, 1H), 2.40 (s, 3H), 2.22-2.14 (m, 1H), 2.04-1.95 (m, 2H), 1.89-1.82 (m, 1H), 1.50-1.40 (m, 1H), 0.87 (t, 3H).

Example 1-4

N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-hydroxycyclopentane-1-carboxamide 4

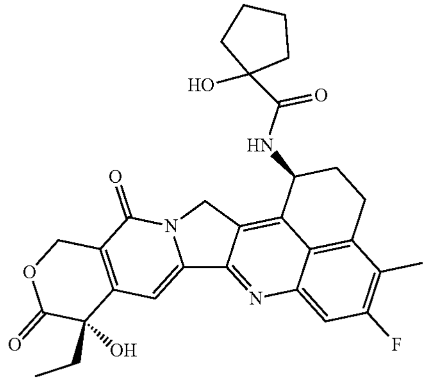

4

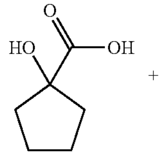

+

4a

-continued

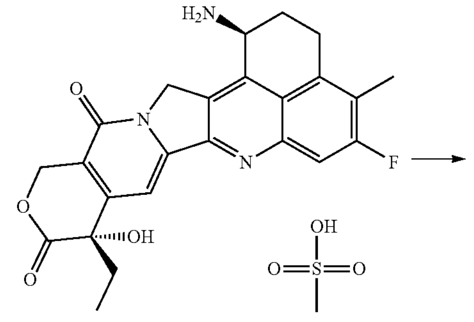

1b

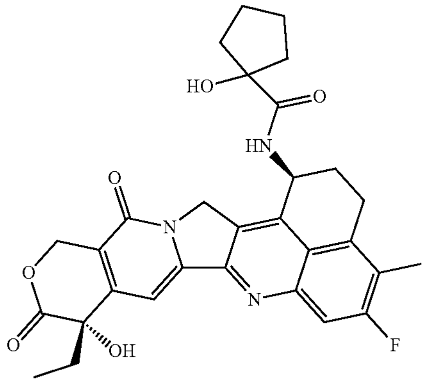

4

To compound 1b (3.0 mg, 5.64 μmol) was added 1 mL of N,N-dimethylformamide. The mixture was cooled to 0-5° C. in an ice-water bath, and a drop of triethylamine was added. The reaction mixture was stirred until it became clear. To the reaction mixture were successively added 1-hydroxy-cyclopentanecarboxylic acid 4a (2.2 mg, 16.9 μmol, prepared as disclosed in Patent Application "WO2013106717") and 4-(4,6-dimethoxy-1,3,5-triazin-2-yl)-4-methylmorpholinium chloride (4.7 mg, 16.9 μmol). After addition, the reaction mixture was stirred at 0-5° C. for 1 h, quenched with 5 mL of water, and extracted with ethyl acetate (10 mL×3). The organic phases were combined, washed with saturated sodium chloride solution (5 mL×2), dried over anhydrous sodium sulfate, and filtered. The filtrate was concentrated under reduced pressure, and the resulting residue was purified by thin layer chromatography with developing solvent system B to give the title product 4 (2.5 mg, 80.9% yield).

MS m/z (ESI): 548.0 [M+1].

$^1H$ NMR (400 MHz, $CDCl_3$): δ 7.73-7.62 (m, 2H), 5.75-5.62 (m, 1H), 5.46-5.32 (m, 2H), 5.26-5.10 (m, 1H), 3.30-3.10 (m, 1H), 2.43 (s, 3H), 2.28-2.20 (m, 2H), 2.08-1.84 (m, 8H), 1.69-1.58 (m, 2H), 1.04-1.00 (m, 2H), 0.89 (t, 3H).

Example 1-5

N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-(hydroxymethyl)cyclopropane-1-carboxamide 5

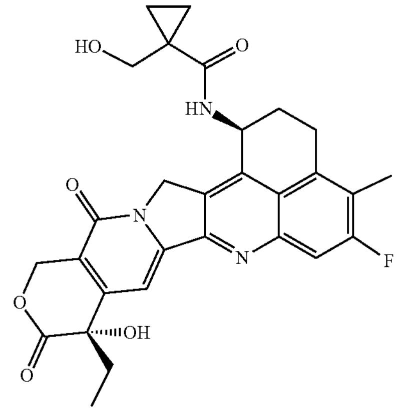

5

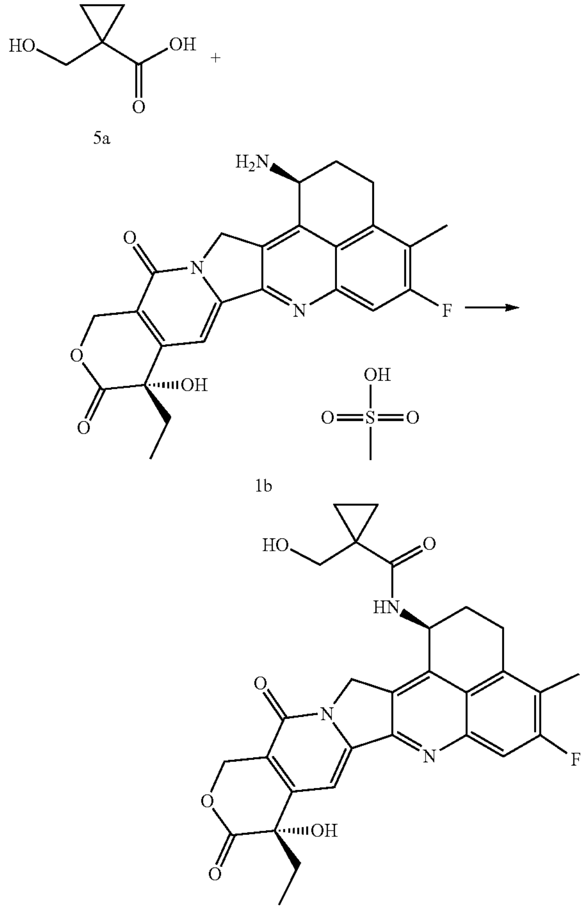

5a

1b

5

To compound 1 b (2.0 mg, 3.76 μmol) was added 1 mL of N,N-dimethylformamide. The mixture was cooled to 0-5° C. in an ice-water bath, and a drop of triethylamine was added. The reaction mixture was stirred until it became clear. To the reaction mixture were successively added 1-(hydroxymethyl)-cyclopentanecarboxylic acid 5a (0.87 mg, 7.5 μmol, prepared as disclosed in Patent Application “WO201396771”) and 4-(4,6-dimethoxy-1,3,5-triazin-2-yl)-4-methylmorpholinium chloride (2 mg, 7.24 μmol). After addition, the reaction mixture was stirred at 0-5° C. for 2 h, quenched with 5 mL of water, and extracted with ethyl acetate (8 mL×3). The organic phases were combined, washed with saturated sodium chloride solution (5 mL×2), dried over anhydrous sodium sulfate, and filtered. The filtrate was concentrated under reduced pressure, and the resulting residue was purified by thin layer chromatography with developing solvent system B to give the title product 5 (1.0 mg, 50% yield).

MS m/z (ESI): 533.9 [M+1].

$^1$H NMR (400 MHz, $CDCl_3$): δ 8.07 (s, 1H), 7.23-7.18 (m, 2H), 6.71-6.64 (m, 1H), 6.55-6.51 (m, 1H), 5.36-5.27 (m, 2H), 4.67-4.61 (m, 2H), 3.53-3.48 (m, 1H), 3.30-3.22 (m, 2H), 3.18-3.13 (m, 1H), 2.71-2.61 (m, 2H), 2.35-2.28 (m, 1H), 2.04-1.91 (m, 4H), 1.53-1.40 (m, 3H), 0.91-0.75 (m, 4H).

Example 1-6

N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-(hydroxymethyl)cyclobutane-1-carboxamide 6

6

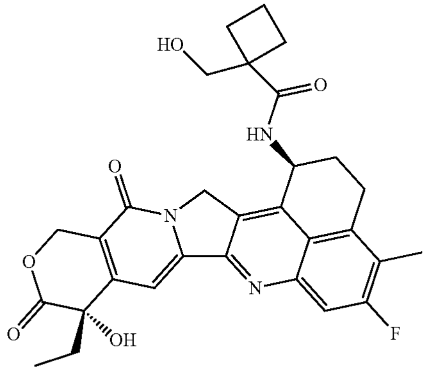

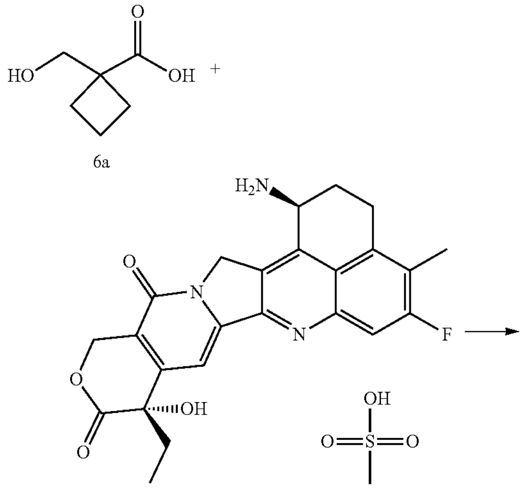

6a

1b

-continued

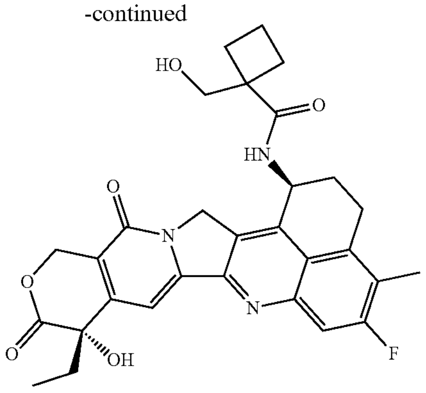

6

To compound 1b (3.0 mg, 5.64 μmol) was added 1 mL of N,N-dimethylformamide. The mixture was cooled to 0-5° C. in an ice-water bath, and a drop of triethylamine was added. The reaction mixture was stirred until it became clear. To the reaction mixture were successively added 1-(hydroxymethyl)cyclobutane-1-carboxylic acid 6a (2.2 mg, 16.9 μmol, prepared as disclosed in "*Journal of the American Chemical Society,* 2014, vol. 136, #22, p. 8138-8142") and 4-(4,6-dimethoxy-1,3,5-triazin-2-yl)-4-methylmorpholinium chloride (4.7 mg, 16.9 μmol). After addition, the reaction mixture was stirred at 0-5° C. for 1 h, quenched with 5 mL of water, and extracted with ethyl acetate (10 mL×3). The organic phases were combined, washed with saturated sodium chloride solution (5 mL×2), dried over anhydrous sodium sulfate, and filtered. The filtrate was concentrated under reduced pressure, and the resulting residue was purified by thin layer chromatography with developing solvent system B to give the title product 6 (2.1 mg, 67.9% yield).

MS m/z (ESI): 548.0 [M+1].

$^1$H NMR (400 MHz, DMSO-$d_6$): δ 7.85-7.62 (m, 1H), 6.88 (br, 1H), 5.87-5.48 (m, 2H), 5.47-5.33 (m, 1H), 5.31-5.06 (m, 1H), 4.25-3.91 (m, 2H), 3.25 (br, 1H), 2.60-2.32 (m, 3H), 2.23 (t, 1H), 2.15-1.95 (m, 3H), 1.70-1.56 (m, 2H), 1.41-1.17 (m, 9H), 1.03 (s, 1H), 0.95-0.80 (m, 2H).

Example 1-7

N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-hydroxycyclobutane-1-carboxamide 7

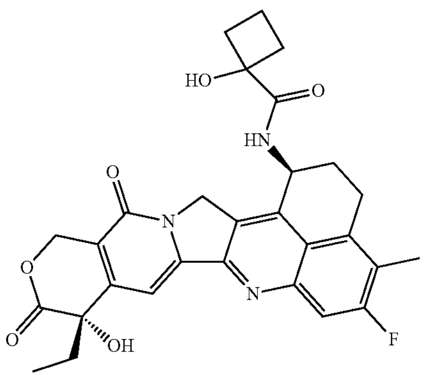

7

-continued

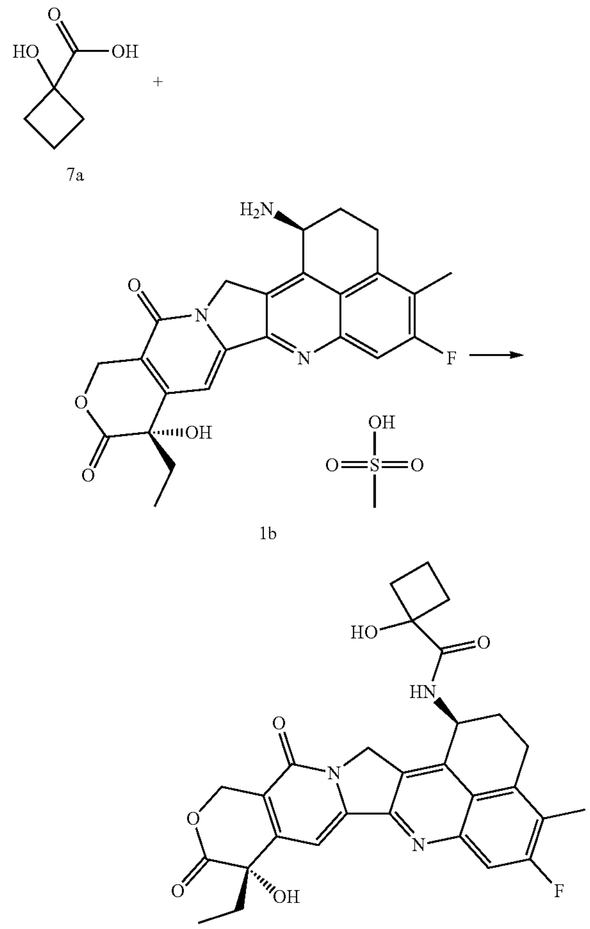

7a

1b

7

To compound 1b (3.0 mg, 5.64 μmol) were added 2 mL of ethanol and 0.4 mL of N,N-dimethylformamide, and the mixture was cooled to 0-5° C. in an ice-water bath, followed by dropwise addition of 0.3 mL of N-methylmorpholine. The reaction mixture was stirred until it became clear. To the reaction mixture were successively added 1-hydroxycyclobutanecarboxylic acid 7a (2.0 mg, 17.22 μmol, supplied by PharmaBlock), 1-hydroxybenzotriazole (2.3 mg, 17.0 μmol) and 1-(3-dimethylaminopropyl)-3-ethylcarbodiimide hydrochloride (3.2 mg, 16.7 μmol). After addition, the reaction mixture was stirred at 0-5° C. for 10 min. The ice-water bath was removed, and the reaction mixture was stirred at room temperature for 2 h, and concentrated under reduced pressure. The resulting residue was purified by thin layer chromatography with developing solvent system B to give the title product 7 (2.5 mg, 83.1% yield).

MS m/z (ESI): 534.0 [M+1].

$^1$H NMR (400 MHz, DMSO-$d_6$): δ 8.28 (d, 1H), 7.75 (d, 1H), 7.29 (s, 1H), 6.51 (s, 1H), 6.12 (s, 1H), 5.59-5.51 (m, 1H), 5.41 (s, 2H), 5.20-5.01 (m, 2H), 3.27-3.17 (m, 1H), 3.15-3.05 (m, 1H), 2.71-2.63 (m, 1H), 2.37 (s, 3H), 2.12-2.05 (m, 1H), 2.03-1.94 (m, 2H), 1.92-1.78 (m, 4H), 1.50-1.42 (m, 1H), 0.90-0.83 (m, 4H).

Example 1-8
1-(((S)-7-benzyl-20-(2,5-dioxo-2,5-dihydro-1H-pyrrol-1-yl)-3,6,9,12,15-pentaoxo-2,5,8,11,14-pentaazaeicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclopropane-1-carboxamide 8
8
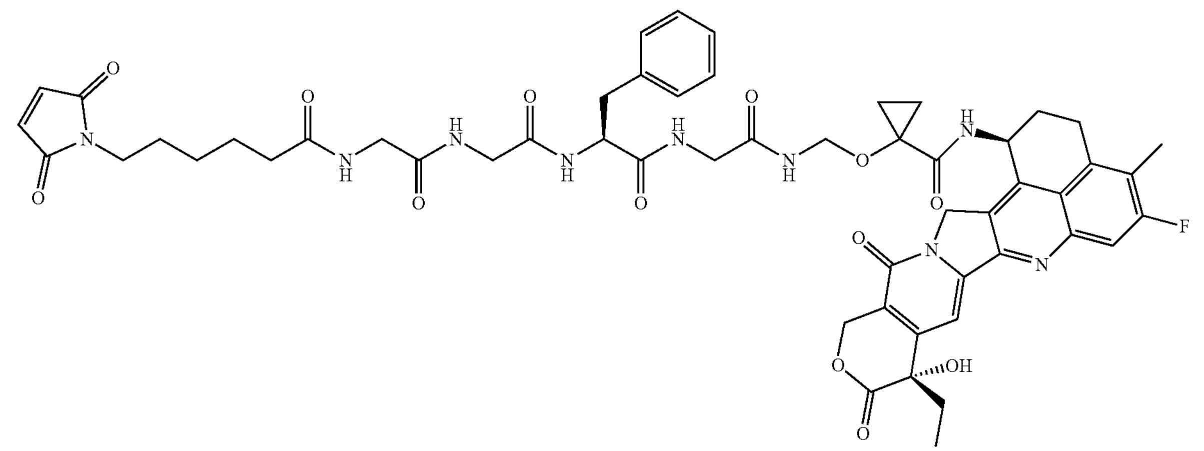
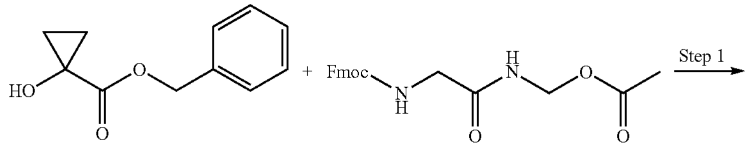
8a 8b
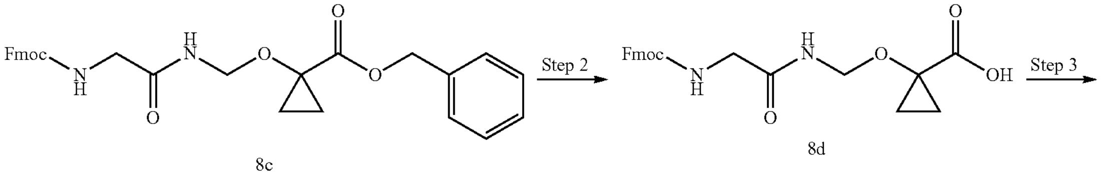
8c 8d
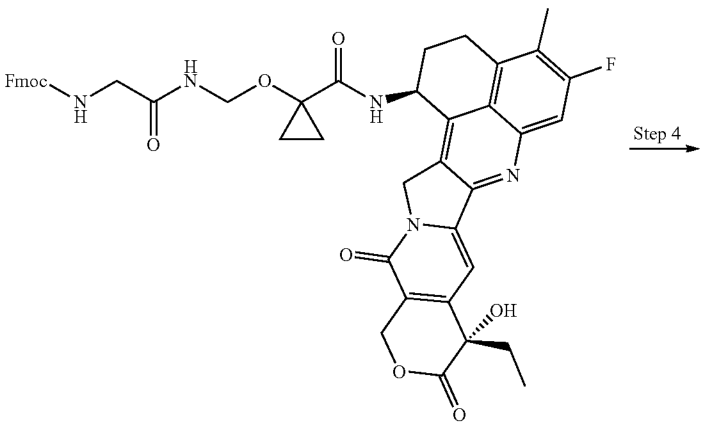
8e -continued

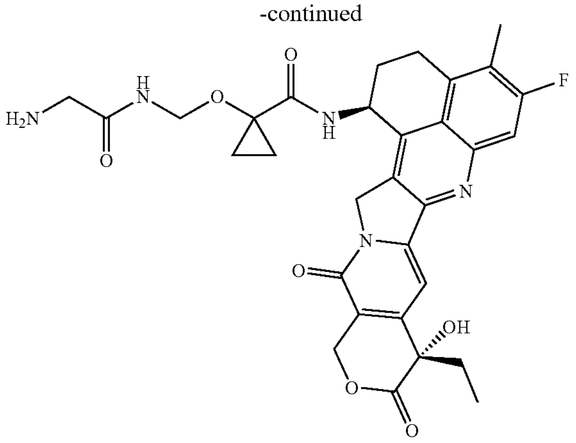

+

8f

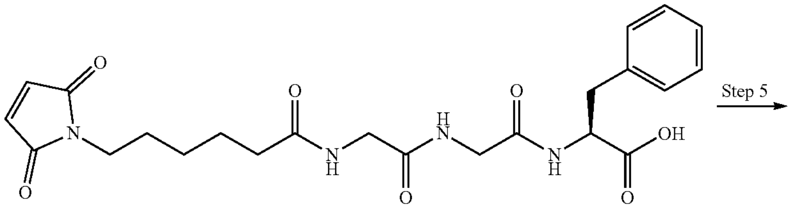

8g

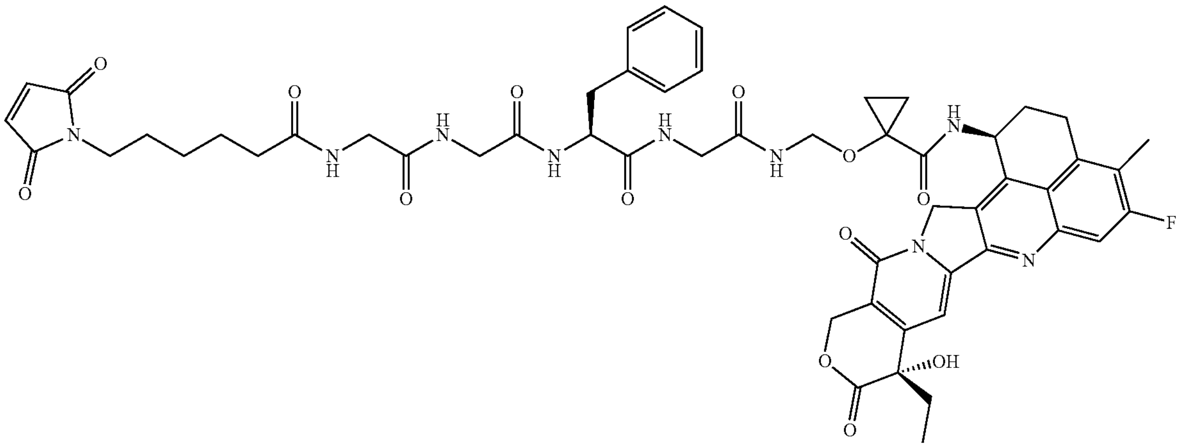

8

Step 1

Benzyl 1-((2-((((9H-fluoren yl)methoxy)carbonyl) amino)acetylamino)methoxy)cyclopropane-1-carboxylate 8c Benzyl 1-hydroxycyclopropane-1-carboxylate 8a (104 mg, 0.54 mmol; prepared as disclosed in Patent Application "US2005/20645") and 2-((((9H-fluoren-9-yl)methoxy)carbonyl)amino)acetylamino)methyl acetate 8b (100 mg, 0.27 mmol; prepared as disclosed in Patent Application "CN105829346A") were added to a reaction flask, and 5 mL of tetrahydrofuran was added. The system was purged with argon three times, and the mixture was cooled to 0-5° C. in an ice-water bath, followed by addition of potassium tert-butoxide (61 mg, 0.54 mmol). The ice bath was removed, and the reaction mixture was warmed to room temperature and stirred for 10 min, followed by addition of 20 mL of ice water and by extraction with ethyl acetate (5 mL×2) and chloroform (5 mL×5). The organic phases were combined and concentrated. The resulting residue was dissolved in 3 mL of 1,4-dioxane, and 0.6 mL of water, sodium bicarbonate (27 mg, 0.32 mmol) and 9-fluorenylmethyl chloroformate (70 mg, 0.27 mmol) were added. The reaction mixture was stirred at room temperature for 1 h. 20 mL of water was added, followed by extraction with ethyl acetate (8 mL×3). The organic phase was washed with saturated sodium chloride solution (20 mL), dried over anhydrous sodium sulfate, and filtered. The filtrate was concentrated under reduced pressure, and the resulting residue was purified by silica gel column chromatography with developing solvent system B to give the title product 8c (100 mg, 73.6% yield).

MS m/z (ESI): 501.0 [M+1].

Step 2

1-((2-((((9H-fluoren-9-yl)methoxy)carbonylamino) acetylamino)methoxy)cyclopropane-1-carboxylic acid 8d Compound 8c (50 mg, 0.10 mmol) was dissolved in 3 mL of a solvent mixture of tetrahydrofuran and ethyl acetate (V:V=2:1), and palladium on carbon (25 mg, 10% loading) was added. The system was purged with hydrogen three times, and the reaction mixture was stirred at room temperature for 1 h. The reaction mixture was filtered through celite, and the filter cake was rinsed with tetrahydrofuran. The filtrate was concentrated to give the title product 8d (41 mg, 100% yield).

MS m/z (ESI): 411.0 [M+1].

Step 3

9H-fluoren-9-yl)methyl(2-(((1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)aminocarbonyl)cyclopropoxy)methyl)amino)-2-oxoethyl)carbamate 8e Compound 1b (7 mg, 0.013 mmol) was added to a reaction flask, and 1 mL of N,N-dimethylformamide was added. The system was purged with argon three times, and the mixture was cooled to 0-5° C. in an ice-water bath, followed by addition of a drop of triethylamine, a solution of compound 8d (7 mg, 0.017 mmol) in 0.5 mL of N,N-dimethylformamide, and 4-(4,6-dimethoxy-1,3,5-triazin-2-yl)-4-methylmorpholinium chloride (7 mg, 0.026 mmol). The reaction mixture was stirred in an ice bath for 35 min. 10 mL of water was added, followed by extraction with ethyl acetate (5 mL×3). The organic phase was washed with saturated sodium chloride solution (10 mL), dried over anhydrous sodium sulfate, and filtered. The filtrate was concentrated under reduced pressure, and the resulting residue was purified by thin layer chromatography with developing solvent system B to give the title product 8e (8.5 mg, 78.0% yield). MS m/z (ESI): 828.0 [M+1].

Step 4

1-((2-Aminoacetylamino)methoxy)-N-((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)cyclopropane-1-carboxamide 8f Compound 8e (4 mg, 4.84 μmol) was dissolved in 0.2 mL of dichloromethane, and 0.1 mL of diethylamine was added. The reaction mixture was stirred at room temperature for 2 h and concentrated under reduced pressure. 2 mL of toluene was added, followed by concentration under reduced pressure; the procedures were repeated twice. The residue was slurried with 3 mL of n-hexane, and the upper n-hexane layer was removed; the procedures were repeated three times. The slurry was concentrated under reduced pressure to give the crude title product 8f (2.9 mg), which was directly used in the next step without purification.

MS m/z (ESI): 606.0 [M+1].

Step 5

1-(((S)-7-benzyl-20- (2,5-dioxo-2,5-dihydro-1H-pyrrol- 1-yl)-3,6,9,12,15-pentaoxo-2,5,8,11,14-pentaazaeicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)cyclopropane-1-carboxamide 8

Crude 8f (2.9 mg, 4.84 μmol) was dissolved in 0.5 mL of N,N-dimethylformamide. The system was purged with argon three times, and the solution was cooled to 0-5° C. in an ice-water bath. A solution of (S)-2(-2-(-2-(6-(2,5-dioxo-1H-pyrrol-1-yl)hexanamido)acetylaminolacetylamino)-3-phenylpropionic acid 8g (2.7 mg, 5.80 μmol, prepared as disclosed in Patent Application "EP2907824") in 0.3 mL of N,N-dimethylformamide was added, followed by addition of 4-(4,6-dimethoxy-1,3,5-triazin-2-yl)-4-methylmorpholinium chloride (2.7 mg, 9.67 μmol). The reaction mixture was stirred in an ice bath for 30 min. Then, the ice bath was removed, and the reaction mixture was warmed to room temperature, stirred for 15 min, and purified by high performance liquid chromatography (separation conditions: chromatography column: XBridge Prep C18 OBD 5 μm 19×250 mm; mobile phase: A-water (10 mmol of $NH_4OAc$), B-acetonitrile, gradient elution, flow rate: 18 mL/min). The corresponding fractions were collected and concentrated under reduced pressure to give the title product 8 (2 mg, 39.0% yield).

MS m/z (ESI): 1060.0 [M+1].

$^1$H NMR (400 MHz, DMSO-$d_6$): δ 9.01 (d, 1H), 8.77 (t, 1H), 8.21 (t, 1H), 8.08-7.92 (m, 2H), 7.73 (d, 1H), 7.28 (s, 1H), 7.24-7.07 (m, 4H), 6.98 (s, 1H), 6.50 (s, 1H), 5.61 (q, 1H), 5.40 (s, 2H), 5.32 (t, 1H), 5.12 (q, 2H), 4.62 (t, 1H), 4.52 (t, 1H), 4.40-4.32 (m, 1H), 3.73-3.47 (m, 8H), 3.16-3.04 (m, 2H), 2.89 (dd, 1H), 2.69-2.55 (m, 2H), 2.37-2.23 (m, 4H), 2.12-1.93 (m, 4H), 1.90-1.74 (m, 2H), 1.52-1.38 (m, 4H), 1.33-1.11 (m, 5H), 0.91-0.81 (m, 4H).

Example 1-9

N-((2R,10S)-10-benzyl-2-cyclopropyl- 1-(((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin- 1-yl)amino)-1,6,9,12,15-pentaoxo-3-oxa-5,8,11,14-tetraazahexadec-16-yl)-6-(2,5-dioxo-2,5-dihydro-1H-pyrrol-1-yl)hexanamide 9-A N-((2S,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)amino)-1,6,9,12,15-pentaoxo-3-oxa-5,8,11,14-tetraazahexadec-16-yl)-6-(2,5-dioxo-2,5-dihydro-1H-pyrrol-1-yl)hexanamide 9-B

9-A

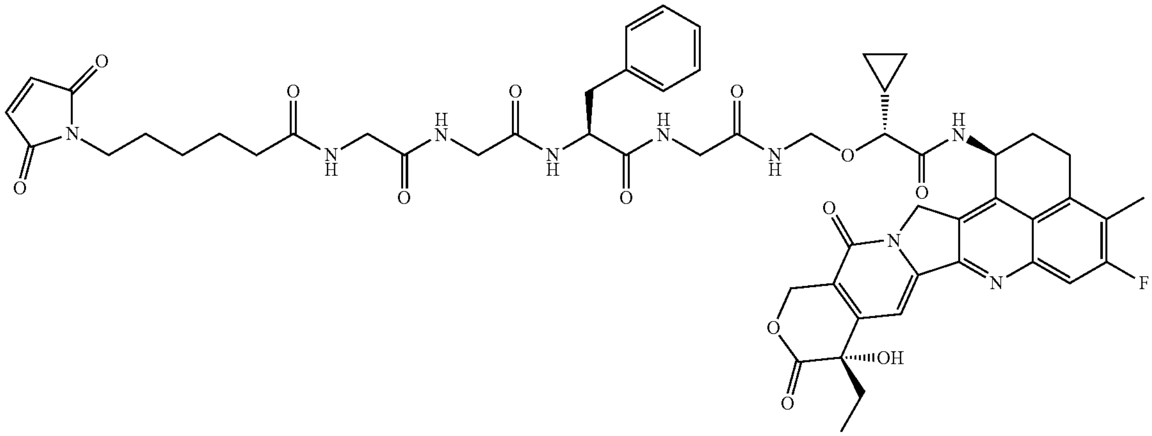

9-B

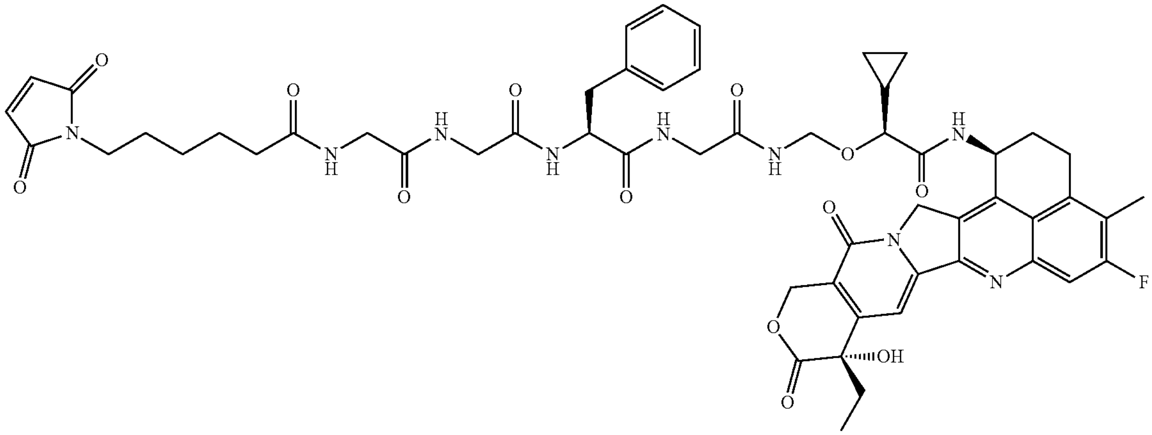

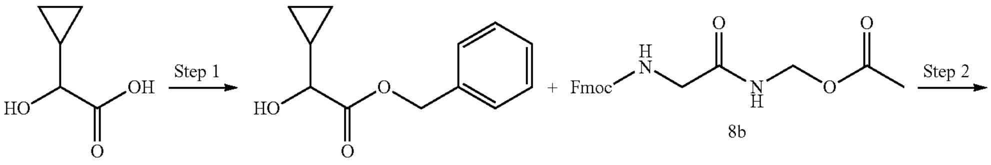

8b

2a

9a

-continued
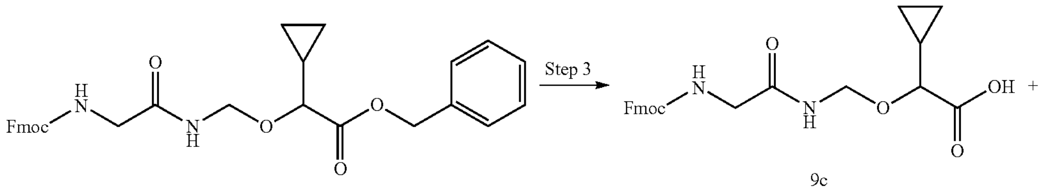
9b 9c
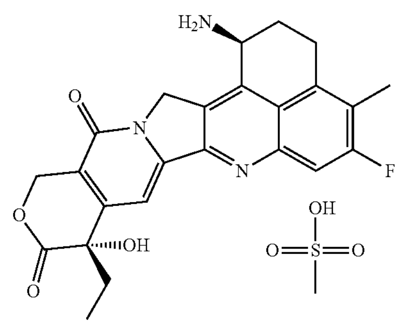
1b
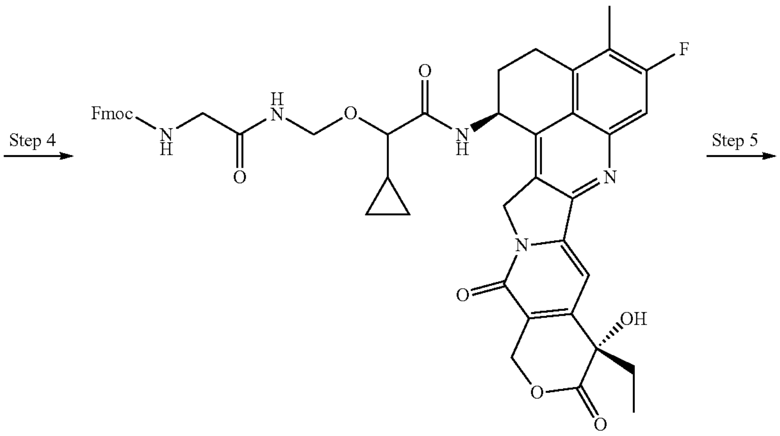
9d
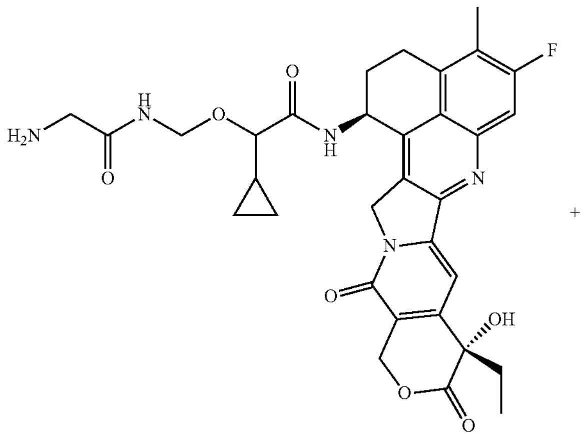
9e
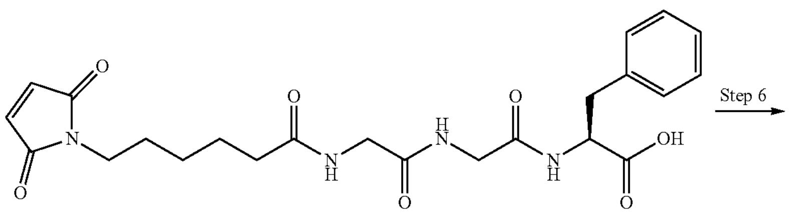
8g -continued

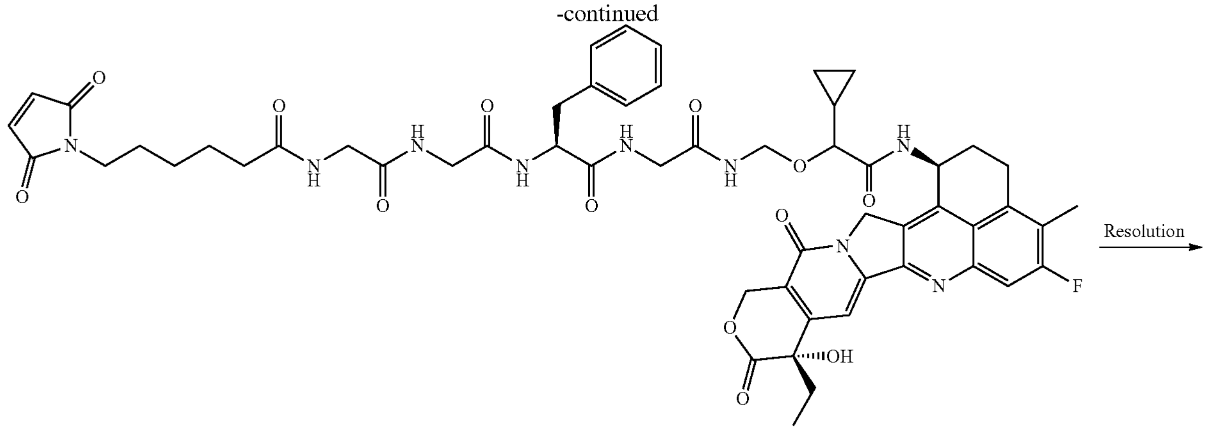

9

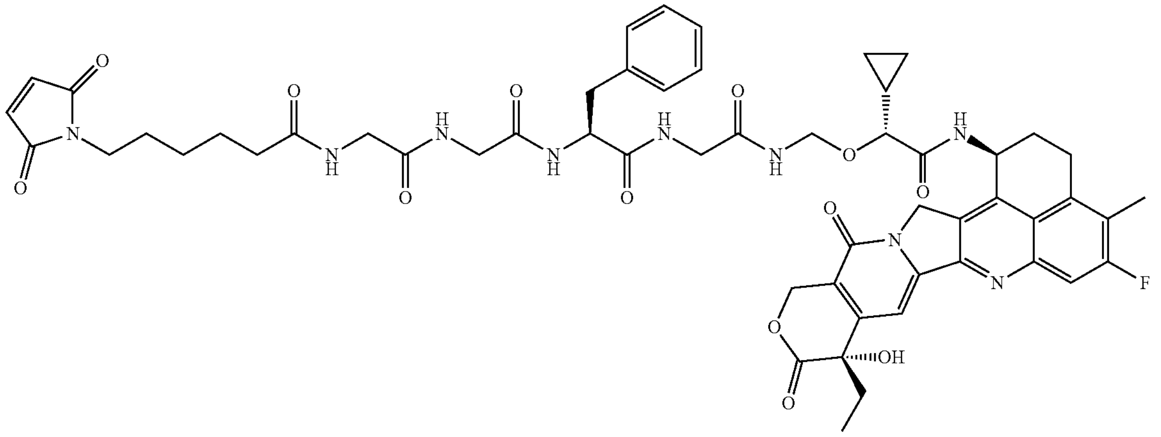

9-A

+

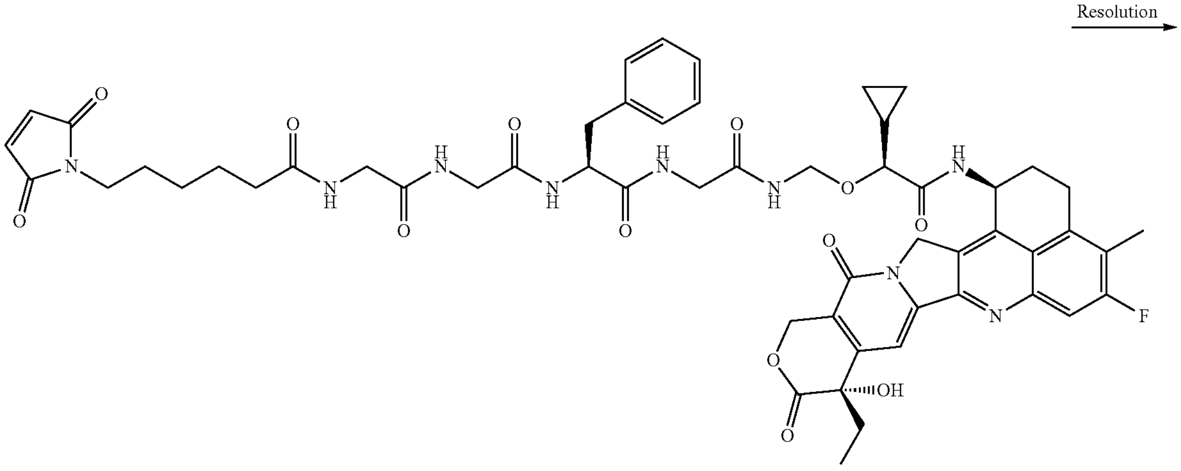

9-B

Step 1

Benzyl 2-cyclopropyl-2-hydroxyacetate 9a

Compound 2a (1.3 g, 11.2 mmol; prepared as disclosed in Patent Application "WO2013/106717") was dissolved in 50 mL of acetonitrile, and potassium carbonate (6.18 g, 44.8 mmol), benzyl bromide (1.33 mL, 11.2 mmol) and tetra-butylammonium iodide (413 mg, 1.1 mmol) were successively added. The reaction mixture was stirred at room temperature for 48 h and filtered through celite, and the filter cake was rinsed with ethyl acetate (10 mL). The filtrates were combined and concentrated under reduced pressure, and the resulting residue was purified by silica gel column chromatography with developing solvent system C to give the title product 9a (2 g, 86.9% yield).

Step 2

Benzyl 10-cyclopropyl-1-(9H-fluoren-9-yl)-3,6-dioxo-2,9-dioxa-4,7-diazaundecan-11-oate 9b Compounds 9a (120.9 mg, 0.586 mmol) and 8b (180 mg, 0.489 mmol) were added to a reaction flask, and 4 mL of tetrahydrofuran was added. The system was purged with argon three times, and the reaction mixture was cooled to 0-5° C. in an ice-water bath, followed by addition of potassium tert-butoxide (109 mg, 0.98 mmol). The ice bath was removed, and the reaction mixture was warmed to room temperature and stirred for 40 min, followed by addition of 10 mL of ice water and by extraction with ethyl acetate (20 mL×2) and chloroform (10 mL×5). The organic phases were combined and concentrated. The resulting residue was dissolved in 4 mL of dioxane, and 2 mL of water, sodium bicarbonate (49.2 mg, 0.586 mmol) and 9-fluorenylmethyl chloroformate (126 mg, 0.49 mmol) were added. The reaction mixture was stirred at room temperature for 2 h. 20 mL of water was added, followed by extraction with ethyl acetate (10 mL×3). The organic phase was washed with saturated sodium chloride solution (20 mL), dried over anhydrous sodium sulfate, and filtered. The filtrate was concentrated under reduced pressure. The resulting residue was purified by silica gel column chromatography with developing solvent system C to give the title product 9b (48 mg, 19% yield).

MS m/z (ESI): 515.0 [M+1].

Step 3

10-cyclopropyl-1-(9H-fluoren-9-yl)-3,6-dioxo-2,9-dioxa-4,7-diazaundecan-11-oic acid 9c Compound 9b (20 mg, 0.038 mmol) was dissolved in 4.5 mL of a solvent mixture of tetrahydrofuran and ethyl acetate (V:V=2:1), and palladium on carbon (12 mg, 10% loading, dry basis) was added. The system was purged with hydrogen three times, and the reaction mixture was stirred at room temperature for 1 h. The reaction mixture was filtered through celite, and the filter cake was rinsed with ethyl acetate. The filtrate was concentrated to give the crude title product 9c (13 mg), which was directly used in the next step without purification.

MS m/z (ESI): 424.9 [M+1].

Step 4

(9H-fluoren-9-yl)methyl(2-(((1-cyclopropyl-2-(((1S,9S)-9-ethyl-5-fluoro-9-hydroxy methyl-10,13-dioxo-2,3,9,10,13,15-hexahydro-1H,12H-benzo[de]pyrano[3',4':6,7]indolizino[1,2-b]quinolin-1-yl)amino)-2-oxoethoxy)methyl)amino)-2-oxoethyl)carbamate 9d Compound 1b (10 mg, 18.8 μmol) was added to a reaction flask, and 1 mL of N,N-dimethylformamide was added. The system was purged with argon three times, and the mixture was cooled to 0-5° C. in an ice-water bath, followed by addition of a drop of triethylamine, crude 9c (13 mg, 30.6 μmol), and 4-(4,6-dimethoxy-1,3,5-triazin-2-yl)-4-methylmorpholinium chloride (16.9 mg, 61.2 μmol). The reaction mixture was stirred in an ice bath for 40 min. 10 mL of water was added, followed by extraction with ethyl acetate (10 mL×3). The organic phases were combined, washed with saturated sodium chloride solution (10 mL×2), dried over anhydrous sodium sulfate, and filtered. The filtrate was concentrated under reduced pressure. The resulting residue was purified by thin layer chromatography with developing solvent system B to give the title product 9d (19 mg, 73.6% yield).

MS m/z (ESI): 842.1 [M+1].

Step 5

2-((2-Aminoacetylamino)methoxy)-2-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)acetamide 9e Compound 9d (19 mg, 22.6 μmol) was dissolved in 2 mL of dichloromethane, and 1 mL of diethylamine was added. The reaction mixture was stirred at room temperature for 2 h and concentrated under reduced pressure. 1 mL of toluene was added, followed by concentration under reduced pressure; the procedures were repeated twice. The residue was slurried with 3 mL of n-hexane and let stand. Then, the supernatant was removed, and the solid was kept. The solid residue was concentrated under reduced pressure and dried using an oil pump to give the crude title product 9e (17 mg), which was directly used in the next step without purification.

MS m/z (ESI): 638.0 [M+18].

Step 6

N-((2R,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)amino)-1,6,9,12,15-pentaoxo-3-oxa-5,8,11,14-tetraazahexadec-16-yl)-6-(2,5-dioxo-2,5-dihydro-1H-pyrrol-1-yl)hexanamide 9-A N-((2S,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)amino)-1,6,9,12,15-pentaoxo-3-oxa-5,8,11,14-tetraazahexadec-16-yl)-6-(2,5-dioxo-2,5-dihydro-1H-pyrrol yl)hexanamide 9-B Crude 9e (13.9 mg, 22.4 μmol) was dissolved in 0.6 mL of N,N-dimethylformamide. The system was purged with argon three times, and the solution was cooled to 0-5° C. in an ice-water bath. A solution of 8g (21.2 mg, 44.8 μmol) in 0.3 mL of N,N-dimethylformamide was added, followed by addition of 4-(4,6-dimethoxy-1,3,5-triazin-2-yl)-4-methylmorpholinium chloride (18.5 mg, 67.3 μmol). The reaction mixture was stirred in an ice bath for 10 min. Then, the ice bath was removed, and the reaction mixture was warmed to room temperature and stirred for 1 h to produce compound 9. The reaction mixture was purified by high performance liquid chromatography (separation conditions: chromatography column: XBridge Prep C18 OBD 5 μm 19×250 mm; mobile phase: A-water (10 mmol of $NH_4OAc$), B-acetonitrile, gradient elution, flow rate: 18 mL/min). The corresponding fractions were collected and concentrated under reduced pressure to give the title products (9-A: 2.4 mg, 9-B: 1.7 mg).

MS m/z (ESI): 1074.4 [M+1].

Single-configuration compound 9-A (shorter retention time):

UPLC analysis: retention time: 1.14 min; purity: 85% (chromatography column: ACQUITY UPLC BEHC18 1.7 μm 2.1×50 mm; mobile phase: A-water (5 mmol of $NH_4OAc$), B-acetonitrile).

$^1H$ NMR (400 MHz, DMSO-$d_6$): δ 8.60 (t, 1H), 8.51-8.49 (d, 1H), 8.32-8.24 (m, 1H), 8.13-8.02 (m, 2H), 8.02-7.96 (m, 1H), 7.82-7.75 (m, 1H), 7.31 (s, 1H), 7.26-7.15 (m, 4H), 6.99 (s, 1H), 6.55-6.48 (m, 1H), 5.65-5.54 (m, 1H), 5.41 (s, 2H), 5.35-5.15 (m, 3H), 4.74-4.62 (m, 1H), 4.54-4.40 (m, 2H), 3.76-3.64 (m, 4H), 3.62-3.48 (m, 2H), 3.20-3.07 (m, 2H), 3.04-2.94 (m, 1H), 2.80-2.62 (m, 1H), 2.45-2.30 (m, 3H), 2.25-2.15 (m, 2H), 2.15-2.04 (m, 2H), 1.93-1.78 (m, 2H), 1.52-1.39 (m, 3H), 1.34-1.12 (m, 5H), 0.87 (t, 3H), 0.64-0.38 (m, 4H).

Single-configuration compound 9-B (longer retention time):

UPLC analysis: retention time: 1.16 min; purity: 89% (chromatography column: ACQUITY UPLC BEHC18 1.7 μm 2.1×50 mm; mobile phase: A-water (5 mmol of $NH_4OAc$), B-acetonitrile).

$^1H$ NMR (400 MHz, DMSO-$d_6$): δ 8.68-8.60 (m, 1H), 8.58-8.50 (m, 1H), 8.32-8.24 (m, 1H), 8.13-8.02 (m, 2H), 8.02-7.94 (m, 1H), 7.82-7.75 (m, 1H), 7.31 (s, 1H), 7.26-7.13 (m, 3H), 6.99 (s, 1H), 6.55-6.48 (m, 1H), 5.60-5.50 (m, 1H), 5.41 (s, 2H), 5.35-5.15 (m, 2H), 4.78-4.68 (m, 1H), 4.60-4.40 (m, 2H), 3.76-3.58 (m, 4H), 3.58-3.48 (m, 1H), 3.20-3.10 (m, 2H), 3.08-2.97 (m, 2H), 2.80-2.72 (m, 2H), 2.45-2.30 (m, 3H), 2.25-2.13 (m, 2H), 2.13-2.04 (m, 2H), 2.03-1.94 (m, 2H), 1.91-1.78 (m, 2H), 1.52-1.39 (m, 3H), 1.34-1.12 (m, 4H), 0.91-0.79 (m, 3H), 0.53-0.34 (m, 4H).

Example 1-10

N-((2S,10S)-10-benzyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)aminocarbonyl)-1,1,1-trifluoro-6,9,12,15-tetraoxo-3-oxa-5,8,11,14-tetraazahexadec-16-yl)-6-(2,5-dioxo-2,5-dihydro-1H-pyrrol-1-yl)hexanamide 10-A N-((2R,10S)-10-benzyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)aminocarbonyl)-1,1,1-trifluoro-6,9,12,15-tetraoxo-3-oxa-5,8,11,14-tetraazahexadec-16-yl)-6-(2,5-dioxo-2,5-dihydro-1H-pyrrol-1-yl)hexanamide 10-B

10-A

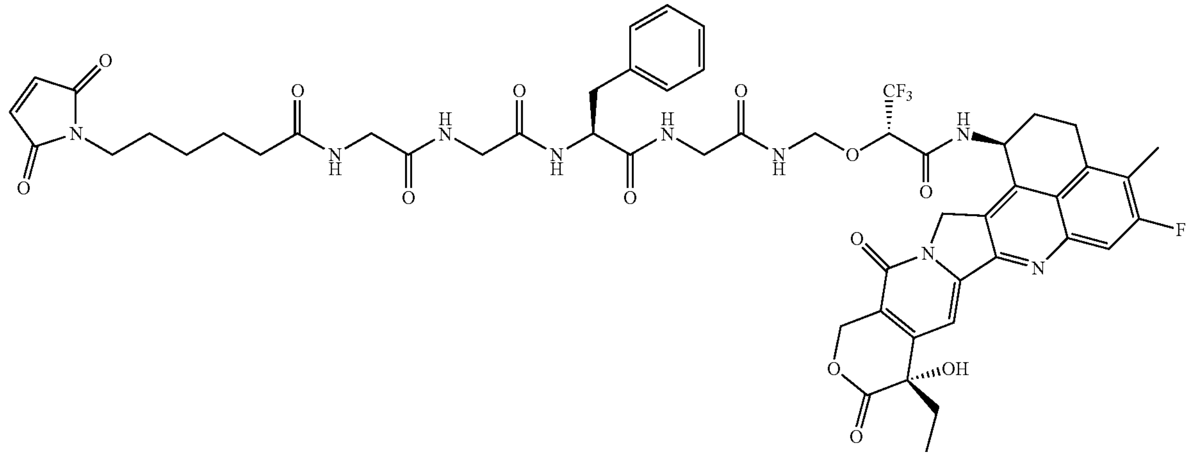

10-B

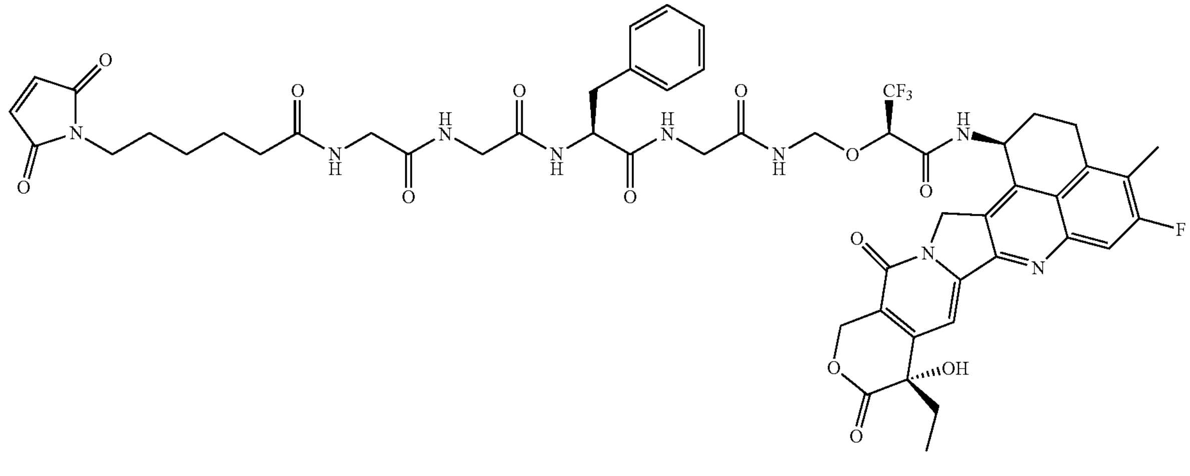

-continued
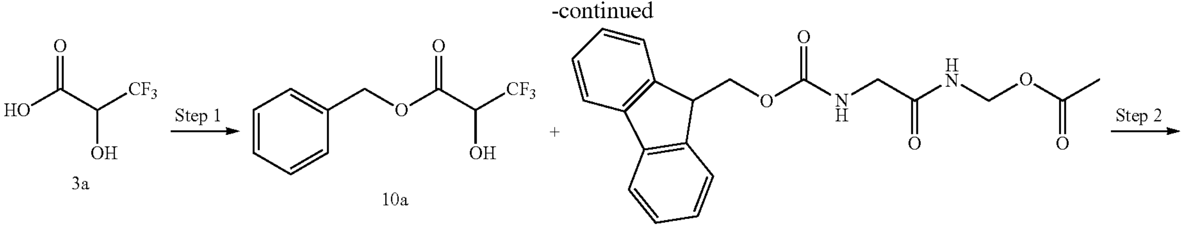
3a 10a 8b
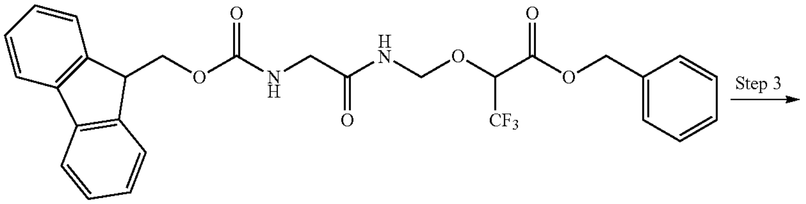
10b
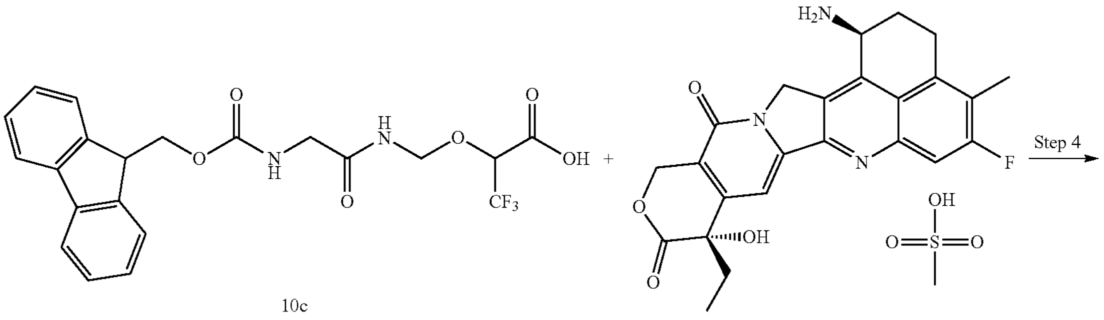
10c 1b
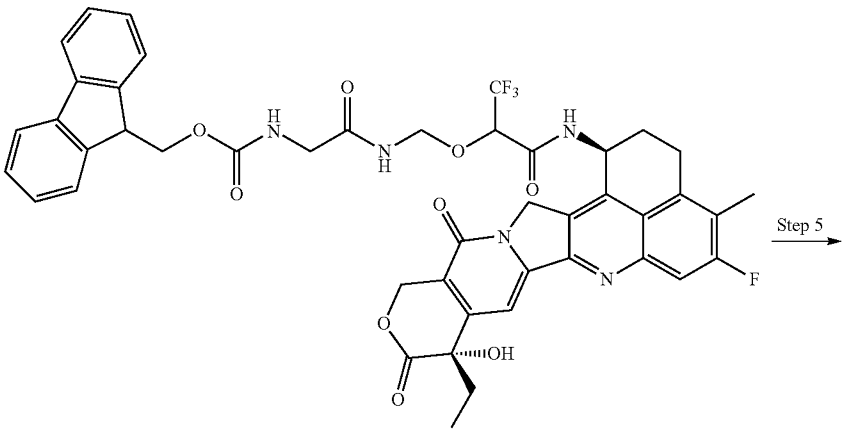
10d -continued
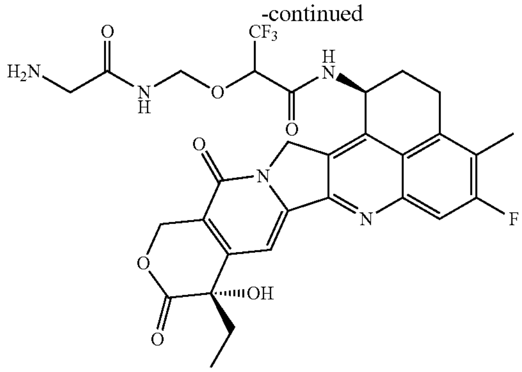
10e
+
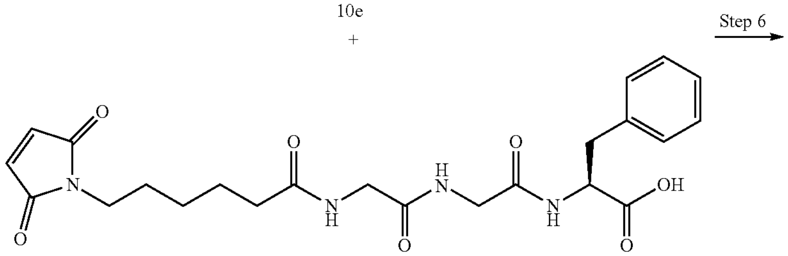
8g
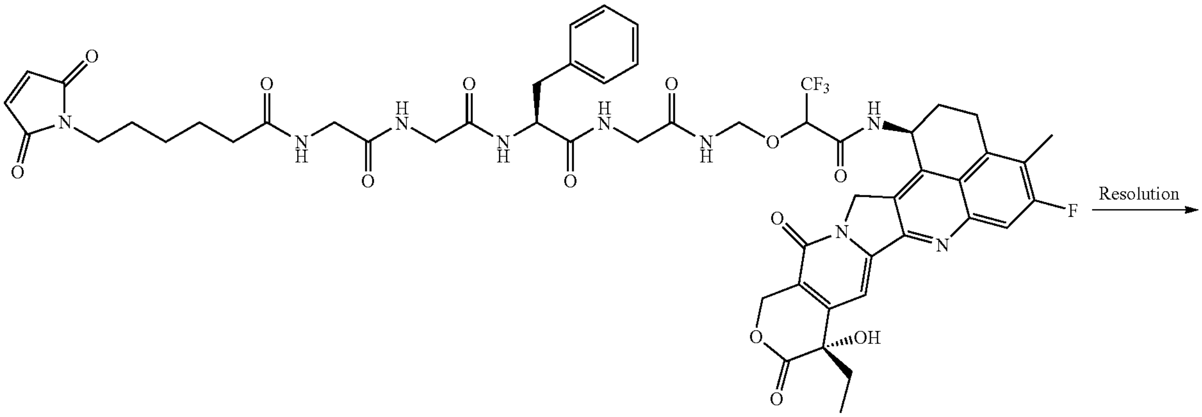
10
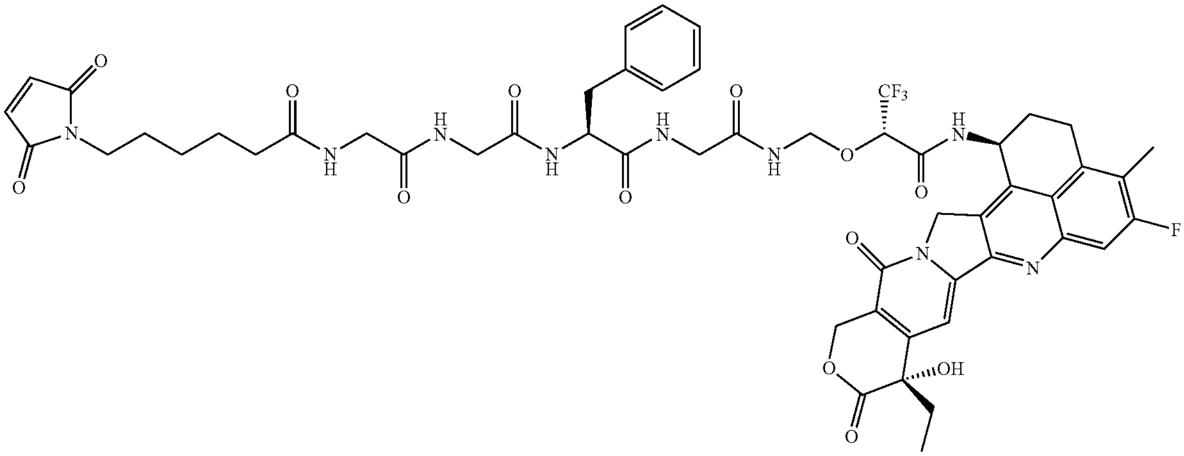
10-A
+

-continued

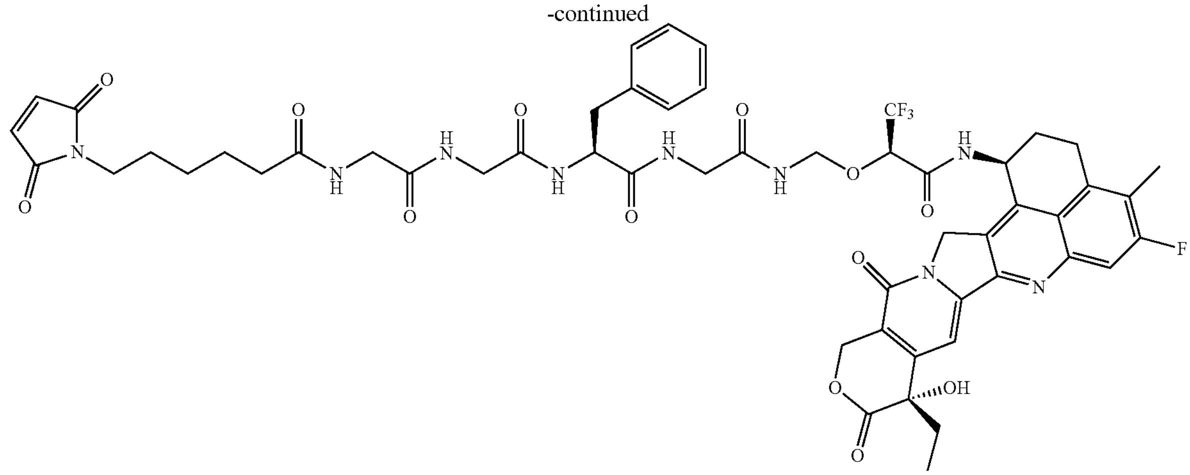

10-B

Step 1

Benzyl 3,3,3-trifluoro-2-hydroxypropionate 10a

Compound 3a (1.80 g, 12.5 mmol) was dissolved in 100 mL of acetonitrile, and potassium carbonate (5.17 g, 37.5 mmol), benzyl bromide (4.48 mL, 37.5 mmol) and tetra-butylammonium iodide (231 mg, 0.63 mmol) were added successively. The reaction mixture was heated to 60° C., stirred for 5 h, cooled to room temperature, and filtered. The filtrate was concentrated under reduced pressure, and the resulting residue was purified by silica gel column chromatography with developing solvent system C to give the title product 10a (980 mg, 33.5% yield).

$^1$H NMR (400 MHz, $CDCl_3$): δ 7.43-7.36 (m, 5H), 5.34 (s, 2H), 4.53 (s, 1H), 3.44 (s, 1H).

Step 2

Benzyl 1-(9H-fluoren-9-yl)-3,6-dioxo-10-(trifluoromethyl)-2,9-dioxa-4,7-diazaundecan-11-oate 10b Compounds 8b (63 mg, 0.17 mmol) and 10a (80 mg, 0.34 mmol) were added to a reaction flask, and 3 mL of tetrahydrofuran was added. The system was purged with argon three times, and the reaction mixture was cooled to 0-5° C. in an ice-water bath, followed by addition of potassium tert-butoxide (38 mg, 0.34 mmol). The ice bath was removed, and the reaction mixture was warmed to room temperature and stirred for 20 min, followed by addition of 10 mL of ice water and by extraction with ethyl acetate (20 mL×2) and chloroform (10 mL×5). The organic phases were combined and concentrated. The resulting residue was dissolved in 2 mL of dioxane, and 0.4 mL of water, sodium bicarbonate (19 mg, 0.23 mmol) and 9-fluorenylmethyl chloroformate (49 mg, 0.19 mmol) were added. The mixture was stirred at room temperature for 1 h. 20 mL of water was added, followed by extraction with ethyl acetate (10 mL×3). The organic phase was washed with saturated sodium chloride solution (20 mL), dried over anhydrous sodium sulfate, and filtered. The filtrate was concentrated under reduced pressure, and the resulting residue was purified by silica gel column chromatography with developing solvent system C to give the title product 10b (51 mg, 55.3% yield).

MS m/z (ESI): 559.9 [M+18].

Step 3

1-(9H-fluoren-9-yl)-3,6-dioxo-10-(trifluoromethyl)-2,9-dioxa-4,7-diazaundecan-11-oic acid 10c Compound 10b (15 mg, 0.28 mmol) was dissolved in 3 mL of a solvent mixture of tetrahydrofuran and ethyl acetate (V:V=2:1), and palladium on carbon (15 mg, 10% loading) was added. The system was purged with hydrogen three times, and the reaction mixture was stirred at room temperature for 1 h. The reaction mixture was filtered through celite, and the filter cake was rinsed with tetrahydrofuran. The filtrate was concentrated to give the crude title product 10c (13 mg).

MS m/z (ESI): 452.9 [M+1].

Step 4

(9H-fluoren-9-yl)methyl(2-((((3-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,1,1-trifluoro-3-oxoprop-2-yl)oxy)methyl)amino)-2-oxoethyl)carbamate 10d Compound 1b (10 mg, 18.8 μmol) was added to a reaction flask, and 1 mL of N,N-dimethylformamide was added. The system was purged with argon three times, and the mixture was cooled to 0-5° C. in an ice-water bath, followed by addition of a drop of triethylamine, a solution of 10c (13 mg, 28.7 μmol) in 0.5 mL of N,N-dimethylformamide, and 4-(4,6-dimethoxy-1,3,5-triazin-2-yl)-4-methylmorpholinium chloride (11 mg, 39.7 μmol). The reaction mixture was stirred in an ice bath for 30 min. 10 mL of water was added, followed by extraction with ethyl acetate (10 mL×3). The organic phases were combined, washed with saturated sodium chloride solution (10 mL×2), dried over anhydrous sodium sulfate, and filtered. The filtrate was concentrated under reduced pressure, and the resulting residue was purified by thin layer chromatography with developing solvent system B to give the title product 10d (16 mg, 97.8% yield).

MS m/z (ESI): 870.0 [M+1].

Step 5

2-((2-Aminoacetylamino)methoxy)-N-((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)-3,3,3-trifluoropropionamide 10e Compound 10d (16 mg, 18.4 μmol) was dissolved in 0.6 mL of dichloromethane, and 0.3 mL of diethylamine was added. The reaction mixture was stirred at room temperature for 2 h and concentrated under reduced pressure. 2 mL of toluene was added, followed by concentration under reduced pressure; the procedures were repeated twice. The residue was slurried with 3 mL of n-hexane and let stand. Then, the supernatant was removed, and the solid was kept; the procedures were repeated three times. The solid residue was concentrated under reduced pressure and dried using an oil pump to give the crude title product 10e (12 mg), which was directly used in the next step without purification.

MS m/z (ESI): 647.9 [M+1].

Step 6

N-((2S,10S)-10-benzyl-2-(((1S,9S)-9-ethyl-5-fluoro-9-hydroxy-4-methyl-10,13-dioxo-2,3,9,10,13,15-hexahydro-1H,12H-benzo 1-yl)aminocarbonyl)-1,1,1-trifluoro-6,9,12,15-tetraoxo-3-oxa-5,8,11,14-tetraazahexadec-16-yl)-6-(2,5-dioxo-2,5-dihydro-1H-pyrrol-1-yl)hexanamide 10-A N-((2R,10S)-10-benzyl-2-(((1S,9S)-9-ethyl-5-fluoro-9-hydroxy-4-methyl-10,13-dioxo-2,3,9,10,13,15-hexahydro-1H,12H-benzo 1-yl)aminocarbonyl)-1,1,1-trifluoro-6,9,12,15-tetraoxo-3-oxa-5,8,11,14-tetraazahexadec-16-yl)-6-(2,5-dioxo-2,5-dihydro-1H-pyrrol-1-yl)hexanamide 10-B Crude 10e (12 mg, 18.5 μmol) was dissolved in 1.0 mL of N,N-dimethylformamide. The system was purged with argon three times, and the solution was cooled to 0-5° C. in an ice-water bath. A solution of 8g (14 mg, 29.6 μmol) in 0.3 mL of N,N-dimethylformamide was added, followed by addition of 4-(4,6-dimethoxy-1,3,5-triazin-2-yl)-4-methylmorpholinium chloride (15 mg, 54.2 μmol). The reaction mixture was stirred in an ice bath for 30 min. Then, the ice bath was removed, and the reaction mixture was warmed to room temperature and stirred for 1 h to produce compound 10. The reaction mixture was purified by high performance liquid chromatography (separation conditions: chromatography column: XBridge Prep C18 OBD 5 μm 19×250 mm; mobile phase: A-water (10 mmol of $NH_4OAc$), B-acetonitrile, gradient elution, flow rate: 18 mL/min). The corresponding fractions were collected and concentrated under reduced pressure to give the title products (2.7 mg, 2.6 mg).

MS m/z (ESI): 1102.0 [M+1].

Single-configuration compound (shorter retention time): UPLC analysis: retention time: 1.18 min; purity: 91% (chromatography column:

ACQUITY UPLC BEHC18 1.7 μm 2.1×50 mm; mobile phase: A-water (5 mmol of $NH_4OAc$), B-acetonitrile).

$^1$H NMR (400 MHz, DMSO-$d_6$): δ 8.97 (d, 1H), 8.85-8.76 (m, 1H), 8.37-8.27 (m, 1H), 8.12-8.02 (m, 1H), 8.02-7.95 (m, 1H), 7.80 (d, 1H), 7.31 (s, 1H), 7.26-7.10 (m, 4H), 6.99 (s, 1H), 6.66 (br, 1H), 6.52 (s, 1H), 5.65-5.54 (m, 1H), 5.41 (s, 1H), 5.37-5.25 (m, 3H), 5.23-5.13 (m, 1H), 4.81-4.68 (m, 2H), 4.51-4.41 (m, 1H), 3.78-3.45 (m, 6H), 3.21-3.13 (m, 1H), 3.02-2.93 (m, 1H), 2.77-2.63 (m, 2H), 2.45-2.29 (m, 3H), 2.24-2.05 (m, 3H), 2.04-1.93 (m, 5H), 1.90-1.75 (m, 2H), 1.52-1.38 (m, 4H), 0.90-0.78 (m, 5H).

Single-configuration compound (longer retention time):

UPLC analysis: retention time: 1.23 min; purity: 90% (chromatography column:

ACQUITY UPLC BEHC18 1.7 μm 2.1×50 mm; mobile phase: A-water (5 mmol of $NH_4OAc$), B-acetonitrile).

$^1$H NMR (400 MHz, DMSO-$d_6$): δ 9.05 (d, 1H), 8.97-8.88 (m, 1H), 8.35-8.27 (m, 1H), 8.11-8.03 (m, 1H), 8.02-7.95 (m, 1H), 7.80 (d, 1H), 7.34 (s, 1H), 7.29-7.13 (m, 4H), 6.99 (s, 1H), 6.66 (br, 1H), 6.54 (s, 1H), 5.64-5.55 (m, 1H), 5.43 (s, 1H), 5.36-5.20 (m, 3H), 4.92-4.85 (m, 1H), 4.82-4.72 (m, 2H), 4.52-4.42 (m, 1H), 3.77-3.48 (m, 6H), 3.21-3.14 (m, 1H), 3.03-2.95 (m, 1H), 2.79-2.65 (m, 2H), 2.47-2.28 (m, 3H), 2.25-2.05 (m, 3H), 2.05-1.94 (m, 5H), 1.91-1.76 (m, 2H), 1.52-1.37 (m, 4H), 0.92-0.77 (m, 5H).

Example 1-11
1-(((S)-7-benzyl-20-(2,5-dioxo-2,5-dihydro-1H-pyrrol-1-yl)-3,6,9,12,15-pentaoxo-2,5,8,11,14-pentaazaeicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclobutane-1-carboxamide 11
11
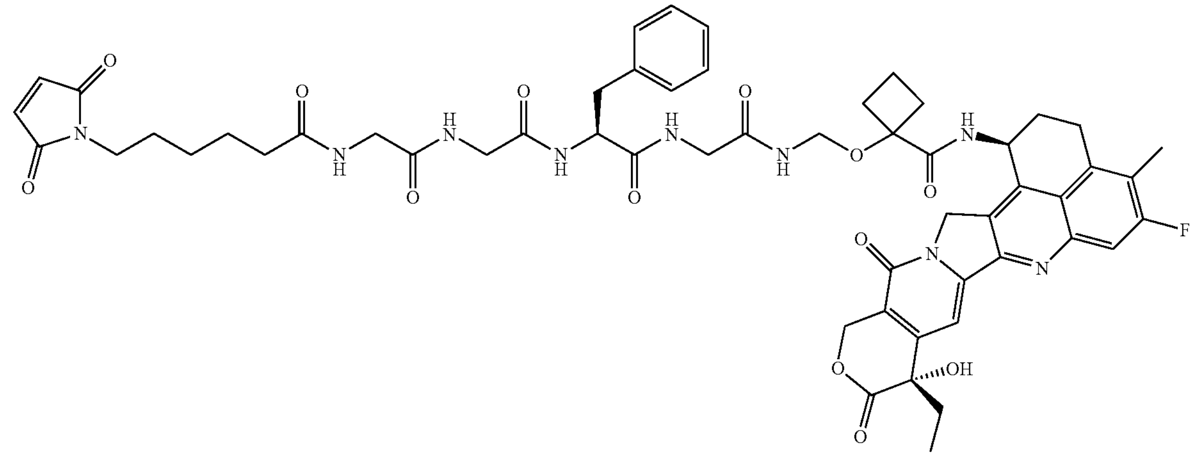
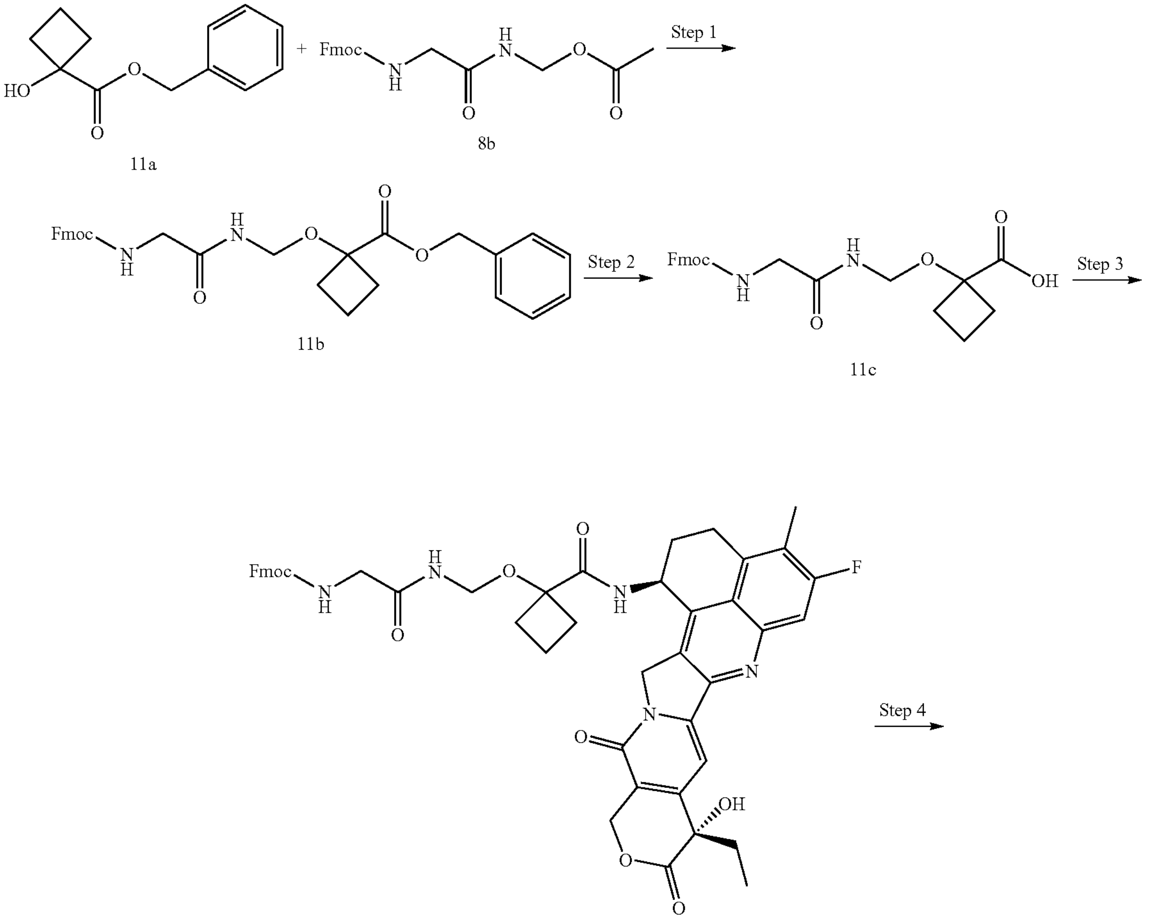
11a
8b
11b
11c
11d -continued

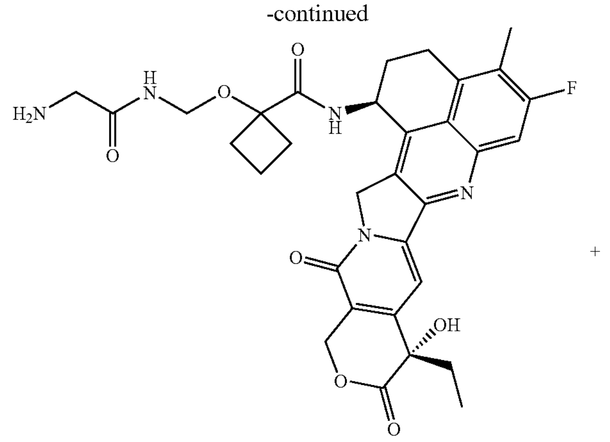

11e

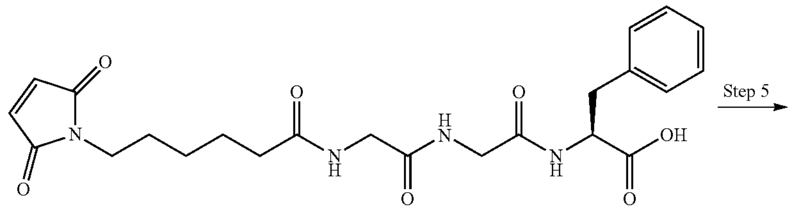

8g

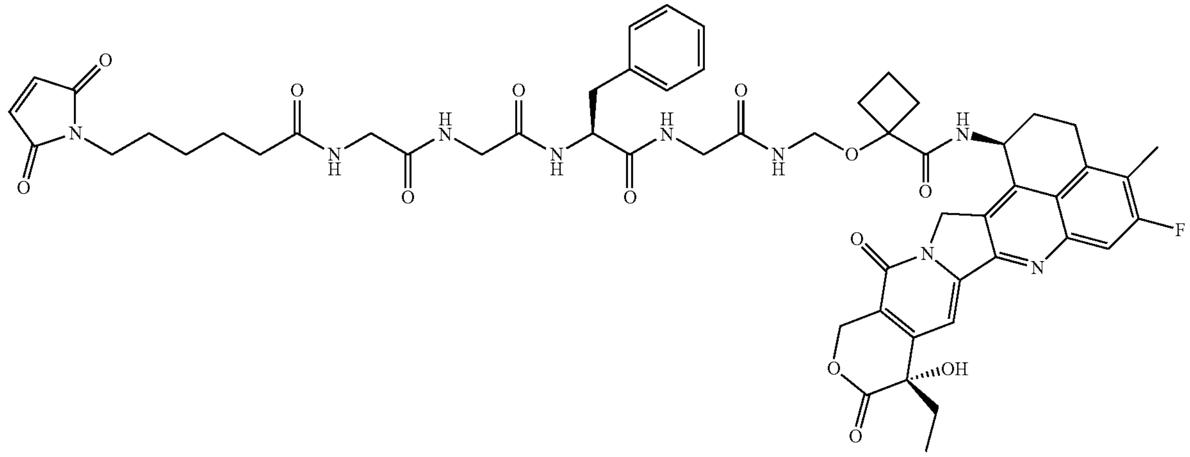

11

Step 1

Benzyl 1-((2-4((9H-fluoren-9-yl)methoxy)carbonyl) amino)acetylamino)methoxy)cyclobutane-1-carboxylate 11b Benzyl 1-hydroxycyclobutane-carboxylate 11a (167 mg, 0.81 mmol, prepared as disclosed in "*Journal of Medicinal Chemistry,* 2013, vol. 56, #13, p. 5541-5552") and 8b (150 mg, 0.41 mmol) were added to a reaction flask, and 5 mL of tetrahydrofuran was added. The system was purged with argon three times, and the reaction mixture was cooled to 0-5° C. in an ice-water bath, followed by addition of potassium tert-butoxide (92 mg, 0.82 mmol). The ice bath was removed, and the reaction mixture was warmed to room temperature and stirred for 10 min, followed by addition of 20 mL of ice water and by extraction with ethyl acetate (5 mL×2) and chloroform (5 mL×5). The organic phases were combined and concentrated. The resulting residue was dissolved in 3 mL of dioxane, and 0.6 mL of water, sodium bicarbonate (41 mg, 0.48 mmol) and 9-fluorenylmethyl chloroformate (105 mg, 0.41 mmol) were added. The mixture was stirred at room temperature for 1 h. 20 mL of water was added, followed by extraction with ethyl acetate (8 mL×3). The organic phase was washed with saturated sodium chloride solution (20 mL), dried over anhydrous sodium sulfate, and filtered. The filtrate was concentrated under reduced pressure, and the resulting residue was purified by silica gel column chromatography with developing solvent system C to give the title product 11b (37 mg, 17.6% yield).

MS m/z (ESI): 514.6 [M+1].

Step 2

1-((2-((((9H-fluoren-9-yl)methoxy)carbonyl)amino)acetylamino)methoxy)cyclobutane-1-carboxylic acid 11e Compound 11b (37 mg, 71.9 μmol) was dissolved in 3 mL of a solvent mixture of tetrahydrofuran and ethyl acetate (V:V=2:1), and palladium on carbon (15 mg, 10% loading) was added. The system was purged with hydrogen three times, and the reaction mixture was stirred at room temperature for 2 h. The reaction mixture was filtered through celite, and the filter cake was rinsed with tetrahydrofuran. The filtrate was concentrated to give the title product 11e (35 mg, 82% yield), which was directly used in the next step.

Step 3

(9H-fluoren-9-yl)methyl(2-(((1-(((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)aminocarbonyl)cyclobutoxy)methyl)amino)-2-oxoethyl)carbamate 11d Compound 1b (10 mg, 0.018 mmol) was added to a reaction flask, and 1 mL of N,N-dimethylformamide was added. The system was purged with argon three times, and the mixture was cooled to 0-5° C. in an ice-water bath, followed by addition of a drop of triethylamine, a solution of compound 11c (13 mg, 0.031 mmol) in 0.5 mL of N,N-dimethylformamide, and 4-(4,6-dimethoxy-1,3,5-triazin-2-yl)-4-methylmorpholinium chloride (25 mg, 0.091 mmol). The reaction mixture was stirred in an ice bath for 40 min. 8 mL of water was added, followed by extraction with ethyl acetate (5 mL×3). The organic phase was washed with saturated sodium chloride solution (8 mL), dried over anhydrous sodium sulfate, and filtered. The filtrate was concentrated under reduced pressure, and the resulting residue was purified by thin layer chromatography with developing solvent system A to give the title product 11d (19 mg, 73.9% yield).

MS m/z (ESI): 842.3 [M+1].

Step 4

1-((2-Aminoacetylamino)methoxy)-N-((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)cyclobutane-1-carboxamide 11e Compound 11d (19 mg, 22.6 μmol) was dissolved in 2 mL of dichloromethane, and 1 mL of diethylamine was added. The reaction mixture was stirred at room temperature for 1.5 h and concentrated under reduced pressure. 1 mL of toluene was added, followed by concentration under reduced pressure; the procedures were repeated twice. The residue was slurried with 4 mL of n-hexane, and the upper n-hexane layer was removed; the procedures were repeated three times. The slurry was concentrated under reduced pressure to give the crude title product 11e (15 mg), which was directly used in the next step without purification.

Step 5

1-(((S)-7-benzyl-20-(2,5-dioxo-2,5-dihydro-1H-pyrrol-1-yl)-3,6,9,12,15-pentaoxo-2,5,8,11,14-pentaazaeicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclobutane-1-carboxamide 11

Crude 11e (2 mg, 3.22 μmol) was dissolved in 0.5 mL of N,N-dimethylformamide. The system was purged with argon three times, and the solution was cooled to 0-5° C. in an ice-water bath. A solution of 8g (1.5 mg, 3.17 μmol) in 0.3 mL of N,N-dimethylformamide was added, followed by addition of 4-(4,6-dimethoxy-1,3,5-triazin-2-yl)-4-methylmorpholinium chloride (2.7 mg, 9.67 μmol). The reaction mixture was stirred at room temperature for 30 min and concentrated to dryness with an oil pump to remove DMF, and the residue was dissolved in DCM and purified directly by thin layer chromatography twice (polarity of developing solvent: DCM/MeOH=10/1) to give the title product 11 (1 mg, 28.8% yield).

MS m/z (ESI): 1073.6 [M+1].

$^1$H NMR (400 MHz, $CDCl_3$): δ 8.70-8.60 (m, 1H), 8.28-8.19 (m, 1H), 8.13-7.91 (m, 3H), 7.79-7.71 (d, 1H), 7.29 (s, 1H), 7.25-7.09 (m, 4H), 6.98 (s, 1H), 6.71-6.62 (m, 1H), 6.55-6.47 (m, 1H), 5.64-5.54 (m, 2H), 5.40 (s, 1H), 5.35-5.27 (t, 2H), 5.17-5.10 (m, 2H), 4.60-4.51 (m, 1H), 4.51-4.35 (m, 2H), 3.93-3.78 (m, 3H), 3.71-3.59 (m, 3H), 3.01-2.88 (m, 3H), 2.70-2.64 (m, 2H), 2.44-2.30 (m, 3H), 2.28-2.14 (m, 3H), 2.11-1.92 (m, 6H), 1.90-1.76 (m, 3H), 1.51-1.39 (m, 4H), 0.92-0.75 (m, 6H).

Example 1-12

(S)-3-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxypropionamide 12-A (R)-3-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxypropionamide 12-B

12-A

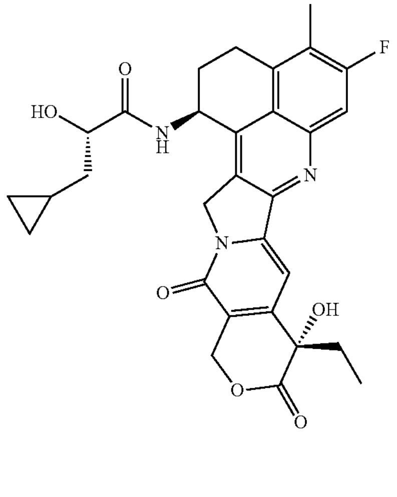

-continued

12-B

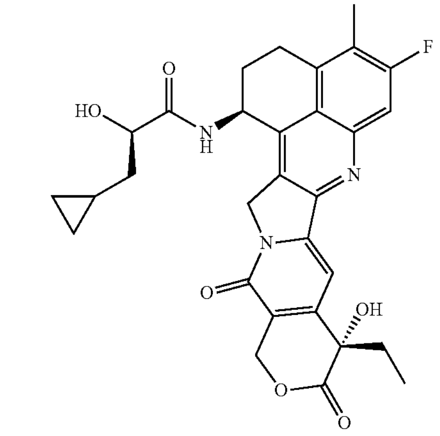

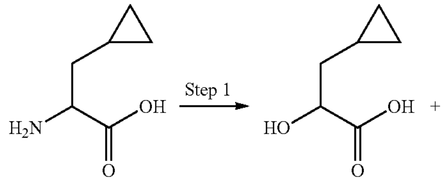

12a

12b

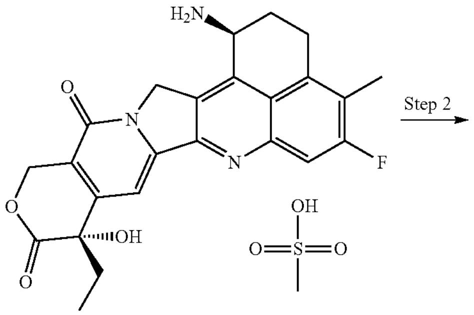

1b

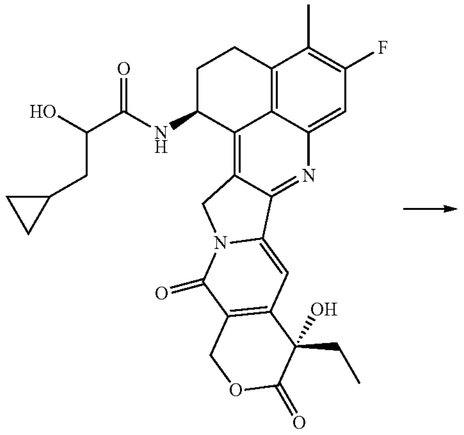

12

-continued

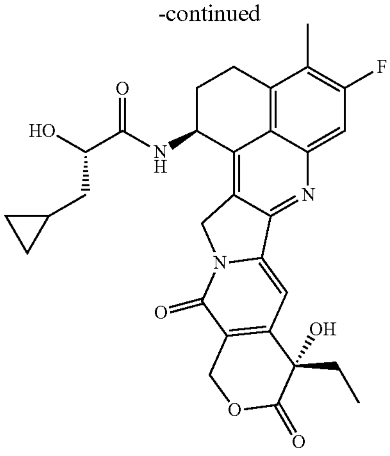

+

12-A

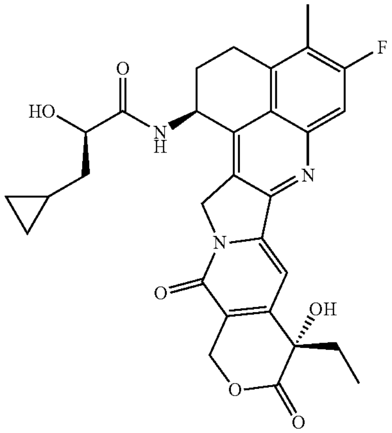

12-B

Step 1

3-Cyclopropyl-2-hydroxypropionic acid 12b

Compound 12a (0.5 g, 3.87 mmol, supplied by Adamas) was dissolved in 35 mL of a solvent mixture of water and acetic acid (V:V=4:1), and the solution was cooled to 0-5° C. in an ice-water bath, followed by dropwise addition of a 2 M aqueous solution of sodium nitrite (0.53 g, 7.74 mmol). The reaction mixture was warmed to room temperature and stirred for 3 h. Solid sodium chloride was added to the reaction mixture to saturate the aqueous phase. The reaction mixture was extracted with ethyl acetate (8 mL×8), dried over anhydrous sodium sulfate, and filtered. The filtrate was concentrated to give the title product 12b (0.45 g, 89.3% yield).

Step 2

(S)-3-cyclopropyl-N-((1S,9S)-9-ethyl-5-fluoro-9-hydroxy-4-methyl-10,13-di oxo-2,3,9,10,13,15-hexahydro-1H,12H-benzo[de]pyrano[3',4': 6,7]indolizino[1,2-b]quinolin-1-yl)-2-hydroxypropionamide 12-A (R)-3-cyclopropyl-N-((1S,9S)-9-ethyl-5-fluoro-9-hydroxy-4-methyl-10,13-di oxo-2,3,9,10,13,15-hexahydro-1H,12H-benzo[de]pyrano[3',4': 6,7]indolizino[1,2-b]quinolin-1-yl)-2-hydroxypropionamide 12-B To compound 1b (45 mg, 0.085 mmol) were added 1.5 mL of ethanol and 1.5 mL of N,N-dimethylformamide. The system was purged with argon three times, and 0.1 mL of N-methylmorpholine was added dropwise. The reaction mixture was stirred until it became clear. To the reaction mixture were successively added compound 12b (90 mg, 0.691 mmol), 1-hydroxybenzotriazole (34 mg, 0.251 mmol) and 1-(3-dimethylaminopropyl)-3-ethylcarbodiimide hydrochloride (49 mg, 0.256 mmol). After addition, the reaction mixture was stirred at room temperature for 3 h and concentrated under reduced pressure, and the resulting crude compound 12 was purified by high performance liquid chromatography (separation conditions: chromatography column: Sharpsil-T C18 5 μm 21.2×250 mm; mobile phase: A-water (10 mmol of $NH_4OAc$), B-acetonitrile, gradient elution, flow rate: 18 mL/min) to give the title products (7 mg, 15 mg).

MS m/z (ESI): 547.9 [M+1].

Single-configuration compound (shorter retention time):

UPLC analysis: retention time: 1.345 min; purity: 72% (chromatography column:

ZORBAX Ecliphase Plus C18 1.8 μm 2.1×50 mm; mobile phase: A-water (5 mmol of $NH_4OAc$), B-acetonitrile).

$^1H$ NMR (400 MHz, DMSO-$d_6$): δ 8.42 (d, 1H), 7.78 (d, 1H), 7.30 (s, 1H), 6.51 (s, 1H), 5.60-5.50 (m, 2H), 5.42 (s, 1H), 5.19 (q, 2H), 4.02-4.00 (m, 1H), 3.21-3.11 (m, 2H), 2.39 (s, 3H), 2.21-2.07 (m, 2H), 2.05-1.95 (m, 1H), 1.92-1.68 (m, 4H), 1.53-1.41 (m, 1H), 0.87 (t, 3H), 0.48-0.34 (m, 2H), 0.14-0.01 (m, 2H).

Single-configuration compound (longer retention time):

UPLC analysis: retention time: 1.399 min; purity: 88% (chromatography column: ZORBAX Ecliphase Plus C18 1.8 μm 2.1×50 mm; mobile phase: A-water (5 mmol of $NH_4OAc$), B-acetonitrile).

$^1H$ NMR (400 MHz, DMSO-$d_6$): δ 8.36 (d, 1H), 7.77 (d, 1H), 7.31 (s, 1H), 6.51 (s, 1H), 5.58-5.51 (m, 1H), 5.48 (d, 1H), 5.42 (s, 1H), 5.20 (q, 2H), 4.09-4.02 (m, 1H), 3.22-3.11 (m, 2H), 2.39 (s, 3H), 2.27-2.06 (m, 2H), 2.05-1.95 (m, 1H), 1.93-1.81 (m, 2H), 1.65-1.43 (m, 2H), 1.32-1.21 (m, 1H), 0.87 (t, 3H), 0.48-0.33 (m, 2H), 0.14-0.01 (m, 2H).

Example 1-13 (Reference Example)

N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxyacetamide

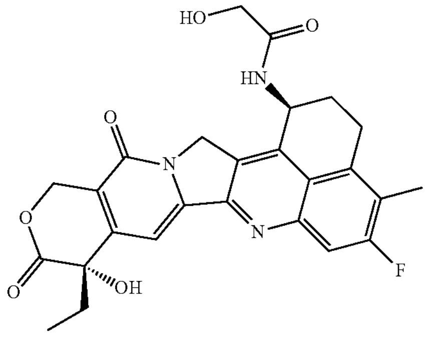

13

The title compound 13 was prepared as disclosed in "Example 76 on page 147 of the specification of Patent EP2907824A1".

Example 1-14

N-((2R,10S)-10-benzyl-2-(cyclopropylmethyl)-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadec-16-yl)-6-(2,5-dioxo-2,5-dihydro-1H-pyrrol yl)hexanamide 14-A N-((2S,10S)-10-benzyl-2-(cyclopropylmethyl)-1-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadec-16-yl)-6-(2,5-dioxo-2,5-dihydro-1H-pyrrol yl)hexanamide 14-B

14-A

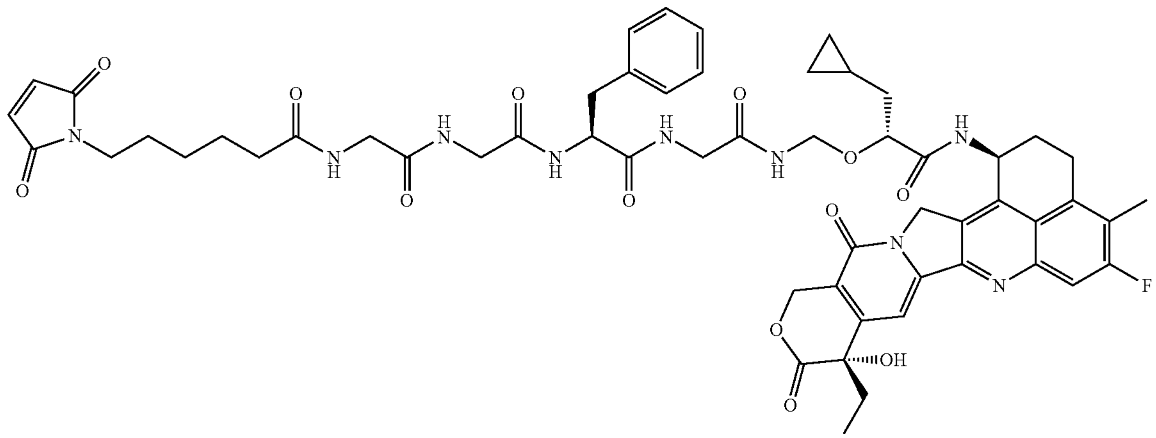

14-B

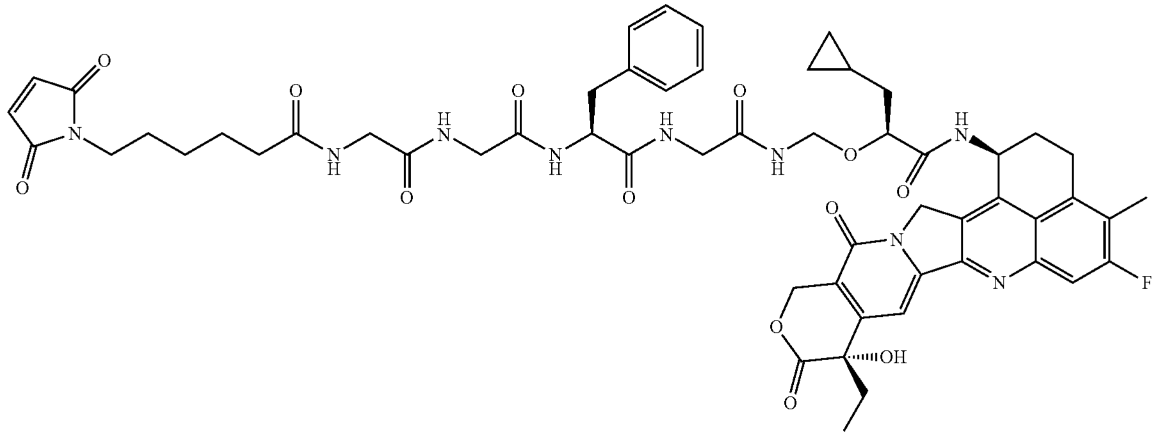

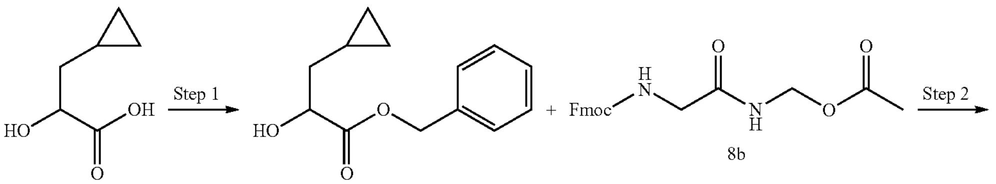

12b 14a 8b

-continued
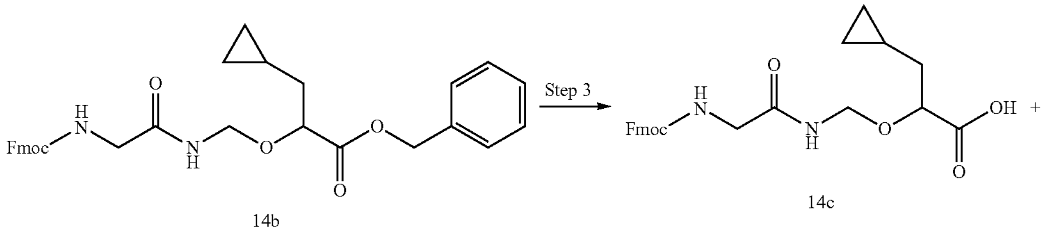
14b 14c
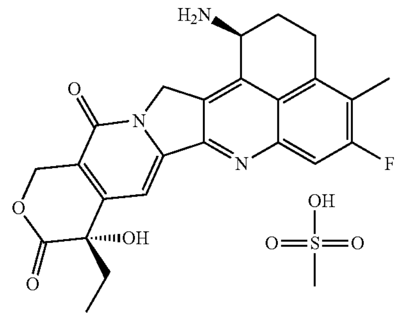
1b
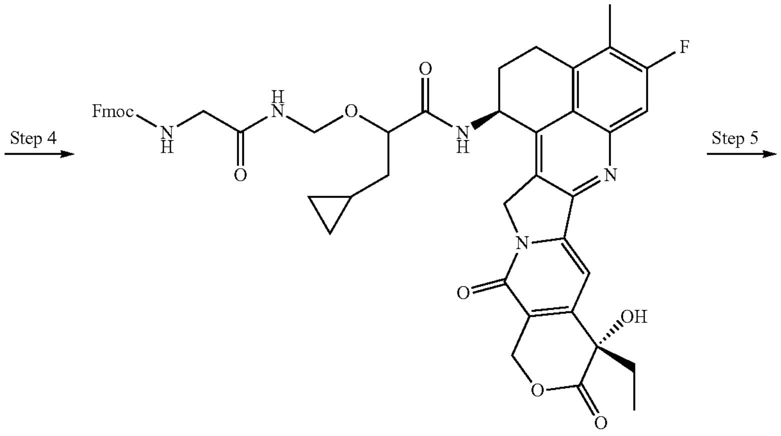
14d
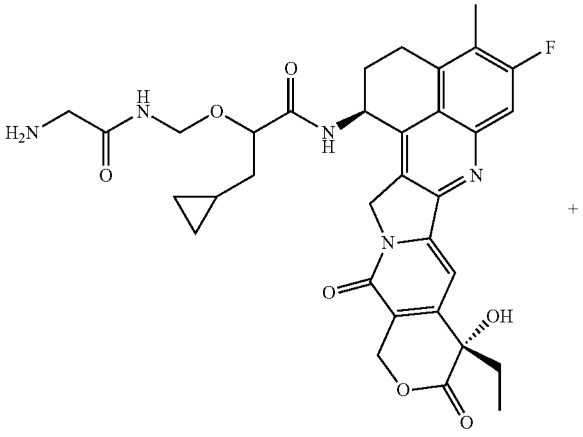
14e
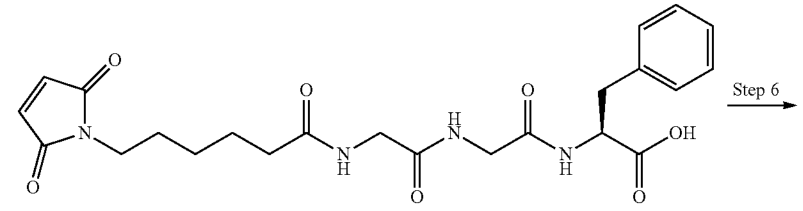
8g -continued
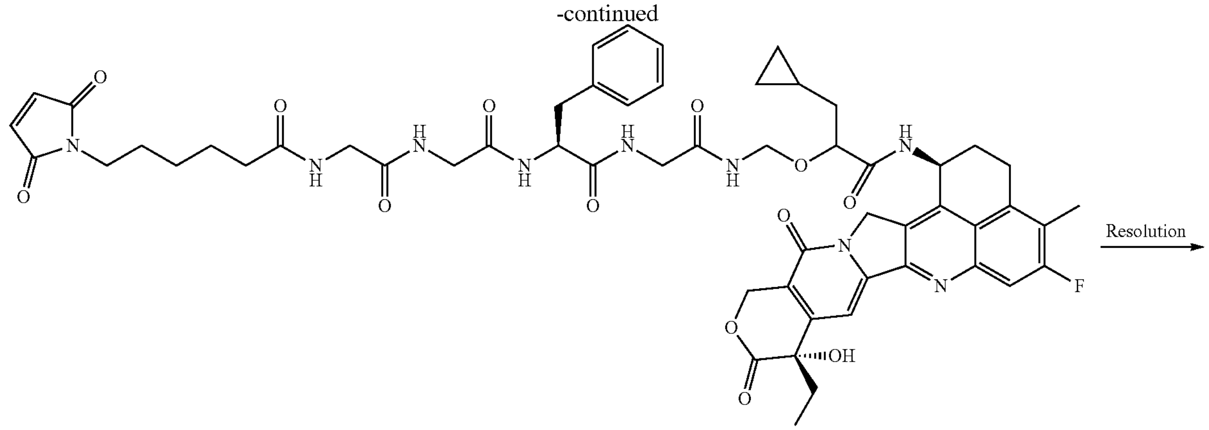
14
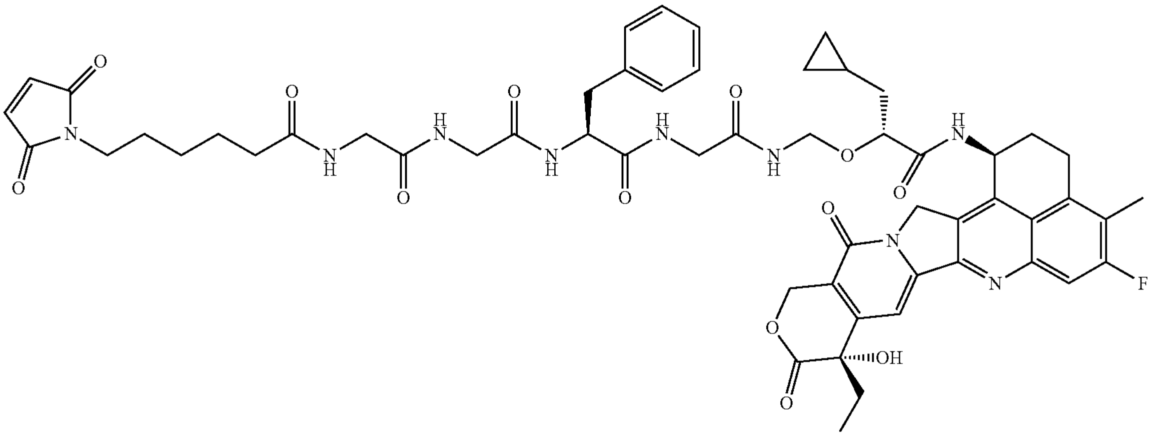
14-A
+
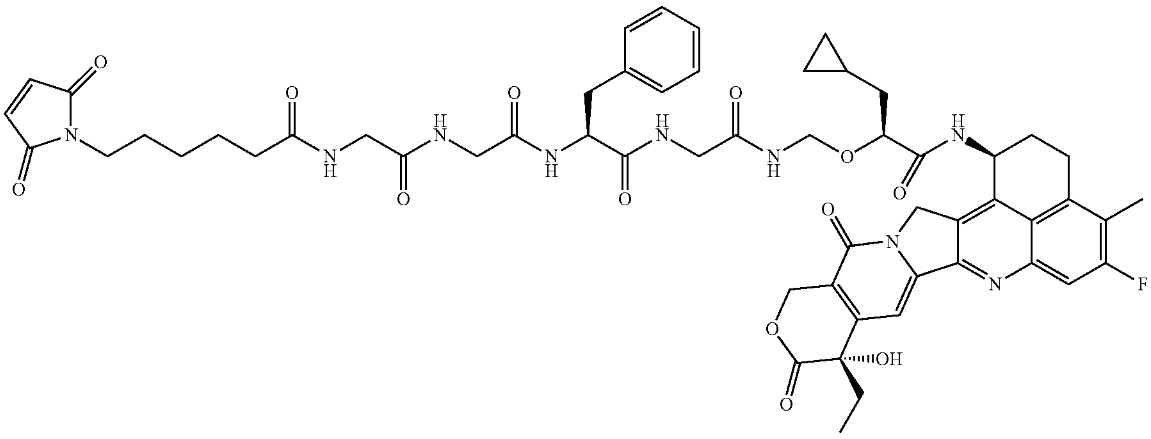
14-B Step 1

Benzyl 3-cyclopropyl-2-hydroxypropionate 14a

Compound 12b (200 mg, 1.54 mmol) was dissolved in 20 mL of acetonitrile, and potassium carbonate (1.06 g, 7.68 mmol), benzyl bromide (0.16 mL, 1.34 mmol) and tetra-butylammonium iodide (28 mg, 0.07 mmol) were added successively. The reaction mixture was stirred at room temperature for 48 h and filtered through celite, and the filter cake was rinsed with ethyl acetate (10 mL). The filtrates were combined and concentrated under reduced pressure, and the resulting residue was purified by silica gel column chromatography with developing solvent system C to give the title product 14a (140 mg, 41.3% yield).

Step 2

Benzyl 10-(cyclopropylmethyl)-1-(9H-fluoren-9-yl)-3,6-dioxo-2,9-dioxa-4,7-diazaundecan-11-oate 14b Compounds 14a (94 mg, 0.427 mmol) and 8b (130 mg, 0.353 mmol) were added to a reaction flask, and 10 mL of tetrahydrofuran was added. The system was purged with argon three times, and the reaction mixture was cooled to 0-5° C. in an ice-water bath, followed by addition of potassium tert-butoxide (79 mg, 0.704 mmol). The ice bath was removed, and the reaction mixture was warmed to room temperature and stirred for 10 min, followed by addition of 20 mL of ice water and by extraction with ethyl acetate (10 mL×4). The organic phase was washed with saturated sodium chloride solution (20 mL), dried over anhydrous sodium sulfate, and filtered, and the filtrate was concentrated under reduced pressure. The resulting residue was purified by silica gel column chromatography with developing solvent system C to give the title product 14b (50 mg, 26.8% yield).

MS m/z (ESI): 529.2 [M+1].

Step 3

10-(Cyclopropylmethyl)-1-(9H-fluoren-9-yl)-3,6-dioxo-2,9-dioxa-4,7-diazaundecan oic acid 14c Compound 14b (27 mg, 0.051 mmol) was dissolved in 3 mL of ethyl acetate, and palladium on carbon (7 mg, 10% loading, dry basis) was added. The system was purged with hydrogen three times. The reaction mixture was stirred at room temperature for 1 h and filtered through celite, and the filter cake was rinsed with ethyl acetate. The filtrate was concentrated to give the crude title product 14c (23 mg), which was directly used in the next step without purification.

MS m/z (ESI): 439.1 [M+1].

Step 4 (9H-fluoren-9-yl)methyl(2-((((3-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)amino)-1-oxopropan-2-yl)oxy)methyl)amino)-2-oxoethyl)carbamate 14d Compound 1b (22 mg, 42.38 μmol) was added to a reaction flask, and 3 mL of N,N-dimethylformamide was added. The system was purged with argon three times, and the mixture was cooled to 0-5° C. in an ice-water bath, followed by dropwise addition of triethylamine (4.3 mg, 42.49 μmol) and addition of crude 14c (23 mg, 51.1 μmol) and 4-(4,6-dimethoxy-1,3,5-triazin-2-yl)-4-methylmorpholinium chloride (17.6 mg, 63.6 μmol). The reaction mixture was stirred in an ice bath for 40 min. 15 mL of water was added, followed by extraction with ethyl acetate (8 mL×3). The organic phases were combined, washed with saturated sodium chloride solution (15 mL), dried over anhydrous sodium sulfate, and filtered. The filtrate was concentrated under reduced pressure. The resulting residue was purified by thin layer chromatography with developing solvent system B to give the title product 14d (29 mg, 79.9% yield).

MS m/z (ESI): 856.1 [M+1].

Step 5

2-((2-Aminoacetylamino)methoxy)-3-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)propanamide 14e Compound 14d (29 mg, 33.9 μmol) was dissolved in 0.8 mL of dichloromethane, and 0.4 mL of diethylamine was added. The reaction mixture was stirred at room temperature for 1.5 h and concentrated under reduced pressure. 1 mL of toluene was added, followed by concentration under reduced pressure; the procedures were repeated twice. The residue was slurried with 3 mL of n-hexane and let stand. Then, the supernatant was removed; and the procedures were repeated three times. The residue was concentrated under reduced pressure and dried using an oil pump to give the crude title product 14e (22 mg), which was directly used in the next step without purification.

MS m/z (ESI): 634.1 [M+1].

Step 6

N-((2R,10S)-10-benzyl-2-(cyclopropylmethyl)-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadec-16-yl)-6-(2,5-dioxo-2,5-dihydro-1H-pyrrol yl)hexanamide 14-A N-((2S,10S)-10-benzyl-2-(cyclopropylmethyl)-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadec-16-yl)-6-(2,5-dioxo-2,5-dihydro-1H-pyrrol-1-yl)hexanamide 14-B Crude 14e (22 mg, 33.9 μmol) was dissolved in 2.5 mL of N,N-dimethylformamide. The system was purged with argon three times, and the solution was cooled to 0-5° C. in an ice-water bath, and 8g (24 mg, 50.8 μmol) and 4-(4,6-dimethoxy-1,3,5-triazin-2-yl)-4-methylmorpholinium chloride (14 mg, 50.6 μmol) were added successively. Then, the ice bath was removed, and the reaction mixture was warmed to room temperature and stirred for 1 h to produce compound 14. The reaction mixture was purified by high performance liquid chromatography (separation conditions: chromatography column: XBridge Prep C18 OBD 5 pin 19×250 mm; mobile phase: A-water (10 mmol of $NH_4OAc$), B-acetonitrile, gradient elution, flow rate: 18 mL/min) to give the title products (2 mg, 2 mg).

MS m/z (ESI): 1088.4 [M+1].

Single-configuration compound (shorter retention time): UPLC analysis: retention time: 1.18 min; purity: 88% (chromatography column: ACQUITY UPLC BEHC18 1.7 pin 2.1×50 mm; mobile phase: A-water (5 mmol of $NH_4OAc$), B-acetonitrile).

Single-configuration compound (longer retention time): UPLC analysis: retention time: 1.23 min; purity: 96% (chromatography column: ACQUITY UPLC BEHC18 1.7 pin 2.1×50 mm; mobile phase: A-water (5 mmol of $NH_4OAc$), B-acetonitrile).

Example 1-15

1-((S)-9-benzyl-22-(2,5-dioxo-2,5-dihydro-1H-pyrrol-1-yl)-5,8,11,14,17-pentaoxo-2-oxa-4,7,10,13,16-pentaazadocosyl)-N-((1S,9S)-9-ethyl-5-fluoro-9-hydroxy-4-methyl-10,13-dioxo-2,3,9,10,13,15-hexahydro-1H,12H-benzo[de]pyrano[3,4':6,7]indolizino[1,2-b]quinolin-1-yl)cyclopropane-1-carboxamide 15

15

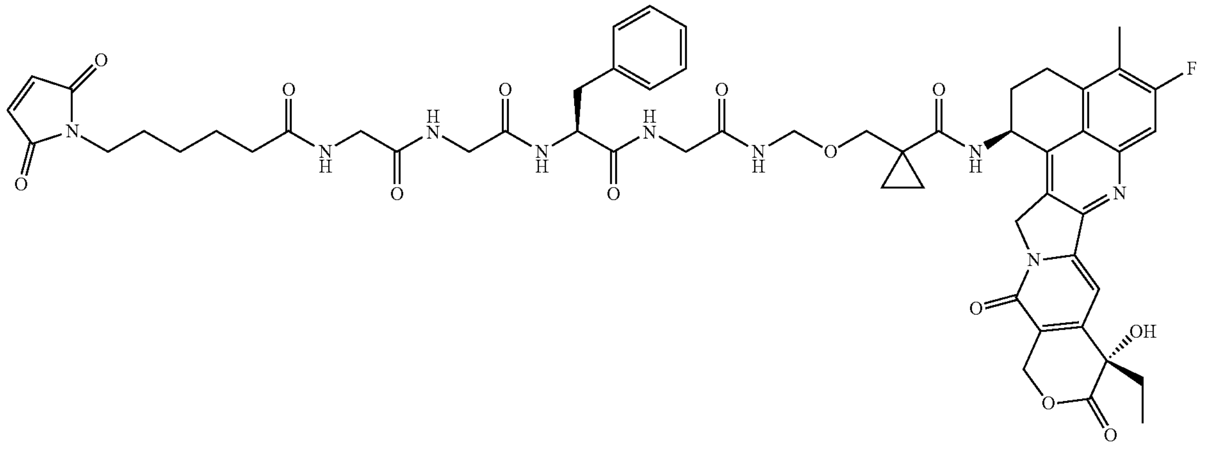

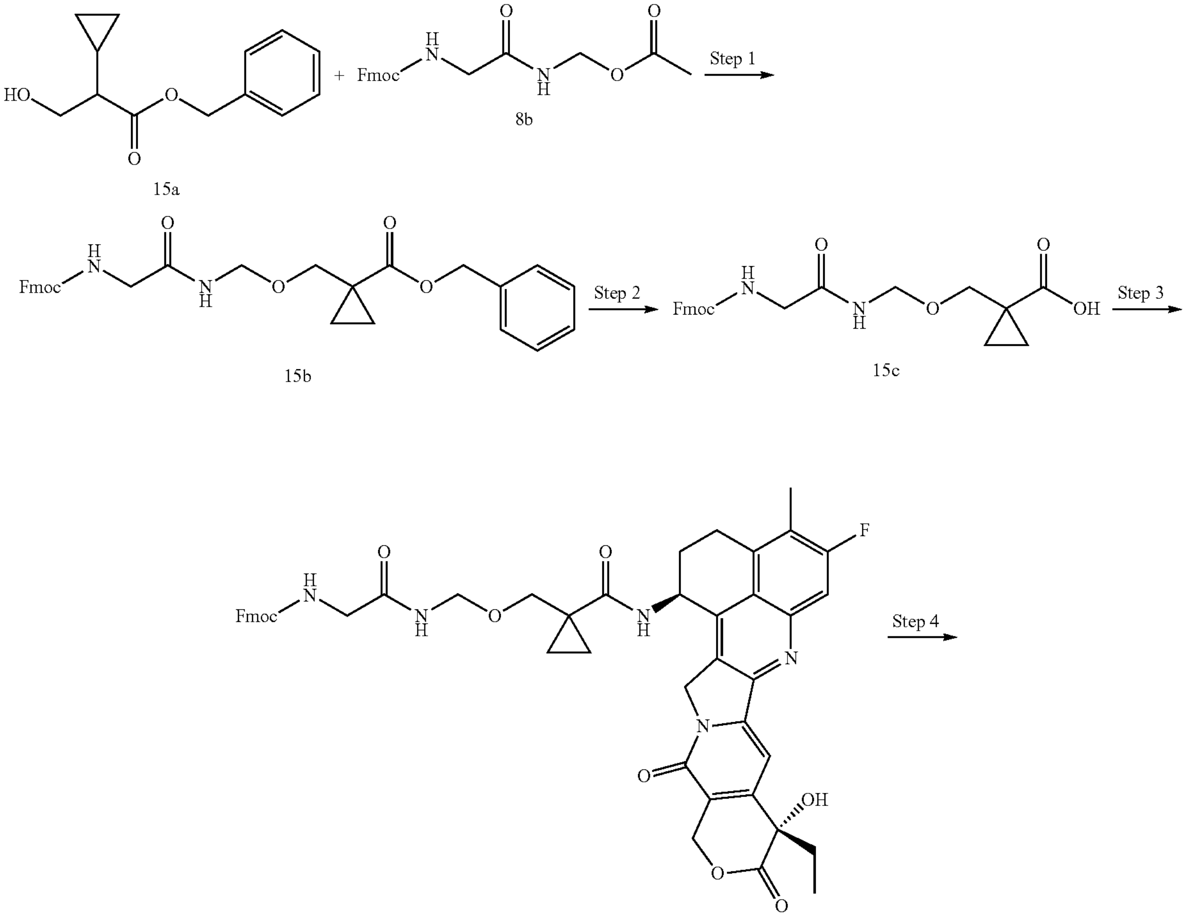

15a 8b 15b 15c 15d

-continued
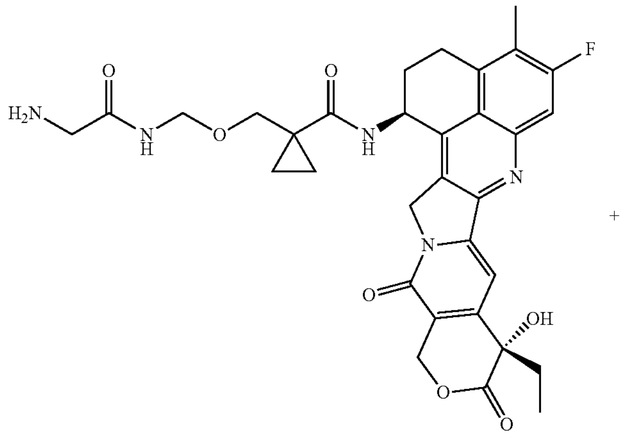
15e
+
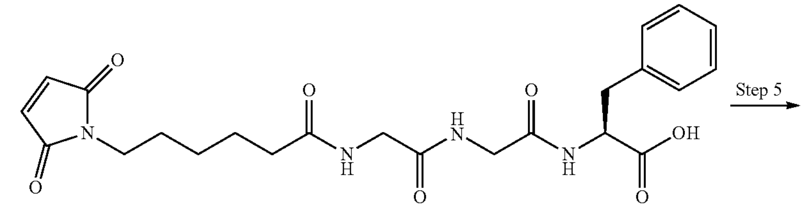
8g
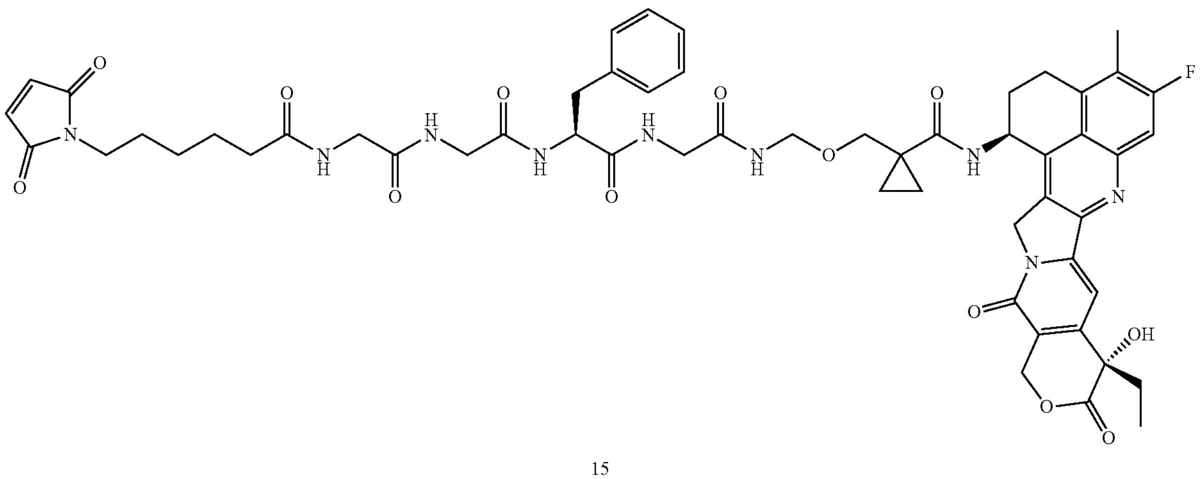
15

Step 1

Benzyl 1-(10-(9H-fluoren-9-yl)-5,8-dioxo-2,9-dioxa-4,7-diazadecyl)cyclopropane-1-carboxylate 15b Compound 8b (500 mg, 1.35 mmol) was added to a reaction flask, followed by addition of 6 mL of tetrahydrofuran, benzyl 1-hydroxymethylcyclopropane-1-carboxylate 15a (233 mg, 1.13 mmol; prepared as disclosed in "Example 22-2 on page 262 of the specification of Patent Application EP2862856A1"). The system was purged with argon three times, and the reaction mixture was cooled to 0-5° C. in an ice-water bath, followed by addition of sodium hydride (54 mg, 1.35 mmol). Then, the ice-bath was removed, and the reaction mixture was warmed to room temperature, stirred for 40 min, and cooled to 0° C., followed by addition of 20 mL of ice water and by extraction with ethyl acetate (5 mL×2) and chloroform (5 mL×5). The organic phases were combined, washed with saturated sodium chloride solution (20 mL), dried over anhydrous sodium sulfate, and filtered, and the filtrate was concentrated under reduced pressure. The resulting residue was purified by silica gel column chromatography with developing solvent system B to give the title product 15b (15 mg, 2.5% yield).

MS m/z (ESI): 515.2 [M+1].

Step 2

1-(10-(9H-fluoren-9-yl)-5,8-dioxo-2,9-dioxa-4,7-diazadecyl)cyclopropane-1-carboxylic acid 15c Compound 15b (15 mg, 0.029 mmol) was dissolved in 2 mL of ethyl acetate, and palladium on carbon (3 mg, 10% loading, dry basis) was added. The system was purged with hydrogen three times, and the reaction mixture was stirred at room temperature for 4.5 h and filtered through celite, and the filter cake was rinsed with ethyl acetate. The filtrate was concentrated to give the title product 15c (11 mg, 89% yield).

MS m/z (ESI): 425.2 [M+1].

Step 3

(9H-fluoren-9-yl)methyl(2-((((1-(((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)aminocarbonyl)cyclopropyl)methoxy)methyl)amino)2-oxoethyl)carbamate 15d Compound 1b (10 mg, 0.021 mmol) was added to a reaction flask, and 1 mL of N,N-dimethylformamide was added. The system was purged with argon three times, and the mixture was cooled to 0-5° C. in an ice-water bath, followed by addition of a drop of triethylamine, compound 15c (11 mg, 0.026 mmol) and 4-(4,6-dimethoxy-1,3,5-triazin-2-yl)-4-methylmorpholinium chloride (10.7 mg, 0.039 mmol). After addition, the reaction mixture was stirred at room temperature for 60 min. 10 mL of water was added, followed by extraction with ethyl acetate (5 mL×3). The organic phase was washed with saturated sodium chloride solution (10 mL), dried over anhydrous sodium sulfate, and filtered. The filtrate was concentrated under reduced pressure, and the resulting residue was purified by thin layer chromatography with developing solvent system B to give the title product 15d (19 mg, 87.0% yield).

MS m/z (ESI): 842.2 [M+1].

Step 4

1-(((2-Amino acetylamino)methoxy)methyl)-N-((1S,9S)-9-ethyl-5-fluoro-9-hydroxy-4-methyl-10,13-dioxo-2,3,9,10,13,15-hexahydro-1H,12H benzo[de]pyrano[3',4': 6,7]indolizino[1,2-b]quinolin-1-yl)cyclopropane-1-carboxamide 15e Compound 15d (19 mg, 22.56 μmol) was dissolved in 2 mL of dichloromethane, and 1 mL of diethylamine was added. The reaction mixture was stirred at room temperature for 1.5 h and concentrated at 0° C. under reduced pressure. 1 mL of toluene was added, followed by concentration under reduced pressure; the procedures were repeated twice. The residue was slurried with 3 mL of n-hexane, and the upper n-hexane layer was removed; the procedures were repeated three times. The slurry was concentrated under reduced pressure to give the crude title product 15e (13.9 mg), which was directly used in the next step without purification.

MS m/z (ESI): 620.1 [M+1].

Step 5

1-((S)-9-benzyl-22-(2,5-dioxo-2,5-dihydro-1H-pyrrol-1-yl)-5,8,11,14,17-pentaoxo oxa-4,7,10,13,16-pentaazadocosyl)-N-((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)cyclopropane-1-carboxamide 15

Crude 15e (13.9 mg, 22.4 μmol) was dissolved in 1 mL of N,N-dimethylformamide. The system was purged with argon three times, and the solution was cooled to 0-5° C. in an ice-water bath, followed by addition of 8g (15.8 mg, 33.4 μmol) and 4-(4,6-dimethoxy-1,3,5-triazin-2-yl)-4-methylmorpholinium chloride (9.3 mg, 33.6 μmol). The reaction mixture was warmed to room temperature, stirred for 60 min, and purified by high performance liquid chromatography (separation conditions: chromatography column XBridge Prep C18 OBD 5 μm 19×250 mm; mobile phase: A-water (10 mmol of $NH_4OAc$), B-acetonitrile, gradient elution, flow rate: 18 mL/min). The corresponding fractions were collected and concentrated under reduced pressure to give the title product 15 (2.5 mg, 10.3% yield).

MS m/z (ESI): 1074.2 [M+1].

$^1H$ NMR (400 MHz, DMSO-$d_6$): δ 8.51-8.37 (m, 1H), 8.22 (t, 1H), 8.14-8.02 (m, 2H), 8.011-7.94 (m, 1H), 7.82-7.73 (m, 1H), 7.29 (s, 1H), 7.26-7.10 (m, 3H), 6.98 (s, 1H), 6.53-6.47 (m, 1H), 5.62-5.50 (m, 1H), 5.45-5.36 (m, 1H), 5.35-5.23 (m, 2H), 5.13-5.02 (m, 2H), 4.61-4.50 (m, 2H), 4.42-4.28 (m, 2H), 3.76-3.61 (m, 3H), 3.60-3.45 (m, 3H), 3.27-3.23 (m, 1H), 3.20-2.81 (m, 7H), 2.75-2.61 (m, 3H), 241-2.28 (m, 3H), 2.23-2.13 (m, 2H), 2.11-2.01 (m, 1H), 2.03-1.94 (m, 1H), 1.90 (s, 1H), 1.87-1.74 (m, 2H), 1.53-1.36 (m, 3H), 1.29-1.08 (m, 4H), 0.90-0.68 (m, 4H).

Example 1-16
1-((S)-9-benzyl-22-(2,5-dioxo-2,5-dihydro-1H-pyrrol-1-yl)-5,8,11,14,17-pentaoxo-2-oxa-4,7,10,13,16-pentaazadocosyl)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclobutane-1-carboxamide 16
16
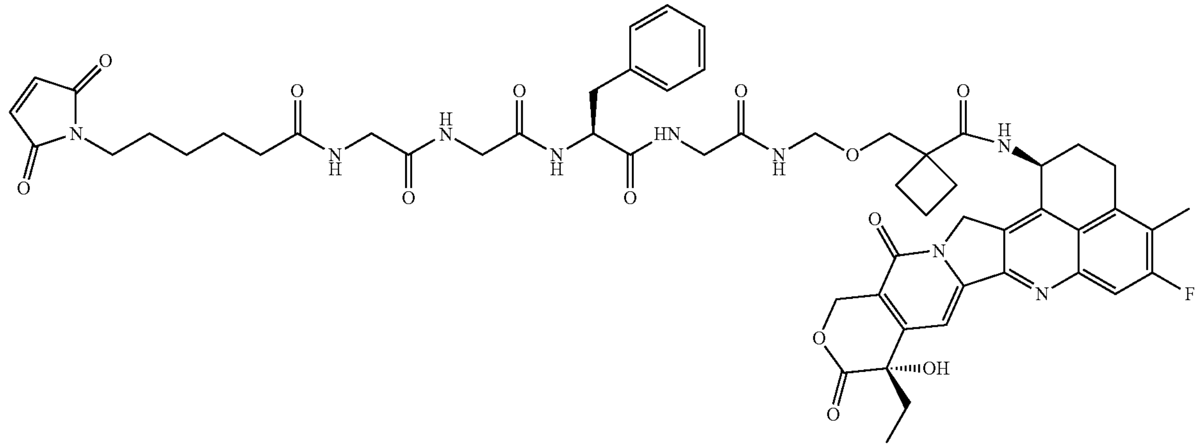
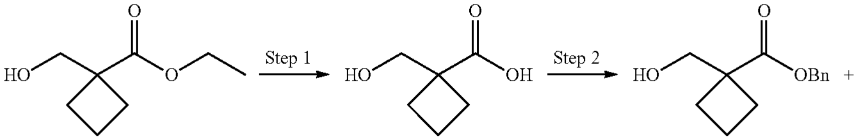
16a 16b 16c
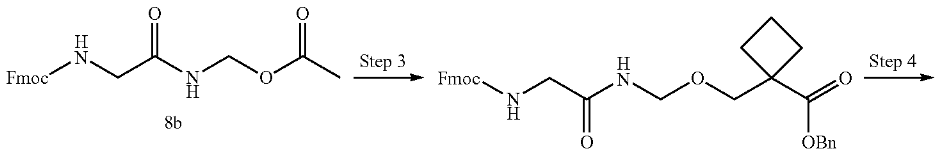
8b 16d
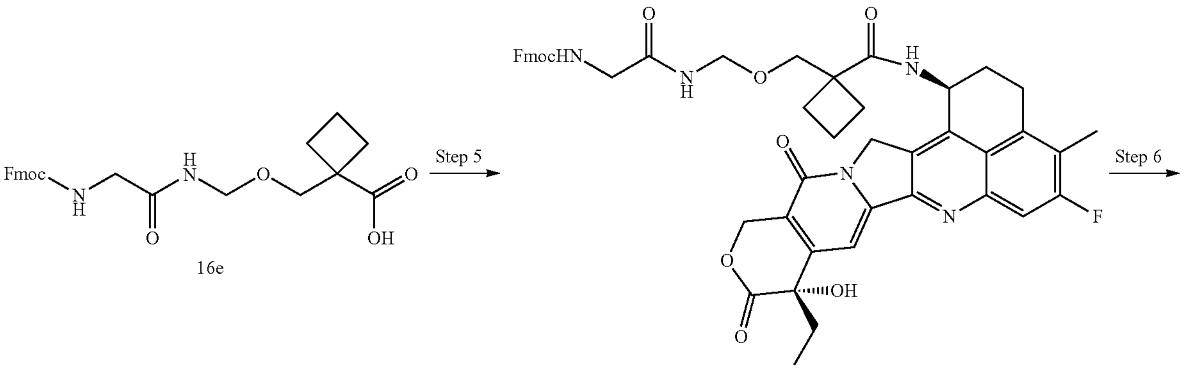
16e 16f -continued

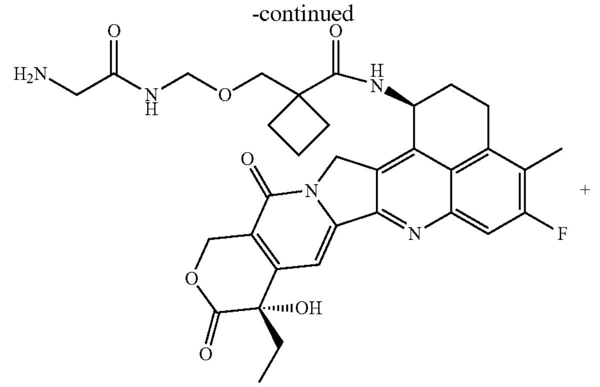

16g

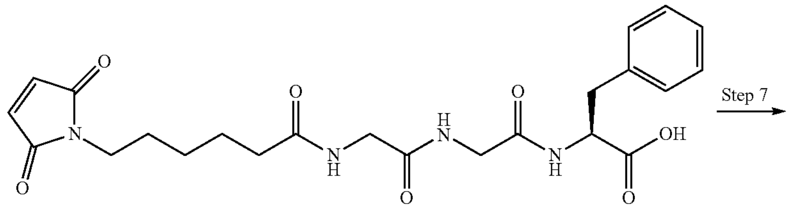

8g

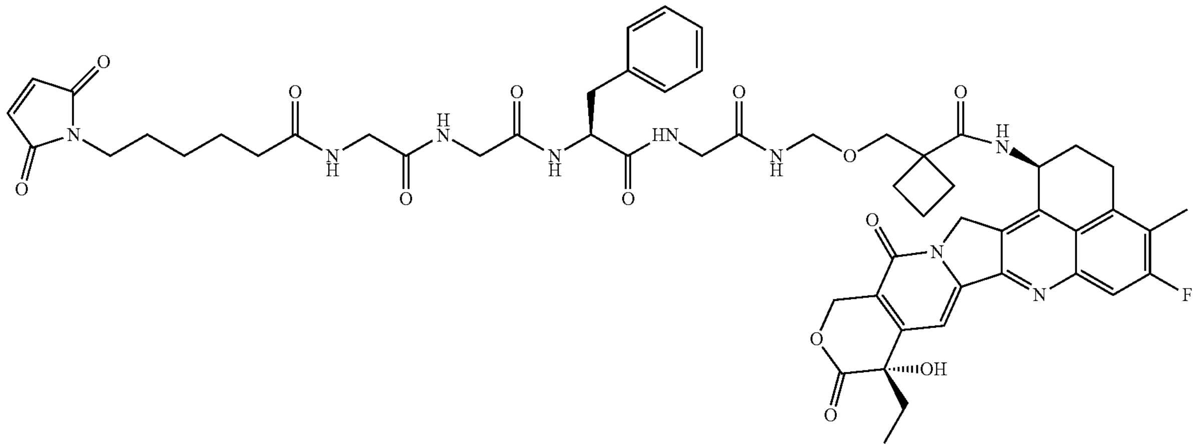

16

Step 1

1-(Hydroxymethyl)cyclobutane-1-carboxylic acid 16b

Ethyl 1-(hydroxymethyl)cyclobutanecarboxylate 16a (250 mg, 1.58 mmol, supplied by Alfa) was dissolved in methanol (2 mL) and water (1 mL), and sodium hydroxide (126 mg, 3.15 mmol) was added. The reaction mixture was warmed to 40° C., stirred for 3 h, cooled to room temperature, and concentrated under reduced pressure to remove the organic solvent. The reaction mixture was reversely extracted with diethyl ether (10 mL) to collect the aqueous phase. The aqueous phase was adjusted to pH 3-4 with 6 N aqueous hydrochloric acid and concentrated under reduced pressure to give a solid. 3 mL of toluene was added, followed by concentration under reduced pressure to dryness; the procedures were repeated three times. The residue was dried using an oil pump to give the crude title product 16b (206 mg), which was directly used in the next step without purification.

MS mlz (ESI, NEG):129.2 [M−1].

Step 2

Benzyl 1-(hydroxymethyl)cyclobutane-1-carboxylate 16c

Crude 16b (206 mg, 1.58 mmol) was dissolved in acetonitrile (15 mL), and anhydrous potassium carbonate (1.09 g, 7.90 mmol), tetrabutylammonium iodide (29 mg, 78.51 μmol) and benzyl bromide (216 mg, 1.26 mmol) were added. The reaction mixture was stirred at room temperature overnight and filtered. The filtrate was concentrated under reduced pressure, and the resulting residue was purified by silica gel column chromatography with developing solvent system C to give the title product 16c (112 mg, 32.1% yield).

MS m/z (ESI): 221.1 [M+1].

Step 3

Benzyl 1-(10-(9H-fluoren-9-yl)-5,8-dioxo-2,9-dioxa-4,7-diazadecyl)cyclobutane-1-carboxylate 16d Compounds 16c (77 mg, 0.35 mmol) and 8b (100 mg, 0.27 mmol) were added to a reaction flask, and 3 mL of tetrahydrofuran was added. The system was purged with argon three times, and the reaction mixture was cooled to 0-5° C. in an ice-water bath, followed by addition of potassium tert-butoxide (61 mg, 0.54 mmol). The reaction mixture was stirred in the ice bath for 10 min 20 mL of ice water was added, followed by extraction with ethyl acetate (5 mL) and chloroform (5 mL×5). The organic phases were combined and concentrated. The resulting residue was dissolved in 3 mL of 1,4-dioxane, and 0.5 mL of water, sodium bicarbonate (27 mg, 0.32 mmol) and 9-fluorenylmethyl chloroformate (71 mg, 0.27 mmol) were added. The reaction mixture was stirred at room temperature for 1 h. 20 mL of water was added, followed by extraction with ethyl acetate (10 mL×3). The organic phase was washed with saturated sodium chloride solution (20 mL), dried over anhydrous sodium sulfate, and filtered. The filtrate was concentrated under reduced pressure, and the resulting residue was purified by silica gel column chromatography with developing solvent system C to give the title product 16d (24 mg, 16.7% yield).

MS m/z (ESI): 551.3 [M+23].

Step 4

1-(10-(9H-fluoren-9-yl)-5,8-dioxo-2,9-dioxa-4,7-diazadecyl)cyclobutane-1-carboxylic acid 16e Compound 16d (12 mg, 22.7 μmol) was dissolved in 1.5 mL of a solvent mixture of tetrahydrofuran and ethyl acetate (V:V=2:1), and palladium on carbon (5 mg, 10% loading) was added. The system was purged with hydrogen three times, and the reaction mixture was stirred at room temperature for 2 h. The reaction mixture was filtered through celite, and the filter cake was rinsed with ethyl acetate. The filtrate was concentrated under reduced pressure to give the crude title product 16e (10 mg), which was directly used in the next step without purification.

Step 5

(9H-fluoren-9-yl)methyl(2-((((1-(((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)aminocarbonyl)cyclobutyl)methoxy)methyl)amino)-2-oxoethyl)carbamate 16f Compound 1b (7.5 mg, 0.014 mmol) was added to a reaction flask, and 1 mL of N,N-dimethylformamide was added. The system was purged with argon three times, and the mixture was cooled to 0-5° C. in an ice-water bath, followed by addition of a drop of triethylamine, a solution of crude 16e (10 mg) in 0.5 mL of N,N-dimethylformamide, and 4-(4,6-dimethoxy-1,3,5-triazin-2-yl)-4-methylmorpholinium chloride (6 mg, 0.026 mmol). The reaction mixture was stirred in an ice bath for 30 min 10 mL of water was added, followed by extraction with ethyl acetate (10 mL×3). The organic phase was washed with saturated sodium chloride solution (10 mL), dried over anhydrous sodium sulfate, and filtered. The filtrate was concentrated under reduced pressure, and the resulting residue was purified by thin layer chromatography with developing solvent system B to give the title product 16f (10.6 mg, 87.8% yield).

MS m/z (ESI): 856.2 [M+1].

Step 6

1-(((2-Aminoacetylamino)methoxy)methyl)-N-((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)cyclobutane-1-carboxamide 16g Compound 16f (10.6 mg, 12.4 μmol) was dissolved in 0.6 mL of dichloromethane, and 0.3 mL of diethylamine was added. The reaction mixture was stirred at room temperature for 2 h and concentrated under reduced pressure. 2 mL of toluene was added, followed by concentration under reduced pressure; the procedures were repeated twice. The residue was slurried with 3 mL of n-hexane, and the upper n-hexane layer was removed; the procedures were repeated three times. The residue was concentrated under reduced pressure to give the crude title product 16g (8 mg), which was directly used in the next step without purification.

MS m/z (ESI): 634.1 [M+1].

Step 7

1-((S)-9-benzyl-22-(2,5-dioxo-2,5-dihydro-1H-pyrrol-1-yl)-5,8,11,14,17-pentaoxo-2-oxa-4,7,10,13,16-pentaazadocosyl)-N-41 S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)cyclobutane-1-carboxamide 16

Crude 16g (8 mg) was dissolved in 1 mL of N,N-dimethylformamide, and 8g (8.8 mg, 18.6 μmol) and 4-(4,6-dimethoxy-1,3,5-triazin-2-yl)-4-methylmorpholinium chloride (5.2 mg, 18.8 μmol) were added. The reaction mixture was stirred at room temperature for 30 min and purified by high performance liquid chromatography (separation conditions: chromatography column: XBridge Prep C18 OBD 5 μm 19×250 mm; mobile phase: A-water (10 mmol of $NH_4OAc$), B-acetonitrile, gradient elution, flow rate: 18 mL/min) to give the title product 16 (1.0 mg, 7.2% yield).

MS m/z (ESI): 1088.0 [M+1].

Example 1-17
(1r,4r)-N—((S)-7-benzyl-1-(1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)aminocarbonyl)cyclopropoxy)-3,6,9,12,15-pentaoxo-17,20,23,26,29,32,35,38,41-nonaoxa-2,5,8,11,14-pentaazatetratridec-43-yl)-4-((2,5-dioxo-2,5-dihydro-1H-pyrrol-1-yl)methyl)cyclohexane-1-carboxamide 17
17
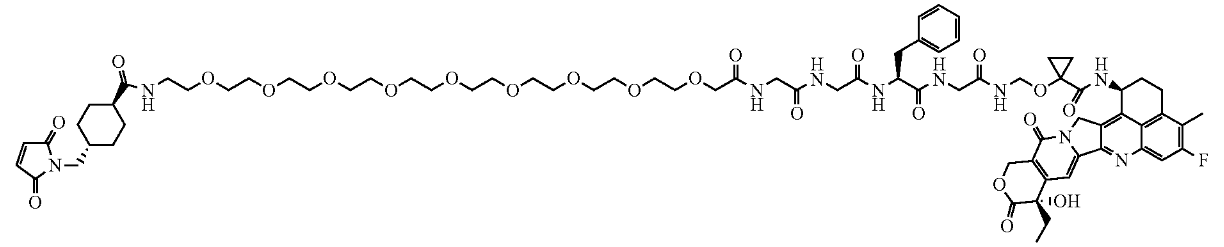
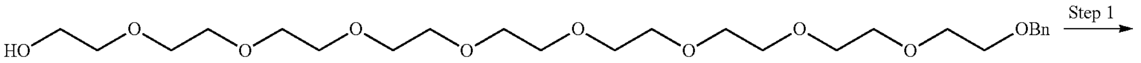
17a
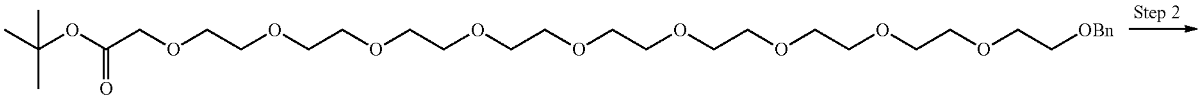
17b
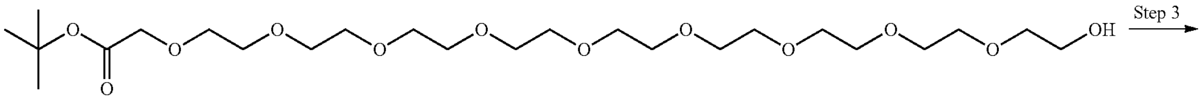
17c
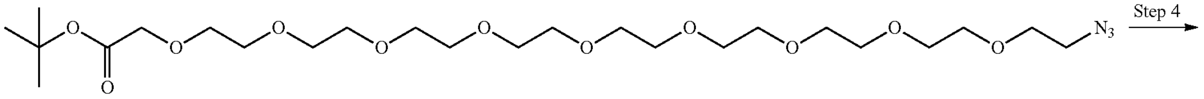
17d
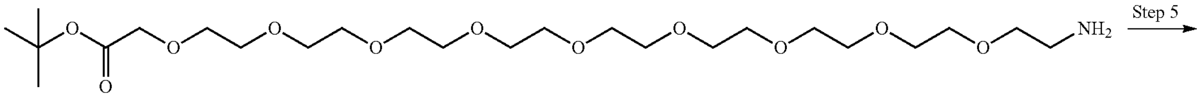
17e
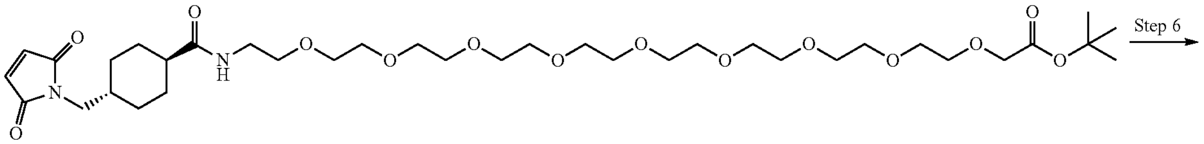
17f
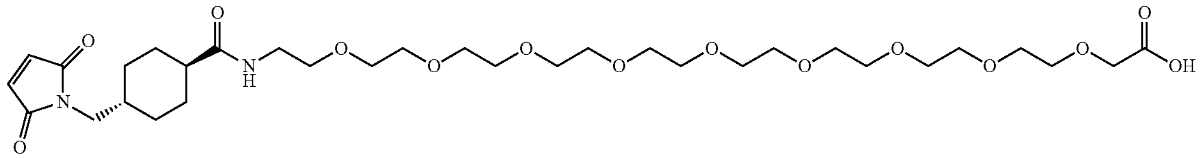
17g -continued
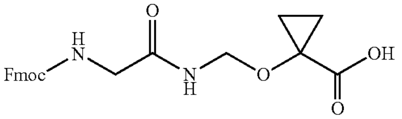
8d
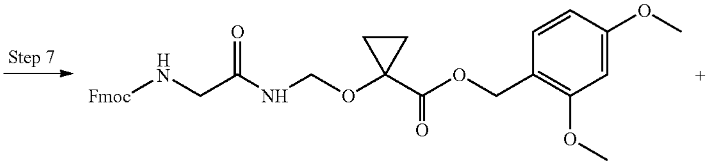
17h
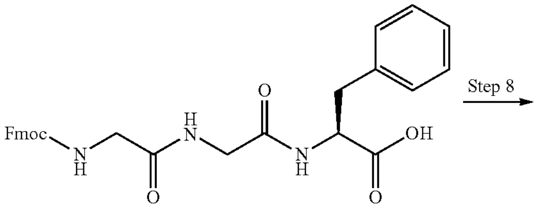
17i
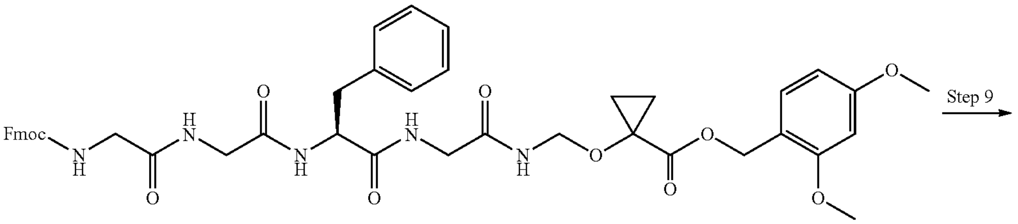
17j
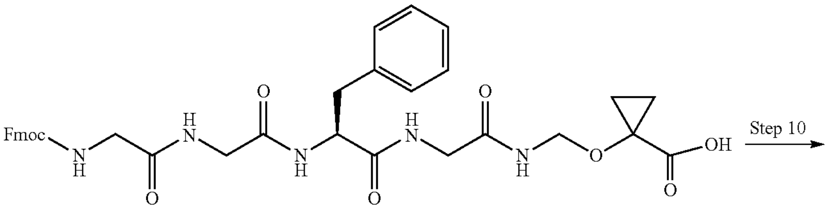
17k
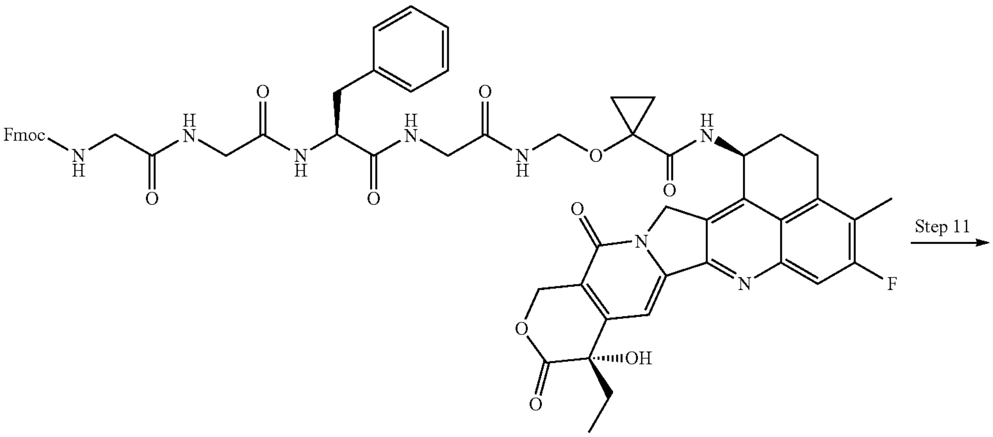
17l
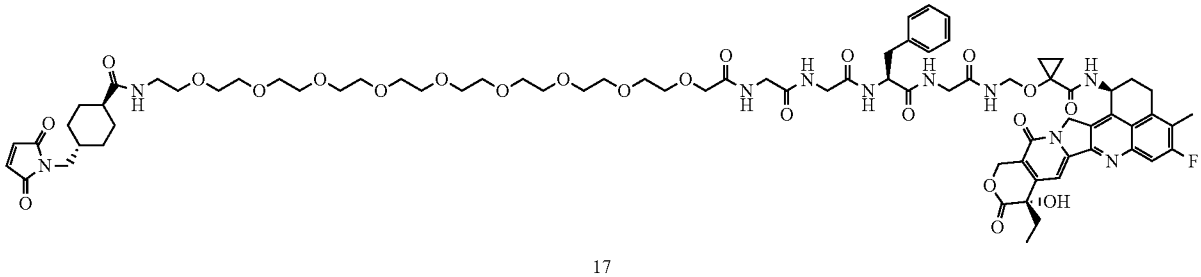
17

Step 1 tert-Butyl 1-phenyl-2,5,8,11,14,17,20,23,26,29-decaoxahentriacontane-31-oate 17b 1-Phenyl-2,5,8,11,14,17,20,23,26-nonaoxaoctacosane-28-ol 17a (0.34 g, 0.67 mmol, supplied by Bide) was dissolved in 10 mL of dichloromethane, and silver oxide (0.24 g, 1.01 mmol), tert-butyl bromoacetate (0.16 g, 0.81 mmol) and potassium iodide (0.07 g, 0.40 mmol) were successively added. The reaction mixture was stirred at room temperature for 3 h, and filtered. The filtrate was concentrated under reduced pressure, and the resulting residue was purified by silica gel column chromatography with developing solvent system B to give the title product 17b (0.42 g, 100% yield).

MS m/z (ESI): 636.3 [M+18].

Step 2 tert-Butyl 29-hydroxy-3,6,9,12,15,18,21,24,27-nonaoxanonacosane-1-oate 17c

Compound 17b (417 mg, 0.67 mmol) was dissolved in 15 mL of tetrahydrofuran, and palladium on carbon (110 mg, 10% loading, dry basis) was added. The system was purged with hydrogen three times, and the reaction mixture was warmed to 60° C., stirred for 3 h, filtered through celite, and the filter cake was rinsed with tetrahydrofuran. The filtrate was concentrated to give the crude title product 17c (357 mg), which was directly used in the next step without purification.

MS m/z (ESI): 546.2 [M+18].

Step 3 tert-Butyl 29-azido-3,6,9,12,15,18,21,24,27-nonaoxanonacosane-1-oate 17d

Compound 17c (357 mg, 0.675 mmol) was dissolved in 10 mL of toluene, and diphenyl phosphoryl azide (279 mg, 1.014 mmol) and 1,8-diazabicycloundec-7-ene (206 mg, 1.353 mmol) were added. The system was purged with argon three times, and the reaction mixture was stirred at room temperature for 2 h, then warmed to 105° C., reacted for 19 h, cooled to room temperature and concentrated. 20 mL of water was added, followed by extraction with ethyl acetate (10 mL×4). The organic phase was washed with saturated sodium chloride solution (20 mL), dried over anhydrous sodium sulfate, and filtered. The filtrate was concentrated under reduced pressure. The resulting residue was purified by silica gel column chromatography with developing solvent system B to give the crude title product 17d (412 mg).

MS m/z (ESI): 571.3 [M+18].

Step 4 tert-Butyl 29-amino-3,6,9,12,15,18,21,24,27-nonaoxanonacosane-1-oate 17e

Compound 17d (230 mg, 0.415 mmol) was dissolved in 8 mL of tetrahydrofuran, and palladium on carbon (58 mg, 10% loading, dry basis) was added. The system was purged with hydrogen three times. The reaction mixture was stirred at room temperature for 2 h and filtered through celite, and the filter cake was rinsed with tetrahydrofuran. The filtrate was concentrated to give the crude title product 17e (220 mg), which was directly used in the next step without purification.

MS m/z (ESI): 528.2 [M+1].

Step 5 tert-Butyl 1-((1r,4r)-4-((2,5-dioxo-2,5-dihydro-1H-pyrrol-1-yl)methyl)cyclohexyl)-1-oxo-5,8,11,14,17,20,23,26,29-nonaoxa-2-azatriundec-31-oate 17f (1r,4r)-4-((2,5-dioxo-2,5-dihydro-1H-pyrrol-1-yl)methyl) cyclohexane-1-carboxylic acid (98.5 mg, 0.415 mmol) was dissolved in 10 mL of dichloromethane, and 2-(7-benzotriazol oxide)-N,N,N',N'-tetramethyluronium hexafluorophosphate (190 mg, 0.500 mmol) and N,N-diisopropylethylamine (162 mg, 1.253 mmol) were added. The system was purged with argon three times, and crude 17e (220 mg, 0.417 mmol) was added. The reaction mixture was stirred at room temperature for 1 h. 15 mL of water was added, followed by extraction with dichloromethane (8 mL×3). The organic phases were combined, washed with saturated sodium chloride solution (15 mL), dried over anhydrous sodium sulfate, and filtered. The filtrate was concentrated under reduced pressure. The resulting residue was purified by silica gel column chromatography with developing solvent system B to give the title product 17f (122 mg, 39.2% yield).

MS m/z (ESI): 747.2 [M+1].

Step 6

1-((1r,4r)-4-((2,5-dioxo-2,5-dihydro-1H-pyrrol-1-yl) methyl)cyclohexyl)-1-oxo-5,8,11,14,17,20,23,26,29-nonaoxa-2-azatriundec-31-oic acid 17g Compound 17f (122 mg, 0.163 mmol) was dissolved in 0.8 mL of dichloromethane, and 0.4 mL of trifluoroacetic acid was added. The reaction mixture was stirred at room temperature for 1 h, diluted with 15 mL of dichloromethane, and concentrated under reduced pressure; 10 mL of n-hexane was added, followed by concentration under reduced pressure; the procedures were repeated twice. Then 10 mL of toluene was added, and the resulting mixture was concentrated under reduced pressure, slurried three times with 10 mL of a solvent mixture of n-hexane:diethyl ether=5:1 until the pH reached 7, concentrated, and dried with an oil pump to give the title product 17g (98 mg, 86.8% yield).

MS m/z (ESI): 691.2 [M+1].

Step 7

2,4-Dimethoxybenzyl 1-((2-((((9H-fluoren-9-yl) methoxy)carbonyl)amino) acetylamino)methoxy) cyclopropyl-1-carboxylate 17h Compound 8d (164 mg, 0.40 mmol) was dissolved in dichloromethane (5 mL), and 2,4-dimethoxybenzyl alcohol (81 mg, 0.48 mmol), 1-ethyl-(3-dimethylaminopropyl)carbonyldiimine hydrochloride (115 mg, 0.60 mmol) and 4-dimethylaminopyridine (5 mg, 0.041 mmol) were added successively. After addition, the reaction mixture was stirred at room temperature for 1 h. 20 mL of water was added, and layers formed after shaking. The aqueous phase was extracted with dichloromethane (8 mL×3). The organic phases were combined, washed with saturated sodium chloride solution (20 mL), dried over anhydrous sodium sulfate, and filtered. The filtrate was concentrated under reduced pressure. The resulting residue was purified by silica gel column chromatography with developing solvent system C to give the title product 17h (124 mg, 55.4% yield).

MS m/z (ESI): 583.1 [M+23].

Step 8

2,4-Dimethoxybenzyl (S)-1-((11-benzyl-1-(9H-fluoren-9-yl)-3,6,9,12,15-pentaoxo-2-oxa-4,7,10,13,16-pentaazaheptadecane-17-yl)oxylcyclopropyl-1-carboxylate 17j Compound 17h (39 mg, 69.6 μmol) was dissolved in 0.6 mL of dichloromethane, and 0.3 mL of diethylamine was added. The reaction mixture was stirred at room temperature for 1 h and concentrated under reduced pressure. 2 mL of toluene was added, followed by concentration under reduced pressure; the procedures were repeated twice. The residue was slurried with 3 mL of n-hexane, and the upper n-hexane layer was removed; the procedures were repeated three times, followed by concentration under reduced pressure. The resulting crude product was dissolved in 2 mL of N,N-dimethylformamide, and (((9H-fluoren-9-yl)methoxy)carbonyl)glycyl-L-phenylalanine 17i (35 mg, 69.8 μmol, prepared as disclosed in "Example 7-12 on page 13 of the specification of Patent Application CN108853514A") and 4-(4,6-dimethoxy-1,3,5-triazin-2-yl)-4-methylmorpholinium chloride (23 mg, 83.1 μmol) were added. The reaction mixture was stirred at room temperature for 1 h. 10 mL of water was added, followed by extraction with ethyl acetate (10 mL×3). The organic phases were combined, washed with saturated sodium chloride solution (10 mL×2), dried over anhydrous sodium sulfate, and filtered. The filtrate was concentrated under reduced pressure. The resulting residue was purified by thin layer chromatography with developing solvent system B to give the title product 17j (48 mg, 83.9% yield).

MS m/z (ESI): 822.0 [M+1].

Step 9

(S)-1-((11-benzyl-1-(9H-fluoren-9-yl)-3,6,9,12,15-pentaoxo-2-oxa-4,7,10,13,16-pentaazaheptadecane-17-yl)oxy)cyclopropane-1-carboxylic acid 17k Compound 17j (48 mg, 58.4 μmol) was dissolved in 1.4 mL of a 3% (v/v) solution of dichloroacetic acid in dichloromethane, and the solution was cooled to 0-5° C. in an ice-water bath, followed by addition of triethylsilane (21 mg, 180.6 μmol). The reaction mixture was stirred in the ice bath for 3 h. The reaction mixture was concentrated under reduced pressure in the ice bath to remove half of the organic solvent. 5 mL of diethyl ether was added, and the resulting mixture was warmed to room temperature naturally and slurried to precipitate a white solid, and filtered. The filter cake was collected and dried with an oil pump to give the title product 17k (33 mg, 84.1% yield).

Step 10

(9H-fluoren-9-yl)methyl((S)-7-benzyl-1-(1-(((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)aminocarbonyl)cyclopropoxy)-3,6,9,12-tetraoxo-2,5,8,11-tetraazatridecan-13-yl)carbamate 17l Compound 1b (20 mg, 42.4 μmol) was added to a reaction flask, and 1 mL of a 10% (v/v) solution of methanol in dichloromethane was added. The system was purged with argon three times, and the mixture was cooled to 0-5° C. in an ice-water bath, followed by addition of a drop of triethylamine. The mixture was stirred until compound 1b was dissolved. Compound 17k (33 mg, 49.1 μmol) was dissolved in 1 mL of a 10% (v/v) solution of methanol in dichloromethane, and then the above reaction mixture was added dropwise, followed by addition of 4-(4,6-dimethoxy-1,3,5-triazin-2-yl) methylmorpholinium chloride (17.6 mg, 63.6 μmol). The reaction mixture was warmed to room temperature and stirred for 1 h. 10 mL of dichloromethane and 5 mL of water were added, and the resulting mixture was stirred for 5 min, and let stand to form layers. The organic phase was collected, and the aqueous phase was extracted with dichloromethane (10 mL×3). The organic phases were combined, washed with saturated sodium chloride solution (10 mL×2), dried over anhydrous sodium sulfate, and filtered. The filtrate was concentrated under reduced pressure. The resulting residue was purified by thin layer chromatography with developing solvent system B to give the title product 17l (37 mg, 80.2% yield).

MS m/z (ESI): 1090.1 [M+1].

Step 11

(1r,4r)-N—((S)-7-benzyl-1-(1-(((1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)aminocarbonyl)cyclopropoxy)-3,6,9,12,15-pentaoxo-17,20,23,26,29,32,35,38,41-nonaoxa-2,5,8,11,14-pentaazatetratridec-43-yl)-4-((2,5-dioxo-2,5-dihydro-1H-pyrrol-1-yl)methyl)cyclohexane-1-carboxamide 17

Compound 17l (15.5 mg, 14.23 μmol) was dissolved in 0.6 mL of dichloromethane, and 0.3 mL of diethylamine was added. The reaction mixture was stirred at room temperature for 1.5 h and concentrated under reduced pressure. 2 mL of toluene was added, followed by concentration under reduced pressure; the procedures were repeated twice. The residue was slurried with 3 mL of n-hexane, and the upper n-hexane layer was removed; the procedures were repeated three times. The reaction mixture was concentrated under reduced pressure and then dried with an oil pump. The resulting crude product was dissolved in 1 mL of N,N-dimethylformamide, and compound 17g (11 mg, 15.92 μmol) and 4-(4,6-dimethoxy-1,3,5-triazin-2-yl)-4-methylmorpholinium chloride (6.0 mg, 21.68 μmol) were added. The system was purged with argon three times, and the reaction mixture was stirred at room temperature for 30 min and purified by high performance liquid chromatography (separation conditions: chromatography column: XBridge Prep C18 OBD 5 μm 19×250 mm; mobile phase: A-water (10 mmol of $NH_4OAc$), B-acetonitrile, gradient elution, flow rate: 18 mL/min). The corresponding fractions were collected and concentrated under reduced pressure to give the title product 17 (6 mg, 27.4% yield).

MS m/z (ESI): 1556.4 [M+18].

$^1H$ NMR (400 MHz, DMSO-$d_6$): δ 8.98 (d, 1H), 8.76 (s, 1H), 8.20 (br, 1H), 8.12-7.95 (m, 3H), 7.93-7.76 (m, 2H), 7.75-7.66 (m, 2H), 7.24 (s, 1H), 7.20-7.05 (m, 6H), 6.97 (s, 1H), 6.64 (br, 1H), 6.55 (d, 1H), 6.47 (s, 1H), 5.61-5.52 (m, 2H), 5.37 (s, 1H), 5.33-5.23 (m, 2H), 5.18 (s, 1H), 5.13 (s, 1H), 5.05 (s, 1H), 5.00 (s, 1H), 4.65-4.55 (m, 2H), 4.53-4.45 (m, 1H), 4.38-4.28 (m, 2H), 3.84 (s, 2H), 3.67 (d, 3H), 3.60-3.40 (m, 33H), 3.18 (d, 1H), 3.15-3.08 (m, 3H), 2.28 (s, 3H), 2.00-1.92 (m, 3H), 1.85 (s, 2H), 1.82-1.73 (m, 2H), 1.68-1.52 (m, 4H), 1.29-1.15 (m, 3H), 0.86-0.76 (m, 5H).

Example 1-18
(1r,4r)-N-((2R,10S)-10-benzyl-2-cyclopropyl-1-(((1S,9S)-9-ethyl-5-fluoro-9-hydroxy methyl-10,13-dioxo-2,3,9,10,13,15-hexahydro-1H,12H-benzo[de]pyrano[3',4': 6,7]indolizino[1,2-b]quinolin-1-yl)amino)-1,6,9,12,15,18-hexaoxo-3,20,23,26,29,32,35,38,41,44-decaoxa-5,8,11,14,17-pentaaza-tetrahexadec-46-yl)-4-((2,5-dioxo-2,5-dihydro-1H-pyrrol-1-yl)methyl)cyclohexane-1-carboxamide 18
18
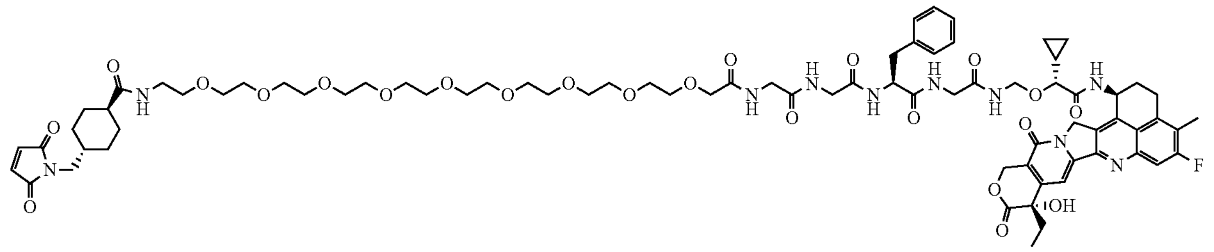
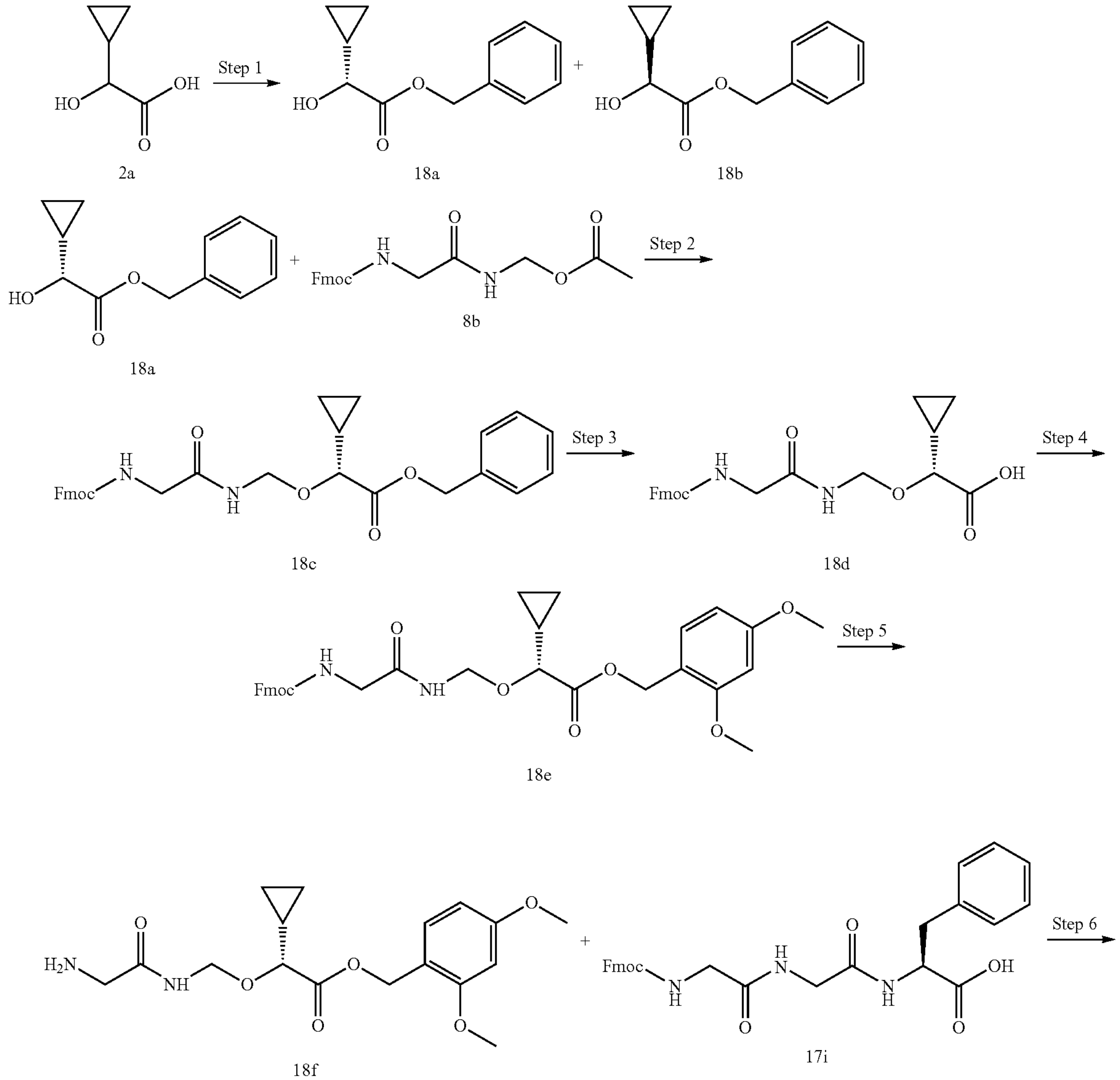
2a
18a
18b
18a
8b
18c
18d
18e
18f
17i -continued
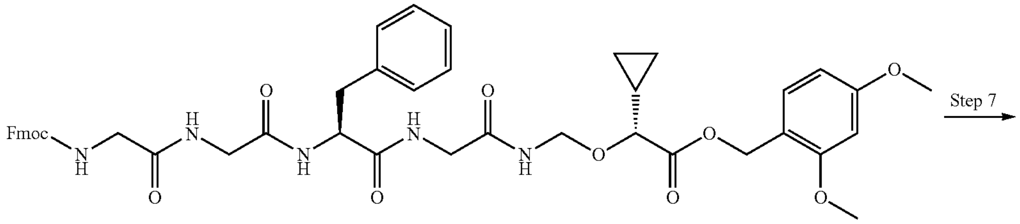
18g
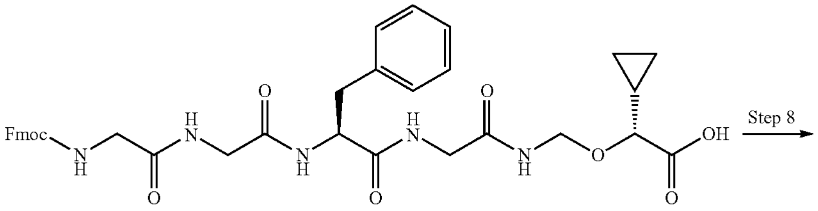
18h
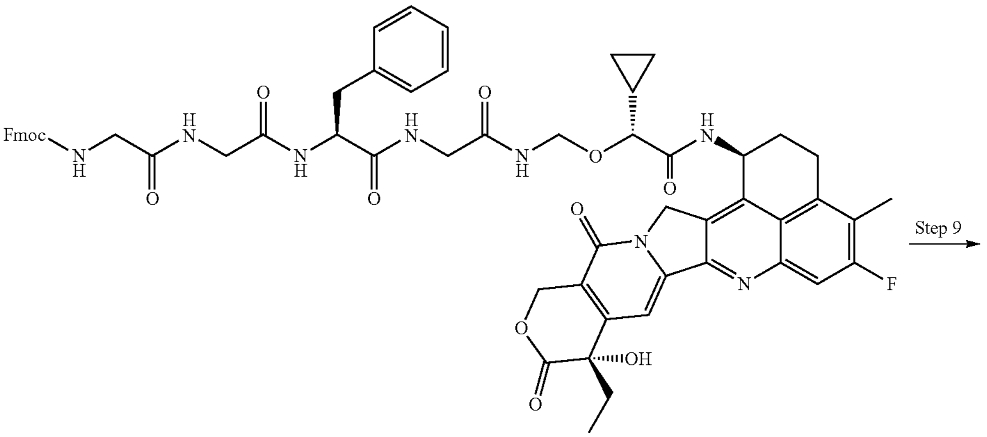
18i
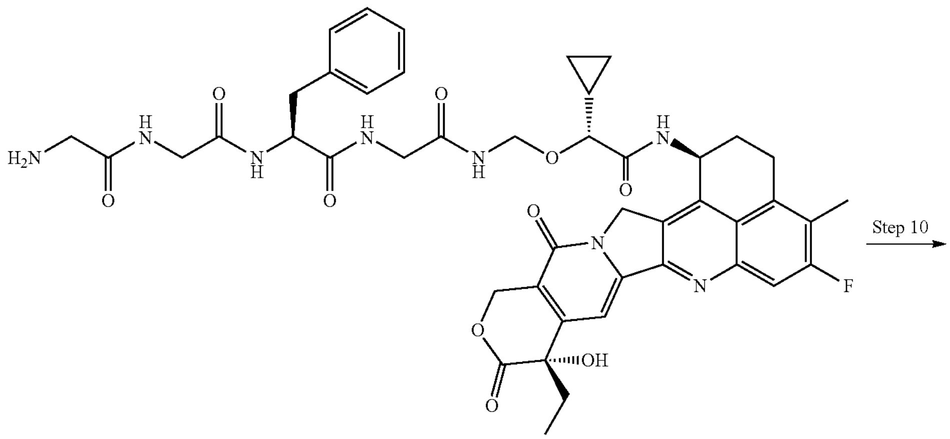
18j -continued

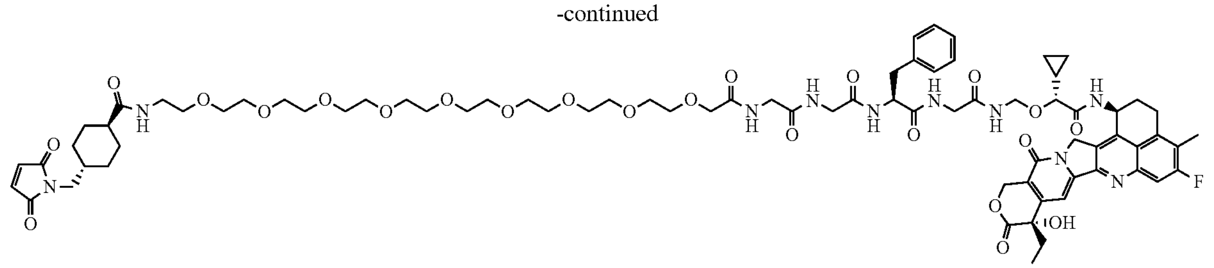

18

Step 1

Benzyl (R)-2-cyclopropyl-2-hydroxy acetate 18a

Benzyl (S)-2-cyclopropyl-2-hydroxyacetate 18b

Compound 2a (7.4 g, 63.7 mmol) was dissolved in 200 mL of acetonitrile, and potassium carbonate (35 g, 253.6 mmol), benzyl bromide (9.3 g, 54.4 mmol) and tetrabutylammonium iodide (500 mg, 1.36 mmol) were added successively. The reaction mixture was stirred at room temperature for 16 h and filtered through celite, and the filter cake was rinsed with ethyl acetate (10 mL). The filtrates were combined and concentrated under reduced pressure, and the resulting residue (4.1 g) was purified by silica gel column chromatography with developing solvent system C and further by chiral resolution to give the title products 18a (1.1 g) and 18b (1.2 g).

Step 2

Benzyl (R)-10-cyclopropyl-1-(9H-fluoren-9-yl)-3,6-di oxo-2,9-di oxa-4,7-diazaundecan-11-oate 18c Compound 8b (3.1 g, 8.41 mmol) was dissolved in tetrahydrofuran (55 mL), and compound 18a (2.0 g, 9.70 mmol) was added. The mixture was cooled to 0-5° C. in an ice-water bath, and potassium tert-butoxide (1.89 g, 16.84 mmol) was added. The mixture was stirred in the ice-water bath for 10 min. Ethyl acetate (30 mL) and water (20 mL) were added, and the resulting mixture was let stand to form layers. The aqueous phase was extracted with chloroform (30 mL×5), and the organic phases were combined, and concentrated under reduced pressure. The resulting residue was dissolved in 1,4-dioxane (32 mL) and water (8 mL), and sodium carbonate (1.78 g, 16.79 mmol) and 9-fluorenylmethyl chloroformate (2.18 g, 8.42 mmol) were added. The resulting mixture was stirred at room temperature for 2 h. Water (30 mL) was added, followed by extraction with ethyl acetate (50 mL×3). The organic phases were combined, washed with saturated sodium chloride solution (30 mL×2), dried over anhydrous sodium sulfate, and filtered. The filtrate was concentrated under reduced pressure. The resulting residue was purified by column chromatography with developing solvent system C to give the title product 18c (1.3 g, 30.0% yield).

MS m/z (ESI): 515.2 [M+1].

Step 3

(R)-10-cyclopropyl-1-(9H-fluoren-9-yl)-3,6-dioxo-2,9-dioxa-4,7-diazaundecan-11-oic acid 18d Compound 18c (1.29 g, 2.51 mmol) was dissolved in ethyl acetate (15 mL), and palladium on carbon (260 mg, 10% loading, dry basis) was added. The system was purged with hydrogen three times, and the reaction mixture was stirred at room temperature for 5 h and filtered through celite, and the filter cake was rinsed with ethyl acetate (20 mL) and methanol (20 mL). The filtrate was concentrated to give the crude title product 18d (980 mg), which was directly used in the next step without purification.

MS m/z (ESI): 425.1 [M+1].

Step 4

2,4-Dimethoxybenzyl(R)-10-cyclopropyl-1-(9H-fluoren-9-yl)-3,6-dioxo-2,9-dioxa-4,7-diazaundecan-11-ester 18e Crude 18d (980 mg, 2.31 mmol) was dissolved in dichloromethane (15 mL), and 2,4-dimethoxybenzyl alcohol (777 mg, 4.62 mmol), 1-ethyl-(3-dimethylaminopropyl) carbonyldiimine hydrochloride (664 mg, 3.46 mmol) and 4-dimethylaminopyridine (28 mg, 0.23 mmol) were added. The reaction mixture was stirred at room temperature for 1 h, and concentrated under reduced pressure to remove the organic solvent. 20 mL of water was added, followed by extraction with ethyl acetate (50 mL×3). The organic phases were combined, washed with saturated sodium chloride solution (30 mL×2), dried over anhydrous sodium sulfate, and filtered. The filtrate was concentrated under reduced pressure. The resulting residue was purified by column chromatography with developing solvent system C to give the title product 18e (810 mg, 61.1% yield).

MS m/z (ESI): 575.0 [M+1].

Step 5

2,4-Dimethoxybenzyl(R)-2-(((2-aminoacetylamino) methoxy)-2-cyclopropylacetate 18f Compound 18e (33 mg, 57.4 μmol) was dissolved in 0.6 mL of dichloromethane, and 0.3 mL of diethylamine was added. The reaction mixture was stirred at room temperature for 1 h and concentrated under reduced pressure. 2 mL of toluene was added, followed by concentration under reduced pressure; the procedures were repeated twice. The residue was slurried with 3 mL of n-hexane, and the upper n-hexane layer was removed; the procedures were repeated three times. The slurry was concentrated under reduced pressure to give the crude title product 18f (21 mg), which was directly used in the next step without purification.

Step 6

2,4-Dimethoxybenzyl(11S,19R)-11-benzyl-19-cyclopropyl-1-(9H-fluoren-9-yl)-3,6,9,12,15-pentaoxo-2,18-dioxa-4,7,10,13,16-pentaazaicosan-20-oate 18g Crude 18f (21 mg, 57.4 μmol) was dissolved in 3 mL of N,N-dimethylformamide, and compound 17i (29 mg, 57.8

μmol) and 4-(4,6-dimethoxy-1,3,5-triazin-2-yl)-4-methylmorpholinium chloride (19 mg, 68.7 μmol) were added. The reaction mixture was stirred at room temperature for 1 h. 10 mL of water was added, followed by extraction with ethyl acetate (10 mL×3). The organic phases were combined, washed with saturated sodium chloride solution (10 mL×2), dried over anhydrous sodium sulfate, and filtered. The filtrate was concentrated under reduced pressure. The resulting residue was purified by thin layer chromatography with developing solvent system B to give the title product 18g (37 mg, 77.1% yield).

MS m/z (ESI): 853.0 [M+18].

Step 7

(11S,19R)-11-benzyl-19-cyclopropyl-1-(9H-fluoren-9-yl)-3,6,9,12,15-pentaoxo-2,18-dioxa-4,7,10,13,16-pentaazaicosan-20-oic acid 18h Compound 18g (37 mg, 44.3 μmol) was dissolved in 1.4 mL of a 3% (v/v) solution of dichloroacetic acid in dichloromethane, and the solution was cooled to 0-5° C. in an ice-water bath, followed by addition of triethylsilane (15.4 mg, 132.4 μmol). The reaction mixture was stirred in the ice bath for 3 h. The reaction mixture was concentrated under reduced pressure in the ice bath to remove half of the organic solvent, and 5 mL of diethyl ether was added. The resulting mixture was warmed to room temperature naturally and slurried to precipitate a white solid, and filtered. The filter cake was collected and dried with an oil pump to give the title product 18h (24 mg, 79.1% yield).

MS m/z (ESI): 708.2 [M+23].

Step 8

(9H-fluoren-9-yl)methyl((2R,10S)-10-benzyl-2-cyclopropyl-1-(((1S,9S)-9-ethyl fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl)amino)-1,6,9,12,15-pentaoxo-3-oxa-5,8,11,14-tetraazahexadec-16-ylicarbamate 18i Compound 1b (30 mg, 63.6 μmol) was added to a reaction flask, and 1 mL of a 10% (v/v) solution of methanol in dichloromethane was added. The system was purged with argon three times, and the mixture was cooled to 0-5° C. in an ice-water bath, followed by addition of a drop of triethylamine. The mixture was stirred until compound 1b was dissolved. Compound 18h (65 mg, 94.8 μmol) was dissolved in 1 mL of a 10% (v/v) solution of methanol in dichloromethane, and then the above reaction mixture was added dropwise, followed by addition of 4-(4,6-dimethoxy-1,3,5-triazin-2-yl)-4-methylmorpholinium chloride (27 mg, 97.6 μmol). The reaction mixture was warmed to room temperature and stirred for 1 h. 10 mL of dichloromethane and 5 mL of water were added, and the resulting mixture was stirred for 5 min, and let stand to form layers. The organic phase was collected, and the aqueous phase was extracted with dichloromethane (10 mL×3). The organic phases were combined, washed with saturated sodium chloride solution (10 mL×2), dried over anhydrous sodium sulfate, and filtered. The filtrate was concentrated under reduced pressure. The resulting residue was purified by thin layer chromatography with developing solvent system B to give the title product 18i (25 mg, 35.6% yield).

MS m/z (ESI): 1104.4 [M+1].

Step 9

(S)-2-(2-(2-aminoacetyl amino)acetylamino)-N-(2-((((R)-1-cyclopropyl-2-(((1S,9S)-9-ethyl-5-fluoro-9-hydroxy-4-methyl-10,13-dioxo-2,3,9,10,13,15-hexahydro-1H,12H-benzo[de]pyrano[3 ',4': 6,7]indolizino[1,2-b]quinolin-1-yl)amino)-2-oxoethoxy)methyl)amino)-2-oxoethoxy)-3-phenylpropanamide 18j Compound 18i (12 mg, 10.9 μmol) was dissolved in 0.6 mL of dichloromethane, and 0.3 mL of diethylamine was added. The reaction mixture was stirred at room temperature for 1.5 h and concentrated under reduced pressure. 2 mL of toluene was added, followed by concentration under reduced pressure; the procedures were repeated twice. The residue was slurried with 3 mL of n-hexane, and the upper n-hexane layer was removed; the procedures were repeated three times. The slurry was concentrated under reduced pressure to give the crude title product 18j (10 mg), which was directly used in the next step without purification.

MS m/z (ESI): 881.0 [M+1].

Step 10

(1r,4r)-N-((2R,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15,18-hexaoxo-3,20,23,26,29,32,35,38,41,44-decaoxa-5,8,11,14,17-pentaaza-tetrahexadec yl)-4-((2,5-dioxo-2,5-dihydro-1H-pyrrol-1-yl)methyl)cyclohexane-1-carboxamide 18

Crude 18j (10 mg) was dissolved in 1 mL of N,N-dimethylformamide, and compound 17g (8.5 mg, 12.3 μmol) and 4-(4,6-dimethoxy-1,3,5-triazin-2-yl)-4-methylmorpholinium chloride (4.6 mg, 16.6 μmol) were added. The reaction mixture was stirred at room temperature for 30 min and filtered. The filtrate was purified by high performance liquid chromatography (separation conditions: chromatography column: XBridge Prep C18 OBD 5 μm 19×250 mm; mobile phase: A-water (10 mmol of $NH_4OAc$), B-acetonitrile, gradient elution, flow rate: 18 mL/min). The corresponding fractions were collected and concentrated under reduced pressure to give the title product 18 (9.5 mg, 56.2% yield).

MS m/z (ESI): 1570.2 [M+18].

$^1H$ NMR (400 MHz, DMSO-$d_6$): δ 8.77 (d, 1H), 8.59-8.55 (m, 1H), 8.42 (d, 1H), 8.37-8.28 (m, 1H), 8.25-8.06 (m, 2H), 7.96-7.86 (m, 1H), 7.86-7.70 (m, 2H), 7.32-7.28 (m, 1H), 7.25-7.14 (m, 3H), 6.67 (m, 1H), 5.96 (s, 1H), 5.80-5.72 (m, 1H), 5.62-5.52 (m, 2H), 5.43-5.30 (m, 3H), 5.28-5.17 (m, 2H), 5.12-5.08 (m, 1H), 4.72-4.35 (m, 8H), 3.95-3.70 (m, 13H), 3.35-3.22 (m, 14H), 2.42-2.32 (m, 3H), 2.05-1.98 (m, 4H), 1.88-1.82 (m, 12H), 1.47-1.39 (m, 3H), 1.32-1.18 (m, 11H), 0.90-0.80 (m, 4H), 0.52-0.37 (m, 3H), 0.32-0.18 (m, 2H).

Example 1-19
(1r,4r)-N-((2S,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15,18-hexaoxo-3,20,23,26,29,32,35,38,41,44-decaoxa-5,8,11,14,17-pentaazatetrahexadec-46-yl)-4-((2,5-dioxo-2,5-dihydro-1H-pyrrol-1-yl)methyl)cyclohexane-1-carboxamide 19
19
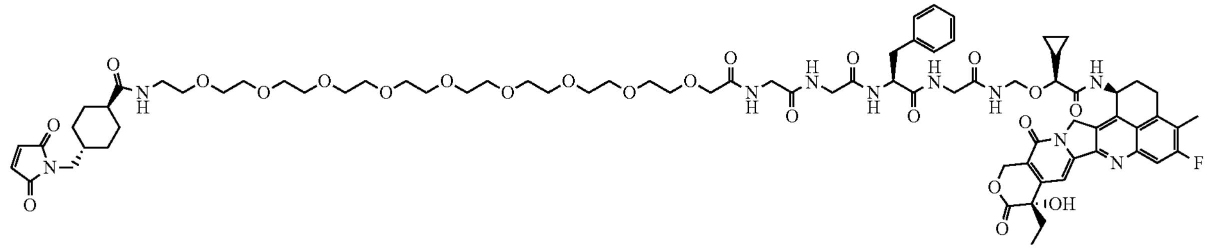
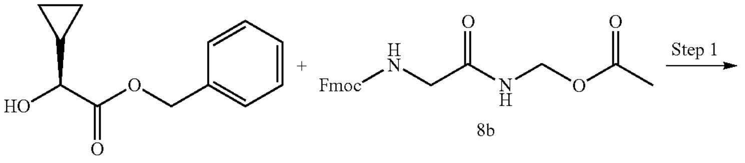
18b
8b
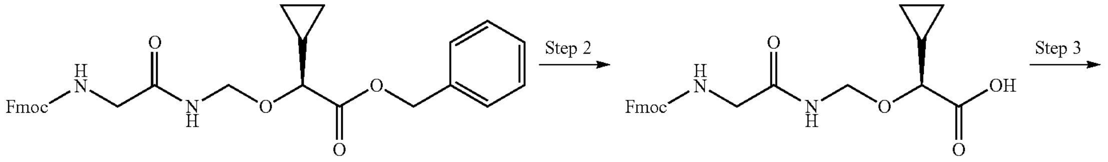
19a
19b
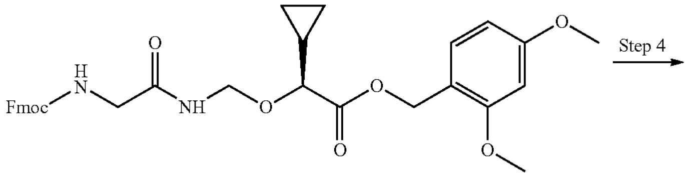
19c
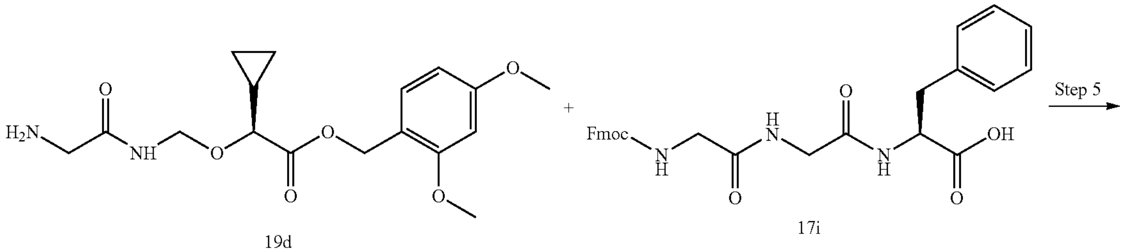
19d
17i
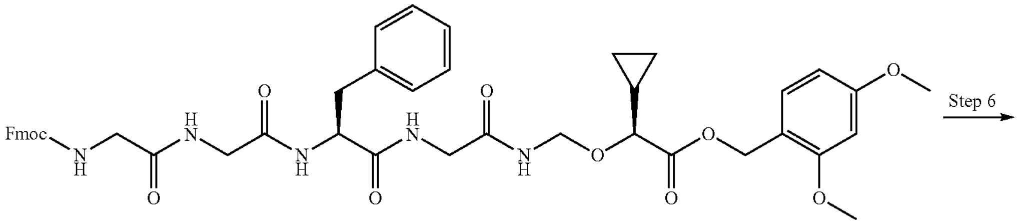
19e -continued
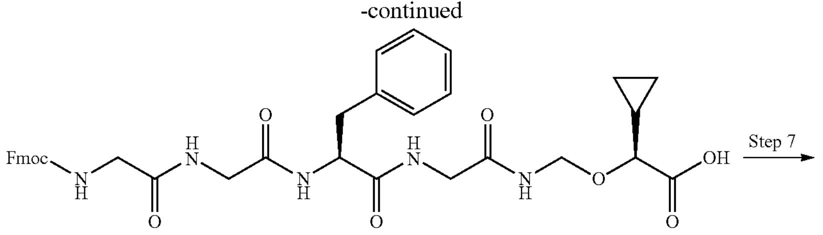
19f
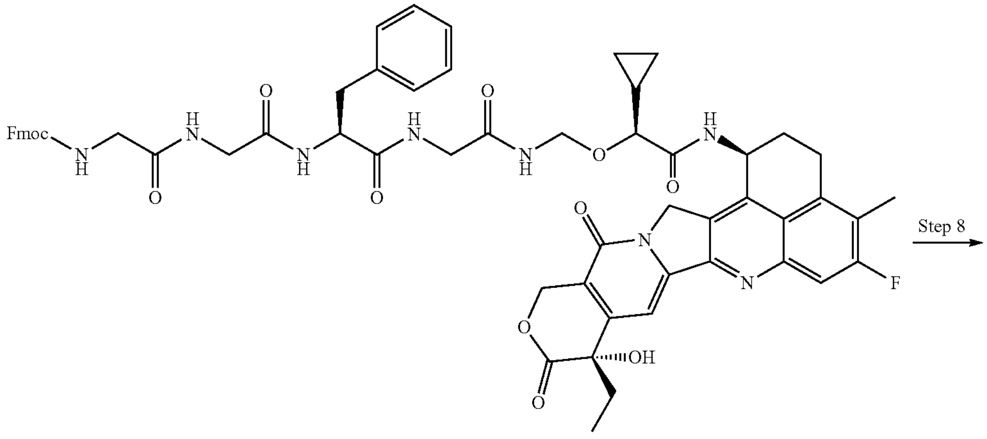
19g
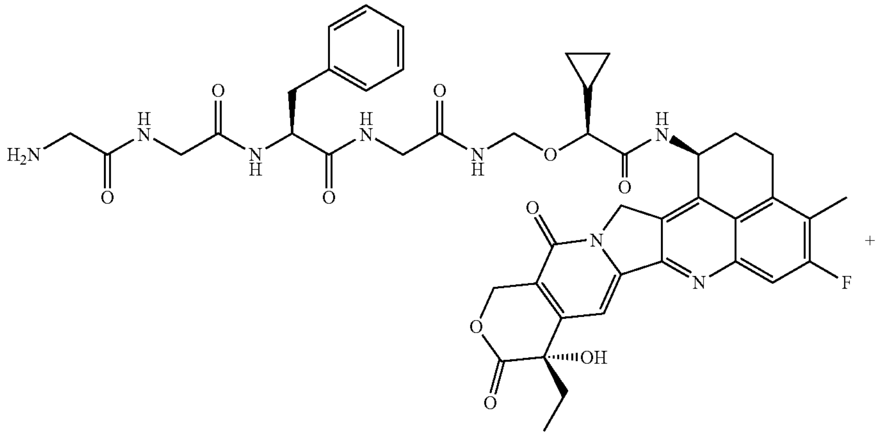
19h
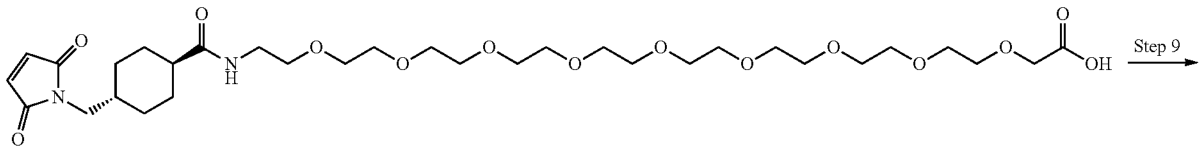
17g
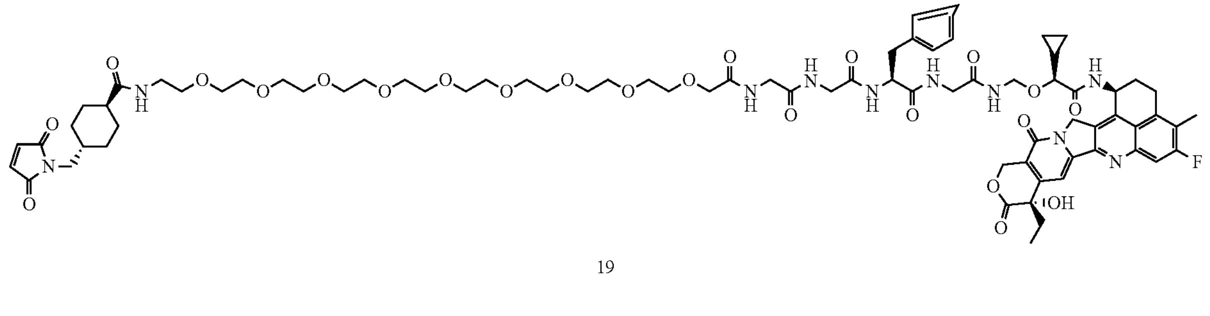
19

Step 1

Benzyl (S)-10-cyclopropyl-1-(9H-fluoren-9-yl)-3,6-di oxo-2,9-di oxa-4,7-diazaundecan-11-oate 19a Compound 18b (252 mg, 1.22 mmol) was added to a reaction flask, and 4 mL of dichloromethane was added. The system was purged with argon three times, and the mixture was cooled to 0-5° C. in an ice water bath, followed by addition of lithium tert-butoxide (98 mg, 1.22 mmol). The reaction mixture was stirred in the ice water bath for 15 min and became clear, and 8b (300 mg, 814.3 μmol) was added. The reaction mixture was stirred in the ice-water bath for 2.5 h. Water (10 mL) was added for liquid separation. The aqueous phase was extracted with dichloromethane (8 mL×2), and the organic phases were combined and washed with water (10 mL×1) and saturated brine (10 mL×2), dried over anhydrous sodium sulfate, and filtered and concentrated to give the crude product. The resulting residue was purified by silica gel column chromatography with developing solvent system C to give the title product 19a (282 mg, 67.2% yield).

Step 2

(S)-10-cyclopropyl-1-(9H-fluoren-9-yl)-3,6-dioxo-2,9-dioxa-4,7-diazaundecan-11-oic acid 19b Compound 19a (280 mg, 0.554 mmol) was dissolved in 8 mL of ethyl acetate, and palladium on carbon (84 mg, 10% loading, dry basis) was added. The system was purged with hydrogen three times, and the reaction mixture was stirred at room temperature for 3 h and filtered through celite, and the filter cake was rinsed with ethyl acetate. The filtrate was concentrated to give the crude title product 19b (230 mg), which was directly used in the next step without purification.

Step 3

2,4-Dimethoxybenzyl(S)-10-cyclopropyl-1-(9H-fluoren-9-yl)-3,6-dioxo-2,9-dioxa-4,7-diazaundecan-11-oate 19c Crude 19b (230 mg, 541.8 μmol) was dissolved in 7 mL of dichloromethane, and 2,4-dimethoxybenzyl alcohol (136.7 mg, 812.7 μmol), 1-ethyl-(3-dimethylaminopropyl) carbonyldiimine hydrochloride (155 mg, 808.5 μmol) and 4-dimethylaminopyridine (6.6 mg, 53.5 μmol) were added successively. The reaction mixture was stirred at room temperature for 16 h, diluted with 10 mL of dichloromethane, washed with water (10 mL×1) and saturated brine (10 mL×2), dried over anhydrous sodium sulfate, and filtered and concentrated to give the crude product. The resulting residue was purified by thin layer chromatography with developing solvent system B to give the title product 19c (159 mg, 51.0% yield).

Step 4

2,4-Dimethoxybenzyl(S)-2-((2-aminoacetylamino) methoxy)-2-cyclopropyl acetate 19d Compound 19c (60 mg, 104.4 μmol) was dissolved in 1 mL of dichloromethane, and 0.5 mL of diethylamine was added. The reaction mixture was stirred at room temperature for 1 h and concentrated under reduced pressure. 2 mL of toluene was added, followed by concentration under reduced pressure; the procedures were repeated twice. The residue was slurried with 3 mL of n-hexane, and the upper n-hexane layer was removed; the procedures were repeated three times. The slurry was concentrated under reduced pressure to give the crude title product 19d (21 mg), which was directly used in the next step without purification.

Step 5

2,4-Dimethoxybenzyl (11S,19S)-11-benzyl-19-cyclopropyl-1-(9H-fluoren-9-yl)-3,6,9,12,15-pentaoxo-2,18-dioxa-4,7,10,13,16-pentaazaeicosa-20-oate 19e Crude 19d (36 mg, 102.2 μmol) was dissolved in 4 mL of N,N-dimethylformamide, and compound 17i (52 mg, 103.6 μmol) and 4-(4,6-dimethoxy-1,3,5-triazin-2-yl)-4-methylmorpholinium chloride (34.6 mg, 125.0 μmol) were added. The reaction mixture was stirred at room temperature for 1 h. 10 mL of water was added, followed by extraction with ethyl acetate (10 mL×3). The organic phases were combined, washed with saturated sodium chloride solution (10 mL×2), dried over anhydrous sodium sulfate, and filtered. The filtrate was concentrated under reduced pressure. The resulting residue was purified by thin layer chromatography with developing solvent system B to give the title product 19e (70 mg, 80.2% yield).

Step 6

(11S,19S)-11-benzyl-19-cyclopropyl-1-(9H-fluoren-9-yl)-3,6,9,12,15-pentaoxo-2,18-dioxa-4,7,10,13,16-pentaazaeicosa-20-oic acid 19f Compound 19e (70 mg, 83.7 μmol) was dissolved in 2.5 mL of a 3% (v/v) solution of dichloroacetic acid in dichloromethane, and the solution was cooled to 0-5° C. in an ice-water bath, followed by addition of triethylsilane (29 mg, 249.4 μmol). The reaction mixture was stirred in the ice bath for 3 h. The reaction mixture was concentrated under reduced pressure in an ice bath to remove half of the organic solvent, and 5 mL of diethyl ether was added. The resulting mixture was warmed to room temperature naturally and slurried to precipitate a white solid, and filtered. The filter cake was collected and dried with an oil pump to give the title product 19f (57 mg, 99.2% yield).

Step 7

(9H-fluoren-9-yl)methyl((2S,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadec-16-yl)carbamate 19g Compound 1b (30 mg, 63.6 μmol) was added to a reaction flask, and 1 mL of a 10% (v/v) solution of methanol in dichloromethane was added. The system was purged with argon three times, and the mixture was cooled to 0-5° C. in an ice-water bath, followed by addition of a drop of triethylamine. The mixture was stirred until compound 1 b was dissolved. Compound 19f (57 mg, 83.1 μmol) was dissolved in 1 mL of a 10% (v/v) solution of methanol in dichloromethane, and then the above reaction mixture was added dropwise, followed by addition of 4-(4,6-dimethoxy-1,3,5-triazin-2-yl)-4-methylmorpholinium chloride (26 mg, 93.9 μmol). The reaction mixture was warmed to room temperature and stirred for 1 h. 10 mL of dichloromethane and 5 mL of water were added, and the resulting mixture was stirred for 5 min, and let stand to form layers. The organic phase was collected, and the aqueous phase was extracted with dichloromethane (10 mL×3). The organic phases were combined, washed with saturated sodium chloride solution (10 mL×2), dried over anhydrous sodium sulfate, and filtered. The filtrate was concentrated under reduced pressure. The resulting residue was purified by thin layer chromatography with developing solvent system B to give the title product 19g (56 mg, 79.8% yield).

MS m/z (ESI): 1103.1 [M+1].

Step 8

(S)-2-(2-(2-aminoacetylamino)acetylamino)-N-(2-((((S)-1-cyclopropyl-2-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-2-oxoethoxy)methyl)amino)-2-oxoethyl)-3-phenylpropanamide 19h Compound 19g (4.6 mg, 4.16 μmol) was dissolved in 1.5 mL of dichloromethane, and 0.75 mL of diethylamine was added. The reaction mixture was stirred at room temperature for 1.6 h and concentrated under reduced pressure. 2 mL of toluene was added, followed by concentration under reduced pressure; the procedures were repeated twice. The residue was slurried with 3 mL of n-hexane, and the upper n-hexane layer was removed; the procedures were repeated three times. The slurry was concentrated under reduced pressure to give the crude title product 19h (4.0 mg), which was directly used in the next step without purification.

Step 9

(1r,4r)-N-((2S,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15,18-hexaoxo-3,20,23,26,29,32,35,38,41,44-decaoxa-5,8,11,14,17-pentaazatetrahexadec-46-yl)-4-((2,5-dioxo-2,5-dihydro-1H-pyrrol-1-yl)methyl)cyclohexane-1-carboxamide 19

Crude 19h (4.0 mg) was dissolved in 1 mL of N,N-dimethylformamide, and compound 17g (2.9 mg, 4.2 μmol) and 4-(4,6-dimethoxy-1,3,5-triazin-2-yl)-4-methylmorpholinium chloride (1.5 mg, 5.4 μmol) were added. The reaction mixture was stirred at room temperature for 40 min and filtered. The filtrate was purified by high performance liquid chromatography (separation conditions: chromatography column: XBridge Prep C18 OBD 5 μm 19×250 mm; mobile phase: A-water (10 mmol of $NH_4OAc$), B-acetonitrile, gradient elution, flow rate: 18 mL/min). The corresponding fractions were collected and concentrated under reduced pressure to give the title product 19 (2.1 mg, 32.4% yield).

$^1H$ NMR (400 MHz, DMSO-$d_6$): δ 8.71-8.62 (m, 1H), 8.59-8.51 (m, 1H), 8.34-8.26 (m, 1H), 8.14-8.02 (m, 2H), 7.95-7.86 (m, 1H), 7.83-7.69 (m, 2H), 7.35-7.31 (m, 1H), 7.29-7.11 (m, 3H), 7.01 (s, 1H), 6.72-6.50 (m, 3H), 5.59-5.50 (m, 2H), 5.42 (s, 2H), 5.38-5.18 (m, 3H), 4.79-4.69 (m, 2H), 4.61-4.42 (m, 3H), 3.91 (s, 2H), 3.79-3.65 (m, 4H), 3.63-3.44 (m, 13H), 3.41-3.30 (m, 2H), 3.26-3.09 (m, 5H), 3.08-2.84 (m, 4H), 2.81-2.64 (m, 3H), 2.42-2.28 (m, 3H), 2.24-2.12 (m, 2H), 2.05-1.93 (m, 4H), 1.89-1.77 (m, 2H), 1.72-1.56 (m, 3H), 1.53-1.38 (m, 3H), 1.34-1.10 (m, 11H), 0.94-0.78 (m, 5H), 0.52-0.35 (m, 3H).

Example 1-20 (Reference Example)

20

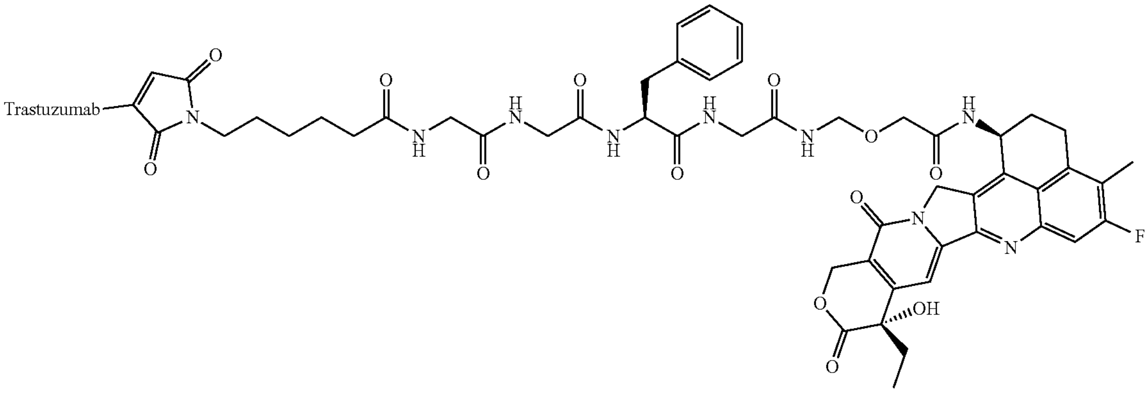

The title compound 20 was prepared as disclosed in "Example 58 on page 163 of the specification of Patent CN104755494A".

The following antibodies can be prepared using a conventional preparation method for antibodies, and can be obtained by, for example, vector construction, transfection of eukaryotic cells such as HEK293 cells (Life Technologies Cat. No. 11625019), and expression purification.

The following is the sequence of trastuzumab:

Light chain

SEQ ID NO: 1

DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Heavy chain

SEQ ID NO: 2

EVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSR

WGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK

The following is the sequence of pertuzumab:

Light chain

SEQ ID NO: 3

DIQMTQSPSSLSASVGDRVTITCKASQDVSIGVAWYQQKPGKAPKLLIY

SASYRYTGVPSRFSGSGSGTDFTLTISSLQPEDFATYYCQQYYIYPYTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Heavy chain

SEQ ID NO: 4

EVQLVESGGGLVQPGGSLRLSCAASGFTFTDYTMDWVRQAPGKGLEWVA

DVNPNSGGSIYNQRFKGRFTLSVDRSKNTLYLQMNSLRAEDTAVYYCAR

NLGPSFYFDYWGQGTLVTVSSASTKGPSVFPLAPSSKSTSGGTAALGCL

-continued

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQK

SLSLSPGK

The following is the sequence of B7H3 antibody 1F9DS:

Light chain

SEQ ID NO: 5

DTVVTQEPSFSVSPGGTVTLTCGLSSGSVSTSHYPSWYQQTPGQAPRML

IYNTNTRSSGVPDRFSGSILGNKAALTITGAQADDESDYYCAIHVDRDI

WVFGGGTKLTVLGQPKANPTVTLFPPSSEELQANKATLVCLISDFYPGA

VTVAWKADGSPVKAGVETTKPSKQSNNKYAASSYLSLTPEQWKSHRSYS

CQVTHEGSTVEKTVAPTEC

Heavy chain

SEQ ID NO: 6

QVQLVQSGGGVVQPGTSLRLSCAASGFIFSSSAMHWVRQAPGKGLEWVA

VISYDGSNKYYVDSVKGRFTISRDNSKNTLYLQMNSLRAEDTAVYYCAR

SARLYASFDYWGQGALVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

Example 1-21. ADC-1

FADC-1

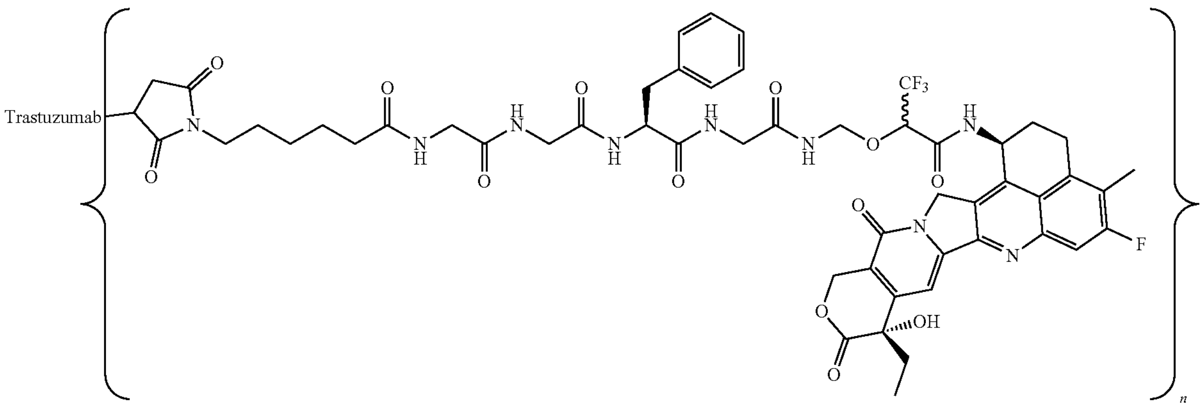

To antibody trastuzumab in aqueous PBS buffer (0.05 M aqueous PBS buffer at pH 6.5, 2.5 mL, 9.96 mg/mL, 0.168 μmol) was added at 37° C. a prepared aqueous solution of tris(2-carboxyethyl)phosphine (10 mM, 0.082 mL, 0.82 μmol). The reaction mixture was shaken on a water bath shaker at 37° C. for 3 h before the reaction was terminated. The reaction mixture was cooled to 25° C. in a water bath and diluted to 5.0 mg/mL, and 2.0 mL of the solution was collected for use in the next step.

Compound 10-shorter retention time compound (2.1 mg, 2.02 μmol) was dissolved in 0.10 mL of DMSO, and the solution was added to the above 2.0 mL of the solution. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-1 of FADC-1 general formula in PBS buffer (5.0 mg/mL, 1.1 mL), which was then stored at 4° C.

Mean calculated by UV-HPLC: n=5.09.

Example 1-22. ADC-2

FADC-1

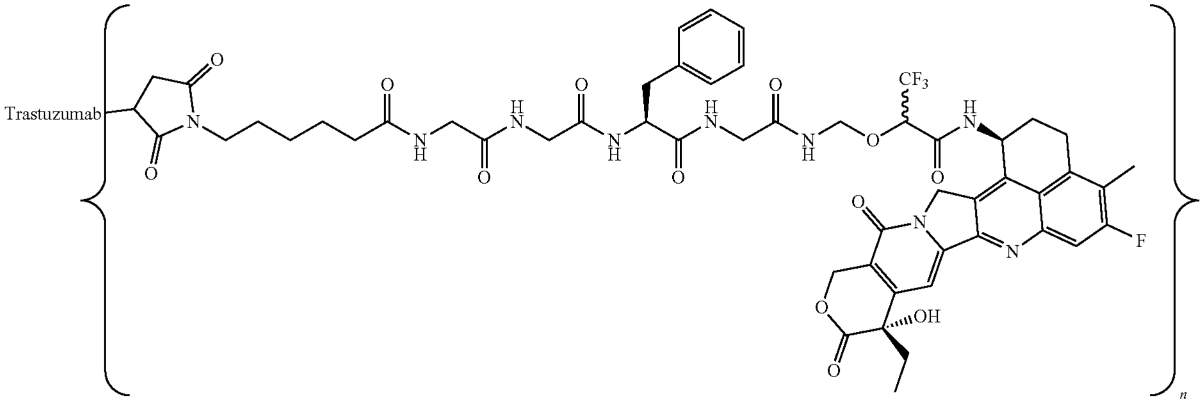

To antibody trastuzumab in aqueous PBS buffer (0.05 M aqueous PBS buffer at pH 6.5, 2.5 mL, 9.96 mg/mL, 0.168 μmol) was added at 37° C. a prepared aqueous solution of tris(2-carboxyethyl)phosphine (10 mM, 0.082 mL, 0.82 μmol). The reaction mixture was shaken on a water bath shaker at 37° C. for 3 h before the reaction was terminated. The reaction mixture was cooled to 25° C. in a water bath and diluted to 5.0 mg/mL, and 2.0 mL of the solution was collected for use in the next step.

Compound 10-longer retention time compound (2.1 mg, 2.02 μmol) was dissolved in 0.10 mL of DMSO, and the solution was added to the above 2.0 mL of the solution. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-2 of FADC-1 general formula in PBS buffer (4.95 mg/mL, 1.1 mL), which was then stored at 4° C.

Mean calculated by UV-HPLC: n=7.39.

Example 1-23. ADC-3

FADC-3

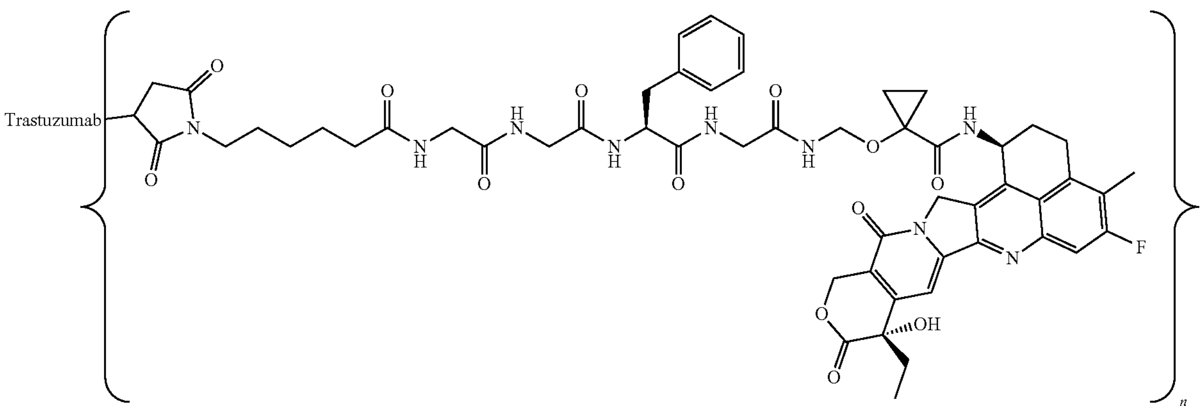

To antibody trastuzumab in aqueous PBS buffer (0.05 M aqueous PBS buffer at pH 6.5, 2.5 mL, 9.96 mg/mL, 0.168 μmol) was added at 37° C. a prepared aqueous solution of tris(2-carboxyethyl)phosphine (10 mM, 0.082 mL, 0.82 μmol). The reaction mixture was shaken on a water bath shaker at 37° C. for 3 h before the reaction was terminated. The reaction mixture was cooled to 25° C. in a water bath and diluted to 5.0 mg/mL, and 2.0 mL of the solution was collected for use in the next step.

Compound 8 (2.1 mg, 2.02 μmol) was dissolved in 0.10 mL of DMSO, and the solution was added to the above 2.0 mL of the solution. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-3 of FADC-3 general formula in PBS buffer (5.24 mg/mL, 1.1 mL), which was then stored at 4° C.

Mean calculated by UV-HPLC: n=7.36.

Example 1-24. ADC-4

FADC-4A

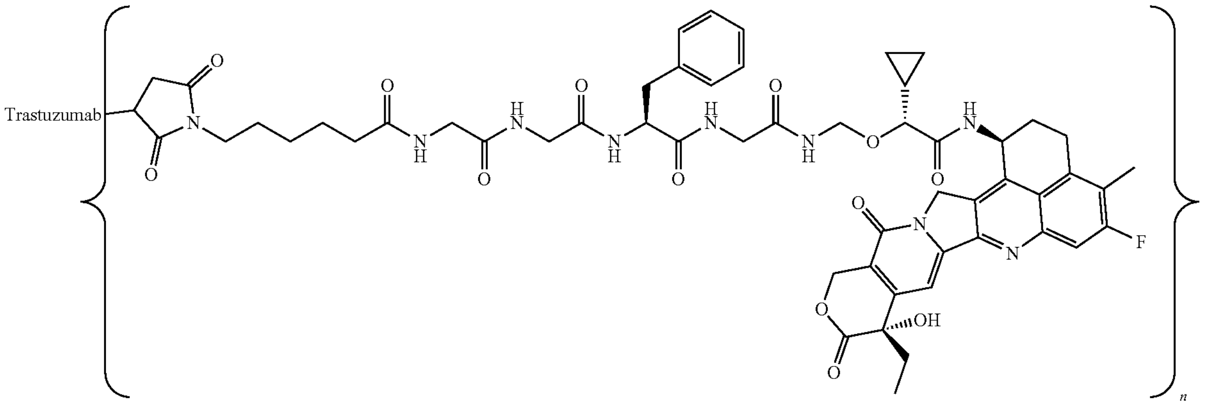

To antibody trastuzumab in aqueous PBS buffer (0.05 M aqueous PBS buffer at pH 6.5, 3.74 mL, 13.38 mg/mL, 0.338 μmol) was added at 37° C. a prepared aqueous solution of tris(2-carboxyethyl)phosphine (10 mM, 0.173 mL, 1.73 μmol). The reaction mixture was shaken on a water bath shaker at 37° C. for 3 h before the reaction was terminated. The reaction mixture was cooled to 25° C. in a water bath and diluted to 6.7 mg/mL, and 1.3 mL of the solution was collected for use in the next step.

Compound 9-shorter retention time compound 9-A (1.0 mg, 0.93 μmol) was dissolved in 0.10 mL of DMSO, and the solution was added to the above 1.3 mL of the solution. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-4 of FADC-4A general formula in PBS buffer (1.72 mg/mL, 2.36 mL), which was then stored at 4° C.

Mean calculated by UV-HPLC: n=7.39.

Example 1-25. ADC-5

FADC-4A

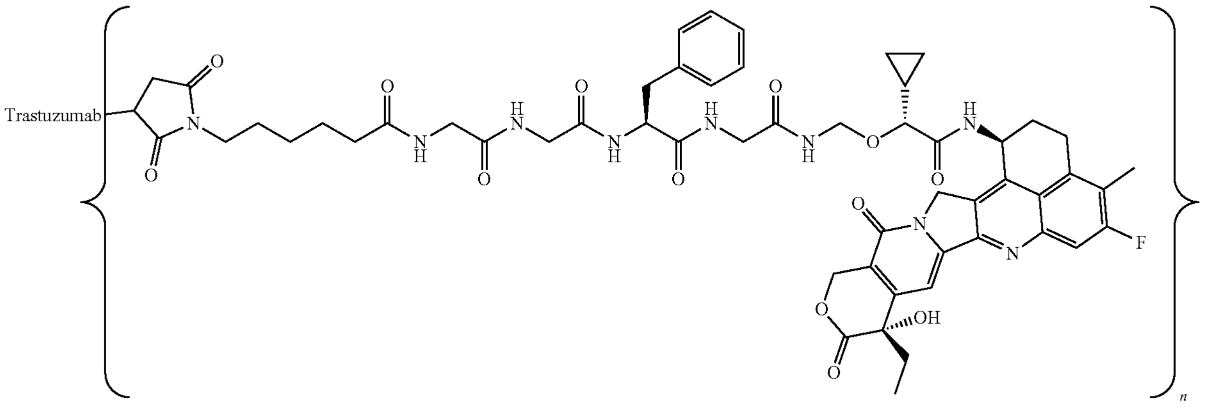

To antibody trastuzumab in aqueous PBS buffer (0.05 M aqueous PBS buffer at pH 6.5, 3.0 mL, 6.70 mg/mL, 0.136 μmol) was added at 37° C. a prepared aqueous solution of tris(2-carboxyethyl)phosphine (10 mM, 0.067 mL, 0.67 μmol). The reaction mixture was shaken on a water bath shaker at 37° C. for 3 h before the reaction was terminated. The reaction mixture was cooled to 25° C. in a water bath, and 0.614 mL of the solution was collected for use in the next step.

Compound 9-shorter retention time compound 9-A (0.5 mg, 0.42 μmol) was dissolved in 0.031 mL of DMSO, and the solution was added to the above 0.614 mL of the solution. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-5 of FADC-4A general formula in PBS buffer (3.08 mg/mL, 0.82 mL), which was then stored at 4° C.

Mean calculated by UV-HPLC: n=3.16.

Example 1-26. ADC-6

FADC-4B

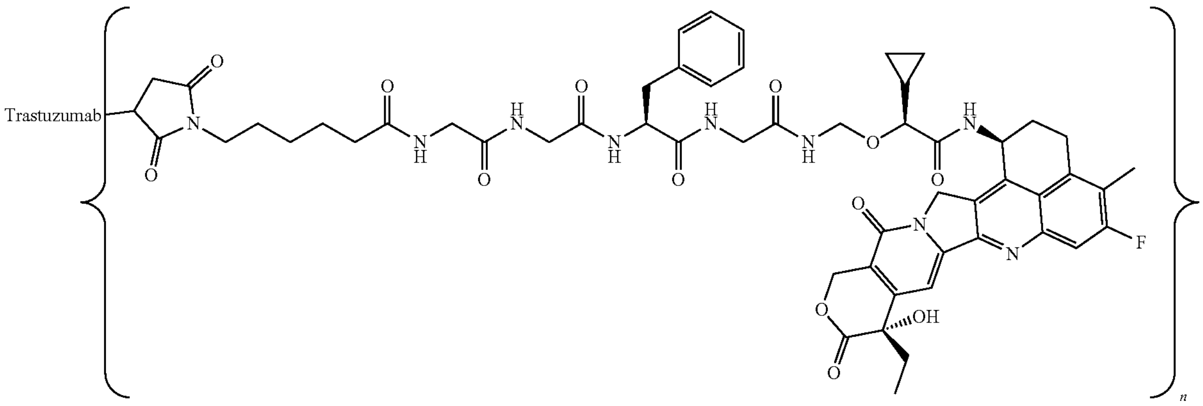

To antibody trastuzumab in aqueous PBS buffer (0.05 M aqueous PBS buffer at pH 6.5, 3.74 mL, 13.38 mg/mL, 0.338 μmol) was added at 37° C. a prepared aqueous solution of tris(2-carboxyethyl)phosphine (10 mM, 0.173 mL, 1.73 μmol). The reaction mixture was shaken on a water bath shaker at 37° C. for 3 h before the reaction was terminated. The reaction mixture was cooled to 25° C. in a water bath and diluted to 6.7 mg/mL, and 0.75 mL of the solution was collected for use in the next step.

Compound 9-longer retention time compound 9-B (0.68 mg, 0.63 μmol) was dissolved in 0.10 mL of DMSO, and the solution was added to the above 0.75 mL of the solution. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-6 of FADC-4B general formula in PBS buffer (1.78 mg/mL, 1.78 mL), which was then stored at 4° C.

Mean calculated by UV-HPLC: n=3.94.

Example 1-27. ADC-7

FADC-7

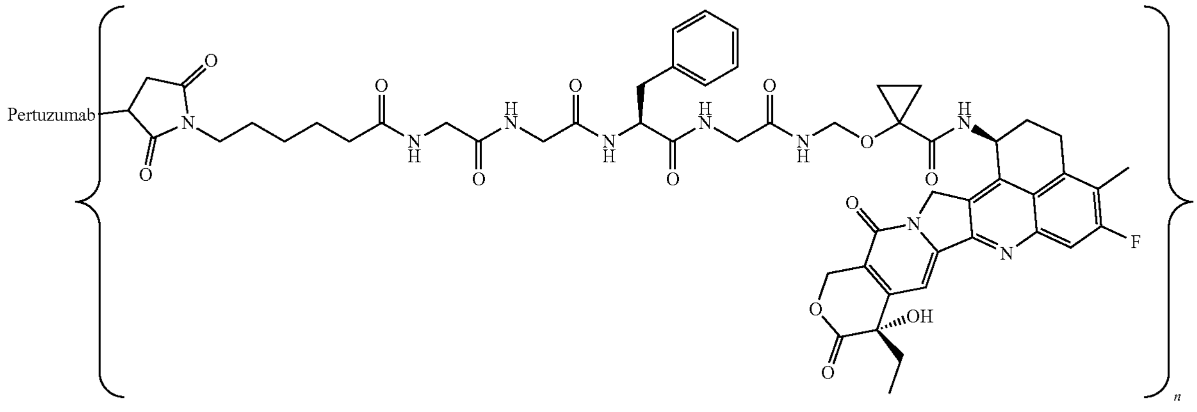

To antibody pertuzumab in aqueous PBS buffer (0.05 M aqueous PBS buffer at pH 6.5, 5.0 mL, 10 mg/mL, 0.338 μmol) was added at 37° C. a prepared aqueous solution of tris(2-carboxyethyl)phosphine (10 mM, 0.173 mL, 1.73 μmol). The reaction mixture was shaken on a water bath shaker at 37° C. for 3 h before the reaction was terminated. The reaction mixture was cooled to 25° C. in a water bath and diluted to 5.0 mg/mL, and 1.0 mL of the solution was collected for use in the next step.

Compound 8 (0.65 mg, 0.6 μmol) was dissolved in 0.1 mL of DMSO, and the solution was added to the above 1.0 mL of the solution. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-7 of FADC-7 general formula in PBS buffer (1.42 mg/mL, 2.15 mL), which was then stored at 4° C.

Mean calculated by UV-HPLC: n=6.91.

Example 1-28. ADC-8

FADC-8

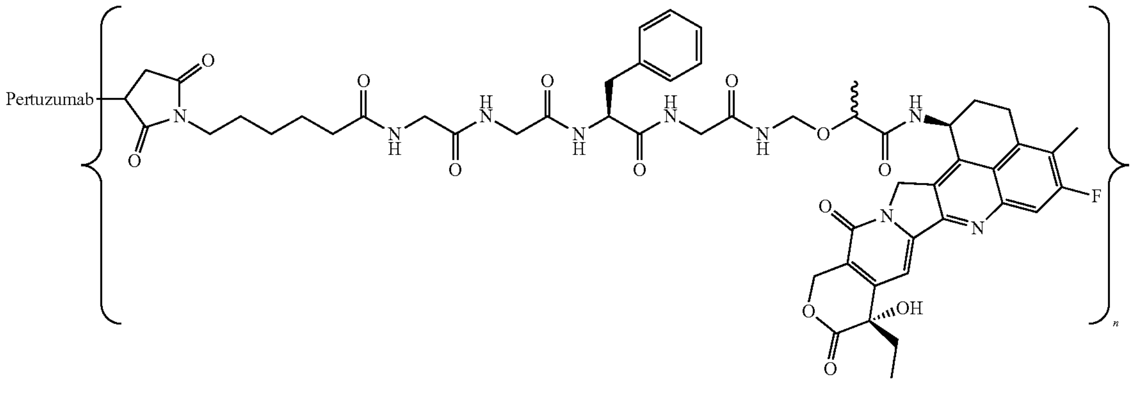

To antibody pertuzumab in aqueous PBS buffer (0.05 M aqueous PBS buffer at pH 6.5, 5.0 mL, 10 mg/mL, 0.338 μmol) was added at 37° C. a prepared aqueous solution of tris(2-carboxyethyl)phosphine (10 mM, 0.173 mL, 1.73 μmol). The reaction mixture was shaken on a water bath shaker at 37° C. for 3 h before the reaction was terminated. The reaction mixture was cooled to 25° C. in a water bath and diluted to 5.0 mg/mL, and 1.6 mL of the solution was collected for use in the next step.

Compound 10-shorter retention time compound (1.04 mg, 1.0 μmol) was dissolved in 0.1 mL of DMSO, and the solution was added to the above 1.6 mL of the solution. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-8 of FADC-8 general formula in PBS buffer (2.14 mg/mL, 2.31 mL), which was then stored at 4° C.

Mean calculated by UV-HPLC: n=6.58.

Example 1-29. ADC-9

FADC-9A

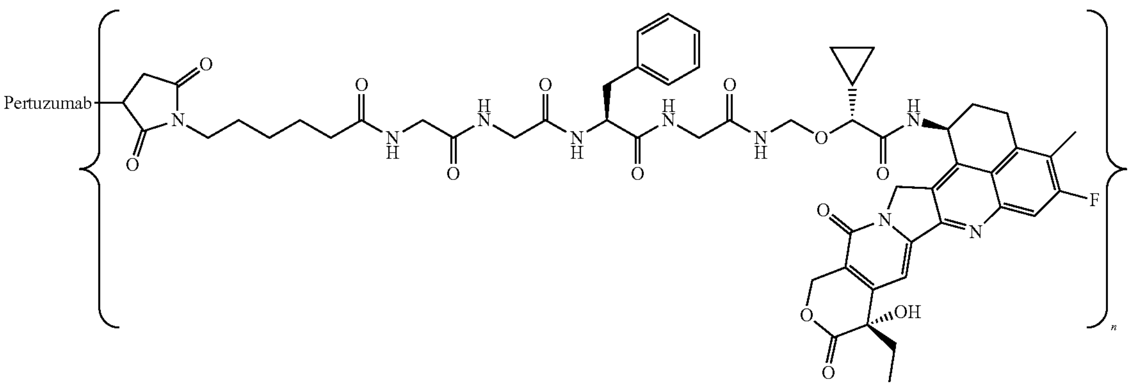

To antibody pertuzumab in aqueous PBS buffer (0.05 M aqueous PBS buffer at pH 6.5, 5.0 mL, 10 mg/mL, 0.338 μmol) was added at 37° C. a prepared aqueous solution of tris(2-carboxyethyl)phosphine (10 mM, 0.173 mL, 1.73 μmol). The reaction mixture was shaken on a water bath shaker at 37° C. for 3 h before the reaction was terminated. The reaction mixture was cooled to 25° C. in a water bath and diluted to 5.0 mg/mL, and 0.8 mL of the solution was collected for use in the next step.

Compound 9-shorter retention time compound 9-A (0.55 mg, 0.5 μmol) was dissolved in 0.1 mL of DMSO, and the solution was added to the above 0.8 mL of the solution. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-9 of FADC-9A general formula in PBS buffer (2.27 mg/mL, 1.11 mL), which was then stored at 4° C.

Mean calculated by UV-HPLC: n=3.16.

Example 1-30. ADC-10

FADC-10

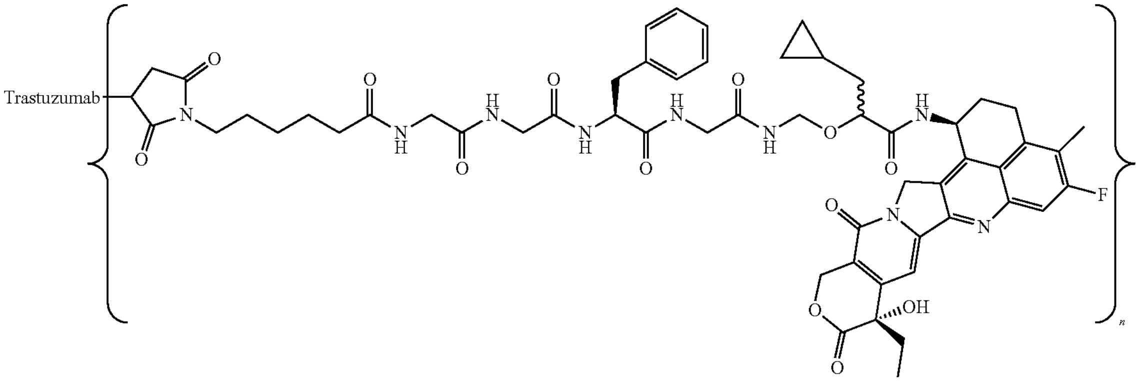

To antibody trastuzumab in aqueous PBS buffer (0.05 M aqueous PBS buffer at pH 6.5, 10.0 mg/mL, 0.574 mL, 38.78 nmol) was added at 37° C. a prepared aqueous solution of tris(2-carboxyethyl)phosphine (TCEP) (10 mM, 19.76 μL, 197.6 nmol). The reaction mixture was shaken on a water bath shaker at 37° C. for 3 h before the reaction was terminated. The reaction mixture was cooled to 25° C. in a water bath.

Compound 14-shorter retention time compound (0.64 mg, 588 nmol) was dissolved in 40 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-10 of FADC-10 general formula in PBS buffer (5.48 mg/mL, 1.03 mL), which was then stored at 4° C.

Mean calculated by UV-Vis: n=6.25.

Example 1-31. ADC-11

FADC-10

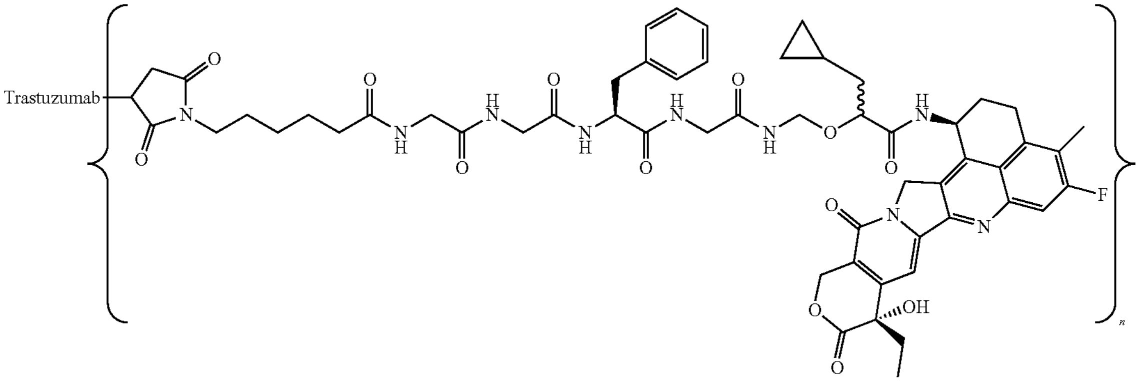

To antibody trastuzumab in aqueous PBS buffer (0.05 M aqueous PBS buffer at pH 6.5, 10.0 mg/mL, 0.646 mL, 43.64 nmol) was added at 37° C. a prepared aqueous solution of tris(2-carboxyethyl)phosphine (TCEP) (10 mM, 22.24 μL, 222.4 nmol). The reaction mixture was shaken on a water bath shaker at 37° C. for 3 h before the reaction was terminated. The reaction mixture was cooled to 25° C. in a water bath.

Compound 14-longer retention time compound (0.72 mg, 662 nmol) was dissolved in 40 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-11 of FADC-10 general formula in PBS buffer (2.13 mg/mL, 1.87 mL), which was then stored at 4° C.

Mean calculated by UV-Vis: n=7.03.

Example 1-32. ADC-12

FADC-12

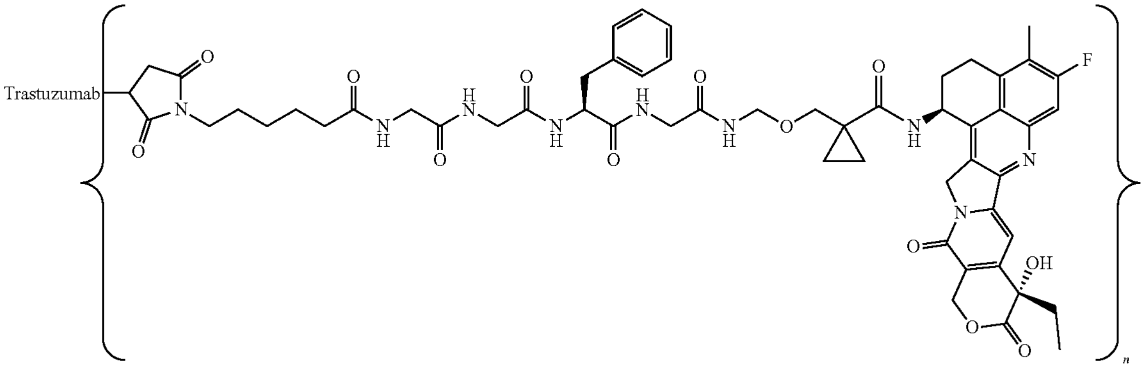

To antibody trastuzumab in aqueous PBS buffer (0.05 M aqueous PBS buffer at pH 6.5, 10.0 mg/mL, 0.726 mL, 49.05 nmol) was added at 37° C. a prepared aqueous solution of tris(2-carboxyethyl)phosphine (TCEP) (10 mM, 25.0 μL, 250.0 nmol). The reaction mixture was shaken on a water bath shaker at 37° C. for 3 h before the reaction was terminated. The reaction mixture was cooled to 25° C. in a water bath.

Compound 15 (0.81 mg, 754 nmol) was dissolved in 40 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-12 of FADC-12 general formula in PBS buffer (3.34 mg/mL, 1.45 mL), which was then stored at 4° C.

Mean calculated by UV-Vis: n=6.93.

Example 1-33. ADC-13

FADC-13

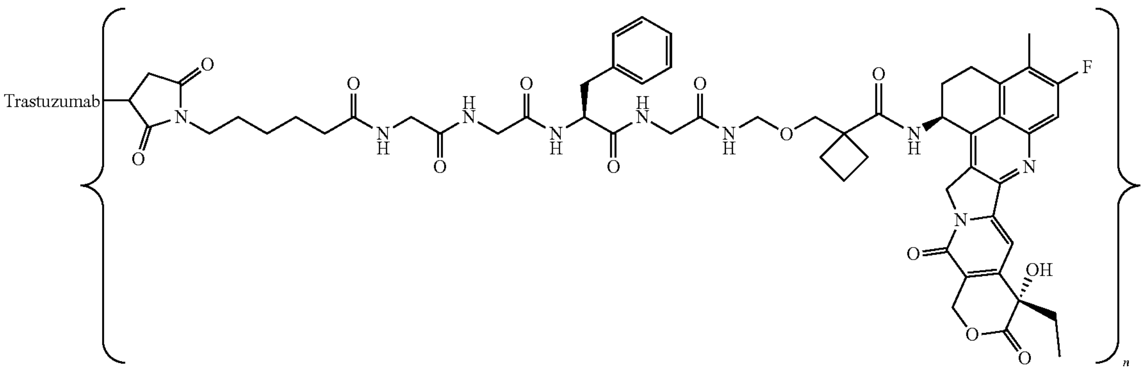

To antibody trastuzumab in aqueous PBS buffer (0.05 M aqueous PBS buffer at pH 6.5, 10.0 mg/mL, 0.287 mL, 19.39 nmol) was added at 37° C. a prepared aqueous solution of tris(2-carboxyethyl)phosphine (TCEP) (10 mM, 9.88 μL, 98.8 nmol). The reaction mixture was shaken on a water bath shaker at 37° C. for 3 h before the reaction was terminated. The reaction mixture was cooled to 25° C. in a water bath.

Compound 16 (0.32 mg, 294 nmol) was dissolved in 20 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-13 of FADC-13 general formula in PBS buffer (2.37 mg/mL, 0.88 mL), which was then stored at 4° C.

Mean calculated by UV-Vis: n=6.53.

Example 1-34. ADC-14

FADC-14

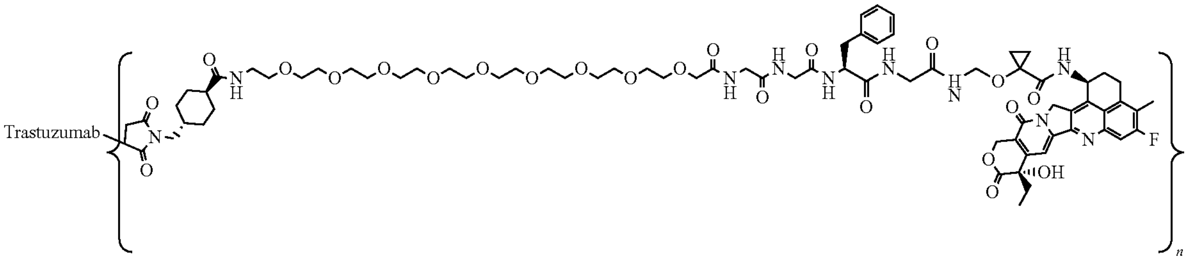

To antibody trastuzumab in aqueous PBS buffer (0.05 M aqueous PBS buffer at pH 6.5, 10.0 mg/mL, 0.592 mL, 40.0 nmol) was added at 37° C. a prepared aqueous solution of tris(2-carboxyethyl)phosphine (TCEP) (10 mM, 20.38 μL, 203.8 nmol). The reaction mixture was shaken on a water bath shaker at 37° C. for 3 h before the reaction was terminated. The reaction mixture was cooled to 25° C. in a water bath.

Compound 17 (0.92 mg, 598 nmol) was dissolved in 40 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-14 of FADC-14 general formula in PBS buffer (0.30 mg/mL, 12.0 mL), which was then stored at 4° C.

Mean calculated by UV-Vis: n=7.61.

Example 1-35. ADC-15

FADC-15

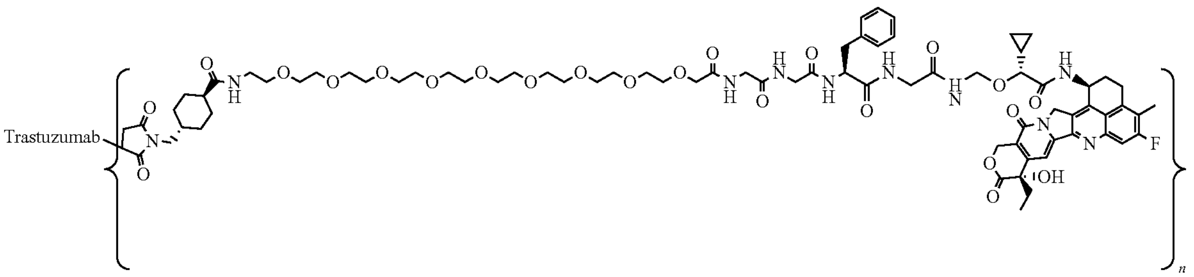

To antibody trastuzumab in aqueous PBS buffer (0.05 M aqueous PBS buffer at pH 6.5, 10.0 mg/mL, 0.592 mL, 40.0 nmol) was added at 37° C. a prepared aqueous solution of tris(2-carboxyethyl)phosphine (TCEP) (10 mM, 20.38 μL, 203.8 nmol). The reaction mixture was shaken on a water bath shaker at 37° C. for 3 h before the reaction was terminated. The reaction mixture was cooled to 25° C. in a water bath.

Compound 18 (0.93 mg, 599 nmol) was dissolved in 40 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-15 of FADC-15 general formula in PBS buffer (0.32 mg/mL, 11.8 mL), which was then stored at 4° C.

Mean calculated by UV-Vis: n=7.89.

Example 1-36. ADC-16

FADC-16

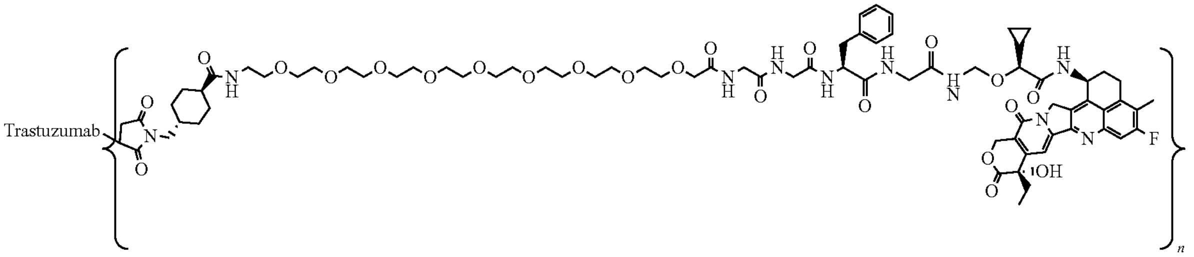

To antibody trastuzumab in aqueous PBS buffer (0.05 M aqueous PBS buffer at pH 6.5, 10.0 mg/mL, 0.53 mL, 35.8 nmol) was added at 37° C. a prepared aqueous solution of tris(2-carboxyethyl)phosphine (TCEP) (10 mM, 18.25 μL, 182.5 nmol). The reaction mixture was shaken on a water bath shaker at 37° C. for 3 h before the reaction was terminated. The reaction mixture was cooled to 25° C. in a water bath.

Compound 19 (0.83 mg, 534 nmol) was dissolved in 35 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-16 of FADC-16 general formula in PBS buffer (0.32 mg/mL, 12.0 mL), which was then stored at 4° C.

Mean calculated by UV-Vis: n=7.43.

Example 1-37. ADC-17

FADC-4A

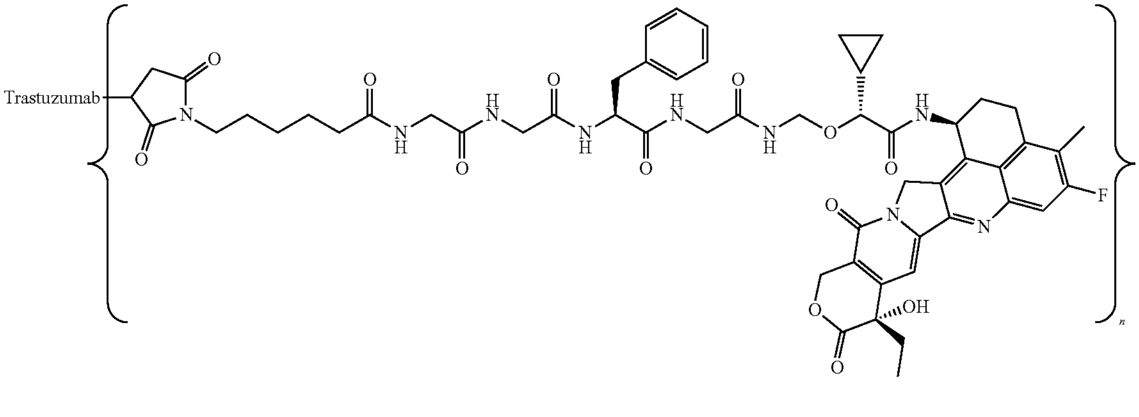

To antibody trastuzumab in aqueous PBS buffer (0.05 M aqueous PBS buffer at pH 6.5, 10.0 mg/mL, 2.0 mL, 135.12 nmol) was added at 37° C. a prepared aqueous solution of tris(2-carboxyethyl)phosphine (TCEP) (10 mM, 43.2 μL, 432 nmol). The reaction mixture was shaken on a water bath shaker at 37° C. for 3 h before the reaction was terminated. The reaction mixture was cooled to 25° C. in a water bath.

Compound 9-shorter retention time compound 9-A (2.22 mg, 2067 nmol) was dissolved in 175 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-17 of FADC-4A general formula in PBS buffer (1.32 mg/mL, 12.0 mL), which was then stored at 4° C.

Mean calculated by UV-Vis: n=5.42.

Example 1-38. ADC-18 (Reference Example)

FADC-18

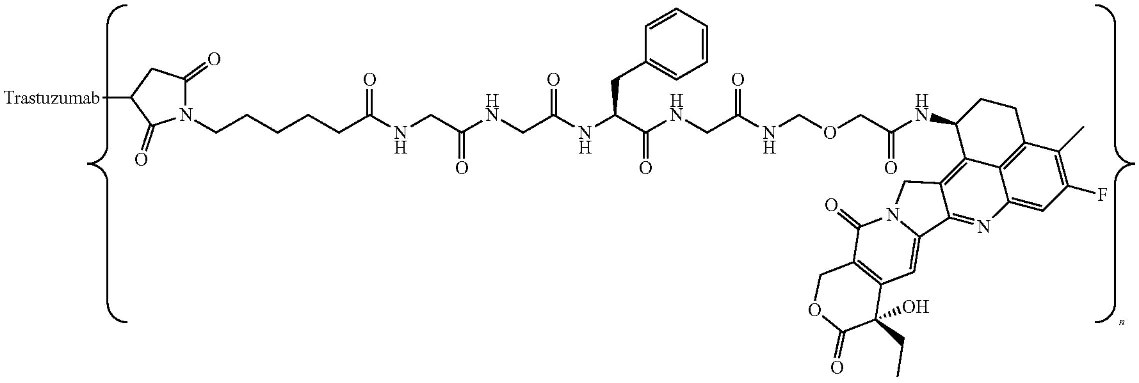

To antibody trastuzumab in aqueous PBS buffer (0.05 M aqueous PBS buffer at pH 6.5, 10.0 mg/mL, 1.5 mL, 101.3 nmol) was added at 37° C. a prepared aqueous solution of tris(2-carboxyethyl)phosphine (TCEP) (10 mM, 51.7 μL, 517 nmol). The reaction mixture was shaken on a water bath shaker at 37° C. for 3 h before the reaction was terminated. The reaction mixture was cooled to 25° C. in a water bath.

Compound 20 (2.0 mg, 1934 nmol) was dissolved in 100 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-18 of FADC-18 general formula in PBS buffer (0.79 mg/mL, 13.0 mL), which was then stored at 4° C.

Mean calculated by UV-Vis: n=7.23.

Example 1-39. ADC-19

FADC-4A

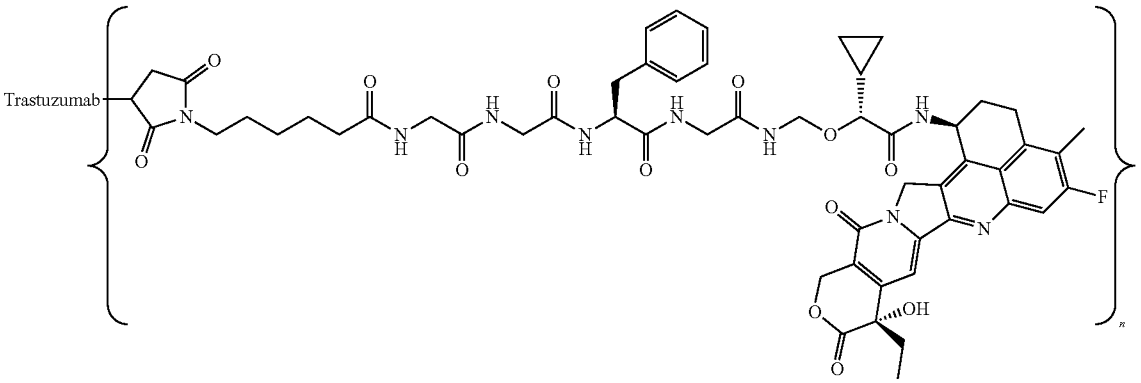

To antibody trastuzumab in aqueous PBS buffer (0.05 M aqueous PBS buffer at pH 6.5, 10.0 mg/mL, 1.36 mL, 91.9 nmol) was added at 37° C. a prepared aqueous solution of tris(2-carboxyethyl)phosphine (TCEP) (10 mM, 46.9 μL, 469 nmol). The reaction mixture was shaken on a water bath shaker at 37° C. for 3 h before the reaction was terminated. The reaction mixture was cooled to 25° C. in a water bath.

Compound 9-shorter retention time compound 9-A (2.0 mg, 1862 nmol) was dissolved in 100 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-19 of FADC-4A general formula in PBS buffer (0.73 mg/mL, 13.0 mL), which was then stored at 4° C.

Mean calculated by UV-Vis: n=6.26.

Example 1-40. ADC-20

FADC-1

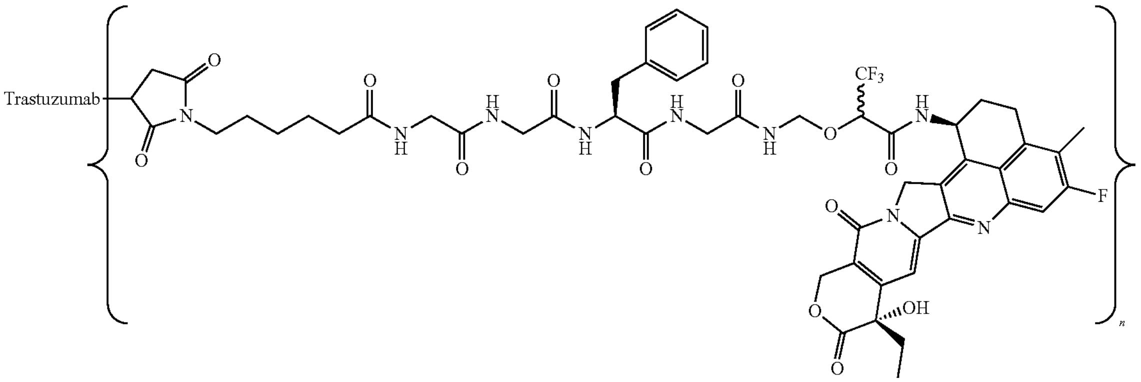

To antibody trastuzumab in aqueous PBS buffer (0.05 M aqueous PBS buffer at pH 6.5, 10.0 mg/mL, 1.5 mL, 101.3 nmol) was added at 37° C. a prepared aqueous solution of tris(2-carboxyethyl)phosphine (TCEP) (10 mM, 51.7 μL, 517 nmol). The reaction mixture was shaken on a water bath shaker at 37° C. for 3 h before the reaction was terminated. The reaction mixture was cooled to 25° C. in a water bath.

Compound 10-longer retention time compound (2.0 mg, 1815 nmol) was dissolved in 100 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-20 of FADC-1 general formula in PBS buffer (0.73 mg/mL, 13.0 mL), which was then stored at 4° C.

Mean calculated by UV-Vis: n=7.43.

Example 1-41. ADC-21 (Reference Example)

FADC-18

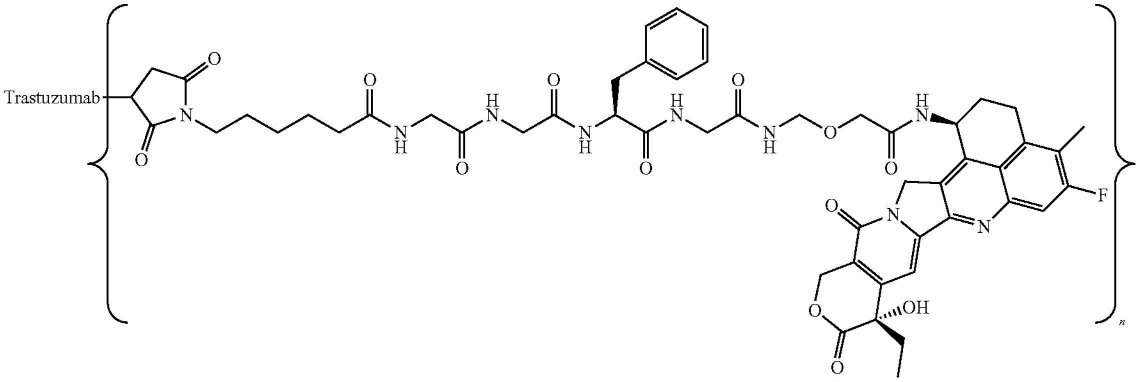

To antibody trastuzumab in aqueous PBS buffer (0.05 M aqueous PBS buffer at pH 6.5, 10.0 mg/mL, 1.86 mL, 125.4 nmol) was added at 37° C. a prepared aqueous solution of tris(2-carboxyethyl)phosphine (TCEP) (10 mM, 63.9 μL, 639 nmol). The reaction mixture was shaken on a water bath shaker at 37° C. for 3 h before the reaction was terminated. The reaction mixture was cooled to 25° C. in a water bath.

Compound 20 (2.07 mg, 2001 nmol) was dissolved in 150 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-21 of FADC-18 general formula in PBS buffer (2.91 mg/mL, 4.44 mL), which was then stored at 4° C.

Mean calculated by UV-Vis: n=7.23.

Example 1-42. ADC-22

FADC-4A

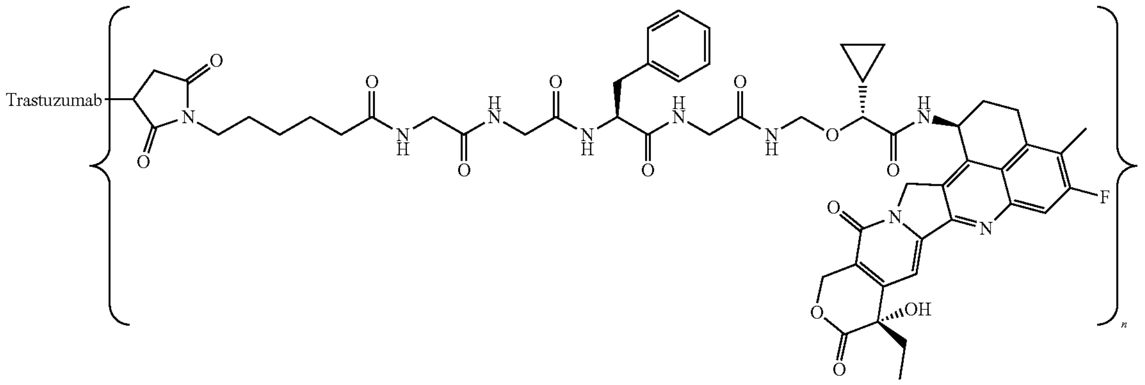

To antibody trastuzumab in aqueous PBS buffer (0.05 M aqueous PBS buffer at pH 6.5, 10.0 mg/mL, 1.88 mL, 127.2 nmol) was added at 37° C. a prepared aqueous solution of tris(2-carboxyethyl)phosphine (TCEP) (10 mM, 64.9 μL, 649 nmol). The reaction mixture was shaken on a water bath shaker at 37° C. for 3 h before the reaction was terminated. The reaction mixture was cooled to 25° C. in a water bath.

Compound 9-shorter retention time compound 9-A (2.1 mg, 1955 nmol) was dissolved in 150 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-22 of FADC-4A general formula in PBS buffer (3.56 mg/mL, 3.98 mL), which was then stored at 4° C.

Mean calculated by UV-Vis: n=6.79.

Example 1-43. ADC-23 (Reference Example)

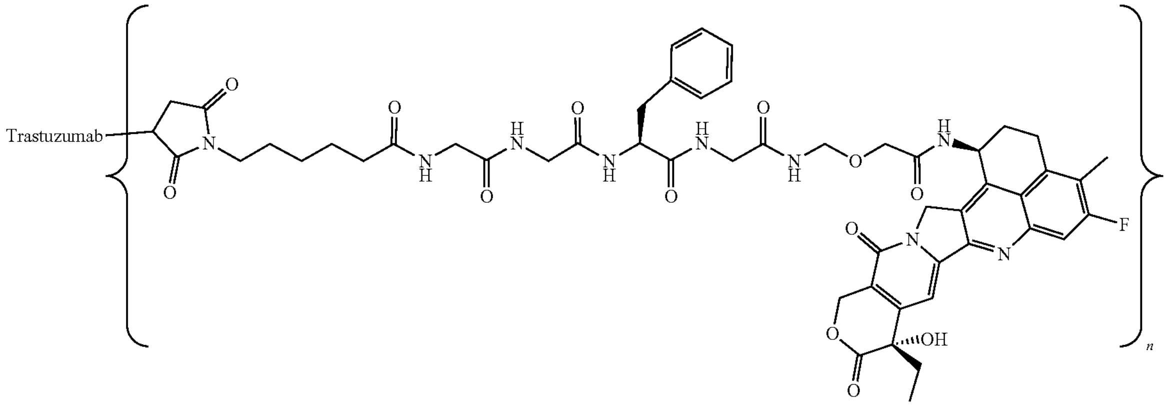

FADC-18

To antibody trastuzumab in aqueous PBS buffer (0.05 M aqueous PBS buffer at pH 6.5, 10.0 mg/mL, 345 mL, 23.31 μmol) was added at 37° C. a prepared aqueous solution of tris(2-carboxyethyl)phosphine (TCEP) (10 mM, 11.89 mL, 118.9 μmol). The reaction mixture was shaken on a water bath shaker at 37° C. for 3.5 h before the reaction was terminated. The reaction mixture was cooled to 25° C. in a water bath.

Compound 20 (362 mg, 350 μmol) was dissolved in 7.12 mL of MeCN and 3.56 mL of DMSO, and the solution was added to the above reaction mixture. The reaction mixture was shaken on a water bath shaker at 25° C. for 3 h before the reaction was terminated. The reaction mixture was purified by desalting through ultrafiltration membranes with 2% (v/v) MeCN and 1% (v/v) DMSO-containing aqueous PBS buffer (0.05 M aqueous PBS buffer at pH 6.5) and aqueous succinic acid buffer (0.01 M aqueous succinic acid buffer at pH 5.3) successively. Then sucrose was added at 60 mg/mL, and tween 20 at 0.2 mg/mL. The mixture was bottled and lyophilized to give a lyophilized powder sample of exemplary product ADC-23 of FADC-18 general formula, which was then stored at 4° C. Mean calculated by UV-Vis: n=7.05.

Example 1-44. ADC-24

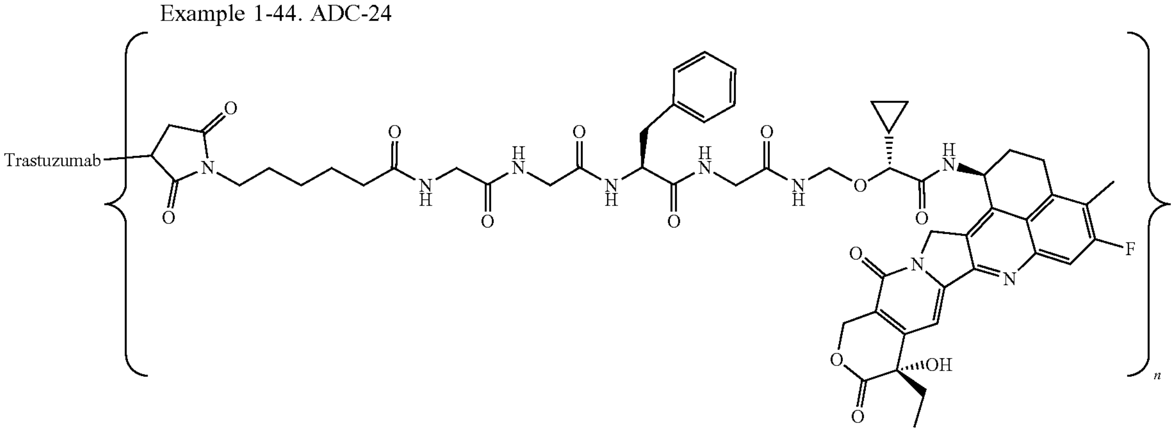

FADC-4A

To antibody trastuzumab in aqueous PBS buffer (0.05 M aqueous PBS buffer at pH 6.5, 10.0 mg/mL, 332 mL, 22.43 μmol) was added at 37° C. a prepared aqueous solution of tris(2-carboxyethyl)phosphine (TCEP) (10 mM, 11.44 mL, 114.4 μmol). The reaction mixture was shaken on a water bath shaker at 37° C. for 3.5 h before the reaction was terminated. The reaction mixture was cooled to 25° C. in a water bath.

Compound 9-shorter retention time compound 9-A (241 mg, 224 μmol) was dissolved in 13.76 mL of MeCN and 6.88 mL of DMSO, and the solution was added to the above reaction mixture. The reaction mixture was shaken on a water bath shaker at 25° C. for 3 h before the reaction was terminated. The reaction mixture was purified by desalting through ultrafiltration membranes with 4% (v/v) MeCN and 2% (v/v) DMSO-containing aqueous PBS buffer (0.05 M aqueous PBS buffer at pH 6.5) and aqueous succinic acid buffer (0.01 M aqueous succinic acid buffer at pH 5.3) successively. Then sucrose was added at 60 mg/mL, and tween 20 at 0.2 mg/mL. The mixture was bottled and lyophilized to give a lyophilized powder sample of exemplary product ADC-24 of FADC-4A general formula, which was then stored at 4° C.

Mean calculated by UV-Vis: n=7.07.

Example 1-45. ADC-25

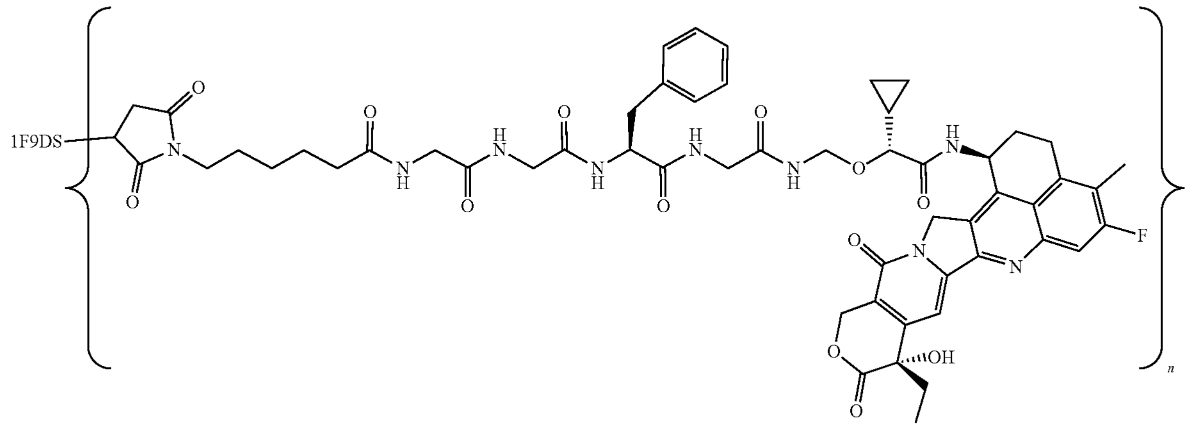

FADC-25

To antibody B7H3 antibody 1F9DS in aqueous PBS buffer (0.05 M aqueous PBS buffer at pH 6.5, 10.0 mg/mL, 2.14 mL, 144.60 nmol) was added at 37° C. a prepared aqueous solution of tris(2-carboxyethyl)phosphine (TCEP) (10 mM, 73.7 μL, 740 nmol). The reaction mixture was shaken on a water bath shaker at 37° C. for 3 h before the reaction was terminated. The reaction mixture was cooled to 25° C. in a water bath.

Compound 9-shorter retention time compound 9-A (3.0 mg, 2793 nmol) was dissolved in 150 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-25 of FADC-25 general formula in PBS buffer (1.28 mg/mL, 13.0 mL), which was then stored at 4° C.

Mean calculated by UV-Vis: n=6.87.

Example 1-46. ADC-26 (Reference Example)

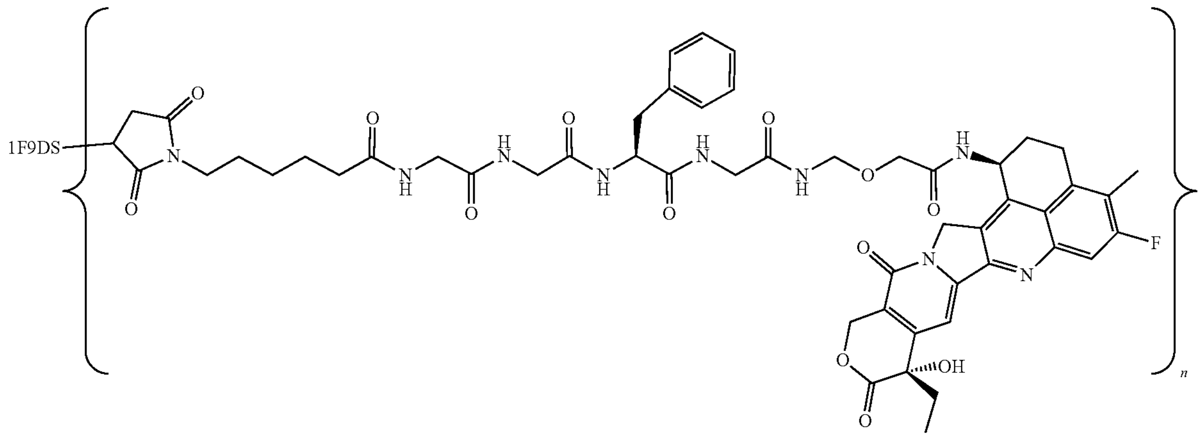

FADC-26

To antibody B7H3 antibody 1F9DS in aqueous PBS buffer (0.05 M aqueous PBS buffer at pH 6.5, 10.0 mg/mL, 0.89 mL, 60.14 nmol) was added at 37° C. a prepared aqueous solution of tris(2-carboxyethyl)phosphine (TCEP) (10 mM, 30.1 μL, 300 nmol). The reaction mixture was shaken on a water bath shaker at 37° C. for 3 h before the reaction was terminated. The reaction mixture was cooled to 25° C. in a water bath.

Compound 20 (1.0 mg, 967 nmol) was dissolved in 100 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-26 of FADC-26 general formula in PBS buffer (1.61 mg/mL, 4.0 mL), which was then stored at 4° C.

Mean calculated by UV-Vis: n=6.15.

Example 1-47. ADC-27

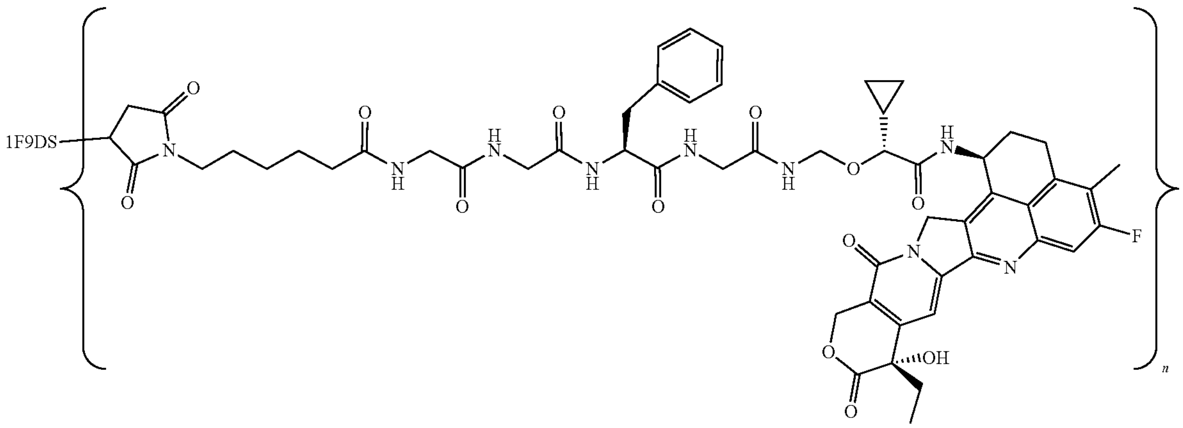

FADC-25

To antibody B7H3 antibody 1F9DS in aqueous PBS buffer (0.05 M aqueous PBS buffer at pH 6.5, 10.0 mg/mL, 0.89 mL, 60.14 nmol) was added at 37° C. a prepared aqueous solution of tris(2-carboxyethyl)phosphine (TCEP) (10 mM, 30.1 μL, 300 nmol). The reaction mixture was shaken on a water bath shaker at 37° C. for 3 h before the reaction was terminated. The reaction mixture was cooled to 25° C. in a water bath.

Compound 9-shorter retention time compound 9-A (1.02 mg, 950 nmol) was dissolved in 100 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-27 of FADC-25 general formula in PBS buffer (1.94 mg/mL, 3.5 mL), which was then stored at 4° C.

Mean calculated by UV-Vis: n=6.11.

Example 1-48. ADC-28 (Reference Example)

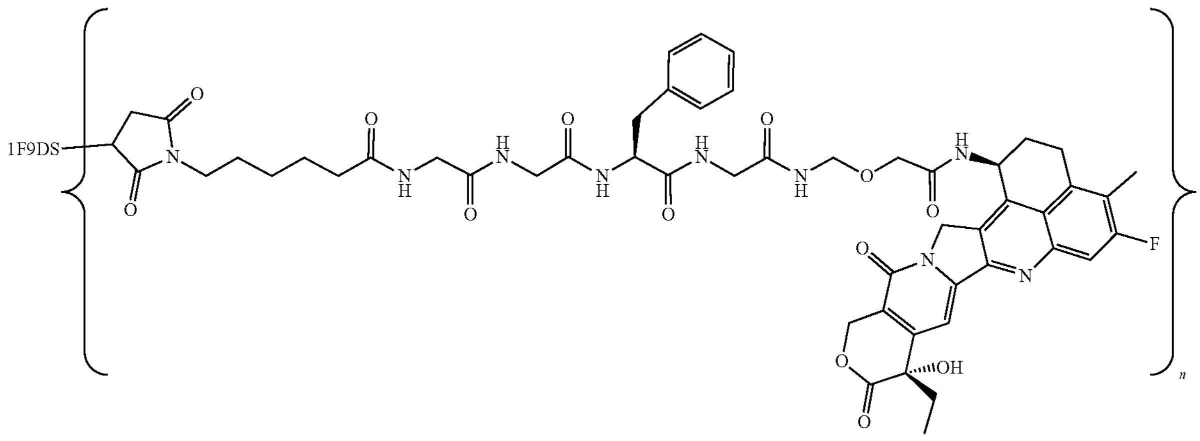

FADC-26

To antibody B7H3 antibody 1F9DS in aqueous PBS buffer (0.05 M aqueous PBS buffer at pH 6.5, 10.0 mg/mL, 2.36 mL, 159.47 nmol) was added at 37° C. a prepared aqueous solution of tris(2-carboxyethyl)phosphine (TCEP) (10 mM, 81.3 μL, 810 nmol). The reaction mixture was shaken on a water bath shaker at 37° C. for 3 h before the reaction was terminated. The reaction mixture was cooled to 25° C. in a water bath.

Compound 20 (3.0 mg, 2901 nmol) was dissolved in 150 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-28 of FADC-26 general formula in PBS buffer (1.29 mg/mL, 13.0 mL), which was then stored at 4° C.

Mean calculated by UV-Vis: n=7.46.

Example 1-49. ADC-29

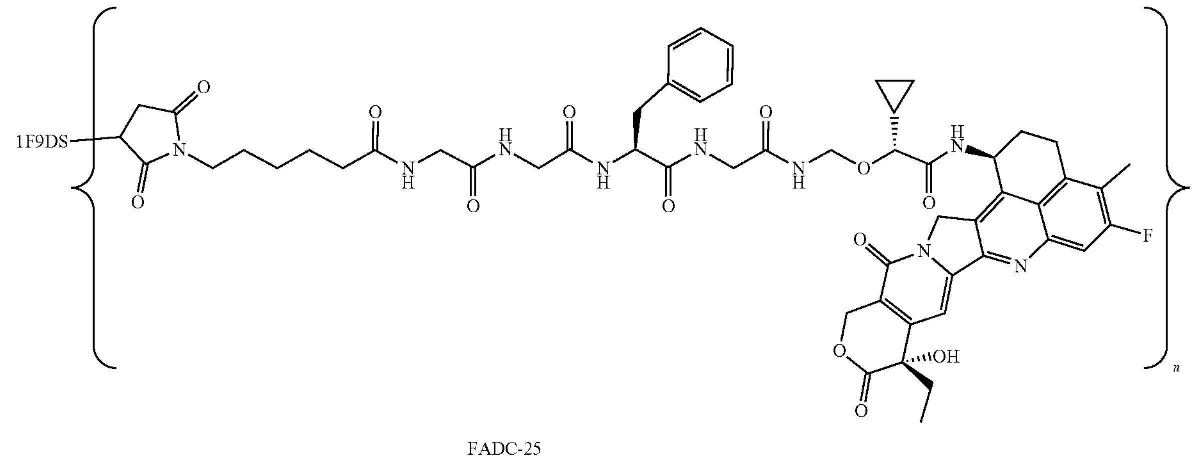

FADC-25

To antibody B7H3 antibody 1F9DS in aqueous PBS buffer (0.05 M aqueous PBS buffer at pH 6.5, 10.0 mg/mL, 0.80 mL, 50.06 nmol) was added at 37° C. a prepared aqueous solution of tris(2-carboxyethyl)phosphine (TCEP) (10 mM, 28.6 μL, 290 nmol). The reaction mixture was shaken on a water bath shaker at 37° C. for 3 h before the reaction was terminated. The reaction mixture was cooled to 25° C. in a water bath.

Compound 9-shorter retention time compound 9-A (1.29 mg, 1201 nmol) was dissolved in 100 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-29 of FADC-25 general formula in PBS buffer (2.63 mg/mL, 2.4 mL), which then was stored at 4° C.

Mean calculated by UV-Vis: n=7.24.

Example 1-50. ADC-30 (Reference Example)

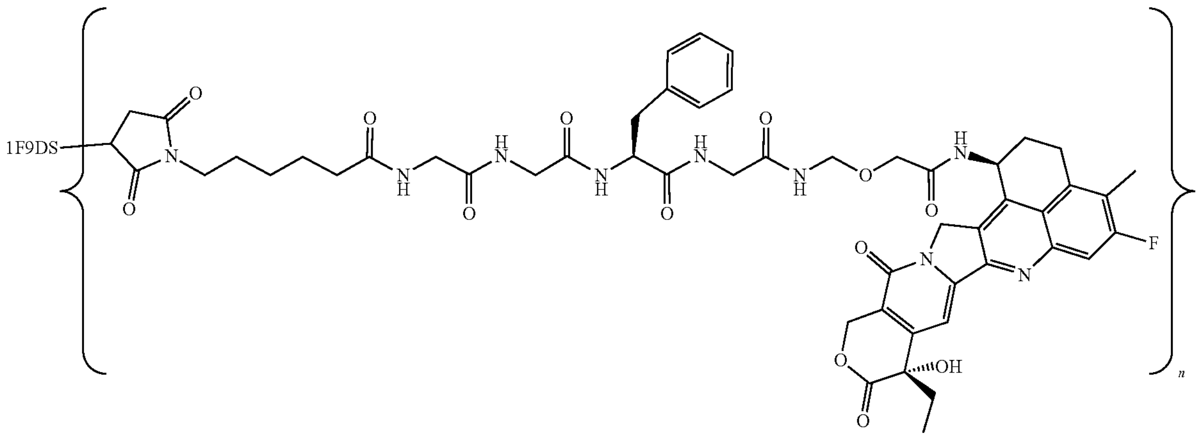

FADC-26

To antibody B7H3 antibody 1F9DS in aqueous PBS buffer (0.05 M aqueous PBS buffer at pH 6.5, 10.0 mg/mL, 0.86 mL, 58.4 nmol) was added at 37° C. a prepared aqueous solution of tris(2-carboxyethyl)phosphine (TCEP) (10 mM, 29.1 μL, 290 nmol). The reaction mixture was shaken on a water bath shaker at 37° C. for 3 h before the reaction was terminated. The reaction mixture was cooled to 25° C. in a water bath.

Compound 20 (1.0 mg, 967 nmol) was dissolved in 100 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-30 of FADC-26 general formula in PBS buffer (1.61 mg/mL, 4.0 mL), which was then stored at 4° C.

Mean calculated by UV-Vis: n=6.15.

Example 1-51. ADC-31

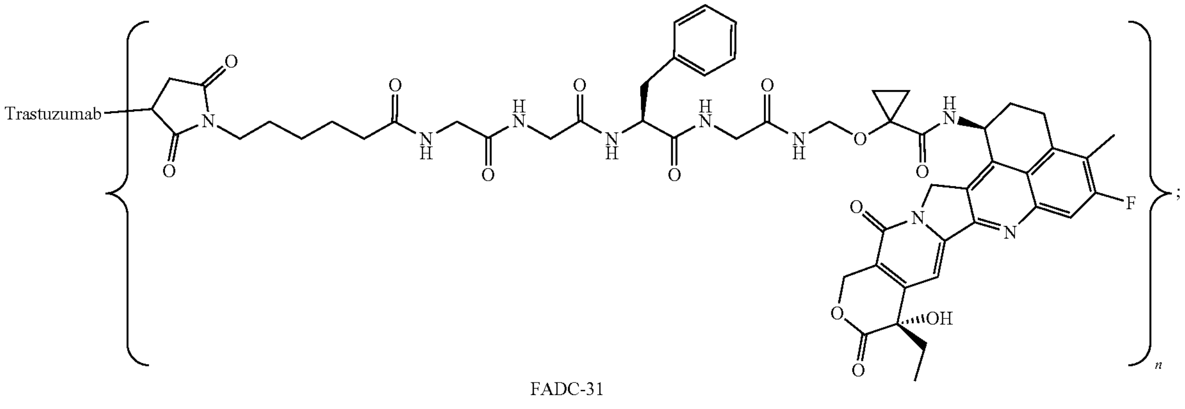

FADC-31

To antibody B7H3 antibody 1F9DS in aqueous PBS buffer (0.05 M aqueous PBS buffer at pH 6.5, 10.0 mg/mL, 0.89 mL, 60.14 nmol) was added at 37° C. a prepared aqueous solution of tris(2-carboxyethyl)phosphine (TCEP) (10 mM, 30.1 μL, 300 nmol). The reaction mixture was shaken on a water bath shaker at 37° C. for 3 h before the reaction was terminated. The reaction mixture was cooled to 25° C. in a water bath.

Compound 8 (1.0 mg, 943 nmol) was dissolved in 100 μL of DMSO, and the solution was added to the above reaction mixture. The reaction mixture was shaken on a water bath shaker at 25° C. for 3 h before the reaction was terminated. The reaction mixture was desalted and purified through a Sephadex G25 gel column (elution phase: 0.05 M aqueous PBS buffer at pH 6.5, containing 0.001 M EDTA) to give exemplary product ADC-31 of FADC-31 general formula in PBS buffer (1.47 mg/mL, 4.5 mL), which was then stored at 4° C.

Mean calculated by UV-Vis: n=6.33.

Example 1-52. ADC-32

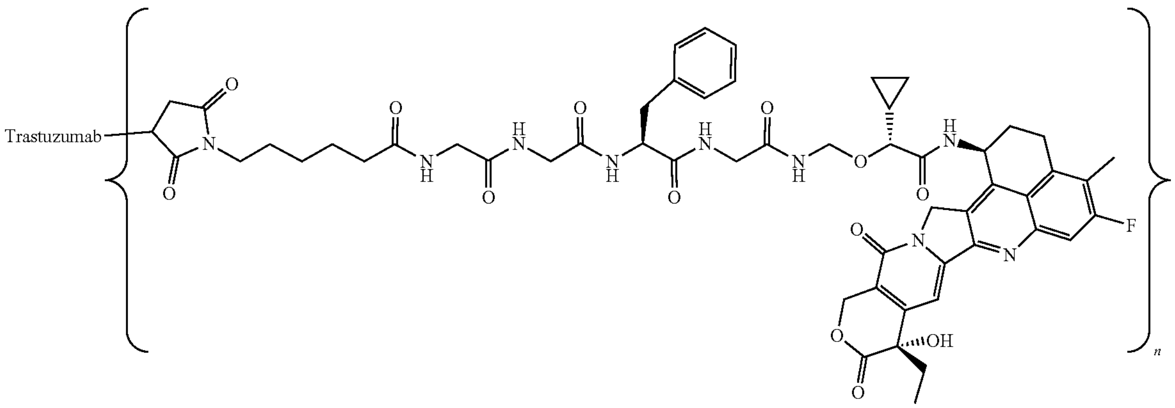

FADC-4A

At 25° C., in a buffer containing 20 mM histidine-hydrochloric acid and 2.5 mM EDTA (pH 5.6), 5.0 g of trastuzumab stock solution (34.44 nmol; trastuzumab was diluted with 20 mM histidine-hydrochloric acid buffer to a final concentration of 15 mg/mL) and 34.64 mg of tris(2-carboxyethyl)phosphine hydrochloride (reducing agent TCEP, Sigma, 120.84 μmol) were stirred in a water bath at a constant temperature for 3 h to give a solution of intermediate I.

Compound 9-shorter retention time compound 9-A (406.2 mg, 378.17 μmol) was dissolved in 9.98 mL of DMSO to give a solution of compound 9-A in DMSO. 23.42 mL of DMSO was added to the above solution of intermediate I in advance, and then the above solution of compound 9-A in DMSO was added to the solution of intermediate I to which DMSO had been added in advance. The reaction mixture was stirred in a water bath at 25° C. for 1 h, quenched with cysteine, and filtered. At 25° C., the reaction mixture was subjected to buffer exchange by 10-fold and 16-fold volume equal-volume ultrafiltration through an ultrafiltration membrane (30 kd) with a 10% (v/v) DMSO-containing aqueous buffer of 20 mM histidine-hydrochloric acid and 2.5 mM EDTA (pH=6.0), and an aqueous buffer of 10 mM histidine-hydrochloric acid (pH=5.5), successively, to remove small molecules and residual solvents, and exemplary product ADC-32 of FADC-4A general formula was obtained.

Mean calculated by HIC: n=6.0.

Example 1-53. ADC-33

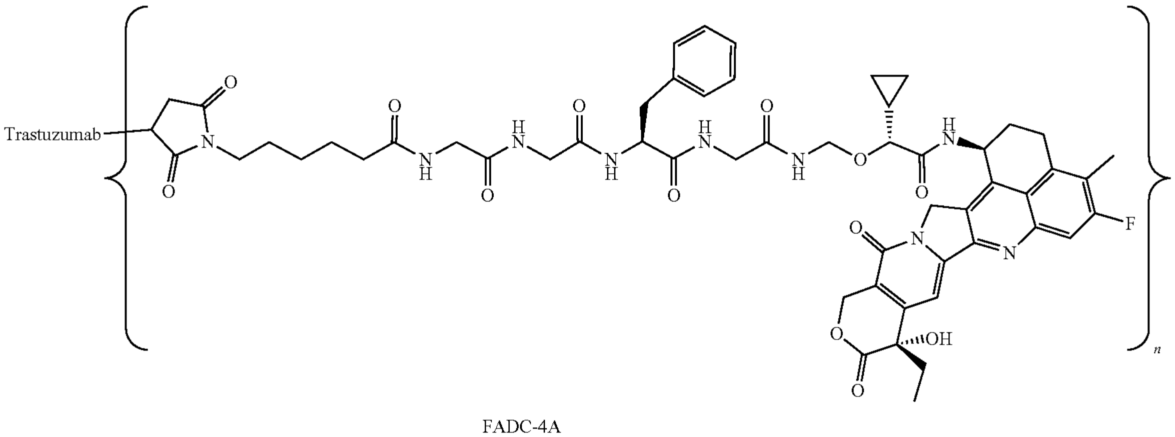

FADC-4A

At 37° C., in a buffer containing 20 mM histidine-hydrochloric acid and 2.5 mM EDTA (pH 6.0), 8.0 g of trastuzumab stock solution (55.11 nmol; trastuzumab was diluted with 20 mM histidine buffer to a final concentration of 15 mg/mL) and 123.95 mg of tris(2-carboxyethyl)phosphine hydrochloride (reducing agent TCEP, Sigma, 432.41 μmol) were stirred in a water bath at a constant temperature for 5 h to give a solution of intermediate I.

Compound 9-shorter retention time compound 9-A (754.7 mg, 702.63 μmol) was dissolved in 15.99 mL of DMSO to give a solution of compound 9-A in DMSO. 37.34 mL of DMSO was added to the above solution of intermediate I in advance, and then the above solution of compound 9-A in DMSO was added to the solution of intermediate I to which DMSO had been added in advance. The reaction mixture was stirred in a water bath at 37° C. for 1 h before the reaction was terminated, and the reaction mixture was filtered. At 25° C., the reaction mixture was subjected to buffer exchange by 8-fold and 16-fold volume equal-volume ultrafiltration through an ultrafiltration membrane (30 kd) with a 10% (v/v) DMSO-containing aqueous buffer of 20 mM histidine-hydrochloric acid and 2.5 mM EDTA (pH=6.0), and an aqueous buffer of 10 mM histidine-hydrochloric acid (pH=6.0), successively, to remove small molecules and residual solvents, and exemplary product ADC-33 of FADC-4A general formula was obtained.

Mean calculated by HIC: n=7.15.

Drug Loading Analysis of ADC Stock Solution

Purpose and Principle of Experiment

An ADC is an antibody cross-linked drug. Its mechanism for treating diseases is to transport toxin molecules into cells depending on the targeting ability of the antibody and kill the cells. The drug loading plays a decisive role in the drug efficacy. The drug loading in the ADC stock solution was determined by ultraviolet-visible spectrophotometry (UV-Vis) or hydrophobic interaction chromatography (HIC).

1. Ultraviolet-Visible Spectrophotometry

Cuvettes containing sodium succinate buffer were placed into the reference cell and sample cell, and the absorbance of the solvent blank was subtracted. Then, a cuvette containing test solution was placed into the sample cell, and the absorbances at 280 nm and 370 nm were determined.

Calculation: the loading in the ADC stock solution was determined by ultraviolet spectrophotometry (instrument: Thermo nanodrop 2000 ultraviolet spectrophotometer), based on the principle that the total absorbance value of the ADC stock solution at a certain wavelength was the sum of the absorbance values of the cytotoxic drug and the monoclonal antibody at that wavelength, namely:

$$A_{280\ nm}=\varepsilon_{mab\text{-}280}bC_{mab}+\varepsilon_{Drug\text{-}280}bC_{Drug} \quad (1)$$

$\varepsilon_{Drug\text{-}280}$: the mean molar extinction coefficient of the drug at 280 nm was 5100;

$C_{Drug}$: the concentration of the drug;

$\varepsilon_{mab\text{-}280}$: the mean molar extinction coefficient of the trastuzumab stock solution or the pertuzumab stock solution at 280 nm was 214,600;

$C_{mab}$: the concentration of the monoclonal antibody stock solution of trastuzumab or pertuzumab;

b: the optical path length was 1 cm.

Similarly, an equation for the total absorbance value of the sample at 370 nm can be given as:

$$A_{370\ nm}=\varepsilon_{mab\text{-}370}bC_{mab}+\varepsilon_{Drug\text{-}370}bC_{Drug} \quad (2)$$

$\varepsilon_{Drug\text{-}370}$: the mean molar extinction coefficient of the drug at 370 nm was 19,000;

$C_{Drug}$: the concentration of the drug;

$\varepsilon_{mab\text{-}370}$: the extinction coefficient of the monoclonal antibody stock solution of trastuzumab or pertuzumab at 370 nm was 0;

$C_{mab}$: the concentration of the monoclonal antibody stock solution of trastuzumab;

b: the optical path length was 1 cm.

The drug loading can be calculated using both equations (1) and (2) as well as the extinction coefficients of the monoclonal antibody and the drug at both wavelengths and their concentrations.

Drug loading $n=C_{Drug}/C_{mab}$

2. Hydrophobic Interaction Chromatography 2.1 HPLC Analysis was Carried Out Under the Following Measuring Conditions:

HPLC system: Agilent high performance liquid chromatograph HPLC system

Detector: DAD detector (measurement wavelength: 280 nm)

Chromatography column: TSKgel Butyl-NPR (4.6 mm×100 mm, 2.5 μm)

Column temperature: 30° C.

Flow rate: 0.5 mL/min

Sample chamber temperature: 4° C.

Mobile phase A: a pH 7.00 aqueous solution containing 1.5 M ammonium sulfate ($(NH_4)_2SO_4$) and 20 mM disodium phosphate ($Na_2HPO_4$).

Mobile phase B: a pH 7.00 mixed solution containing 75% 20 mM disodium phosphate ($Na_2HPO_4$) and 25% isopropanol.

Gradient program: 0.0% B to 0.0% B (0 mM to 3.0 min), 0.0% B to 100.0% B (3.0 min to 30.0 mM), 100.0% B to 100.0% B (30.0 min to 33.0 min), 0.0% B to 0.0% B (33.1 min to 40.0 min), Sample injection amount: 50 μg 2.2 Data Analysis Based on the current data, because of the characteristics of the column, based on the difference in salt concentrations, the antibody drug conjugate was eluted in ascending order according to the number of bound drugs. Therefore, the distribution of the number of conjugated drugs was obtained by measuring the area of each peak. According to the elution order, the peaks were DO (antibody with no drug linker bound), D2, D4, D6 and D8. The drug loading DAR (n) was calculated as:

TABLE 1

Drug loading calculation by hydrophobic interaction chromatography

| Name | Number of linked drugs | Weighted peak area percentage |
|---|---|---|
| D 0 | 0 | Peak area of D 0 × number of linked drugs |
| D 2 | 2 | Peak area of D 2 × number of linked drugs |
| D 4 | 4 | Peak area of D 4 × number of linked drugs |
| D 6 | 6 | Peak area of D 6 × number of linked drugs |
| D 8 | 8 | Peak area of D 8 × number of linked drugs |

Drug loading n = Σ(weighted peak areas)/100

Biological Evaluation

Test Example 1-1: Test for Inhibition of In Vitro Proliferation of Tumor Cells by Compounds Disclosed Herein I. Purpose This experiment is intended to determine the inhibitory activity of the pharmaceutical compounds of the present disclosure against the in vitro proliferation of U87MG cells (Cell Bank, Chinese Academy of Sciences, Cat #TCHu138) and SK-BR-3 tumor cells (human breast cancer cells, ATCC, Cat #HTB-30). The cells were treated in vitro with a compound at different concentrations. After 6 days of culture, the proliferation of the cells was determined using a CTG (CellTiter-Glo® Luminescent Cell Viability Assay, Promega, Cat #G7573) reagent, and the in vitro activity of the compound was evaluated according to the $IC_{50}$ value.

II. Method

The method for testing the inhibition of the in vitro proliferation of U87MG cells was described below as an example for the method for assaying for the inhibitory activity of the compounds of the present disclosure against the in vitro proliferation of tumor cells. The method was also applicable to, but not limited to, the test for the inhibitory activity against the in vitro proliferation of other tumor cells.

1. Cell culture: U87MG and SK-BR-3 cells were cultured in a 10% FBS-containing EMEM medium (GE, Cat #SH30024.01) and a 10% FBS-containing McCoy's 5A medium (Gibco, Cat #16600-108), respectively.

2. Cell preparation: U87MG and SK-BR-3 cells growing at log phase were collected, washed once with PBS (phosphate buffered saline, Shanghai BasalMedia Technologies Co., Ltd.), and then digested with 2-3 mL of trypsin (0.25% Trypsin-EDTA (1×), Gibico, Life Technologies) for 2-3 min; after being fully digested, the cells were eluted with 10-15 mL of a cell culture medium; the eluate was centrifuged at 1000 rpm for 5 min, and the supernatant was discarded; then the cells were resuspended in 10-20 mL of a cell culture medium to form single-cell suspensions.

3. Cell plating: the U87MG and SK-BR-3 single-cell suspensions were each well mixed, and their cell densities were adjusted with a cell culture medium to $2.75\times10^3$ cells/mL and $8.25\times10^3$ cells/mL, respectively; the density-adjusted cell suspensions were each well mixed and added to a 96-well cell culture plate at 180 μL/well. To each of the peripheral wells of the 96-well plates was added 200 μL of media only. The plates were incubated in an incubator (37° C., 5% $CO_2$) for 24 h.

4. Compound preparation: the compound was dissolved in DMSO (dimethyl sulfoxide, Shanghai Titan Scientific Co., Ltd.) to prepare a stock solution at an initial concentration of 10 mM.

Small-molecule compounds were at an initial concentration of 500 nM. Drug formulation was performed as follows.

Different test samples at concentration 100 μM (30 μL) were added to the first column of a 96-well U-bottom plate, and 20 μL of DMSO was added to each well of the second column through the eleventh column. The samples in the first column (10 μL) were added to the 20 μL of DMSO in the second column, and the mixtures were well mixed. The mixtures (10 μL) were added to the third column, and so on to the tenth column. The drugs in the plate (5 μL per well) were transferred to EMEM media (95 μL), and the mixtures were well mixed for later use.

ADCs were prepared at an initial concentration of 10 nM or 500 nM as follows.

Different test samples at concentration 100 nM or 5 μM (100 μL) were added to the first column of a 96-well plate, and 100 μL of PBS was added to each well of the second column through the eleventh column. The samples in the first column (50 μL) were added to the 100 μL of PBS in the second column, and the mixtures were well mixed. The mixtures (50 μL) were added to the third column, and so on, by 3-fold dilution, to the tenth column.

5. Sample adding: the test samples prepared at different concentrations (20 μL) were added to the culture plate, with two duplicate wells set for each sample. The plate was incubated in an incubator (37° C., 5% $CO_2$) for 6 days.

6. Color developing: the 96-well cell culture plate was taken out, and 90 μL of CTG solution was added to each well, followed by 10 mM of incubation at room temperature.

7. Plate reading: the 96-well cell culture plate was taken out and tested in a microplate reader (BMG labtech, PHER-Astar FS) for chemiluminescence.

III. Data Analysis

Data were processed and analyzed using Microsoft Excel and Graphpad Prism 5. The experimental results are shown in the Table 2 below.

TABLE 2

$IC_{50}$ values of the small-molecule fragments of the present disclosure in inhibiting in vitro proliferation of SK-BR-3 cells and U87 cells

| | $IC_{50}$ (nM) | |
|---|---|---|
| Compound No. | SK-BR-3 | U87 |
| 1 | 0.12 | 0.23 |
| 2-shorter retention time 2-B | 0.33 | 0.86 |
| 2-longer retention time 2-A | 8.11 | 2.31 |
| 3-shorter retention time | 0.36 | 0.83 |
| 3-longer retention time | 1.67 | 2.98 |
| 4 | 1.9 | / |
| 5 | / | 4.81 |
| 6 | / | 1.83 |
| 7 | / | 1.95 |

Conclusion: The small-molecule fragments of the present disclosure have significant inhibitory activity against the proliferation of SK-BR-3 cells and U87 cells, and the chiral centers have certain influence on the inhibitory activity of the compounds.

Test Example 1-2: Test for Inhibition of In Vitro Proliferation of HER2-Targeted Tumor Cells by Antibody Drug Conjugates of the Present Disclosure This experiment was intended to determine the inhibitory activity of the HER2-targeting antibody drug conjugates of the present disclosure against the in vitro proliferation of SK-BR-3 (human breast cancer cells, ATCC, Cat #HTB-30) and MDA-MB-468 (human breast cancer cells, ATCC, Cat #HTB-132). The cells were treated in vitro with a compound at different concentrations. After 6 days of culture, the proliferation of cells was determined using CTG reagents, and the in vitro activity of the compound was evaluated according to $IC_{50}$ value.

The test method of Test Example 1 was followed. SK-BR-3 and MDA-MB-468 cells were used in the tests, and the cell culture media were a 10% FBS-containing McCoy's 5A medium (Gibco, Cat #16600-108), a 10% FBS-containing EMEM medium (GE, Cat #SH30024.01), and a 10% FBS-containing L-15 medium (ThermoFisher, Cat #11415-114). The cell densities of the three strains of cells were adjusted to $8.33\times10^3$ cells/mL, $8.33\times10^3$ cells/mL and $1.39\times10^4$ cells/mL with cell culture media, respectively, and the density-adjusted cell suspensions were well mixed and added to 96-well cell culture plates at 180 μL/well. The related compounds were tested, and the results are shown in Table 3 below.

TABLE 3

$IC_{50}$ values of the antibody drug conjugates of the present disclosure in inhibiting in vitro proliferation of tumor cells with HER2 targets

| | $IC_{50}$ (nM) | |
|---|---|---|
| Compound No. | SK-BR-3 | MDA-MB-468 |
| ADC-3 | 0.43 | >50 |
| ADC-4 | 0.30 | >50 |
| ADC-6 | 0.48 | >50 |
| ADC-7 | 0.14 | >50 |
| ADC-9 | 0.95 | >50 |
| ADC-10 | 1.36 | >50 |
| ADC-11 | 0.73 | >50 |
| ADC-12 | 0.82 | >50 |
| ADC-13 | 0.47 | >50 |
| ADC-14 | 0.53 | >50 |
| ADC-15 | 0.38 | >50 |
| ADC-16 | 0.49 | >50 |
| ADC-17 | 0.37 | >50 |

Conclusion: the HER2-targeting antibody drug conjugates of the present disclosure showed significant inhibitory activity against the proliferation of HER2-positive SK-BR-3 cells while showed weak inhibitory activity against the proliferation of HER2-negative MDA-MB-468 cells, exhibiting good selectivity.

Test Example 1-3: Plasma Stability Test for Her2-ADC

Samples ADC-19, ADC-18 and ADC-20, human plasma, monkey plasma (Shanghai Medicilon Inc.) and a solution of 1% BSA (Sigma) in PBS (Sangon Biotech (Shanghai)) were each filtered through a 0.22 μm filter for sterilization. ADC-19, ADC-18 and ADC-20 were each added to the sterile plasma or 1% BSA solution in PBS at a final concentration of 200 μg/mL. The resulting mixture was incubated in a cell incubator at 37° C. The day of incubation was defined as day 0. Samples were taken on days 7, 14 and 21 and tested for the free toxin.

25 μL of samples were taken out to a 96-well plate; 50 μL of an internal standard working solution (100 ng/mL camptothecin solution in acetonitrile) and 150 μL of acetonitrile were added; the mixture was vortexed for 5 min and centrifuged for 10 min (4000 rpm), and 5 μL of the resulting samples were used for LC/MS/MS (Applied Biosystems, USA) analysis.

The results showed that: ADC-19 was fairly stable in both human and monkey plasma, as well as a solution of 1% BSA in PBS, with a release rate of free toxin of no more than 2.1% at the highest, and tended to be stable on day 14, see FIG. 1A.

Figure 1B:
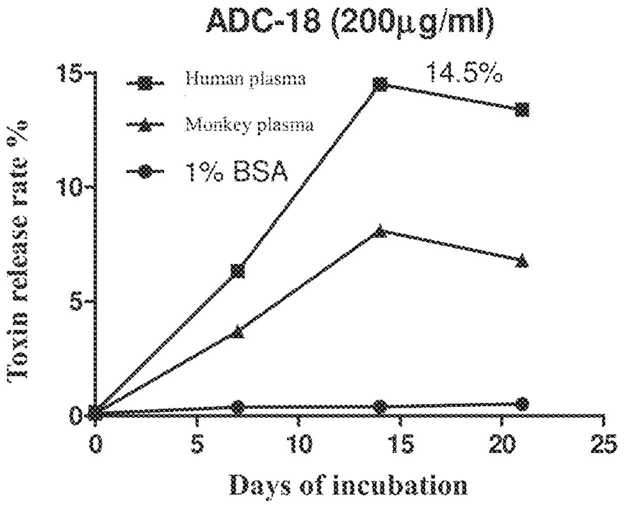
FIG. 1B shows the results of plasma stability test for ADC-18 of the present disclosure.

ADC-18 was poorly stable in human and monkey plasma with release rates of free toxin of 14.5% and 8.10% at the highest, respectively. It was relatively stable in 1% BSA solution in PBS, see FIG. 1B.

Figure 1C:
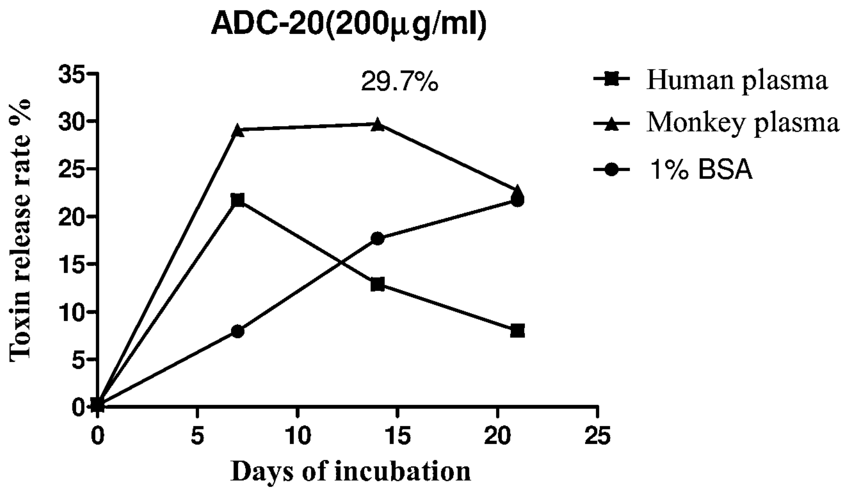
FIG. 1C shows the results of plasma stability test for ADC-20 of the present disclosure.

ADC-20 was poorly stable in human plasma, monkey plasma, and a solution of 1% BSA in PBS, with release rates of free toxin of 21.7%, 29.7% and 21.7% at the highest, respectively. It was in a degraded state in the solution of 1% BSA in PBS, see FIG. 1C.

Test Example 1-4: Evaluation of Drug Efficacy on JIMT-1 Tumor-Bearing Mice

I. Purpose

With nu/nu nude mice used as test animals, Her2-ADC antibodies T-DM1, ADC-21 and ADC-24 were administered by intraperitoneal injection, and then their efficacy was evaluated in trastuzumab (Herceptin)-resistant human breast cancer cell strain JIMT-1 xenograft tumor nude mice.

II. Test Drugs and Materials

1. Test drugs

T-DM1 (prepared by reference US20050169933)

ADC-21: 3 mg/kg

ADC-21: 10 mg/kg

ADC-24: 3 mg/kg

ADC-24: 10 mg/kg

Blank control (Blank): PBS

2. Preparation method: all prepared by dilution in PBS.

3. Test animals nu/nu nude mice, purchased from Beijing Vital River.

III. Method

Mice were inoculated subcutaneously on the right flank with JIMT-1 cells (Nanjing Cobioer) ($5\times10^6$ cells/mouse, with 50% artificial basement membrane). After 8 days, the tumors grew to a size of 203.09±11.94 $mm^3$, and the animals were randomized into κ groups of 8 (d1).

The drug was administrated by intraperitoneal injection for a total of 2 times. The tumor volumes and body weights were measured twice a week and the results were recorded. Excel 2003 statistical software was used. The mean values were calculated as avg; the SD values were calculated as STDEV; the SEM values were calculated as STDEV/SQRT; and the inter-group difference P-values were calculated as TTEST.

Tumor volume (V) was calculated as: $V=1/2\times L_{long}\times L_{short}^2$

Relative volume (RTV)=$V_T/V_0$

Tumor inhibition rate (%)=$(C_{RTV}-T_{RTV})/C_{RTV}$ (%)

Where $V_0$ and $V_T$ are the tumor volumes at the beginning and end of the experiment, respectively. $C_{RTV}$ and $T_{RTV}$ are the relative tumor volumes of the blank group (Vehicle, PBS) and the experimental groups, respectively, at the end of the experiment.

IV. Results

Figure 2:
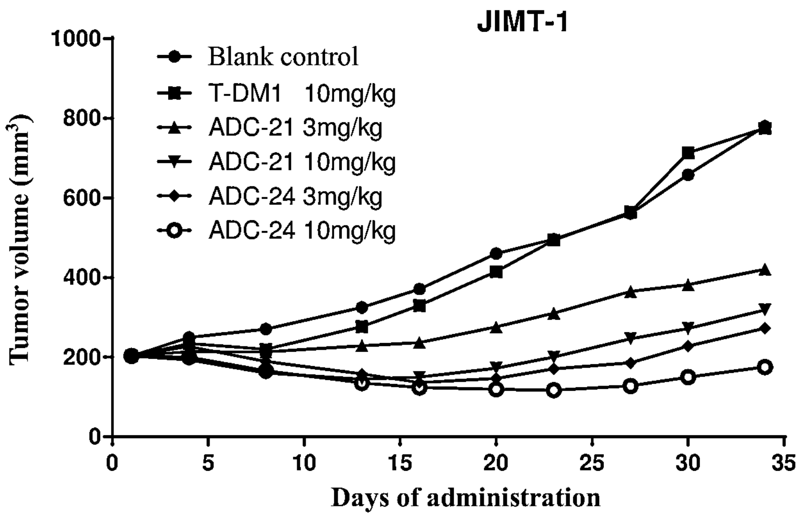
FIG. 2 shows the evaluation of the efficacy of ADC-21 and ADC-24 of the present disclosure in JIMT-1 tumor-bearing mice.

The experimental results are shown in FIG. 2. The experiment ended after two intraperitoneal injections were performed and then observation was performed for 34 days. T-DM1 (10 mg/kg) had no inhibition effect on tumors; 3 mg/kg of ADC-21 had the tumor inhibition rate of 46.22% (P<0.01); 10 mg/kg of ADC-21 had the tumor inhibition rate of 56.77% (P<0.001); 3 mg/kg of ADC-24 had the tumor inhibition rate of 62.77% (P<0.001); 10 mg/kg of ADC-24 had the tumor inhibition rate of 76.32% (P<0.001). Under the condition of the same dosage, the tumor inhibition effect of the ADC-24 was significantly better than that of the ADC-21.

Test Example 1-5: Evaluation of Drug Efficacy on SK-BR-3 Tumor-Bearing Mice

I. Purpose

With nu/nu nude mice used as test animals, Her2-ADC antibodies ADC-21 and ADC-22 were administered by intraperitoneal injection, and then their efficacy was evaluated in human breast cancer cell SK-BR-3 xenograft tumor nude mice.

II. Test Drugs and Materials

1. Test drugs

ADC-21: 1 mg/kg

ADC-21:6 mg/kg

ADC-22: 1 mg/kg

ADC-22: 6 mg/kg

Blank control (Blank): PBS.

2. Preparation method: all prepared by dilution in PBS.

3. Test animals nu/nu nude mice, purchased from Beijing Vital River.

III. Method

Mice were inoculated subcutaneously on the right flank with SK-BR-3 cells (ATCC) ($5\times10^6$ cells/mouse, with 50% artificial basement membrane). After 20 days, the tumors grew to a size of 153.34±11.73 $mm^3$, and the animals were randomized into 5 groups of 8 (d0).

The drug was administrated by intraperitoneal injection for a total of 1 time. The tumor volumes and body weights were measured twice a week and the results were recorded. Excel 2003 statistical software was used. The mean values were calculated as avg; the SD values were calculated as STDEV; the SEM values were calculated as STDEV/SQRT; and the inter-group difference P-values were calculated as TTEST.

Tumor volume (V) was calculated as: $V=1/2\times L_{long}\times L_{short}^2$

Relative volume (RTV)=$V_T/V_0$

Tumor inhibition rate (%)=$(C_{RTV}-T_{RTV})/C_{RTV}$ (%)

Where $V_0$ and $V_T$ are the tumor volumes at the beginning and end of the experiment, respectively. $C_{RTV}$ and $T_{RTV}$ are the relative tumor volumes of the blank control group and the experimental groups, respectively, at the end of the experiment.

IV. Results

Figure 3:
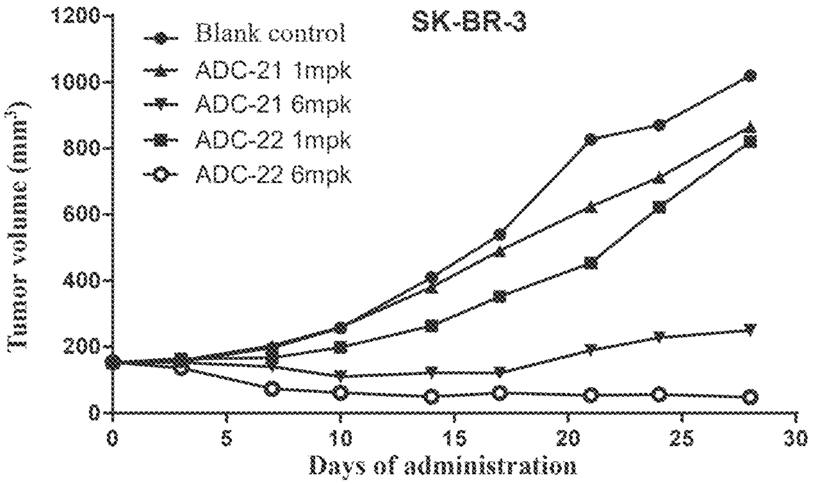
FIG. 3 shows the evaluation of the therapeutic effect of ADCs on human breast cancer cell SK-BR-3 xenograft tumor nude mice.

The experimental results are shown in FIG. 3. The experiment ended after one intraperitoneal injection was performed and then observation was performed for 28 days. 1 mg/kg of ADC-21 had the tumor inhibition rate of 15.01%; 6 mg/kg of ADC-21 had the tumor inhibition rate of 77.4%, and had significant difference compared with that of the blank control (P<0.001). 1 mg/kg of ADC-22 had the tumor inhibition rate of 19.82%; 6 mg/kg of ADC-22 had the tumor inhibition rate of 98.38% (P<0.001). Under the condition of the same dosage of 6 mg/kg, the tumor inhibition effect of the ADC-22 was significantly better than that of the ADC-21.

Test Example 1-6: Plasma Stability

Sample ADC-25 was well mixed with each of human plasma, monkey plasma and 1% BSA solution in PBS at a final concentration of 100 μg/mL, and then the mixtures were sterilized by filtration and incubated in a 37° C. water bath. The day of incubation was defined as day 0. Samples were taken on days 7, 14 and 21 and tested for the free toxin. Samples at different time points were taken out, left to cool to room temperature, and well mixed by vortexing. 25 μL of each of the samples was added to a 96-well plate, followed by the addition of 50 μL of an internal standard working solution (100 ng/mL camptothecin solution in acetonitrile) and 150 μL of acetonitrile. The resulting mixtures were vortexed for 5 min and centrifuged at 4000 rpm for 10 min. 5 μL of the supernatant was collected for LC/MS/MS analysis.

Figure 4:
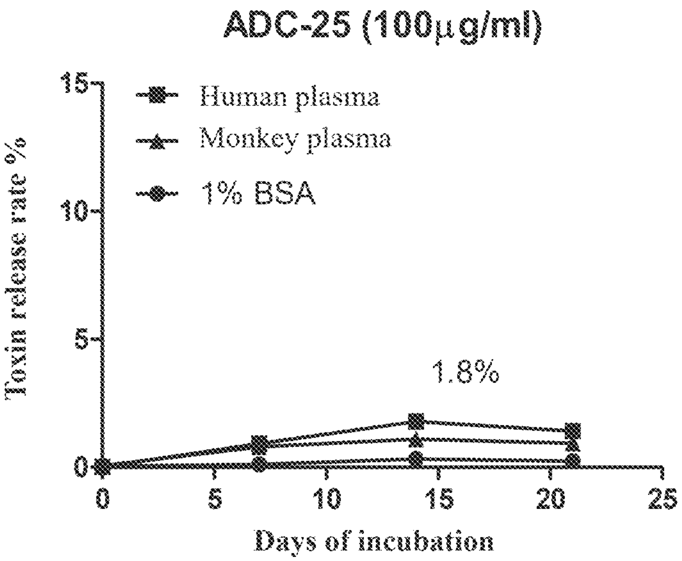
FIG. 4 shows the results of plasma stability test for ADC-25 of the present disclosure.

The results showed that: ADC-25 was fairly stable in both human and monkey plasma, as well as a solution of 1% BSA in PBS, with a release rate of free toxin of no more than 2% at the highest, and tended to be stable on day 14, see FIG. 4.

Test Example 1-7: Evaluation of Efficacy of ADCs Against Human Brain Astrocytoma U87MG Nude Mouse Xenograft Tumor I. Purpose With BALB/cA-nude mice used as test animals, the efficacy of the ADC compounds of the present disclosure against human brain astrocytoma U87MG nude mouse xenograft tumors was evaluated in this experiment.

II. Test Drugs and Materials

1. Test drugs

ADC-27 (3 mg/kg)

ADC-26 (3 mg/kg)

Blank control (Blank): PBS buffer at pH 7.4.

2. Preparation method: PBS buffer at pH 7.4.

3. Test animals

BALB/cA-nude mice: purchased from Shanghai Jiesijie Laboratory Animal Co., Ltd.

III. Method

Six to seven-week-old laboratory female BALB/cA-nude mice were inoculated subcutaneously with human brain astrocytoma U87MG cells (human brain astrocytoma, Cell Bank, Chinese Academy of Sciences, Cat #TCHu138). On the tenth day after inoculation of the cells, the animals were randomly grouped (DO), 8 animals per group, administered by intraperitoneal injection once a week for a total of 3 times, and tumor volumes and body weights were measured 2-3 times per week and the data were recorded.

Tumor volume (V) was calculated as follows:

$$V=1/2\times a\times b^2$$

where a and b represent length and width, respectively.

Relative volume (RTV)=$V_T/V_0$

Tumor inhibition rate (%)=$(C_{RTV}-T_{RTV})/C_{RTV}$ (%)

Where $V_0$ and $V_T$ are the tumor volumes at the beginning and end of the experiment, respectively. $C_{RTV}$ and $T_{RTV}$ are the relative tumor volumes of the control group (Blank) and the experimental groups, respectively, at the end of the experiment.

IV. Results

Intraperitoneal injection (i.p.) administration was given once a week for a total of 3 times; after observation for 22 days, 3 mg/kg of ADC-27 had the tumor inhibition rate of 63.3% (P<0.0001), and 3 mg/kg of ADC-26 had the inhibition rate of 49.1%. ADC-27 showed a stronger anti-tumor efficacy than ADC-26.

Figure 5:
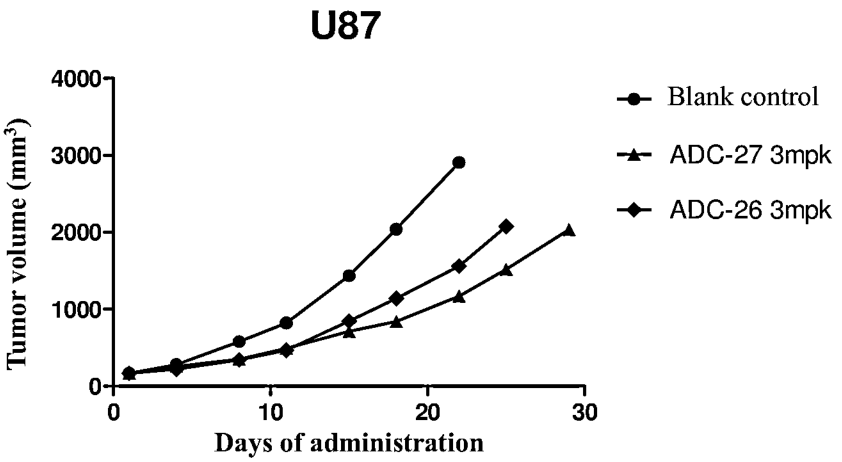
FIG. 5 shows the efficacy of the ADCs of the present disclosure against human brain astrocytoma U87MG nude mouse xenograft tumors.

The weights of all animals in each group were normal in the administration process, and the ADCs had no obvious toxic or side effect. The results are shown in Table 4 and FIG. 5. The detected antibodies could effectively inhibit the growth of U87MG xenograft tumor in tumor-bearing nude mice, and showed dose dependency.

TABLE 4

Efficacy of administered antibodies against human brain astrocytoma U87MG nude mouse xenograft tumors (D22)

| | Mean tumor volume ($mm^3$) | | | | Relative tumor volume | | Tumor inhibition rate (%) |
|---|---|---|---|---|---|---|---|
| Group | Day 0 | SEM | Day 22 | SEM | Day 22 | SEM | Day 22 |
| Blank control | 167.06 | 17.74 | 2906.96 | 327.6 | 17.76 | 1.63 | — |
| ADC-27 3 mpk | 167.07 | 16.06 | 1172.48 | 80.27 | 7.55 | 0.95 | 63.3*** |
| ADC-26 3 mpk | 167.73 | 17.63 | 1561.03 | 303.37 | 8.83 | 1.17 | 491*** |

***indicates P < 0.001

Test Example 1-8: Evaluation of Efficacy of ADCs Against Pleural Effusion Metastatic Human Pharyngeal Cancer Cell Detroit 562 Nude Mouse Xenograft Tumors I. Purpose With BALB/cA-nude mice used as test animals, and the efficacy of the ADC compounds of the present disclosure against pleural effusion metastatic human pharyngeal cancer cell Detroit 562 nude mouse xenograft tumors was evaluated in this experiment.

II. Test Drugs and Materials

1. Test drugs

ADC-29 (3 mg/kg)

ADC-28 (3 mg/kg)

Negative control ADC (3 mg/kg): antibody drug conjugate formed by coupling non-B7H3-targeted antibodies to compound 20.

2. Preparation method: all prepared by dilution in PBS.

3. Test animals

BALB/cA-nude mice: purchased from Changzhou Cavens Laboratory Animal Co., Ltd.

III. Method

Six to seven-week-old laboratory female BALB/cA-nude mice were inoculated subcutaneously with pleural effusion metastatic human pharyngeal cancer cells Detroit 562 cells (ATCC, Cat #ATCC® CCL-138™). On the tenth day after inoculation of the cells, the animals were randomly grouped (DO), 8 animals per group, administered by intraperitoneal injection once a week for a total of 3 times, and tumor volumes and body weights were measured 2-3 times per week and the data were recorded. Tumor volume (V) was calculated as follows:

$$V=1/2\times a\times b^2$$

where a and b represent length and width, respectively.

Relative volume (RTV)=$V_T/V_0$

Tumor inhibition rate (%)=$(C_{RTV}-T_{RTV})/C_{RTV}$ (%)

Where $V_0$ and $V_T$ are the tumor volumes at the beginning and end of the experiment, respectively. $C_{RTV}$ and $T_{RTV}$ are the relative tumor volumes of the control group (negative control) and the experimental groups, respectively, at the end of the experiment.

IV. Results

The drugs were administered by intraperitoneal injection once a week, and a total of 3 injections were administered. On day 28 of observation, tumor inhibition rates of the test ADCs ADC-29 3 mg/kg (3 mpk) and ADC-28 3 mg/kg mg/kg (3 mpk) reached 72.27% ($P<0.001$) and 56.2% ($P<0.001$), respectively. ADC-29 showed a stronger anti-tumor efficacy than ADC-28.

Figure 6:
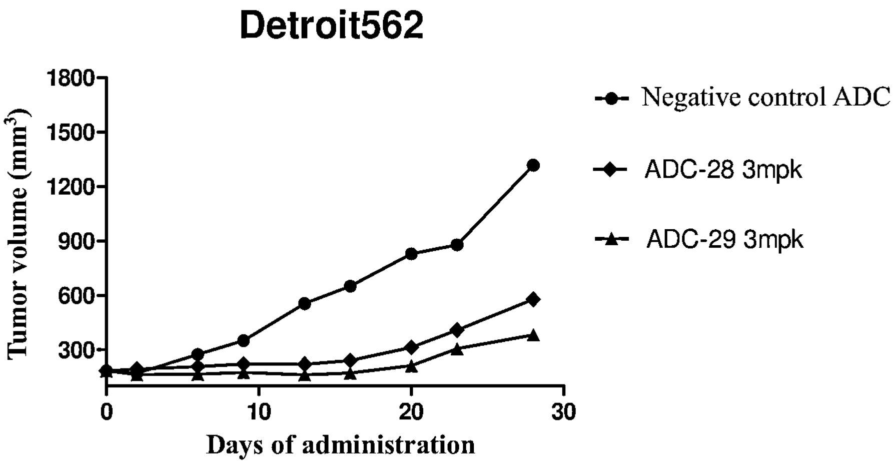
FIG. 6 shows the efficacy of the ADCs of the present disclosure against pleural effusion metastatic human pharyngeal cancer cell Detroit 562 nude mouse xenograft tumors.

The weights of all animals in each group were normal in the administration process, and the ADCs had no obvious toxic or side effect. The results are shown in Table 5 and FIG. 6. The detected antibodies could effectively inhibit the growth of Detroit 562 xenograft tumor in tumor-bearing nude mice, and showed dose dependency.

TABLE 5

Efficacy of administered antibodies against Detroit 562 xenograft tumors in tumor-bearing nude mice (D28)

| | Mean tumor volume ($mm^3$) | | Mean tumor volume ($mm^3$) | | Relative tumor volume | | Tumor inhibition rate (%) |
|---|---|---|---|---|---|---|---|
| Group | Day 0 | SEM | Day 28 | SEM | Day 28 | SEM | Day 28 |
| Negative control | 182.70 | 6.79 | 1317.99 | 223.20 | 7.47 | 1.46 | — |
| ADC-29 3 mpk | 182.59 | 6.50 | 381.48 | 105.76 | 2.07 | 0.58 | 72.27*** |
| ADC-28 3 mpk | 182.57 | 6.92 | 578.07 | 160.13 | 3.43 | 1.09 | 56.2*** |

***indicates $P < 0.001$

Test Example 1-9: Evaluation of Drug Efficacy on U87-MG Tumor-Bearing Mice

I. Purpose

With Balb/c nude mice used as test animals, the efficacy of the B7H3-antibody drug conjugate after intraperitoneal injection was evaluated on a human glioblastoma cell U87MG xenograft tumor model of the mice.

II. Test Drugs and Materials

1. Test drugs

ADC-30 1 mg/kg

ADC-30 3 mg/kg

ADC-31 1 mg/kg

ADC-31 3 mg/kg

Blank control (Blank): PBS

2. Preparation method: all prepared by dilution in PBS.

3. Test animals

BALB/cA-nude mice: purchased from Shanghai Slac Laboratory Animal Co., Ltd.

III. Method

Mice were inoculated subcutaneously on the right flank with U87MG cells (human brain astrocytoma, Cell Bank, Chinese Academy of Sciences, Cat #TCHu138) ($2.5\times10^6$ cells/mouse). After 14 days, the tumors grew to a size of 167.49 $mm^3$, and the animals were randomized into 5 groups of 8 (d1).

The drug was administrated by intraperitoneal injection once a week, and a total of 3 injections were given. The tumor volumes and body weights were measured twice a week and the results were recorded.

Excel 2003 statistical software was used. The mean values were calculated as avg; the SD values were calculated as STDEV; the SEM values were calculated as STDEV/SQRT; and the inter-group difference P-values were calculated as TTEST.

Tumor volume (V) was calculated as: $V=1/2\times L_{long}\times L_{short}^2$

Relative volume (RTV)$=V_T/V_0$

Tumor inhibition rate (%)$=(C_{RTV}-T_{RTV})/C_{RTV}$ (%)

Where $V_0$ and $V_T$ are the tumor volumes at the beginning and end of the experiment, respectively. $C_{RTV}$ and $T_{RTV}$ are the relative tumor volumes of the blank control group (Vehicle) and the experimental groups, respectively, at the end of the experiment.

IV. Results

Figure 7:
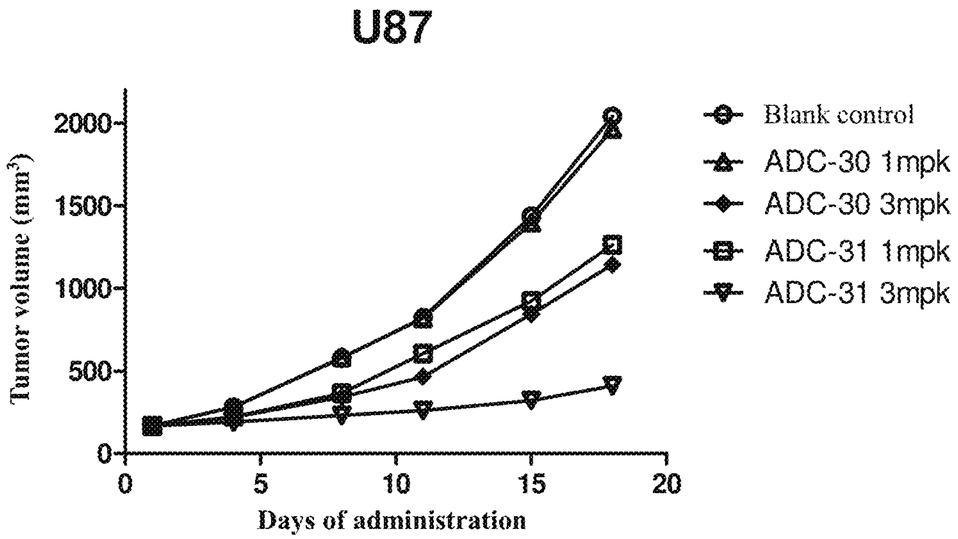
FIG. 7 shows the efficacy of the ADCs of the present disclosure against human glioblastoma U87MG nude mouse xenograft tumors.

The experimental results are shown in FIG. 7. The drugs were administrated by intraperitoneal injection once a week, and a total of 3 injections were administered. On day 18 of observation, tumor inhibition rates of test ADCs ADC-30 1 mg/kg, ADC-30 3 mg/kg, ADC-31 1 mg/kg and ADC-31 3 mg/kg reached 0.31%, 45.23% ($P<0.0001$), 39.22% ($P<0.01$) and 80.24% ($P<0.0001$), respectively. Under the condition of the same dosage, the tumor inhibition effect of the ADC-31 was significantly better than that of the ADC-30.

II. Formulation

The equipment used in the formulation preparation and determination and the calculation method for results are shown below.

SEC Molecular Exclusion Chromatography:

This is a method for analyzing the separation of absolute by the relative relationship between the pore size of the gel pores and the size of the polymer sample molecule coil. SEC % (SEC monomer content percentage)=A monomer/A total×100% (A monomer represents the peak area of the main peak monomer in the sample, and A total represents the sum of all peak areas).

Instrument for SEC measurement: Agilent 1260; column: waters, XBrige BEH200 Å SEC (300×7.8 mm 3.5 μm).

CE Capillary Gel Electrophoresis:

This is a method of moving the gel into a capillary as a supporting medium for electrophoresis and separating according to the molecular weight of the sample under a certain voltage.

Reduced CE purity percentage=A main peak/A total×100% (A main peak represents the light chain main peak area+the heavy chain main peak area, and A total represents the sum of all peak areas).

Instrument for CE measurement: Beckman model plus800

Turbidity Measurement:

The degree to which light is hindered from passing through a water layer indicates the ability of the water layer to scatter and absorb light. It is related not only to the suspended matter content but also to the particle composition, size and shape as well as the reflection performance of its surface. In comparing the absorption values of the same protein sample at the same concentration at the same wavelength (within near ultraviolet and visible wavelength regions), the greater the absorption value is, the greater the turbidity is, the more the protein molecules in the sample tend to aggregate. The instrument for measurement was a multifunctional microplate reader (Molecular Devices M5). Samples in the same volume were added to a 96-well plate and the absorbance values were read.

Osmotic Pressure Measurement:

The freezing point method was used for measuring the osmotic pressure. The freezing point of a solution is measured by using a high-sensitivity temperature-sensing element on the basis of the proportional relation between the freezing point depression value and the molar concentration of the solution, and then converted into the osmotic pressure through electric quantity. Manufacturer of instrument: Loser, model: OM815.

Protein Concentration Determination:

Because the toxin in the antibody drug conjugate absorbed light at 280 nm, the protein concentration was corrected using the following formulas:

$$A_{280}=C_d\times\varepsilon_{280d}+C_{mab}\times\varepsilon_{280mab}$$

$$A_{370}=C_d\times\varepsilon_{370d}$$

where Cd represents the toxin concentration, Cmab represents the protein concentration, 6280d represents the extinction coefficient of the toxin at 280 nm, ε280mab represents the extinction coefficient of the protein at 280 nm, 6370d represents the extinction coefficient of the toxin at 370 nm, ε280mab=1.49 mg-1*cm-1*mL, ε280d=5000 (molar extinction coefficient of toxin at 280 nm)/1074.13 (molecular weight of toxin)=4.65 mg-1*cm-1*mL, and ε370d=19000 (molar extinction coefficient of toxin at 370 nm)/1074.13 (molecular weight of toxin)=17.69 mg-1*cm-1*mL; the above extinction coefficients were mass extinction coefficients.

Instrument for protein concentration measurement: ultraviolet-visible spectrophotometer; model: Nano Drop oneC; optical path length: 1 mm.

Illustratively, a molecular weight of the naked antibody is 145.181 kDa, and a molecular weight of the toxin is 1074 Da; if the mean DAR value is 5.7, the calculated ADC molecular weight will be 151.317 kDa, which is 1.042 times that of the naked antibody. Illustratively, if the ADC DAR value is 5.7 and the concentration of the naked antibody protein is 20.00 mg/mL, the ADC concentration will be 20.84 mg/mL.

Example 2-1. Screening for Buffer Systems and pH Values for Formulations 20 mg/mL (protein concentration based on naked antibody) ADC-33 formulations (containing no saccharide, surfactant and other buffers except for the following buffer systems) were prepared using the following buffer systems:

1) 10 mM histidine-sodium acetate, pH 5.0
2) 10 mM histidine-sodium acetate, pH 5.5
3) 10 mM histidine-sodium acetate, pH 6.0
4) 10 mM histidine-sodium acetate, pH 6.5
5) 10 mM histidine-histidine hydrochloride, pH 5.5
6) 10 mM succinic acid-sodium succinate, pH 5.5
7) 10 mM citric acid-sodium citrate, pH 5.5

Samples were taken for a high-temperature stability study (40° C.) and a shaking study (25° C., 300 rpm). The shaken sample contained 0.1 mg/mL polysorbate 80 (PS80), and the other samples contained 0.4 mg/mL PS80. Each formulation was filtered, and a container was filled with it, plugged and capped. The samples were subjected to the forced degradation experiments described above and examined for appearance, SEC and turbidity.

The results are shown in Table 6. The results show that where histidine-sodium acetate was used as the buffer, the appearances of the samples gradually worsened, the turbidities increased, and the SEC monomer proportion decreased, as the pH value increased within pH 5.0-6.5. At pH 5.5, the sample containing 10 mM histidine-sodium acetate and the sample containing 10 mM histidine hydrochloride were similar in appearance and SEC %, and were superior to those containing 10 mM succinic acid-sodium succinate or 10 mM citric acid-sodium citrate. Surprisingly, the formulation containing 10 mM succinic acid-sodium succinate was significantly superior in turbidity to the other formulations after the shaking study.

TABLE 6 pH and buffer system stability results

| No. | Conditions | Appearance | Turbidity A550 | SEC % |
|---|---|---|---|---|
| 1 | D 0 | Clear and transparent | 0.051 | 95.9 |
| | 40° C. D 12 | Slightly opalescent | 0.058 | 92.0 |
| | Shaking D 12 | Slightly opalescent | 0.055 | 95.0 |
| 2 | D 0 | Clear and transparent | 0.050 | 95.8 |
| | 40° C. D 12 | Slightly opalescent | 0.061 | 91.6 |
| | Shaking D 12 | Slightly opalescent | 0.056 | 93.3 |
| 3 | D 0 | Clear and transparent | 0.051 | 95.4 |
| | 40° C. D 12 | Slightly opalescent | 0.061 | 91.0 |
| | Shaking D 12 | Slightly opalescent | 0.060 | 91.3 |
| 4 | D 0 | Clear and transparent | 0.050 | 94.4 |
| | 40° C. D 12 | A large amount of particles like a haze of smoke | 0.085 | 89.3 |
| | Shaking D 12 | Slightly opalescent | 0.058 | 87.4 |
| 5 | D 0 | Clear and transparent | 0.051 | 95.5 |
| | 40° C. D 12 | Slightly opalescent | 0.065 | 90.9 |
| | Shaking D 12 | Slightly opalescent | 0.060 | 93.1 |
| 6 | D 0 | Clear and transparent | 0.053 | 95.7 |
| | 40° C. D 12 | Slightly opalescent, fine particles | 0.055 | 89.7 |
| | Shaking D 12 | Slightly opalescent | 0.053 | 91.5 |
| 7 | D 0 | Clear and transparent | 0.057 | 95.5 |
| | 40° C. D 12 | Opalescent | 0.063 | 88.8 |
| | Shaking D 12 | Opalescent | 0.059 | 89.3 |

Note:
in the table, "D" indicates day; for example, D 12 indicates 12 days, and D 0 indicates the start of the experiment; the same applies below.

Example 2-2. Screening for Surfactant Species 20 mg/mL (protein concentration based on naked antibody) ADC-32 formulations containing different polysorbate surfactants and each containing 10 mM succinic acid-sodium succinate (pH 5.0) buffer and 80 mg/mL sucrose were prepared. Each formulation was filtered, and a container was filled with it, plugged and capped. The samples were subjected to a high-temperature stability study (40° C.) and a shaking study (25° C., 300 rpm) and examined for appearance, SEC and reduced CE.

The results are shown in Table 7. There were no significant differences in appearance, SEC and reduced CE between the PS20 (polysorbate 20)-containing formulations and the PS80-containing formulations under different conditions, which indicates that both PS20 and PS80 were able to stabilize ADC-32 effectively.

TABLE 7

Results of the screening for polysorbate species

| Polysorbate species | Conditions | Appearance | SEC % | Reduced CE % |
|---|---|---|---|---|
| PS80 | D 0 | Clear and transparent | 99.1 | 98.7 |
| 0.2 | Shaking D 15 | Clear and transparent | 97.2 | 98.4 |
| mg/mL | 40° C. D 15 | Clear and transparent | 95.4 | 98.3 |
| PS20 | D 0 | Clear and transparent | 99.0 | 98.7 |
| 0.2 | Shaking D 15 | Clear and transparent | 97.7 | 98.7 |
| mg/mL | 40° C. D 15 | Clear and transparent | 95.4 | 98.2 |

Examples 2-3. Screening for Surfactant Concentrations

Samples containing 0, 0.1, 0.2, 0.4 and 0.6 mg/mL PS80 were prepared. Each sample also contained 10 mM succinic acid-sodium succinate (pH 5.0), 80 mg/mL sucrose and 20 mg/mL (protein concentration based on naked antibody) ADC-32. The samples were filtered to remove bacteria and particles and diluted with 0.9% NaCl such that the ADC-32 concentration was 0.2 mg/mL. The dilutions were examined for appearance and insoluble microparticles.

The results are shown in Table 8. Where the PS80 concentration in the formulation was at 0-0.2 mg/mL, as the concentration increased, the increase in the insoluble microparticles in the dilution became smaller and there were fewer and fewer visible particles. Where the concentration was at 0.2-0.6 mg/mL, there were no differences in insoluble microparticles between the dilutions and the appearances were good.

TABLE 8

Results of the screening for PS80 concentrations

| PS80 concentration | Time | Appearance | Insoluble microparticles/100 mL ≥2 μm | ≥10 μm | ≥25 μm |
|---|---|---|---|---|---|
| 0 mg/mL | 0 h | Clear and transparent, occasional particles | 8892 | 458 | 33 |
| | 4° C. 24 h | Distinct particles | 39408 | 4317 | 100 |
| 0.1 mg/mL PS80 | 0 h | Clear and transparent, occasional particles | 5267 | 525 | 17 |
| | 4° C. 24 h | Clear and transparent, occasional particles | 13342 | 508 | 0 |
| 0.2 mg/mL | 0 h | Clear and transparent | 2733 | 308 | 17 |
| PS80 | 4° C. 24 h | Clear and transparent | 4050 | 283 | 17 |
| 0.4 mg/mL | 0 h | Clear and transparent | 1367 | 175 | 17 |
| PS80 | 4° C. 24 h | Clear and transparent | 3267 | 433 | 8 |
| 0.6 mg/mL | 0 h | Clear and transparent | 2933 | 267 | 0 |
| PS80 | 4° C. 24 h | Clear and transparent | 4167 | 192 | 0 |

Examples 2-4. Screening for Sugar Species

Different samples containing 80 mg/mL sucrose, trehalose and mannitol were prepared. Each sample also contained 10 mM succinic acid-sodium succinate (pH 5.0), 0.2 mg/mL PS80 and 20 mg/mL (protein concentration based on naked antibody) ADC-32. The samples were filtered to remove bacteria and particles. Each formulation was filtered, and a container was filled with it, plugged and capped. The samples were subjected to a high-temperature stability study (40° C.) and a −35° C./4° C. freezing/thawing cycle study and examined for appearance, SEC and reduced CE.

The results are shown in Table 9. Under freezing/thawing conditions, sucrose was superior to trehalose and mannitol in appearance. Sucrose and trehalose were superior to mannitol in SEC results. At 40° C., sucrose was slightly superior to trehalose in reduced CE results.

TABLE 9

Results of the screening for saccharide species

| Saccharide species | Conditions | Appearance | SEC % | Reduced CE % |
|---|---|---|---|---|
| 80 mg/mL sucrose | D 0 | Clear and transparent | 99.23 | 97.44 |
| | 5 freezing/thawing cycles | Clear and transparent | 98.88 | 97.54 |
| | 40° C. D 17 | Clear and transparent | 95.05 | 98.04 |
| 80 mg/mL trehalose | D 0 | Clear and transparent | 99.23 | 97.33 |
| | 5 freezing/thawing cycles | A small amount of fine particles | 98.83 | 98.36 |
| | 40° C. D 17 | Clear and transparent | 95.38 | 96.50 |

TABLE 9-continued

Results of the screening for saccharide species

| Saccharide species | Conditions | Appearance | SEC % | Reduced CE % |
|---|---|---|---|---|
| 80 mg/mL mannitol | D 0 | Clear and transparent | 99.20 | 97.55 |
| | 5 freezing/thawing cycles | Distinct fine particles | 90.24 | 96.72 |
| | 40° C. D 17 | Clear and transparent | 95.29 | 97.28 |

Figure 8:
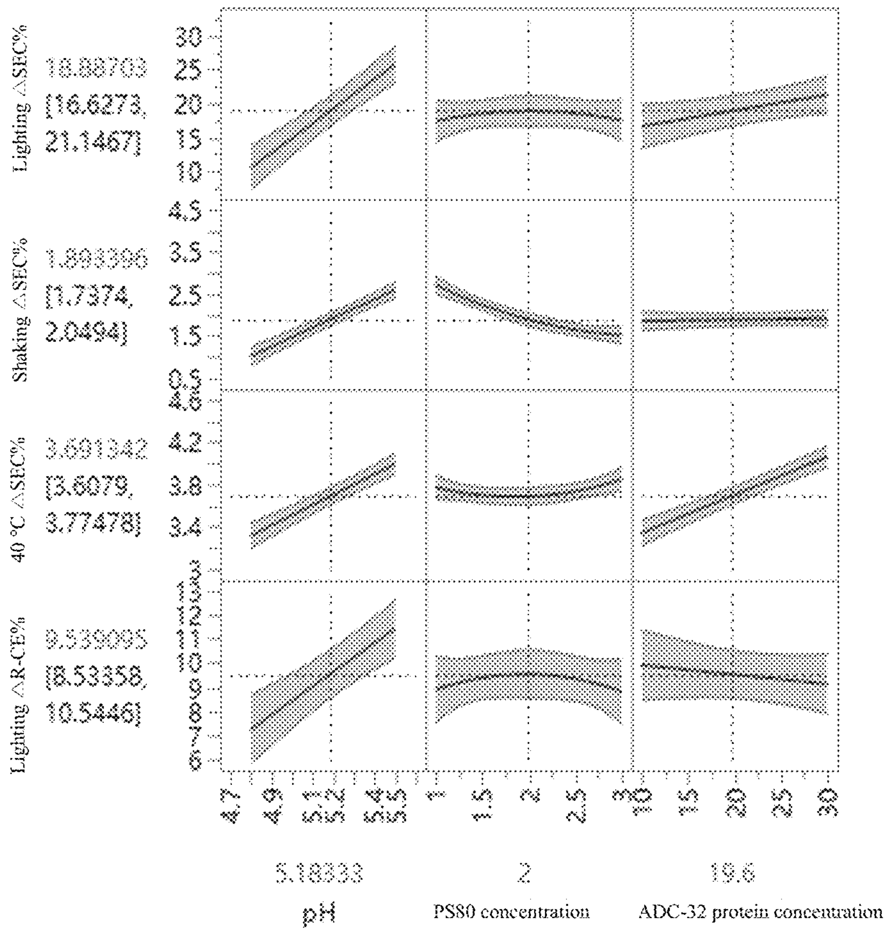
FIG. 8 shows fitted tendency graphs for a formula screening experiment, wherein the PS80 is in a unit of $10^{-4}$ g/mL, and the ADC-32 protein concentration (based on naked antibody) is in a unit of mg/mL.

Examples 2-5. Screening for pH, Antibody Drug Conjugate Concentrations and Polysorbates With 10 mM succinic acid-sodium succinate as the buffer and 80 mg/mL sucrose as the stabilizer, formulas were designed with respect to the pH, ADC-32 protein concentration (based on the naked antibody) and the polysorbate concentration, as shown in Table 10. A high-temperature stability study (40° C.), a lighting study (4° C., 4500 Lx) and a −35° C./4° C. freezing/thawing cycle study were conducted, and the results were statistically analyzed using the least square method with SEC and reduced CE as evaluation indexes. The results are shown in Table 11 and FIG. 8. The formulations of the present disclosure are shown to be highly pH-dependent. Under lighting, shaking and 40° C. conditions, as the pH increased, there was a greater decrease in SEC; similarly, under lighting conditions, as the pH increased, reduced CE increased, and there was a greater decrease in the monomer peak, which suggests that the formulations of the present disclosure should be at low pH values to have improved stability. Under shaking conditions, as the PS80 concentration increased, there was a downward trend toward SEC. There were no differences in the effects PS80 had on SEC and reduced CE under the other conditions. As the ADC-32 protein concentration increased, there was a greater decrease in the SEC monomer peak at 40° C. There were no differences in the effects the ADC-32 protein concentration had on SEC and reduced CE under the other conditions.

TABLE 10

Formula designs for screening experiments

| Formula No. | pH | PS80 ($10^{-4}$ g/mL) | ADC-32 protein concentration (mg/mL, based on naked antibody) |
|---|---|---|---|
| 1 | 5.0 | 1.7 | 10 |
| 2 | 5.2 | 1 | 30 |
| 3 | 5.5 | 3 | 10 |
| 4 | 4.8 | 2 | 30 |
| 5 | 4.8 | 1 | 20 |
| 6 | 5.5 | 1 | 10 |
| 7 | 5.5 | 2 | 30 |
| 8 | 4.8 | 3 | 16 |
| 9 | 5.5 | 2 | 20 |
| 10 | 5.2 | 3 | 30 |
| 11 | 5.2 | 2 | 20 |
| 12 | 5.2 | 2 | 20 |

TABLE 11

Results of the screening for formulas

| No. | Conditions | Appearance | SEC % | ΔSEC % | Reduced CE % | ΔReduced CE % |
|---|---|---|---|---|---|---|
| 1 | D0 | Clear and transparent | 99.2 | 0.0 | 99.0 | 0.0 |
| | Lighting D10 | Clear and transparent, yellowish | 88.9 | 10.3 | 91.5 | 7.5 |
| | Shaking D15 | Clear and transparent | 97.8 | 1.4 | 99.0 | 0.0 |
| | 40° C. D15 | Clear and transparent | 96.0 | 3.2 | 97.9 | 1.1 |
| 2 | D0 | Clear and transparent | 98.9 | 0.0 | 98.7 | 0.0 |
| | Lighting D10 | Clear and transparent, yellowish | 79.4 | 19.5 | 90.5 | 8.2 |
| | Shaking D15 | Clear and transparent | 96.3 | 2.6 | 99.1 | −0.4 |
| | 40° C. D15 | Clear and transparent | 94.7 | 4.2 | 97.9 | 0.7 |
| 3 | D0 | Clear and transparent | 98.9 | 0.0 | 98.7 | 0.0 |
| | Lighting D10 | Clear and transparent, yellowish | 77.2 | 21.7 | 87.2 | 11.5 |
| | Shaking D15 | Clear and transparent | 96.9 | 2.0 | 97.5 | 1.2 |
| | 40° C. D15 | Clear and transparent | 95.1 | 3.8 | 98.2 | 0.5 |
| 4 | D0 | Clear and transparent | 99.0 | 0.0 | 98.7 | 0.0 |
| | Lighting D10 | Clear and transparent, yellowish | 86.3 | 12.7 | 91.4 | 7.3 |
| | Shaking D15 | Clear and transparent | 97.7 | 1.3 | 98.8 | −0.1 |
| | 40° C. D15 | Clear and transparent | 95.3 | 3.7 | 98.1 | 0.6 |
| 5 | D0 | Clear and transparent | 99.1 | 0.0 | 98.7 | 0.0 |
| | Lighting D10 | Clear and transparent, yellowish | 90.0 | 9.1 | 92.1 | 6.7 |
| | Shaking D15 | Clear and transparent | 97.5 | 1.6 | 98.4 | 0.4 |
| | 40° C. D15 | Clear and transparent | 95.7 | 3.4 | 98.0 | 0.7 |
| 6 | D0 | Clear and transparent | 98.9 | 0.0 | 98.9 | 0.0 |
| | Lighting D10 | Clear and transparent, yellowish | 76.2 | 22.8 | 86.9 | 12.0 |
| | Shaking D15 | Clear and transparent | 95.0 | 4.0 | 98.5 | 0.4 |
| | 40° C. D15 | Clear and transparent | 95.2 | 3.7 | 98.1 | 0.8 |
| 7 | D0 | Clear and transparent | 98.7 | 0.0 | 98.3 | 0.0 |
| | Lighting D10 | Clear and transparent, yellowish | 68.2 | 30.5 | 86.8 | 11.4 |
| | Shaking D15 | Clear and transparent | 96.1 | 2.6 | 98.9 | −0.6 |
| | 40° C. D15 | Clear and transparent | 94.3 | 4.4 | 97.7 | 0.6 |
| 8 | D0 | Clear and transparent | 99.2 | 0.0 | 99.0 | 0.0 |
| | Lighting D10 | Clear and transparent, yellowish | 88.3 | 10.9 | 91.8 | 7.2 |
| | Shaking D15 | Clear and transparent | 98.1 | 1.0 | 98.9 | 0.1 |
| | 40° C. D15 | A small amount of small particles | 95.8 | 3.4 | 98.5 | 0.5 |
| 9 | D0 | Clear and transparent | 98.9 | 0.0 | 97.6 | 0.0 |
| | Lighting D10 | Clear and transparent, yellowish | 73.8 | 25.1 | 87.1 | 10.5 |
| | Shaking D15 | Clear and transparent | 96.3 | 2.6 | 97.7 | −0.1 |
| | 40° C. D15 | Clear and transparent | 94.7 | 4.1 | 97.1 | 0.5 |
| 10 | D0 | Clear and transparent | 98.9 | 0.0 | 98.1 | 0.0 |
| | Lighting D10 | Clear and transparent, yellowish | 80.9 | 18.0 | 90.4 | 7.7 |
| | Shaking D15 | Clear and transparent | 97.3 | 1.6 | 99.0 | −1.0 |
| | 40° C. D15 | Clear and transparent | 94.8 | 4.2 | 98.5 | −0.5 |
| 11 | D0 | Clear and transparent | 99.1 | 0.0 | 98.7 | 0.0 |
| | Lighting D10 | Clear and transparent, yellowish | 80.5 | 18.6 | 88.7 | 10.0 |
| | Shaking D15 | Clear and transparent | 97.2 | 1.9 | 98.4 | 0.3 |
| | 40° C. D15 | Clear and transparent | 95.4 | 3.7 | 98.3 | 0.3 |
| 12 | D0 | Clear and transparent | 99.0 | 0.0 | 98.7 | 0.0 |
| | Lighting D10 | Clear and transparent, yellowish | 78.2 | 20.8 | 88.4 | 10.3 |
| | Shaking D15 | Clear and transparent | 97.1 | 1.9 | 99.1 | −0.4 |
| | 40° C. CD15 | Clear and transparent | 95.4 | 3.6 | 97.9 | 0.8 |

Examples 2-6. Lyophilization Process Development

A 20 mg/mL (protein concentration based on naked antibody) ADC-33 stock solution containing 10 mM succinic acid-sodium succinate pH 5.0, 80 mg/mL sucrose and 0.2 mg/mL PS80 was prepared, filtered, bottled and then lyophilized according to the lyophilization process parameters 1 (see Table 12). The lyophilization sample was in the form of a white powder cake with a flat surface and contained 1.05% water. The bottom of the powder cake was slightly depressed in the center. The sample was reconstituted with water for injection, and the pH value was measured. The results are shown in Table 13. The ionic strength (≥10 mM) was high enough for buffering. The formula included 80 mg/mL sucrose, which could meet the iso-osmotic requirement.

TABLE 12

Lyophilization process parameters 1

| Lyophilization process parameter | Temperature setting (° C.) | Time setting (min) | Retention time (h) | Degree of vacuum (Pa) |
|---|---|---|---|---|
| Pre-freezing | 5 | 10 | 1 | N/A |
| Pre-freezing | −45 | 50 | 2 | N/A |
| Primary drying | −25 | 120 | 40 | 10 |
| Secondary drying | 25 | 60 | 8 | 1 |

TABLE 13

Final formula pH and osmolality results

| pH of buffer | Osmotic pressure of stock solution | pH of stock solution | pH after reconstitution |
|---|---|---|---|
| 5.00 | 298 mosm | 5.06 | 5.06 |

A 20 mg/mL (protein concentration based on naked antibody) ADC-33 stock solution containing 10 mM succinic acid-sodium succinate pH 5.0, 80 mg/mL sucrose and 0.2 mg/mL PS80 was prepared, filtered, bottled and then lyophilized according to the lyophilization process parameters 2 (see Table 14). The surface of the powder cake was flat and showed no wrinkles and depressions. 0.89% water was contained. The lyophilization process could meet the requirement for product quality.

TABLE 14

Lyophilization process parameters 2

| Lyophilization process parameter | Temperature setting (° C.) | Time setting (min) | Retention time (h) | Degree of vacuum (Pa) |
|---|---|---|---|---|
| Pre-freezing | −5 | 10 | 1 | N/A |
| Pre-freezing | −45 | 40 | 2 | N/A |
| Primary drying | −20 | 120 | 35 | 10 |
| Secondary drying | 25 | 60 | 8 | 1 |

A 20 mg/mL (protein concentration based on naked antibody) ADC-32 stock solution containing 10 mM succinic acid-sodium succinate pH 5.0, 80 mg/mL sucrose and 0.2 mg/mL PS80 was prepared, filtered, bottled and then lyophilized according to the lyophilization process parameters 3 (see Table 15). The surface of the powder cake was flat and showed no depressions. The bottom edge of the powder cake slightly shrank. 1.17% water was contained. The lyophilization process could substantially meet the requirement for product quality.

TABLE 15

| Lyophilization process parameters 3 | | | | |
|---|---|---|---|---|
| Lyophilization process parameter | Temperature setting (° C.) | Time setting (min) | Retention time (h) | Degree of vacuum (Pa) |
| Pre-freezing | −5 | 10 | 1 | N/A |
| Pre-freezing | −45 | 40 | 2 | N/A |
| Primary drying | −15 | 120 | 30 | 10 |
| Secondary drying | 25 | 60 | 9 | 1 |

Examples 2-7. Long-Term Stability Data

A 20 mg/mL (protein concentration based on naked antibody) ADC-32 stock solution containing 10 mM succinic acid-sodium succinate pH 5.0, 80 mg/mL sucrose and 0.2 mg/mL PS80 was prepared, filtered and bottled, and then pilot batches of finished products of the stock solution were formulated according to the lyophilization process parameters 2, subjected to long-term storage at 2-8° C., reconstituted and then tested. The results are shown in Table 16. Compared to the products on DO, those under 2-8° C. M3 conditions showed SEC, reduced CE and free toxin levels within acceptable ranges (SEC %≥93%; reduced CE %≥95%; free toxin level ≤330 ppm). The SEC slightly decreased by 0.5%, while both the reduced CE and free toxin level remained unchanged.

TABLE 16

| Long-term stability data results | | | | |
|---|---|---|---|---|
| Batch No. | Conditions | SEC % | Reduced CE % | Free toxin |
| P1927 | D 0 | 97.6 | 99.3 | <5 ppm |
| | 2~8° C. M 3 | 97.2 | 99.2 | <5 ppm |
| P1929 | D 0 | 97.8 | 99.3 | <5 ppm |
| | 2~8° C. M 3 | 97.2 | 99.2 | <5 ppm |

Note:
in the table, "M" represents month; for example, M 3 represents 3 months.

The invention claimed is:

1. A pharmaceutical composition, comprising an antibody drug conjugate and a succinate buffer, wherein the antibody drug conjugate has a structure of general formula as follows:

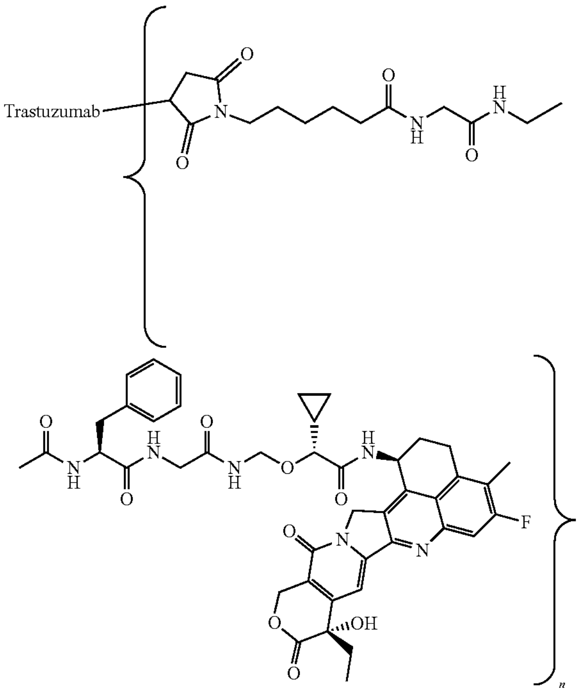

wherein:

n is a decimal or an integer from 1 to 10;

the pharmaceutical composition is at a pH of 4.5 to 5.2.

2. The pharmaceutical composition according to claim 1, wherein the pharmaceutical composition further comprises a surfactant of polysorbate.

3. The pharmaceutical composition according to claim 2, wherein the surfactant is at a concentration of about 0.01 mg/mL to about 1.0 mg/mL.

4. The pharmaceutical composition according to claim 1, wherein the composition further comprises a saccharide selected from the group consisting of sucrose, mannitol, sorbitol and trehalose.

5. The pharmaceutical composition according to claim 4, wherein the saccharide is at a concentration of about 60 mg/mL to about 90 mg/mL.

6. The pharmaceutical composition according to claim 1, wherein the antibody drug conjugate is at a concentration of about 1 mg/mL to about 100 mg/mL.

7. The pharmaceutical composition according to claim 1, wherein the succinate buffer is at a concentration of about 5 mM to about 50 mM.

8. The pharmaceutical composition according to claim 1, comprising the following components:

(a) the antibody drug conjugate at about 10 mg/mL to about 30 mg/mL, (b) a polysorbate at about 0.05 mg/mL to about 0.5 mg/mL, (c) a saccharide at about 60 mg/mL to about 90 mg/mL, and (d) a succinate buffer at about 5 mM to about 20 mM; the pharmaceutical composition being at a pH of 4.8 to 5.2.

9. The pharmaceutical composition according to claim 1, wherein n is a decimal or an integer from 3 to 8.

10. A lyophilized formulation comprising an antibody drug conjugate, wherein the formulation can be reconstituted to form the pharmaceutical composition according to claim 1.

11. A method for preparing a lyophilized formulation comprising an antibody drug conjugate, comprising a step of lyophilizing the pharmaceutical composition according to claim 1.

12. A lyophilized formulation comprising an antibody drug conjugate, obtained by lyophilizing the pharmaceutical composition according to claim 1.

13. A reconstituted solution comprising an antibody drug conjugate, obtained by reconstituting the lyophilized formulation according to claim 10.

14. An article of manufacture, comprising a container containing the pharmaceutical composition according to claim 1.

15. The pharmaceutical composition according to claim 1, wherein the pharmaceutical composition is at a pH of 4.8 to 5.2.

16. The pharmaceutical composition according to claim 1, wherein the pharmaceutical composition is at a pH of 5.0 to 5.1.

17. The pharmaceutical composition according to claim 2, wherein the surfactant is polysorbate 80 or polysorbate 20.

18. The pharmaceutical composition according to claim 2, wherein the surfactant is polysorbate 80.

19. The pharmaceutical composition according to claim 2, wherein the surfactant is at a concentration of about 0.05 mg/mL to about 0.5 mg/mL.

20. The pharmaceutical composition according to claim 4, wherein the saccharide is sucrose.

21. The pharmaceutical composition according to claim 1, wherein the antibody drug conjugate is at a concentration of about 10 mg/mL to about 30 mg/mL.

22. The pharmaceutical composition according to claim 1, wherein the antibody drug conjugate is at a concentration of about 20 mg/mL to about 22 mg/mL.

23. The pharmaceutical composition according to claim 1, wherein the succinate buffer is at a concentration of about 5 mM to about 20 mM.

24. The pharmaceutical composition according to claim 1, wherein the pharmaceutical composition comprises:

(a) the antibody drug conjugate at about 20 mg/mL to about 22 mg/mL, (b) polysorbate 80 at about 0.2 mg/mL, (c) sucrose at about 80 mg/mL, and (d) a succinate buffer at about 10 mM; the composition being at a pH of 5.0 to 5.1.

* * * * *